(12) United States Patent
Arnold et al.

(10) Patent No.: US 7,368,264 B2
(45) Date of Patent: May 6, 2008

(54) SLC1A1 MARKER FOR ANXIETY DISORDER

(75) Inventors: Paul Daniel Arnold, Toronto (CA); Margaret A. Richter, Toronto (CA); James Lowery Kennedy, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 0 days.

(21) Appl. No.: 11/591,244

(22) Filed: Oct. 31, 2006

(65) Prior Publication Data

US 2007/0099224 A1 May 3, 2007

Related U.S. Application Data

(60) Provisional application No. 60/731,472, filed on Oct. 31, 2005.

(30) Foreign Application Priority Data

Dec. 23, 2005 (CA) .................................. 2528222

(51) Int. Cl.
*C12P 19/34* (2006.01)

(52) U.S. Cl. .................................................... 435/91.2
(58) Field of Classification Search ................ 435/91.1
See application file for complete search history.

(56) References Cited

U.S. PATENT DOCUMENTS 5,210,015 A    5/1993  Gelfand et al. ................. 435/6
5,487,972 A    1/1996  Gelfand et al. ................. 435/6

FOREIGN PATENT DOCUMENTS

WO    WO/95/13399    5/1995

OTHER PUBLICATIONS

Dickel et al. Arch. Gen. Psychiatry, vol. 63, pp. 778-785, Jul. 2006.*
S.A. Rasmussen et al., "The Epidemiology and Differential Diagnosis of Obsessive Compulsive Disorder" J. Clin. Psychiatry, vol. 53, 4 suppl., pp. 4-10 (1992).
J. Alsobrook et al., "Segregation Analysis Of Obsessive-Compulsive Disorder Using Symptom-Based Factor Scores", American Journal of Medical Genetics (Neuropsychiatric Genetics) vol. 88, pp. 669-675 (1999).
R. R. Anholt et al., "Quantitative Genetic Analyses Of Complex Behaviours In Drosophila", Nature Reviews Genetics, vol. 5, pp. 838-849 (2004).
P. D. Arnold et al., "Association Of A Glutamate (NMDA) Subunit Receptor Gene (GRIN2B) With Obsessive-Compulsive Disorder: A Preliminary Study", Psychopharmacology (Berl), vol. 174, pp. 530-538 (2004).
P. D. Arnold et al., "Glutamate Transporter Gene SLC 1 A 1 Associated With Obsessive-Compulsive Disorder", Arch. Gen. Psychiatry, vol. 63 (7), pp. 769-776. (2006).
J. C. Barrett et al., "Haploview: Analysis And Visualization Of LD And Haplotype Maps", Bioinformatics, vol. 21, Issue 2, pp. 263-265 (2005).
S. Bhattacharyya et al., "A Family Genetic Study Of Clinical Subtypes Of Obsessive-Compulsive Disorder", Psychiatric Genetics, vol. 15, No. 3, pp. 175-180 (2005).
O. J. Bienvenu et al., "The Relationship Of Obsessive-Compulsive Disorder To Possible Spectrum Disorders: Results From A Family Study", Biological Psychiatry, vol. 48, pp. 287-293 (2000).
Y. L. Bronstein, et al., "Neurochemistry Of Frontal-Subcortical Circuits". In: Lichter D, Cummings J, eds. Frontal-subcortical circuits in psychiatric and neurological disorders. New York: Guilford Press, pp. 59-91 (2001).
G. Carey et al., "Twin And Family Studies Of Anxiety, Phobic And Obsessive Disorders", In: Klein D, Rabkin , J, eds. Anxiety:New Research And Changing Concepts. New York:Raven Press; pp. 117-136 (1981).
M. C. Cavallini et al., "Complex Segregation Analysis For Obsessive Compulsive Disorder And Related Disorders", American Journal of Medical Genetics (Neuropsychiatric Genetics) vol. 88, pp. 38-43 (1999).
N. Chabane et al., "Early-Onset Obsessive-Compulsive Disorder: A Subgroup With A Specific Clinical And Familial Pattern?", Journal of Child Psychology Psychiatry; vol. 46, No. 8, pp. 881-887 (2005).
B. Conne et al., "The 3' Untranslated Region Of Messenger RNA: A Molecular 'Hotspot' For Pathology?", Nature Medicine, vol. 6, No. 6, pp. 637-641 (2000).
R. Delorme et al., "Frequency And Transmission Of Glutamate Receptors GRIK2 And GRIK3 Polymorphisms In Patients With Obsessive Compulsive Disorder", Clinical Neuroscience and Neuropathology, vol. 15, No. 4, pp. 699-702 (2004).
D. Denys et al., "Symptom Dimensions In Obsessive-Compulsive Disorder: Factor Analysis On A Clinician-Rated Scale And A Self-Report Measure", Psychopathology vol. 37, pp. 181-189 (2003).

(Continued)

*Primary Examiner*—Gary Benzion
*Assistant Examiner*—Cynthia B Wilder
(74) *Attorney, Agent, or Firm*—Winston & Strawn LLP

(57) ABSTRACT

The present invention provides methods for diagnosing or identifying susceptibility of a subject to an anxiety or mood disorder. One method involves testing a sample obtained from the subject for the presence of a polymorphism in Intron 10 of the SLC1A1 gene. The presence of allele G or allele A of the A/G polymorphism rs301434 indicates that the patient is susceptible to an anxiety disorder. An alternate method involves testing a sample obtained from the subject for the presence of a polymorphism in the 3' untranslated region of the SLC1A1 gene. The presence of allele C of C/G polymorphism rs3087879 indicates that the patient is susceptible to an anxiety disorder. Furthermore, a method is provided that involves testing a sample obtained from the subject for the presence of a haplotype in the SLC1A1 gene, wherein the combined presence allele G of the A/G polymorphism rs301434 and allele C of C/G polymorphism rs3087879 indicates that the patient is susceptible to a mood disorder.

20 Claims, 33 Drawing Sheets

OTHER PUBLICATIONS

M. B. First et al., "Structured Clinical Interview for DSMIV Axis I Disorders", Patient Edition. (SCID-I, version 2.0). New York: Biometrics Research Department, New York State Psychiatric Institute (1996).
W. K. Goodman et al., "The Yale-Brown Obsessive Compulsive Scale: I. Development, use, and reliability", Arch Gen Psychiatry, vol. 46, pp. 1006-1011 (1989).
W. K. Goodman et al., The Yale-Brown Obsessive Compullsive Scale (Y-BOCS), Arch Gen Psychiatry, Diagnostic and Statistical Manual of Mental Disorders, Fourth Edition. (vol. 46:1006-1011) Washington, DC American Psychiatric Association, 1994), SCID (Structured Clinical Interview for DSM-IV, or FIGS (Family Interview for Genetic Studies, (1989).
I. I. Gottesman, et al., "The Endophenotype Concept In Psychiatry: Etymology And Strategic Intentions", American Journal of Psychiatry; vol. 160, pp. 636-645 (2003).
G. L. Hanna et al., "Familial And Sporadic Subtypes Of Early-Onset Obsessive-Compulsive Disorder", Biological Psychiatry, vol. 57, pp. 895-900 (2005).
J. M. Hettema et al., "A Review And Meta-Analysis Of The Genetic Epidemiology Of Anxiety Disorders". American Journal of Psychiatry; vol. 158, pp. 1568-1578 (2001).
G. L. Hanna et al., Genome-Wide Linkage Analysis Of Families With Obsessive-Commpulsive Disorder Ascertained Through Pediatric Probands, American Journal of Medical Genetics (Neuropsychiatric Genetics) vol. 114, pp. 541-552 (2002).
D. Hien et al., "Structured interview for DSM-IV childhood diagnoses (KID SCID)", Unpublished manuscript (1999).
Y. H. Huang et al., "Glutamate Transporters Bring Competition To The Synapse", Current Opinion in Neurobiology, vol. 14, pp. 346-352 (2004).
Inouye E., "Similar And Dissimilar Manifestations Of Obsessive-Compulsive Neurosis In Monozygotic Twins", American Journal of Psychiatry, vol. 121, pp. 1171-1175 (1965).
International HapMap Consorium, "The International HapMap Project", Nature, vol. 426, pp. 789-796 (2003).
Y. Kanai et al., "The Glutamate/Neutral Amino Acid Transporter Family SLC 1: Molecular, Physiological And Pharmacological Aspects", . Pflugers Arch—Eur J. Physiol., vol. 447, pp. 469-479 (2004).
D. Lahiri et al., "A Rapid Non-Enzymatic Method For The Preparation Of HMW DNA From Blood For RFLP Studies", . Nucleic Acids Resesearch, vol. 19, pp. 5444 (1991).
N. Laird et al., "Implementing A Unified Approach To Family Based Tests Of Association", Genetic Epidemiology, vol. 19 (Suppl 1) pp. S36-S42 (2000).
M. B. Lanktree et al., "PedSplit: Pedigree Management For Stratified Analysis", Bioinformatics, vol. 20 No. 14, pp. 2315-2316 (2004).
J. F. Leckman et al., "Symptoms Of Obsessive-Compulsive Disorder", American Journal of Psychiatry, vol. 154 (7) pp. 911-917 (1997).
J. F. Leckman et al., "Obsessive-Compulsive Symptom Dimensions In Affected Sibling Pairs Diagnosed With Gilles De La Tourette Syndrome", . American Journal of Medical Genetics (Neuropsychiatric Genetics) vol. 116B, pp. 60-68 (2003).
D. Mataix-Cols et al., "A Multidimensional Model Of Obsessive-Compulsive Disorder", American Journal of Psychiatry, vol. 162 (2) pp. 228-238 (2005).
G.C. Mathews et al., "Neuronal Glutamate Uptake Contributes To GABA Synthesis And Inhibitory Synaptic Strength", Journal of Neuroscience, vol. 23 (6) pp. 2040-2048 (2003).
E.C. Miguel et al., "Obsessive-Compulsive Disorder Phenotypes: Implications For Genetic Studies". Molecular Psychiatry, vol. 10, pp. 258-275 (2005).
C. Murray et al., "Global Burden Of Disease: A comprehensive assessment of mortality and disability from diseases, injuries and risk factors in 1990 and projected to 2020". vol. 1, Harvard: World Health Organization (1996).
G. Nestadt et al., "Complex Segregation Analysis Provides Compelling Evidence For A Major Gene Underlying Obsessive-Compulsive Disorder And For Heterogeneity By Sex", Am. J. Hum. Genet., pp. 1611-1616 (200).

G. Nestadt et al., "A Family Study Of Obsessive-Compulsive Disorder", Arch Gen Psychiatry, vol. 57, pp. 358-363 (2000).
H. Nicolini "Segregation Analysis Of Obsessive Compulsive And Associated Disorders. Preliminary results", Ursus Medicus, vol. 1, pp. 25-28 (1991).
E. J. Nordstrom et al., "A Transgenic Model Of Comorbid Tourette's Syndrome And Obsessive-Compulsive Disorder Circuitry", . Molecualr Psychiatry, vol. 7, pp. 617-625 (2002).
D. Pauls et al., "A Family Study Of Obsessive-Compulsive Disorder", AJP: American Journal of Psychiatry, vol. 152, pp. 76-84 (1995).
K.A Phillips, "The Obsessive-Compulsive Spectrums", Psychiatr. Clin. North Am., vol. 25(4), pp. 791-809 (2002).
D. Rosenberg et al., "Toward A Neurodevelopmental Model Of Obsessive Ccompulsive Disorder", Biological Psychiatry, vol. 43, pp. 623-640 (1998).
D. Rosenberg et al., "Decrease In Caudate Glutamatergic Concentrations In Pediatric Obsessive Compulsive Disorder Patients Taking Paroxetine". Journal of American Academy of Child Adolescent Psychiatry, vol. 39, pp. 1096-1103 (2000).
D. Rosenberg et al., "Genetic And Imaging Strategies In Obsessive-Compulsive Disorder: Potential Implications For Treatment Development", Biological Psychiatry, vol. 48, pp. 1210-1222 (2000).
D. Rosenberg et al. "Reduced Anterior Cingulate Glutamatergic Concentrations In Chlldhood OCD And Major Depression Versus Healthy Controls". Journal of American Academy of Child Adolescent Psychiatry, vol. 43:9, pp. 1146-1153 (2004).
M. Rufer et al., "Temporal Stability Of Symptom Dimensions In Adult Pateints With Obsessive-Compulsive Disorder", . Journal of Affective Disorders, vol. 88(1), pp. 99-102 (2005).
L. Scahill et al., "Children's Yale-Brown Obsessive Compulsive Scale: Reliability And Validity", Journal of American Academy of Child Adolescent Psychiatry, vol. 36(6),, pp. 884-852 (1997).
J.P. Sepkuty et al., "A Neuronal Glutamate Transporter Contributes To Neurotransmitter GABA Synthesis And Epilepsy", Journal of Neuroscience, vol. 22 (15) pp. 6372-6379 (2002).
Y, Shigeri et al., "Molecular Pharmacology Of Glutamate Transporters, EAATs and VGLUTs", . Brain Research Reviews, vol. 45, pp. 250-265 (2004).
R.S. Spielman et al., "Transmission Test For Linkage Disequilibrium: The Insulin Gene Region And Insulin-Dependent Diabetes Mellitus (IDDM)", . Am. J. Hum. Genet., vol. 52, pp. :506-516 (1993).
D. O. Stram, "Tag SNP Selection For Association Studies", Genetic Epidemiology, vol. 27, pp. 365-374 (2004).
L. J. Summerfeldt et al., "Symptom Structure In Obsessive-Compulsive Disorder: A Confirmatory Factor-Analytic Study", . Behaviour Research and Therapy, vol. 37, pp. 297-311 (1999).
J. Veenstra-Vander Weele et al., "Genomic Organization Of The SLC 1A1/EAAC1 Gene And Mutation Screening In Early-Onset Obsessive-Compulsive Disorder", Molecular Psychiatry, vol. 6, pp. 160-167 (2001).
V. L. Willour et al., "Replication Study Supports Evidence For Linkage To 9p24 In Obsessive-Compulsive Disorder", Am. J. Hum. Genet., vol. 75, pp. :508-513 (2004).
G. Zai, et al., "Evidence For The Gamma-Amino-Butyric Acid Type B Receptor 1 (GABBRI) Gene As A Susceptibility Factor In Obsessive-Compulsive Disorder", . American Journal of Medical Genetics (Neuropsychiatric Genetics) vol. 134B, pp. 25-29 (2005).
H, Zhang et al., "Genomewide Scan Of Hoarding In Sib Pairs In Which Both Sibs Have Gilles De La Tourette Syndrome", Am. J. Hum. Genet., vol. 70, pp. 896-904 (2002).
J. Zoharet et al., "Is There Sexual Dimorphism In Obsessive-Compulsive Disorder?", Neuroscience Biobehavioral Reviews, vol. 23, pp. 845-849 (1999).
S. E. Stewart et al., "Obsessive Compulsive Disorder (OCD) Phenotypes in Pediatric OCD", American Academy of Child and Adolescent Psychiatry/Canadian Academy of Child Adolescent Psychiatry Joint Annual Meeting, pp. 56 (2005).

* cited by examiner

FIGURE 1

[SEQ ID NO:1]

SNP 7 = A/G polymorphism (R) at pos 4572082 in Intron 10
chromosome:NCBI35:9:4571757:4572407:-1

CAGGGCACTGAATTGAGAAATAGCTGATCCTGTCCAAGGTACAAGCATTTACTCCTGACT

GCTCCTTTTTGCCAGTAGATGCACTTTGTGGGAAAGAAAGATCTGGAATCCAGGAGGGGC

AGCCAGGTGAACTTTATTACCAGGTATTTAAAAAGATCCCTCTTGGTAAGATCAGCTGAG

GCAGTAGGGATTTTTTTCTTTGTAATGTGCAGTCTCTTTATCAGCAACATCTTCCTTATT

TTAATTGGATCATTCTGAAGGAAACAAGGGTTCAACATGCCCTGAAAAATCCCTTGACTT

GGATAAGCTGGAGGCCACACCTACA

R

TGCTTTCTGGAGACAAGTCCTTGCCCTTGGGCCA

AGGCCTGAACTGTTGCCCGGGTTCCACTGTGTTGAAAGGTGAAAATGTAAAAATTGGCAA

TTTAAACTGGAAGAATCCCTGATTCTATCCACACATTCATATTCTTTGGGGCTAAAAAAA

GCCAGAGTTCTTAGGAAGCTGATTCTACTGCCCATTCATCTGCCTACTGAGGTGTTGCAG

AAAGCATTTGAGGGTACAGTCAAACACAGGCCAGAGTTTTTTGACAAGTGTATTTTCATT

CAGTGGTTTTGACCACCAAATTATAGTAAATTAGAGATTTCTGGGGCTGTA

FIGURE 2

[SEQ ID NO:2]

SNP 8 = A/G polymorphism (R) at pos 4572843 in Intron 10
chromosome:NCBI35:9:4572518:4573168:-1

GCCAGTCGACAGCAATGATCAGGGTGACATCCTCGGCGGGCAGGCCCACGGCACTCAGCA

CAATCACCATGGTCACCAGGCCAGCCTGGGGCACGCCAGCAGCTCCGATGCTGGCAGATG

TGGCCGTGATACTGCAGAAACATACCAGCAGGAAAGGAGTTAGACACTTACCTCTCCCGT

TAAAGCCCTGGCCTGAAATGGTTACTCCCGCTTAGTCCCGATGGCTATTACTGCTGTGTC

CCTAAATTGGGTAGTTAGAATCTGTGACTTGCTGAGCCCCAGCTCTGCCTCATTACAGGA

TTAGAGCTGTGGGGGGAGGGGACT

R

TGAGGGGTATGATGCCATCTCCTTGCAGACGGAG

ATATGGCACATCACTCTAATGCAAGGAAGAACTGCATAAGTGGCACCAAAAAATAAGTAA

GAGAGATACTCAAGAGGAAAGCAGGAGTTTACTAAATGGGGTGTTAATAGGAGGCTTCGT

GTACTCATCTATGTATACATACACTCATCCTAAATAAGTGCCAGGTACCTCTGCACCTGC

CTTCCTACTCCCTTGTTCCATCTACTCACCACCCAATAATTTACTGAGCACCTAATATAT

GGCAGGAATTTAAGTTGCCCTGAAGGATGGACAGAAGGATAGTTGTAGGGG

FIGURE 3

[SEQ ID NO:3] SNP 9 = C/G polymorphism (S) at pos 4576808 (3065 on cDNA sequence)

```
   1 agcggaggag ccgggcgcgc ctgccacgca aaactaccgg gctggcaggg cggcgggcgc
  61 ggtgcgcgat cccgggtggc ggcggcaacg gcggtggtga cggcggcgac tgcagcggcc
 121 ggctctcacc tctcccctgt gcaccgcat ctcgccgcgc cgccgagcag ccagcagtcc
 181 ccgggtcgcc cagcccacgc gcgcacggcc gagcccagcg cacaatagcg gcgacagcca
 241 tggggaaacc ggcgaggaaa ggatgcgagt ggaagcgctt cctgaagaat aactgggtgt
 301 tgctgtccac cgtggccgcg gtggtgctag gcattaccac aggagtcttg gttcgagaac
 361 acagcaacct ctcaactcta gagaaattct actttgcttt tcctggagaa attctaatgc
 421 ggatgctgaa actcatcatt ttgccattaa ttatatccag catgattaca ggtgttgctg
 481 cactggattc caacgtatcc ggaaaaattg gtgtgcgcgc tgtcgtgtat tatttctgta
 541 ccactctcat tgctgttatt ctaggtattg tgctggtggt gagcatcaag cctggtgtca
 601 cccagaaagt gggtgaaatt gcgaggacag gcagcacccc tgaagtcagt acggtggatg
 661 ccatgttaga tctcatcagg aatatgttcc ctgagaatct tgtccaggcc tgttttcagc
 721 agtacaaaac taagcgtgaa gaagtgaagc ctcccagcga tccagagatg aacatgacag
 781 aagagtcctt cacagctgtc atgacaactg caatttccaa gaacaaaaca aaggaataca
 841 aaattgttgg catgtattca gatggcataa acgtcctggg cttgattgtc ttttgccttg
 901 tctttggact tgtcattgga aaaatgggag aaaagggaca aattctggtg gatttcttca
 961 atgctttgag tgatgcaacc atgaaaatcg ttcagatcat catgtgttat atgccactag
1021 gtattttgtt cctgattgct gggaagatca tagaagttga agactggaa atattccgca
1081 agctgggcct ttacatggcc acagtcctga ctgggcttgc aatccactcc attgtaattc
1141 tcccgctgat atatttcata gtcgtacgaa agaaccctttt ccgatttgcc atgggaatgg
1201 cccaggctct cctgacagct ctcatgatct cttccagttc agcaacactg cctgtcacct
1261 tccgctgtgc tgaagaaaat aaccaggtgg acaagaggat cactcgattc gtgttacccg
1321 ttggtgcaac aatcaacatg gatgggactg cgctctatga agcagtggca gcggtgttta
1381 ttgcacagtt gaatgacctg gacttgggca ttgggcagat catccaccatc agtatacgg
1441 ccacatctgc cagcatcgga gctgctggtc tgcccgagcc tggcctggtg accatggtga
1501 ttgtgctgag tgccgtgggc ctgccgccg aggatgtcac cctgatcatt gctgtcgact
1561 ggctcctgga ccggttcagg accatggtca acgtccttgg tgatgctttt gggacgggca
1621 ttgtggaaaa gctctccaag aaggagctgg agcagatgga tgtttcatct gaagtcaaca
1681 ttgtgaatcc ctttgccttg gaatccacaa tccttgacaa cgaagactca gacaccaaga
1741 agtcttatgt caatggaggc tttgcaggag acaagtctga caccatctca ttcacccaga
1801 cctcacagtt ctagggcccc tggctgcaga tgactggaaa caaggaagga catttccgtg
1861 agagtcatct caaacactgc ttaaggaaaa gagaaacact aatggccaag tgtacatttg
1921 atttgatata cagacctcca gattattttc tatatttgga ttcacagcct ttgcgctctg
1981 ggttttggga tttgggtgtg gggtaagttg aagggaaatc aatttaaagg aaagttctat
2041 tatctgggtt ttagaaattc tataagagac aaagtttgga agtacataaa gtaataactg
2101 ttagaattag gtaatggata tgaaagagaa aatgctttct catgcataga caagtgtttt
2161 gggttcttaa aaaaaatatt ctgtcattgg ttacaaattt ttactcaggc tttctattgg
2221 catggattc ctttgacctc tcactttttt ataattata atgcatctaa accacctgtc
2281 cccagttaat gtgccaaaat gtcaattttt aacttatctc cagccaattt caaagaaaac
2341 agaccaggcat agttctgcaa taacagtttt aagatgggca tagggtttgg aagaaagaga
2401 gaaggattct ttttcaatg tactgtattg ggacgctggt aactgttaac ccagtgttca
2461 gcatagagct atatatatat atatgtgtat atatttatta ttttcatata atttgccaga
2521 cagagatcag aattgaaccg tcaatgtgaa ataaagagtt ctccttgtac ttgaataata
2581 accacgattc caacccaggt ctgctttggg gcttatcaga actcctttct aaggagcact
2641 agaatgagaa atcatgttgt tcgatcgttt cacatcgtta tatcagctct aaagcagaga
2701 tgtattatgt tgatactcca aggtggcata gccattcatt tacaacttcc agatttgagc
2761 tgcctggagg gaatccatat cagctctgca taagattata tacaaagctg tcactcacaa
2821 aaggctggat gtgctttcat ccaactggaa ggcttattc ttccaagttc attcatactc
2881 aaagaggcca gtactttgcc atccttgcac tttctgttat cagggcccaa ataacagtgg
2941 caagctacca actaagttgt attttaataa agattccatg ggttgaacaa gccacgttgc
3001 agaaaaagag cttcccctaa cctgggttgt tgcagagtaa atcccacgac ataagctggt
3061 atcaSt ggtt cgggggaaat agttccattc tatgactctt gtctcctcct ccaggaggac
3121 tgttctaact agtaatcttg gccctattca ttacatcctc tgcttgtcat tctgctaatt
3181 tatgaagata gtttattata gtctgtactt cagttctcat cttgtaaata atgcttaaca
3241 taaacttgta cttacactga aatccaaaat agtcatgttt ctgcagtatt ctgtagccaa
3301 cttaaacctg tgctttcatg tttaagaaat gagaaattgt gccaaagata gcagaagagt
3361 agataagtgc tcagtattga cgacctacat ctgaaatcta caacataatg atactgaatt
3421 gttatgtaaa catcataaat agtaaataat gattcaatgt gaatttttaaa atgcaaatat
3481 tgctattgtt tataggaaat aaatctaaat ataaacgaaa aaaaaaaaaa aaa
```

FIGURE 4

[SEQ ID NO:4]

SNP 9 = C/G polymorphism (S) at pos 4576808 (3065 on cDNA sequence)

>9 dna:chromosome chromosome:NCBI35:9:4480440:4577260:1

```
AGCAGGAGGAGCCGGGCGCGCCTGCCACGCAAAACTACCGGGCTGGCAGGGCGGCGGGCG
CGGTGCGCGATCCCGGGTGGCGGCGGCAACGGCGGTGGTGACGGCGGCGACTGCAGCGGC
CGGCTCTCACCTCTCCCCTGTGCACCCGCATCTCGCCGCGCCGCCGAGCAGCCAGCAGTC
CCCGGGTCGCCCAGCCCACGCGCGCACGGCCGAGCCCAGCGCACAATAGCGGCGACAGCC
ATGGGGAAACCGGCGAGGAAAGGATGCGAGTGGAAGCGCTTCCTGAAGAATAACTGGGTG
TTGCTGTCCACCGTGGCCGCGGTGGTGCTAGGTGAGCGGCGCGGCGGGTGGGCGATGCGC
GCACCCTCACGCGCTCTCTGCGCCCAGGCCGCGTGCGGCTGAGGGTGGGCTTGGCGCTGG
CGCACTCCATGCAGGGTCCCTCGATGCCCCCTCGGCCTTAGCCTCGGGCCCCCTGCGGGG
GCTTTCCCCCAAGCGCTCTAATTACTGCACACCAAGAACAAAGCTCCTCTGGGACTCCCA
TTTGAGTGCTCCTTGAGCTGCTGGTTCCTGCTCTACCCAAAATGATCAAAGGGGCTTGGG
GGTAGAAAGGGAAGCAAGTAGCTCTTGGTTCTGCTCGTTTGAAAACAGGGTTCGATTTTT
TTCTTTGTTAATCCCGCACCGTATCTCCCCCTATCACCGCCACCTTCCTCACCCCACACC
CCCAGCCTCGCTGCGCGGGCAGAGATTGAGTGTGGATTACAGTTCTCAGTCGAATTGGAA
GAGGCACCCTGGCCTCCGGGATGGGCCGGACCCTTAGGGGAGGGAGGCTGAGAACGCTGT
CGCCGCTCATCCTGGGCAGTGCGTGGAAAGGTGCCTTCCCACGCGGCGAGCGCCGACTGC
CTGCACCCGGGCTCTGAAAAGCTGCCAGATTCGTGCCTGAATTCTGGGATGTGCCACTGT
GGCCCGCGGGAGGTCACCGGGGAAGAGAGCTAAGAGAACTCAGCCGTCTCTTCTCCTGCC
TTCCTTGCTCTCCACGTTGTTTTTGTATTTAAGATAATGTTTAAGCCATCCTTGCCTGTT
TTTAAACAAGGGTGTATTTAAGTGATCCACCCCTCACAGATCACTGGACCAGGTGGATGT
CTGAGCCATTGCTCAGAGGTATGAGTTATTCCTATTTAGATTCTGATTTTTTACCAAGGT
TGTGTGTTTCTAGCTCCGGCCCGGGGATGCACTTCCTTGGGATTAGCGCCATATCTGTCG
CCTTCCCAGTGATAGCTCCTCAGCAGGTGAGGGCTGTTGCACCCTCTGAGGAATGTGGAT
TCCTCGGCAGGCTCCACCTTCCCCTTGGAAACTGCAGCTGTGTTTGCTGAAAAGGCAAGT
GGGGACAGCTTGTTTCCTCCCAACCTCAGGTACCTTCCTCTCCAACTGCTGCTCCTAAAT
CTCAGAATATATGGTGTTGCTTGCTTCTCCTCCGAACCGCCCCCTCCCCTCAGGGTGGGG
ATAGGGCATGGAAATGGCCTTTGGAAGTTAATGGGATTCTTGGGGTCAGATTGGATTCTC
CAGAACCTTGGGGAAAGGAAAGTCAGGTTTCTAGTAAATAAATAACATCCTGGAATGGCC
CTAGCAGAGGCTATTTGTAGGAGGAAAGGAGAGAAGTACAGAAGCAAATCTTGACTATTT
CCCCCAAGAAGTGCCAAGTGGTTTTGGAACTTTTTTTTTCGGTTTTGAACATTTTTAAG
GGAAAGTTTATCCTACTCTACCATATTTAAATAGCATACGCTACAAAGAACGACTTGATT
TCCTTTAGGCCAAAGAGAAGAGATGGCCTTGTTTGTTTTCCTAGTGATAAGAGTCGAGGA
TTAATTGTTAAATCTCTTTTTGAAGACTGAGAGATGCCAGGGCAAGGTGGCTCATGCCTA
TAACCCCAGTTACTCGGGAGGCTGAGGCAGGAGAATTGCTTGAACCCAGAAGGCAGAGGT
TGAAGTCAGCCAAGATTGTGCCACTGCACTCCGCCTGGGTGACAGAGCAAGAATCCACC
AAAAAAAAAAAAAAAAAGGAAAAGGACTTTTAGAGGGCCAGGCACGGTGACTCACACC
TATAATCCCAATATTTTGGGAGGCCAAGGAAGGAGGATTGCTTGAGCCCAGGAGTTGGAG
ACCAGCCTGGGCAACATGGCAAATGCCATCTCTACAAAAAAGTACAAAAATTAGCGTGG
TGGTGCACATCTGTAGTCCTAGCTACTCAGGAGACTGAGGTGGGAGGATCACCTGAGCCC
AGGGAGGTCGAGGCTGCAGTGAGCCGTGATCGTGACTCTGCACTCCAGCCTGGGCAACAA
GAATGAGACCTTGTCTAAAAGAAAAAAAAAAAGACTTTGCAGGATAAACATTGGCTTG
AGTCTCCTCCTGATTCCCTGTGGAAGTGGAGTTATCCTGCCTTTTCAGCATGGGCTCT
CCAGAGATACTCACTTGCTACCCAAGTGTTGCACACCACTCGTCAGCATGCGATTCACTG
GAGACTGGTTTGGAGAAGGTTTTAAGCAATTGTTCCCTGGCCTTTGGAATCAGTTGCGTG
AATAAGAAGAAGTACATGCTCATTTTGCAGACATGGCCTTTGGTCTCAGATGGGCACTTT
CCTCCAATTTTAATGTCTGTGAGCCCCAAGAGCTTAGTTTGAGTACTTTTCTCCAGAAAG
```

FIGURE 4 (Continued)

```
GAAAGTCACCACTTAAAAATCAAGTGCCCAGCTGAAATCTTCCTAGATATTTGTTCCTTC
AGATGGCAACAAAGGGCAGTCCTGCTTCTGGTCTGAGAAGTCTCAAACCTAGACCACCCC
CGATATGCCCATTAACAGGGGTCCTTTTCTTGTCCTTTTTCTTCAGAGTACTGGGCCTGA
GTGGAAACTCATACTTGTTTGTGTAGTCTGTAAGGGCTGATTTGTTTAATTGACAGTGAA
ATTCCAGTGACTTATAACAGTGGCACTGAGTCTATTCATAAACCCTTGCTAGATAATGAT
AGTAAGAGCTTATTTTATAACTGCCTTAACTGATCCAGAAAAATCGCAAGAGCTCTAATG
CAGCCTCCCTTTTGGACTTTTCAGCATGTGGAACTTAAAGAAGAAAAAAACTGTGAAAT
TTATTAACTATCATGACAAAACATCTTCTTCTGATTATAGCCGTTCAAATGTTTGGTCCC
TGACCAGGTGCAGTGGCTCAGACTTGTAATCCTAGGACTTTGGAAGGCCAAGGTAGGAGG
AATGAGTGAGTTCAGGAGTTTGAGACCAGCCTGATCTCATCTCTATTTCTAAAAAAAATA
ATTTAAAGAAATAATAATGCAATGAAATGTTCAGTCACTACTATAATTCAGTAGCCCTAA
TACTTTGAAATATTTGATTATAGAAATAAGAGGCAAAGATTTTATGAGCCAGCTTAAAG
CCTGATTTTTCAAGATACAGCACATGAGGGGAAATGTAATAAGGGTCATCTTTATTAGGT
GTGGAAGTTCACTCTTTTCATGGACAAGGAAATGCTAAGAACTAAACATTTCTCAAATTC
TTGTTCACAAGATGAAGGGATTCAATAGTTAGGTGACCATCTTTTTAAATTTCTGCGACA
CCCTACATGGTCCTGAAAATAGTATCTTGGATTTTCACAGGAAAATCCTCTGCTAAAATA
CCACTAGAAACACTTTCACGGCTTTCATTACAATTCTTATAGGCTTATTCTCTGCTTCCA
TAGAATGGTAGAATGAGCACAGAGCCTGGAGTGAAGAGTCCTTGGGATTTGAATTCTGGT
ACTATCAAGCTCTATCATGCAGGCAAACTGTGTATTTCCCTACAAGCCTCAATTTCCTCA
TCTGGAAATTGGAGATATTACTTATTACTTCGTTTGTTATTAGAGGTGTGAAAGATACTC
AGTTGTGTGGCTGGCATATATTCAGCACTCAATAGTTGTTATTTTAAGGTAAATCTGAAT
AATTTGATTATGAGAAAATTAATATTTTCTTATGAAATAAATTCTCTCATAGTATGTCTC
TTTCTGTGTCCTGCTTAGTGTCCCGCCTATAATTTAGGGTGACTCAAGTGTTTTGATGAC
CTGCTCTGTCTGAGCTAATAACTGTCCCTGTAGTATTATTCATTTCTTTAAAGAGGAAAT
GGAAAGAATGAATCATTTATTTTTGTGCCCCACCGGCTAATCCTCAATTCATTTAAATAT
AATATTTAAATATATAATTTATATAAATATAATTTAAGTATGTAAATTCTGAAGGAAGGT
TTTATGCTCTAAGTGGGAATTCTGTCCAAGCAGAATTACTGAGTGAGAATTCTGCCAGCC
TTCTAATGCGGGTCATCCAATAATGATTATATAGTATATGATGTTGTTAAGGCACTTCTT
ATATCCTCACCCTATTCACAATATAATACCTAATCTTTCTCTCCAGACCAGTTATGCCAT
TACTTCTGTCATTTGAAAAATCTGTGATTTCAACTTAGAGCTATTCAGAAAAAGCAATAG
GTATTGGCATTTACATGACAGAGCTGGCAAGCTTATTCATTCTAAATTGTTTTCTTTGGA
GCGCTAAGGAAGCAATCATGCATAGATTCTGATTCCATTATCTAAAATCAGAAACAGCTC
CTTCATGGTCTTAGCAATACCCTTGCCCAGCCTCGTGTCTCTACCCTGGAGCTCATGTAG
CGTGCATCTGGCAGTGCTAATTTGAGACGTGGCATAGGCTTTCCCGCTTTGTCTGTGAAG
CCCCTGAGGACAGGGCCCAGCGGCGGTTCACGCTGGTTCCAGGCCCAGCCCCTCACCTGC
ATAGAACCTTGGCTCAGCAGTGTTTAGGAATATCCCTGTAATAATCAACACTTAAGCCAT
TCATTCATTTAACAGATATGTATCAGACCCCCACTGTGCACCAGGGATTGTTCTACAGCC
GGGTCACACAGCATGTCCTCATGGGACTTAATGTTCAAGTAGAGAGAGGTAGACCATAAA
TAGAATACATAGGTAACCTACTGTATAGAGCATGTTAGATGAGAATAGTGTTCTGGAGTA
GTATAGAGCAGGGAGTGGGCTGGCAAGGTGGGGGGTTGCAATTTTAAACAGGGTGACAGG
GGAGGCCATACTGAGAAGGTGACAGTTGAATCAAGACGGAGGAGAGGTGAAGGAACAAGT
TGCACAGGTATCTGGGGAGCATCCTAGTTTGTGTGAGAAACATCAAGGAGTAGAATGAGG
GAGGGAAAGAGTAGGAGGAGATGAAGTGGAGGTGAGGCTGGGGGCAGAGCAATAGGGTGG
TTCAGGTCCAAGGTCCAGGAAAGGGGAAATGGGTGCCTCAGCTGAGCAGCCAGGAGTGGA
ACAGAATGAAAAGACAGCTGCTTGAGGTTAACCTGCAGGGCTTGGCTGGATTTGGTCCAA
GGGAGAAGGCAGTGGCTATCTCCAGCAAAACAGAGAGTCCTGGAAGGGGCACCGACTTGG
AAAAGAACATGGCATGTTCCACGGTGGACGTGTTGAGTTTGAGGAGCCAGAAGGGTGTTT
GGGTAAAGGTAGGCAGCAAACACCTGGCTAAGTGAGTCTGGTGCTCAGGAGACAAATGTG
GAGTGGAGTGTCGACTTAAGACAGCATGTCAGGGACCTGGTTAAGGCTTTGGGAATGAAT
GAACCTATCCTGGGAGAAAAGGGAGAAGAGAAGACCAAAGACAGAGTTCTGGACAACCCC
AACATTGGAGGTCTGGGAAGAGAAGGGGCCCACAGGAGAAACCGGACGTGGTGTGATAGA
AATTAAGAACAGGAACAGTGATGGGTGAGAGGCTCGGGGGCAGGAGTGAGAGGGTCTGAG
GAGGAAGTTCAACAGCGTTGGGGATACAAAGGACAGGGATGTGACCTTCTGGGCTTTTAT
TTGGAGGCACTTAGGTGTGAAAGAATTCAGAGAAAGTGGAAGTCACGTTTAAGATCCAGA
GAGTATTTTTCTTTCTTTTTTTAAGAGACAGGGTCTCGTTTTGTTGCCCAGGCTGGTCTT
```

FIGURE 4 (Continued)

```
GAATGCCTGGCTTCAAGCTGTCCTCCTGCCTCAGCCTCCCAAAGTGCTAGGATTACAAGT
GCAAGCCACTGCACTCAGCCTTGTTTTGTTTTGTTTTTGTTTGTTTTTTGTTTTTTAAGG
AGACTTGAGTCTGACTGAACCTGAAGAGAAGTGATCATTAAAAATAAAAATGCAGCTGAG
CATGGTGACTCATGTCTGTAATCCCAGCACTTTGGGAGGTGAAGGTGGGAGGACTGCTTG
AGGCTAGGAGTTCAAGACCAGCCTGGGCAACACAGCAGGACCCCTGTCTCTGCAAAATAA
AAATTAAATTAGCCAGGCACGATGGTGCGTGCCTGTGGCCCCAACTACTCAAGAGGCTGA
TGTGGGAAGATCACATGAGGCCAGGAGTTCCAGGCTGCAGGGAGCTTGATCACATCATTG
TACACTCCAGCTGAGGTGACAGTGCAAGATCCTGTCTCTGAAAAATAATAATAATAAATG
CAGAAGAGAGAGAAAATAATGAATGCTGTTGGGTGGAGTGAGGCCTGGGACAGTAGAAGA
CAGTGTGAAATGGAGGGACCTAGTTGGGGATTGGCCAGAGAACGGGACTTTATACTCCTG
AGATGGAAGGGAGGAGTTAAGGGTGAAGCATTGTATTCCTTTCCTGTGGCTGCCCTAACA
AATTACCACAAACCGGGTGGTTTTAAAAAACAGAAATTTTTTTTGAGACTTAGGTGTAT
CCATTACTCTGTGCCAAGAACTGTTCTGAGTGCTATATAGGTATTAAATGATTTAATCTT
TCCATCAAGCATATTTTCAGGAAACAGAGGCACAGAGAATTAAGAAACTTGCCCAAGGTC
GAGGGCAGAGCCGGGATTCAAACCCTGGAAGTCTGGCTCTAGAGCCTCTGCTTCTAACCA
CTATCCTCTCCCGCTGCTGTGTGATATTATTACCCTATATTCTGATGTTTCTGCCTCCCT
CACCAATTCAGGAACCCTAAGGGAAGGACGTTTGTGTTGCTCTTCTCTGTGCCCATAGTA
CCTATCACATTGCACAGTAGGGTGAATACATTTGTTGAATTGCTGAGCCATTTATGACCC
AGAGAGTTAGTAAAATGTTGTCCTTGTTTGTCAAGGGAACAAATGAGCCTAAAGCTTAAA
TCAAACTCTATTACCTCCATAAATTCTCCTCTGCCTGTTTCAGCCCCCTCTGATCTATGT
CAGCAACATAGATTAACACTTGATGAATCTATATAAATATCAAGCATGTTGATCTTTTCT
TTCTCAAAACTAGATTACAGACCCCTTGAGGTCCCTCTTATTACATTTCACAGGCACTAA
AAAATAAAATGAGGCCATAAAGTAATGAGACTGACTCTTAACTGTTTTTTTAATTTTTAA
AAAAGTATATCTGATACCTATACTCTCTGAGTCTTTGTTTCTTATTAACAAGAAAGGGAC
TTAGATTAGCTGGGAGAGCAAAGAAGATTCTATTCATGCATCTATTACCACTTATAGGTA
GTGGACTATCTGGTATGATCTTTATTGAAAAAGAGTTGAAAACAAAAGTCTGAAATTGAT
TACTGCTGTCTGGCACTGGCTTAGGATCAGGAACTAGTGGTATGCGTGCTGAGTAATTGT
TGACTTGGGTTATAAAACCTCTGAGAGTCCTTCTAGCTTTAAGAACCTTTAGCTTTATGA
CTGTATATTCATTCCTCAGTTCATTGCTGGGAGCCAGAGGAACTCTTCTGTAAGGAGCTA
AGGGGGTTCAAAGGGCATTACAAGATGATAAAATGACCTAGACATTGAGTCAACTGTTCT
GTGTTTGAACTGCTGATCAGTGACATAGGGATAATCATGTAAATTGTATATGGGCTATT
ACCATGGTAATATGTTCTATGTCAGTATTATTAGATGGTTTATTACAACAGTAATAGAAG
GTCTAATATATGTATGTTTTGGACTTTATATGTCTCTAATTTAAAATATTTGCAAAGTA
CACAATACTCCAAAAACACTAAATAAAATAATAGTTTCTTCAAAATGACAGGAATAGCCT
AGTTCCTATATCCTCAAAACCAGTGATTTCCACAACAATAATCAGTTTGACATAGGGAAA
ACAAAAAAAAGCATAGTTATTCATATATAATGGGGACTTTTGCTTTCAATGAGGAATATA
GCTTTATGTTTATGTATTTCTGAAAAGTGATGAAAACAGACAAGGTTGCTAGTTTAGTCA
TATATATTTAATTTGTATTAATATATTTATTCCATAGCATGCCACAGACATGACAATATT
AGCAAAATAATGAGCACTACTAATTAGTTTCCATAATATTTTCTAGAAATTTGGGAGTTG
CTAGTGAGTTAAGTTCATCTGCAAAAAAATATATATATATGTGTGTGTGTGTATATAT
ATGATATTGCTTATACTTTCTCTAAAATACTGAGAGATATGTGGTCTCTGTCTCTGTATA
TATTACATGTATACATACATATACATATGTATGTATTATATACATAATATATACATATAT
ATTATATATGTATATATAATCTTATATATTATATATAAGATTATATATTATATATATATA
AGATTACATATTTATATGTATATATATATCTTTTTTTTTTTGAGAACAAGTCTCACTC
TGTCACCTAGGCTGGAGTGCAGTGGCACGATCTTGGCTCACTGCAACCCCTGCCTCCCAG
GTTCAAGCGATTCTTCTGCCTTAGCCTCCCGAGTAGCTGGGATTACAGGTGCCCACCACC
ACACCCAGCGAATTTTTGTATTTTTAGTAGAGACAAAGTTTCACCATGTTGGCCAGGCTG
GTCTCGAACTCCTGACCTCAGGTGATCCACCCACGTTGGCCTCCCAAAGTGCTGGGATTA
CAGGCATGAGTCACGGGGCCCAGCCATATATTATGTATCTCCATCTATCTTATCTCCTTA
GTTAAGTACCTTAGAGAAGAGATCCTTCTGGCCTCGCCAAAGTTCTACATATTAAAGAAT
TAGGAAAAGAAACTGGGCTTTGAATGCTTATGCCTGGTGTTTTCATTTTTGCAACTAAAT
CAGAATCAGATTTGAAGCATCACTGAAATGATTCTGATTTTTGGTTGTTCTATGCAAGGT
ATATATGACTCAAGTCTATCAAAACTCCAACAAAATGATCTAAACACAAAATTATAAAAT
GAATCTTTAAAATGATTTTACATATTAGACTCTGCACATGCAGGTTGGTATATACAATCT
TAATGCCTCCTATGAGGAAGACTGAATATAAATTGCTAGTGGTTGGCAAATATTGAATAT
```

FIGURE 4 (Continued)

```
CTTGTTAGATGTTGCTTAATTTAAGATACGGTGTTTTATTTAGTACAGTAAAACTACAAA
ATTGAAGTTGCTCACCTGTTAAAAATTTGAGCACTGGGCATAAGAAATAAAGAAAGCTTC
AAATGAAAACACGCTGTGTAGAAAATTTTTGTGTGCAAATTCAGGATGTGGTGGAGCTCA
GGTGGGTAAAGCCTGGGTTATGTCAGACAAGGTAGGATTAGGAATCAGTTGTTAGAGAGC
ATGTATGCATGTGAGAGCACTTGCTTATAAAGAGAGAAAGCTTTCCACATTAATTGCTTG
TGAGAAATTGTGATTACCTTTAACAGAGCCGAGACTGAAAATAACTGTCCTAGGGAGTCC
GTGACACACTGGCCTGGTGCCAGGGAAGCTGTGTTCGCCTGAGGTATTGCAAATTTCCCG
TGTCGCTGGAGATTTGGGGTCACAGATGCTGTGACAACTCAAGCACTCTCGAAGAAAATG
AACTCATTTTAGATGACATTGAGTGGCCCGTTTAAACTCCCCATAGCAGTGTCTATTAAA
GTAGAAAGTGTTTTAAATGGCCTTTTCTATTTTGTTTGTTTTATTTTGAGACAGAGTCTC
ACTCTGTCACCCAGGCTGGAGTGCAGTAGTGCGATCTCGGCTACTGCAACCTCCACCTCC
CAGGTTCAAACAATTCTCCTGCCTCAGCCTCCCGGGTAGCTGGCAGTACAGGTGCCTGCC
ACCACAACTGGCTAATATTTTCTATATGTTTAGTAGAGACGGGGTTTCACCATGCTGGCC
AAGCTGCTCTCGAACTGTTAACTGCAGGTAGTCTGCCCGCCTCGGCCTCCCAAAGTGCTG
GGATTACAGGTGTGAGCCACTGCACTGCGCCCAAGAAACTGATTTAGAAAGAGTTAATAC
ATTATACTTGCTGAGGAACAGCCCCAAACTGCAACAAAGAGTACTCTGTTGTAATTAGTA
CAGCCCACAGTAACACCTCTGTTAATAGAAAGGAAGTGTTTCAGTGACTCACTCTTTTTC
AGAAATTTTACTACTTTACTTTGAAAATTATCTGCTGACTGCCTGTTCCGTTACCAAAGG
TAGAATATTTCCTTTCCAATAAATAGTCCTATACTTTCTGGGATGGACAGATCTCATCCC
AGCTCACAGATGCTTCATGTTCCTCTCCCAGGCCCAGCCTCGGCTATGTGAGCTCCGGGC
AGCGGTTCCCACTCAGCCAAGACAGGGAGGGATACAGTGCCCTGTTCTCTACCACTAATC
CCCAGACCCAGCCCTGAGAAGATAAGACGTCCCACCAGTCCTGCACTCATGCTGAGGTCA
CCACTCCCGAGCCCTTTCTTAGTCTCAGAGTCCCTAACCGTGTCCAACACAGGACAATTG
TCACAGCAGATCTCCGCATGTCTAGGAAGGCTCTTGATAGTAGAAAGTGTTTTAAATGGC
CTTTTCTATTTTGTTTTGTTTTGAGACAGAGTCTCACTCCGTCACCCAGGCTGGAGTGTA
GTAGTGTGATCTCGGCAACTGCAACCTCCACCTCCCAGGTTCAAACAATTTTCCTGCTAT
CATCATGTGACTCTCTGCTTGGTCTGCATGTTGAAGCAATAGCAGACTTTGGGACTGGAA
CTTGGCTTCGGAAACACCCTCAGAGAGGGTCCACATGGCCACATGGTGTGTTTATTCTTA
TAATCTCTCTGAGACAACTATTTGGGTATAACACTTCCAGATGTAGTTAAAACTACAGCA
CTTTGGCCAGGTACGGTGCTCACGCCTGTAATCCCAGAACTTTGGGAGGCCGAGGTGGGC
AGATCACCTGAGGTCAGGAGTTCAAGACCAGCCTGACCAACATGGAGAAACCCCATCTCT
ACTAAAAATACAAAATTAGCCAGGTATGGTGGTGCATGCCTGTAATCCCAGCTACTGGGG
AGGCTGAGGCAGGAGAATTGCTTGAACCCTGGAGGCAGAGGTCGCAGTGAGCCGAGATCA
CGCCATTGCACTCCAGCCTGGGCAATGAGAGCTAAACTCCATCTCCAAAACAAAACAAAA
CAAAACAAAACAAAGAAAACTACAGCACTTACTCAACCAAGGGGGAAATCCTTATAGGAG
AGAGCTTAGGTGAGAATGTACAATTATTTTTCTACCATTGTTCTATTGCTTAAGAGTTAC
CTCGTTACTAATAATTCAGTAAGGAATTAAGTCAACATAAAAAAATGCACCATCACCAGA
AATGCCTAAACTACAGAGAGCCTAATCTCTGAGCCTCTCCCCATTACTGGAAAATAAACT
GATACTGTTCAACTTCTGTGGGTATCTCAAAGACTTGTTTTCTGAGCCACTTAGCAGGTT
TCATTTAAGATTTCCCCAAATTATGGGCCAGGCACAGTGGCTCACATCTGTAATTCTAGC
ACTTTGGGAGGCCAAGGCATACAGATGGCTTGAGCCCAGGAGTCCAAGACCAGCCTGGGC
AACATGGTGACACCTCATCTCTACAAATAATACAAAAATTAACCAGGTGTGGTGGGTCAC
GCCTGTAGTCCCAGCTACTCAGGGGCTGAGGTGAGAGGATCACTTGAGCCCGGGAGGTT
GAGTCTGCAGTGAGCCAAGATCACACCACAGCACTCCTGCCCGGGTGATAGAATGAGACC
CTGTCTCCAGAAAAAAAAAAAAAAAAAAAAAAAAGATTCCCTGAAGTATGAGACATTGA
GAGAGAAAGTGAGAGTGACATATTTTCTCCCTTGAAAAGTTCTCTTTGGCTAACCAACCC
TAATATCAATATTTATTGAGAATTTACCACGAGTTTTATGTACATTTATCTCCCATTTGA
CCCTCAGTACAATGAGTTAGGGGGTTCCCATTTTACCAGATGAGGAAACTGAAATTTACA
AGGCTTAGGTCATGTAGCTGAGCACACAGAGCTAGGATTAGCACCCAGGACTGTCTGATT
CCAAAGCTTAGGTTACTAATTATTAATCATTAAGCAAGTCTTCTTCCTTCCTAGTAAACC
TTGATACACCTACACCTAATTGGTAGTTAGAACCATACTTGGAGACAGGCTTCTTTCTTG
CAAAGTGGCCAAATAAAGCCTATTCTCCTCCTTCTTGCTTCATCCTTTCTCAGTCTTGTA
GCTCATCTTTATTGCGTGTGGTTAGTCCTTTCCGCTACGCTTCTCCTACATAAACCTTCT
GTTTGAGCTTGAATTCTAGTGAAACTCATCTAGTTGCTTTCCCAGAACTGTTGTACTTTC
ATGCCCTAATCCTTTTGCTCAAATGTTTCACTCACTGTTATCCTGCCTATCCTTGAAGAT
```

FIGURE 4 (Continued)

```
GGATTTAATTACCACTTTTATGTTGTAGACTTCTCTGACTGCAGTTGGAGATAATCTCCC
TTCTCTACATTCTTAACCCTTGATTTATATGCATAAATTATCACCATTAGCACCACCATT
CCCACGTCTGTTCTGTGGCAGACATCACTGATTACAGTACTCTTCACTACTGAGCTCTGT
CATGGCCTCAGAATCCTCGAAACTTTGCTCCAGGCAACCACTGTTAATCAAACAGAATTG
GTGCCTAAGATGAAAAGTATTGTTTGTTGCTGGGAAAAGTTTATTCATTTGGCAATCAAT
TAGGAACTGAATTTAAATTGAGCAAGTACTGATGTTACTGATAAGAGAAGCAGAGTCAAA
GTCTGTATTTTGTCCTCTCAGTCCATTGGTGGCAATACATCCACAATCACTAACATGATC
CTGAGTGTGGTAAATGCTGCAAGGAGGCTGCAGCATGCTGTGGGCCTTCAAAGAAGGTGC
AACTGGGAAAGTTCCTGGAGGAGGCCATAATTGGAATGGCCTTGAGCAGGTGTGGTAGGA
TTTCTGGGCTTGAAGACTGGAACGAGCAAGTCTGTATAAAGGTGATGATACACATAAGGA
GGGCTTATCATCTCTTAGGTTCAATTTCAGTATTACATGGAACTATAATTAATATATGT
GTTGCTGTGCTTTCGCACTTTTTCTTACCTGTTTCCTAAGGACAAGAATGCAATACTACA
CAGGTCTGTCACATCATAGCATCCAGCATTGTACTTACTTCACAGGAGGTGCCCCCAGAT
ATATCTGACTGATTACAACCTTCTTCACTGAAGAATTAAAACAGGTAAATCTTTGATGAA
CCAATCCCATTGATCCCCTAGAAGCCCACTCAGTTGTATGAGTTTTTGAGTGAAGACCAT
GAGGAACTCTTATGCTAGCCTAAGTCATCCCAAACATACTTAACTCCTGGAATGGGGACC
CCAGAAGAAGAGCAAGTCTGGTTGCTAACAGTTTTGAAGCCATTTTATTGTGAGCACTGC
ATGACCCTGAAGCTCCCAGACTGGAGAGCATCTCTGTACCCTAAGGAAGATCTGATCTTC
TCAAGAAACCAGCACCAGAACCCACCTGATCTCCAGATAATTCTCTGGGCTAATTAGAGA
AAATGGAAGATCCATCTCTTTTTCCATAATTGGGCTACAGCTTGGCACTGAATCAACCCT
GGATGGTAGAGCCTTTTCAGCTACGGTATTTAGCAACTCTTACACCATTCATTGAATTTA
TTTCTGGATTTTCCCCCTCCAAGTGTCCTTTCACATCCTTATCCAAATTCTGCCCACTTC
TCTCCCTGTCTGGAGATTATTTCTATGATAAGAAATTAATTAGCCTGTCTGTACTACCTG
TTCCAGGAGACTTTGAACAACTGCGTGGGTAAACACTAGATGTGGTCACCAAAGAGTCGG
AAAATAAGTTTTTACTTTTTCATTAGCAAAAGTTAATTGTCAACCAGGAGATGTAACAGG
CTTGCTCCATTTCTGCTGCCGCTTCTTGGATTTCTTTCTTGCATGTGGAGAATTTCCTGA
GGTTTCACCAGACTGAAGAGATTCTGAGTTCTTGAAGTGATGGAGATAAAGATCTTGTTG
TCATAAAACAGCAAAGAGCACTGTGATTGGGTTTGAAAGATTTTTGATTGTGTTATGGAC
AGTGCTCTTACTGGTTTTTAAAAAGTTGATGTTTTCTTCTGTGTAAATTTAAATAATTTC
TTTAAAGGCAGTAAGCTTTTATATTTAATATACCTTTCACTGTGCAATCACAACAGGAAG
ATTTTCTAAATTAGACATCTTTACCTTGAAGAAGAAACTTGTCTGTTTCAGTGTCTTTTT
GTAGCAAGATTGACCAAAACAAGTGGTAAATAAGTCTGTAATATTTAACTGTCATGAAAT
ACCTTTGCTAATAAGGAAATGGCCTCGGTTTGGATTAGGTGGAGTTTCGTGTGTGCGATG
TGGGGGTGTATGTGTACATATATTTCTTTTTTTTTTTTTTTTTGAGATACAGCCTCAC
TATGTCGCCCAGGCTGGAGTGCAGCGGCATGATCTTGGCTCACTGCAACCTCCGCCTCCC
AGGTTCAAGCGATTCTCCTGCCTCAGCCTCCCAAGTAGCTGGGATTACAGATGTGCAACA
CCATGCCTAGCTAATTTTTTTGTATTTTTAATAAAGATGGGGTTTCACCATGTTGGCCAG
GCTGGTCTTGAACTTCTGACCTCAGGTGATCCACCTGCCTTGGCCTCCCAAAGAGCTGGG
ATTACAGGGGTGAGCCACCGCACCCGGCCCATATTTCCTTTTTTTATACTGGATAGCAAT
ATAGGGTCTTGTCTTTCACCTTTTAAGTTCACAGAACAGTTTGTCCTGACCACACATAAG
TTACCAGTATAATGTTTTATGAAGGTTTAGAAATGAGCTCCCAGAAAAATAATATTTTAA
TATCTACAAATAAATAATCTGAGGATGTTTCTCAATTCAGCATCAATGCTGGGTTGTGCC
TTGTGGATTTCCATTGGCTCTACGTGCAAAAGATTAAGTTAGTTAGAATGAGGAAGACAT
TTTTAATTACTGTGAAATTCTTTGTTGTTGTTGTTGTTTTTCTTTTTGTTTTGGGAA
GGTGTCTCACACTGTTACCCAGGCTGGAGGGCAGTGGCATGATCTTGGCTCACTTCAACC
TTCACCTCCTGGGTTCAAGCAATTCTGCTGCCTCAGCCTCCCGAGTAGCTGGGATTATAG
GCATGTGCCACCACGCCCAGCTAATTTTTGTACTTTTAGTTTTTGGGATGGAGAGTCTCT
GTCACCCAGAATGGAGTGCAGTGGCACCAACTCAGCTCACTGCAACCTCCGCCTTCCGAG
TTCAAGCGATTCTCCTGCCTCAGCTTCCCAAGTAGCTGGGATTACAGGTGCCCACCACCA
CGCCTGGCTAATTTTTGTATGTTTTAGTAGAGAGGGGGTTTCACCATGTTGGCCAGGCT
GGTCTTGAACTCCTGACCTCAAGTGATCCACTCACCTCTGCCTCCCAAATTGCTGGGATT
ACAGGCTCCTGCCGTCTGACTTAATTTTTGTACTTTTAGTAGAGACGGGGTTTCGCCATG
TTAGCCAGGCTGGTCTAGAACTCATGACCTTAAGTGATCCACCTGCCTCAGCCTCCCAAA
GTGCTGGGATTACAGGCATGAGCCATCATGCCCGGCCAAATTACTATGAAATTCTATCCT
GCCAGTGCTTTAGAATAACTTGCATTTTAAAGTACATTTGCACATTTTACATATAATGCT
```

FIGURE 4 (Continued)

```
ATATGGTTGTGTTTGGGCTTTGTGTACAGATGACTTTTGTTATTAAGTGGAAAAGGCCTG
AAATATGCTGTTCTATGTTAAGTAAATTGATATAACCTAAGAAAAGATCTTGTTGCCAAT
TCAGAAACCATAACCTTAAATAGCATGCCTGGGTCTCCTCTGTATCTGGTTTAACATCTG
CATTGAATATTGGTATTTTCCAATAATCTCCAACTAGCTTATTTATTTTGAAAAAAAAAA
ATAGAAATCTACGTCTACTTTTGCTTAAGTGGAAATACTTGAGTAATGCTTGGTTGCTTT
TTTAACCTCAAGTCAGTAACTGTGAAAGACTGGACTTACTGCACCTAAGATCTAGAACCC
TGAAGTTATCTAATTGGTGCTCATCACTGAGCTTGTGTAGGCTTCCTGAAGCCTATTCAG
GGCCCTGTGTACTAGGGAAAAGGGTTGGCAGATCACAGTGTGTGGAGTATGCAGCCAGTA
ATTCTTTCTTAGATTCTCTCTCCCCTCTTAGAACCTCCCCTCATTTCCCAGGGAACATCT
GTTTTCCATGAGGGCAGTACTAAGGGGCTGAAGATTCCCACAGACATATAATAAAAGGT
TCCAAGAGTAGGCTGGCGGCAGTGGCTCACGCCTGTAATCCCAGCACTTCGGGAGGCCGA
GGTGTGTGAATCACTAGGTCAGGAAATGGAGACCATCCTGGATAACATGGTGAAACCCCC
TCTCTATTAAAAATACAAAAAAAAATTAGCTGAGCGTGGTGGTGGGCACCTGTAGTCCCA
GCCACTTGGGAGGTTGAGGCAGGAGAATGGCGTGAACCCGGGAGGTGGACCTTGCAAGTG
AGCCAAAGTGGCGCCACTGCACTCCAGCCTGGGTGACACAGCAAGACTCTGTCTCAAAAA
AGAAAAAAAAAATAGATTCCAAGAGTAAACAAAATCCTCAAGTGTTACTGTGCAAAGAT
TATACTCACCATGTTTGATTTTTTTGGTCTCTGGTGGTCATCCCAGATGCATTCACAGTC
ATTTCTGGACCTTTAATGTAATCCACTGTTGTTATTAAATGAGCTGATCCACATGGAGTT
ACTTTTTGAAATCATGAAGTTCCTTATGAATGTTTGTTATTGTGTCTTAAATTCTTTAAA
TTCTTAAAATATGTCTTAACTCACTTAAAGATAAAAGTAAATGTTTCTGTGGTCCTTCTG
GGAGTGGGGAAAGTTACAACTCCACAAATGTTAAGAGAGAAGGGTGAACAGTTAGCAGTC
AGGCAGCATGGTTGGGAGTCATGAGGAAGAGCATTCAAGATGACACAAGTTTTGTAAGCA
GACCTAAGGAACGGGCTGAAGAATGTTGTGGAGACCCAGGTACTTCGACTTAGCATTCTG
AGTTCAGAGTTCGCCCAGGAGTTCCAGGCTTGTGGCAGGTTTAGAAAATCCAGGATGATC
GGCCACCTTCTTTCTCCCAGAGGTCGATCTGATCTTAAGTTGTACCTGACTAAAACCTGC
TGCAGGAGAGATGGTCAGATTTTATTTACACACAGGGAGATGGCTTCCTAAGATTGTGTA
GTGAACCAAGAAGGTGTTTACAGGCATGTGAAACTGGCTATTGTAAAGAGGCAGTGATCT
GGGACACGTGATGTTAGTTAAAGTGGAGGAAAAGGTGTACCCTTCAAGCAGAGGATTCCA
GGGCCTCTCCAAACCGTACAAGTCTGAGCCAAGGGACAGAAATTCCATCAGTGGCTTGGA
AGCCAAATATTTGCCCTGATACTGAGGAAGGGAAAGAGTGGAACGTGACCGTGGGATAGA
TAAAGGGTCTTCACAGGAATGCAAACAAGATGATAGGTAGAATCACCCATGAGATTAGCA
AACAAATCACTTTAAGAGGAAAAAAGTAGAATAAAGAGAGTCAACCACAGGTAGAAAATG
CAAGACTTTGGAATCCACAAGTCATAGATATGTATCTCGGGAAATAATCCAAGCACACAT
GCATGGTACTGATACACCTGTGGGAGAGTGAGAGTCTGGTTGTCCCGAGACTGATAGATT
CACCCACCTGCTGGGCTCTAAGCCAGTTGGATATTTGCTCGAGAGACTAGATTCCTGTGG
GCTGGTCCTAACTTTCCCAACTAAGCTCACCCTCACTTGAGCCCAAAGGACTCCTAAGAC
TCCATCCCCAGGAGGCATCCCCAGGTGAGGAGCTGGGCACTTGAATTGTCATGTGTACAG
CACCATAGCCATTGTAAAAGGAGAACATCTCACAAGTCAGGAGTTACTGGAGAGACTGTT
TATGACACACTTCTGGGTTCGATGGCCCTGAGACAATAAATTCATCCACATTCCTGTGGC
CCAGTTTTCATGCTTTGCTCATGACATCCTCCCTCAGTGATTTTCTCCTGCCTTTCATAA
TCAGGTTTGATGAGCAAAGGTTAGAAAGTGCAGTGGCTTCCTGGGCATGTGCATTAAATA
GCAATTAAAATGCAGTCCTGGTTCGGCTCAATGCAGCAGGTGTCAATCAAACACCTACAG
TGTGTCAAGCTTGATGCCGGGGCGGTGGGTACAGGAATGAGCAGACAAATGCTTCTGCC
TTGGGAGCTTGAGATGAAAGGGAAGGAGAGCACGAATTAGACCTGTTTGAGGGGGTAATA
GAAATTCAGATAAAACTGAGTAGGGTCCAGAGGAGAGATTCTTTCCACCTGAGAAGACAG
CCTAGGAAAGGCTTTCTGGAGGAGGTGGCTTTTTAACTAGGCTTTAAGGGGTGGGTAGGA
GTTTATTAGGCAGAGATAGTGGCAAAGGGCTTTCAAGGGAGGGCGATCTGTGTGAACAAG
AGTGTGAAAGCAAAAAAGCATGTAAACAAAAAAGCATGGAGCATCTTTAAGAAATAGCAA
GGAGTTTGCTGTGACTGGATCTGCTGGGATTGGGGGGTGAGAAGGACATGCAGGCCTGTA
TTGGTTAGGGACCTGGCAGGAAGCAGACTCAAAAGAGTTTCACTGAGCAGAATTGAATCA
AGGGACTATTTATAGAGTTCAGCAGGGTAAAAGGAATCAGCAAGGGATGGTGAGGCACCC
AGGGATGAATAACTGGGAAGCTATTAGCTCATCTAGGCCTGAACAGACAAGAGAGGGTGA
TGGGGTTTCCACAGTACAGTGAGGGCTGAGTTGTGGCAGGGAACCAAAAGGCAGGGCCTA
TGTGGCTGCAGAAGAACAGGGGAAGGGAGGGCGGGAGAAAATAAAAAAAAAAACCCAACC
TCTGTCTCTTTCTACCATTAAGATCTACAGCTACTGCCTCTCATTTGCTAAACCCAGCCA
```

FIGURE 4 (Continued)

```
AAACCAGAGGCAAGGAACCCTGGATCAGCCCTCCCAGTGCACAGAGCAGGACAAAGAAAG
ACAGAGGGTGAATCGGAGGGCAAATGGAGAGTGACTAGCACAGAGCCATATGGCATGAGG
TGCCATGCTGAAAGGTTTTCTCGGGACATCAAGAAGTGTTGAAAAGATACAAAGTCTAGG
AATGATGGCAGGGAAATTATTATTTATTTACTGAGATGGAATCTTGCTCTGTCCCCCAGG
CTGGAGTGCAGTGGTATGATCTCAGCTCACTGCAACCTCTGCCTCCCAGGTTCAAGCAAT
TCTCTTGCCTCGGCCTTCCAAGTAGCTGGGATTACAGGCATGTGCCACCATGCCTGGCTA
ATTTTTTCATTTTTAGTAGAAATGGGGTTTTGCTGTGTTGGCCAGGCTGGTTTCAAACTC
CTGACCTCAAGTGATCCGCCCACCTTGGCCTCCCAAAGTGCTGGGATTACAGGCATGAGC
CACTACGCCCAGTCTATTTTGATAACATCTGGTGATACTGGTGGCTGTTGCTTAAGGGCA
TTATGGGAAATGAGAGGTAAGAATGGCTTCCACAGCCTCTAGCTATATACCAGCAGGACC
ATCTCCTGCTGTTCACACAAGCCTAGCCCTAGGCCTCTACATCTAGAAAGCATTGCCCGT
GCATCTACCAGCCTTTCTTCCATGCAAGGAGGGCAAATGTGGCTGGCGGAGAAGGCACCT
AGAATACCAGTGGCAGCTTCTCTGTCTCCCCACTATAATTTAGGACTCTTCTAATTGTAA
GCAACAGAAAATCCAGTTCAAACAGGCTTAATCCAGAAAGGTGTAAGGAGGCGGGGGTGA
CATATAAAATTTATGGCTCAGATACCATAAGAGTCTAGAAACAGTACCTGGCTTCCAGTA
CAGGGGTTTAATATCATCTGGACCTGTTGTCTCCTTACATACAGTCTCTTTACACCTGTG
TCATTTTCACTCCCAAGCAAGACTCTTCCCTGGTGTTGATACAGCTGCCAGCACAGGTCA
AGGTTTCTTTTTCCCAGTTCCACACCCAGCAGGAGAGATAAAGTTTCTGATCCCTATTAG
TTCAAACAAGACTCCATGGCCTTAGCCTTAGGCTAACTCAGCCCTGAGTCAGAGCTCCAT
TCCTCAATATAGTCTTGGGACCAAAGGAACATGGTGATCTGATTGGCTAGACCAGGGTCC
CTCCCTCATCCTACCATGTTCCCCAAGCTTCTGGACTACTTAGGGCTTCAGCTCCACCG
TAAACAAATTGAGAGTTAGAAGGTATGCTGTTCACTGCAGGGACAAGGGATACTGTCCCT
TAGCAAGAGCAACAGACCTGCCTTTTATCTGTTATGTTCTTGAGCTATTTCCTGAAAGCA
ATCAATACAACACTCATAAGTTAAATTTTATTGAATTCATAGTTACAAAAGCCAGGAAGT
CGTTTAGTTATTAACCACATGGTTTGAAATTGATGGAATTGAGACAGAAATCACTTTAAA
AACTGAGAGAGGGTGTCATAGTCTGTTCTGGCTGCTGTAACAACATCCCACAGACTACGT
AGCTTATAAACAACAGACATTTATTTCTTATAGTTCTGGAGGCCAGGATGTCCAAGATCA
AGGTGCCATTAGATTCCGTGTCTGCTGAGGGCCCACCTCCTGGCTCATGAATGATGCCTT
CTAGCTGTTTCCTCACACAGTGGAAGTGGCAAGGCAGCTCTCTGGGACTCTTTCAAAAAG
GCACTAATCCCATTCAGGAGGGCTCTCCCCTCACGACCTAATCACCTCTCAAGGGCCCCA
CCTTCTAACACCATCACATTGATGATTAGGTTTCAAAATATGAATTTGAAGGAGGACATA
CACATTCATACCATAGCAGAGGAGAAGAAAAATTAAGCATGTTTTGCCTTAAACTCTTAA
GAATTCTACACACACACACACACACACACACACACACTACACTACACTACAGCTTA
TATTTAATGCTGAAAGTCTGAATGCTTTCCCCCTAAGAGCAGGAATAAGGCAAAGGTGTC
CATTCTCACCATTTCTTTTGAATATCTCACTGGAAACCTGGGCCAGTGCAACAGGGCAAG
AAAAAGAAATAAAAGGCATTTTGAAAAGAAAGAAACAAAACTGTCCCTATTCACAGATGG
CATGATTTTCTACACAGGAAATCCCAAGAAATTACAAAATAAATTTTAAGACTAATAAGT
GATTTTAGCAGGGCTGCAAGATACAAGGTTAACACACAAAAATCACTTGTTATTTCTATA
TGTTAACAATGTACAACTGAAAATGAAATTTAAATACATTGTGTGACATAGCTCCAAAA
GGTAAGGATTAGGTATGTAACAAAATATATATAGGATCTATACTCTGACAATTATAAAAC
ACTGATGAAAGAAATCAATGAATGCCAAAGTAAATGGAGAGACATAAGTTGTTCATGGAT
TGGATGACTCAACATAGTAATGATGTCAGTTCTCCCATAATTGATGTATAGATTTAATGC
AATTCTGATCTAAATCCCAGCAGGGATTTTGTAGATATACCAGACAAGCTGATTCTAAA
ATTCATATGGAGGCAGGGTGCGGTGGCTCACACCTGTAATCCCAGCACTTTGGGAGGCTG
AGGTGGGCAGATTGCTTGAGCTCAGGAATTGAACACCATCTTGGGCAACGTGGCAAAACT
CTACAAAAAAATACAAAACTTAGCCAGGCATGGTGGCATGCGCCTGTAGTCCCAGCTACT
TGGTAGGCTGAGGTGGGAGGATTGCTTGAGCCCGGGAGATTGAAGCTGCAGCGAGCCATG
ATCACGCCACTGCACTCAAGCCTGGGTGACAGAGTGAGATCCTGTCTCCAAAAAAAACAA
ACAACAAATAAAACTCATATGGAAAGATAAAGGCATTAGAAGAGCTAAAATAATTATGAA
AAAGAAGAAAGTTGGAGGAATCATCCTATCTTATTTCAATATGGTTTTCAAGATATCAAG
TGTAATATTGGTGAAAAGGTAGACATGGCAAAAACTGCAATTACTTTTGCACCAACCTAA
TAGATGAATGAAGCAGAACAGAGATTCCAGAAATAGACCCATAGAAATATGCCCAGTTGG
TCTTTTTTATTTTTTTTTAAATTGAGACAGGGTCTCACTCTGTCTCCCAGGTTGGAGTGC
AGCAGCATGATTGTAGCTCATTGCAGCCTTGAACTCCTGGGCTCAAGAAGTCCTCCTGCT
TCAGACTCTCAAAGTGCTGAGATTGCAGGTGTGAGCCACTGTACCTGGCCCTCCAATTGA
```

FIGURE 4 (Continued)

```
TTTTTGACAAAGGTGCAAAAGCTATTCAAAGAGCAAAGGATAGTCTTTCCAACAAATGGT
ATTGGAACAACTAGACATCATATGCAGAAAAAAAATGAACCTCAACCTAAAATCACATT
ACATTCAAAAATTAACTCCAAAAGGAAAAGAGTAAGATATAAGACTTTTAGAAGAAAACA
TAGGGGTAAAATCTACATGAGCTGGAGTTAGGCAAAGAGATCTAGATGCCAAAGCACAAT
TCATAAAAGAAAAAATTGGTAAGTTGGACTTTAACAAATAAATCTCTTTCTCTCCAAAA
GGCACTTAAGAGAATGAACAAACAAGCTACAGACTGGGAGAAAAGAATTGCAGATCATAT
ATCCAACTTGTCTAAATTTGTATCCAGAATATATAGAGAAACTCTCAAAACTAAGTAATA
AGAAAACAAATGATCAAACTTTAAAAATAGGCAAAACCTGAACAGACACTTCACCGAAGA
GGGTATACTGATGGCAAATAAACACATGAAAAAATATTCAGCATCGTTGGCCGTTAGGGA
AAAGTGAATTAAAACCACAATAAGATGCCAGTAAATACCTATTAGAGTGGCTAAAAAAAA
ATACAACACCAAGTGCTGATGAGGATGTGGAGCAACTGGTACTATTAAACACTGCTGATA
TGGGAATATAAAATGGTACAGCCACTCTAAAAAACAATTTGGCACTTTCTTATCACCTTA
AATACAGCTTTATGATATGGCACAGCAGTCCCACTCCTGTGTATAGGTCCTAGAGAAAGG
AAAACATGTTCACACAAAAATCTGTATGTGAGTGTTTATAGCAGCACTCTGCATAATCAA
TCAAAATGGGAGACGAGTCAAATATTCTTCAATAAGTAAATAAACTACTGTCTATCCATA
AAACGTGATCTATTCAGCAAGAGAAAGGAACATACCATTGATACGTACAAAACTCAGATG
AATCTTAGAGGCATTATAGTCAGTGAAAAAACCAGTCTCACAACTTACATAGAATATGAT
TCCATCTGCATGATAGCCTCAAAAAGACAAAACCATAGTGGTGGAAAACAGACTAGTGGT
TGCTAGAGGTTAGGAATGGAGAAAGGTGTGACTAGAAAGATACAGCATGAGAGAGCTCTT
TGGCGTGATGGAGCTGTTCTATATTCTAATTTTGATGGTGGCTATAAGAATTTTAACATG
TTAACCATAGAACTGTACACTAAAATAGTCAATTTTATTGTATGATCAACACATGTACAC
ACACATACAAACATGCCCTTAAGAGTCAGTTGGTGCATACATGTCCAGCATTTGCAAGAG
AGGGTCTGTGTTTACTGGTGGGGAATTCCTGTTTTCTACTGAGTTCTCATCCCTGAAAAG
AGCAAAACCTTGAGTGGCCTGATGCTGCCGTAATTCCCATTGAGGATATCTGACCTAATT
GTTTTGGGTATTGTTGGGCATGGAAGGTTCACTAACATCTTAAGATAACATTCACACGGC
CAGCCAGAGCCTCCCTGGTTATCTGGCTTGGGGACGCACATGTCACATGGATCTTGGAGG
AGGTTGGGAAGGCTTTCCAAATACACTTGGGCTGAGTTTTGAAGTCACTGAAATGGTAAT
CAGATAAATGAGAGAGCAGAGGGAGCAATAAATAAAGGCTCAAAGACATGAGCGCAGGGC
AGAACTGACACAGTGGGCATGGTTGGGGTTGGGGCTGGGGCTAGGGTGGGTCAGAGAGCT
TGCATGCCACCCTATGTTAGGGGACCACTGAAGGGGCTTTAAGCTGGAGAGTGACTCCGC
CAGATTTGCATCCTGGAAAGATAGCTCTGACTTAGTTTGCAGAATGAACTGGCAGAGACA
AGATTGTATGCAGAAAGAGTTTTAGGAAGTTGATGAAGTAGCCTTGGTGAGAAATGCAGC
GGACCTGAACCAAGACAGTGTCAGAGGCCATCACTCACTTTACATTACATTACATTACTT
TACATTACAGTGTAAAGGCCATCACTCACTTGTCTTCTGACTGGGCTGGCAGGATTCAAG
CAGCCGGGGCTCCTGTATCCCTTTTCTCGCTGACTCTCTCTCTCCTCTTCTCTTTCTCTC
TCTCTCTCCCCAACCCCCACCCCCACTATACTCCCTCTTGCTCTGGTTTTCCCATGTTG
CCTCTCCAGCATGGCAGCTTCAAGGCAGCTGGACTTCTTACATGATGCTTCAGGGCTTCA
AAGTGAGTGTCCCAAGAAGAAAACTAATCAGATGCTGGCCTCTTCTAACCTATCTCAGAT
TTCACATAGCCTCACTACTGCTGCATTTTGTCTATCAAGGTGATCACGAAGGCCAACCCA
GCTTCAAGAGACAGGGACAGAGCCTCCATTTTCTGATGGGAAGAGTATCAGATATTCTAT
AGGCCTATTTTTAAAGTACCAGGGGACCCAGAATGAAAAGTCTGAGGTTTTCTGAAGGGA
GGATAGATACGTTTATTTTTCCTTTGTTGGGTCTCATGTGCAGGTATCCAGGTAGAGTCC
CAGCAGGTAATTGTATATTGAGTTTGTCACTGGGGAAACAGCATGAGGCAACAGATAGAG
ATGGAAATGGAAGCTATAAAACAGATGGGATCCCTGTGGGAGAGTGTGCTGCCCAAGAA
GAGGGTGGAAGACAAACCCTTGATGAACATCAACAATGTCAAAGGTGGAGAGATGAGAAC
TTATCCAGCTGGCTGAGTTCCTCTAGACATCCAACTGGTTTTCACTCCTAGAGTACTGCA
GTCTGAGACTTCTCTGGGATTCAGTATTCTCTTGGTAAAAGAGTCATCTTTCCAGCAGGA
CTGAACCCTTGCTTGCCCAGATCAAGGGTCCTCTTCCACCTCTCACAGCTGGCTGCTGAG
TCAGAACCTCCTACCTTCCTCCCAAGGCCAGGCTGTGTTGTGGAGCCTTCTGTCCTGTGT
GTTTCCAGTATGGGACAAGGCACTAGATCCTCCACCCTCTTCCCAGTTAGCTATGTTCCC
TGGAGTAAAAGAGTCTTTGAACAAGTTGTTAGGAAAGTTTCTCCTCTTCAACCACTTCAA
AATGTCCTTTTGAGTGTAAGCCACATCCAAATAATTAGTCTTCAGTTCCAGATCCTGTTA
GAGAGCCACACTGGTACAGGAGCTTTCCTGATTCCTCTTTTGTGAGTTGCCATAAAGAAA
GAGGAAATGACCTATAATCTATGAAAGAGCCAGGTTCTAAAACAGATCATTCTGACTTCA
GAGCTCAGCCCTTCACCCTAGGCATCCCTCCAAGAGACACCAGCATGAACTTACCCAGAA
```

FIGURE 4 (Continued)

```
CGGGCCTGAACATTTGAACAACTGAACACAATACACCCCAGCTGGCTCCTGGCAGATTGC
ACTCCAGTGTGGTGAGTTTAATTTGAGCAAGCAGTTGAAATAAAACAGGGCTGGCTGTGG
GGATGTGGCAGAGCCAGAATGGCTTCTCTTGATCTTTTTTTTCTCTCTGGGAAACAAGAT
GAATTAATGAACTGATTCATACTCCCTTTTACCCAAAGTCTGAAATAAACCACCCTTATC
ATCTCATCAAACCTTTACCCGACCCAAACTATGGATCTGGGATTCTTACTCTTCTCTTGC
CTTCAATCTATCCCACTCCTGATGAAGTTCCTTCCCAACTTCCAATCCCATGGGCTTCAC
TTTCCTGCCTATAAACAGCTGTCAACTGCCTGATTTCCCTATGCTAATCCATTCTACACA
TTTTAACCAGGCTTTTCTCCAATCTAGGCTGGCTTTTACACAAACATGTTCAATGGCTAT
TCATTATCCTTAAAAACTAATCTTTGTATATTATAGTTTAACACACGGTTTATCTCATTT
TATCCTCACAATGAACCCATTATATGGAAGGGAACTTAGGGTCAGAGAAGTATAAATTCT
CCTCCCTGGCATTCAAGGGCTTTCATGGTGTGCCCCAAGTGATTTCCTAGTCTTGGTTTT
CTAAACCACCCCTCAAGCACCAGCCAAACTACTGACTGAACACACTCTTATCACCTCTTT
ATGGAAGAAACAGAACTTTGGTGTCCAACAGAACTGGATATCGAAGCTGGCCATGTGACT
TTGGACAAGTTTCCTAACCTGTGTTACATTATTATCTTTATCTGTAAATAACAGGCTTTT
TAGATCAGATGATTAAATAAAATAACGTATTATAAAAGTGTTTGGGCCTTAGGCACCTGA
CACGTTAATTTCTTCTTCCCCTGCCCCTCTGTCTTTAGGTGTTCTCTCCACTCTCCACCG
TCCTCAATAGTCCCCGCCTAGTGAATTCCTTCTCACTCTCACATCCAAGGTTCATCTAAA
ATTCTTTCTTAATCTCACCTAGTGTGAATTTCAAGGGTAGCTCTGAACTCCTACAACTTT
GGGGTGGCCGTTCCTATAGACTAGCTTGTTCTCTTGTCTTCTGTCTTGTCCTGCCTACTA
GAATACAATTTCTCAGTGGCAGGAGCAGCGTCCTCTCTTTGACCTCACAACATAGCACCT
CTGTGGTGCTGGCACGAAGAAGTCATCCAGAAAACATTTGTAAGATTGACTCAAGACCAC
GGGAGGCTTCTTGTGTTCCACGTGCTGATTTCCTGATTGCTGTGATATTTGCTTTCGGCT
GAACACTGGTCACCTTCCCTCTTCTGTTATTGTGTACCAGAATGAAAGATGACAGCCAGG
AGGAAGTTTGCTTGCAGAGGTATGTGGGCTGAGCTCACAAAATTTAACAATTGTTTTTAG
CTTTTGTTCACATTTTAAAAATTGGGTGGTCTCACACAAAGACCTAGATTTTTAGTTTCT
CTTTAAAAATTCAGGAGAAAAGGCCACCATGGACCCTCACTTTCATGTGATGGGGCTTGG
GCAGAGACATCAAGACCACCACAGACCCATGGGCCTGCTTCCCTCACTTCTGCCCTGATC
CCTGTAGCCTTGTACGTTTGCAGTCTTTGATGTCAACTGAAAATTGTTGAAATGTATTTC
AACCCTATCTTTAAGAATGAAGTTGTAGCCGAGCACGGTGGCTCACGCCTGTAATCCCAG
CACTTTGGGAGGCTGAGACAGGTGGATCACTTGAGGTCAGGAGTTCAAGACCAGCCTGGC
CAACATGGGAAACTCCATCTCTACTAAAAATAAATAATAAAAAAACTTAGCCAAGCATG
GTGGTGGGTGCCTGTAATCCCAGCTACTCAGGAGGCTGAGGCAGGAGAATTGCTGAACCT
GGGAGGCAGAGGTTGCAGTGAGCCGAGATCTCACCATTGCACTCCAGCCTAGGTGAAAGA
GCGATATTCCACCTCAAAAAAAAAAAAAAAAAAAAAAAAGAATGAAGTCCTTACTTTTT
TTTTGATTTTAGGACAGATGACCAAGGAGGTGTTACTTCCTTGAGTGGTGAAAAGGTTCT
TCTACTGCATGGGGTTTTTTGTGGTTTTGTTTTTTTTTGTTTTTGAGATAAGGTCTCAC
TCTGTCACCCAGGCTGGAGTGCAGTGGCATGATCTCAGCTCACTGAAGCCTCAGCAGCCT
GAGCTCAAGCGATCATCCCACTTTAGCTTCCCTAATAGCTGGGATTACACACGTGGGCCA
CTGCGCCTGGCCTACAGTATGGTTTTTAAATATCTTTGTGCTCTCCCTCTGTAGACATCT
TTCATTTGCTTAGAATCTGTGGTGATGGAGGCCTCATGCCCTATTCCAACTCCAGCTGCC
TGTCAATGTAGTGTCTGTAGCTTCTTTCACATGGAGAAGCTATCAGTCCCATTCTGTCCA
TCAAGGTAGAGTGAAAAATATCAGGTCACTCTGCTGCCTCTACCACCTTTCAGCACTGAT
GGCTCCACTCCCTGAGGGGAGAGGCACAAGTGACAGGGAAGGAAGAAAGAAGAAGAATTT
TCTCACTTTGTGATTTATTGCATTTAATTCTCACCCTGAGTCTGAGTTGGGTATCATTCC
TTCTTGACTTATAGCAAAATCAAGGCACATAGAGGCTGTCCTTTATGCTCCATCCCAAAG
CTAGAAAATAAATGATGAGTGGTTTGGGCCCGGTTGTGTCTAATTGTGTCATGTTTTTTC
ACTATTCTGTCTGCCTTAGGGTCTCCAACCCCTTTCAGCTGTATTTATAAGACTGATGTT
TGCAGAACTGTTTATTAGTTTGCAGGACTGTTTATTAGACAACTACAAACGGAGCTGAAA
TAAAACTTTGGTTTCTGTTTGCTCTAAAGAGAAGTTTCTGTTCAATCCTCCACTGGGAGT
GTGTCTTTAGGCCTCTAAATTTTATACCATAACTATTTGTATAATTTGAATGGTCTCCAA
TGAAATGGATACAAATAATAATAAATACATTCTAAAATAGCAATAATGCATGACATTGGT
TTAGATCACAGTGTTTCCTATGTACATTTTCTCTTTGGGTTCACCCAACATTCTCGAGAT
ACCCTCACTCAAGTTTTTAGATAAAGCAATCAAAAAGCAAGAGGATTTAAATGACATAGG
TAAGTATGCATGTGGTAGAAATGGAATTAGAATCCAGATTCTTAGCTCCTCTTTTCATTA
TCTGATCCTGCTTGGTTTTTACTCACACCAGGCAATAATTTTGAAAGCTCTGCTCTCTCT
```

FIGURE 4 (Continued)

```
ACTTGTGATATTATTATCTGTTGTTATTATTCAATCATAAATATTTATTGAGCCTTCCTG
CAGGCCAAGGGCAGGGCTAAGTCCTGTGCATTCATTATTTCACTTAATGCTCAGGACAGC
CATATGACATAGGTACTCTTCTCATTTCTCTTTAACTGATGAGGATACAGAGGCTTAGAG
GGATTCAGTAACTTATGTAAGGTCACACTGCTAGTAACTGGTAGGACATACTCAACTCCA
GATAGGTGACTCATGGAAATTTCTGCTGTGTCTTACATCTTCACCTAGATTGTAAACCAC
ATGGGGACCCGGACCACATGTCCTCCACAGAGCTTAGCAAAGTGGTTGTATGCACAGGTA
TGCAAGTCATTAATTAATGACAGTTGATTTTTCTCGGCCATTAGCTTTTATTTTACTTT
ATCTATAGGGATTTTCAGATCACACTGTTCTCAAAATAATCCTGGTTTTCTGTTGGCTGT
TTTGATTTATCTTTAGACACTGTAATTGAAAATTAAGCTCTTAAGCATCTCCTTTACAGG
CTATGTTCCACAATCTGTAATCACAACTTTTCTTTAAATTGATCATCATCTTTTGAGCTG
TTAATAAACATGTCTGGCTTCATTTGGGTTTTCAAATTGTTATTTCCAGACGGTGAGACT
TTCAGATCTGATAGGCTCACACACATCCTGCCAAGTGGAAGTTTGAGCAAAATGTCACAT
CTTTGGCAATATTTGTGCTATTAGTATGATGATTAAAGGAAAAAGAAAAGTTTCACTGTG
ATGTCAGCAGCTTTCCCACCTCATGAAAAGCCATCAAATTATCAACCAATCAAAATTAA
ATGAATCCCATTTAATTTTATTATTATCTATTTTTCTTTTTTCCCGTTTTAAAAATGAA
TTTGGTTCATTTGCTTTCTGCTTCTGGATTTGCCTGTTCTGGACATTTCATATAAATGGA
ATCATATAATACATGGACTTTTGTGACTGGCTTCTTTGGCTTGTTTCACTTAGTGTAATG
TTTTCAAGGCTCATCCATACCACAGCATGCAGCAGTGCTTTATTCCTTTTTATGGCTGAA
TATTATTCCATTGGATAGAGATACAATATTTTGTTTATCCAATAATAAATTGGGCACTTA
GATTGTTTTCACATTTGGCTATTAGGAATAATGTTGTTGTGAACATTTCTTGTACAGTTT
TTGTGTAAGGACATGTTTTCAATTCCAGAGGCTATATATCTAGGCATGCAATTGCTGGGT
CACATGGTAACTCTATGTTTAATTTTTGAGGAACTGCCAAACAGTCTTCCACAGAGGCTG
CAACATTTTACATTCTCACCAAAAAGGCAAAAAGATTCCAGTTTCTCCACATCCTCACCA
ACATATATCATTTTCTCTTTTTTGTGTTTTTTAAAAATAGCCATTCTAATGAGTACAAAG
TAACATCTTATTGTGGTTTTGATTTATATTTCCCTAATGACTAATAATATTCGACATCTT
TTTATATGCTTACTGTCCATTTGTATATCTTCATTGGAGAAATGTCTATTCAAATATTTT
GTCTATTTTTAACAATTTGGTTGTCTTTTCATTGTTGAGTTGTAAGAATTCTTTATGTAT
TCTAGACCCTTACCAGATACATAATTTGCACACTTCTCTTTTTTGAATAAATTGCAAAGC
AACATTTTTCAAAAAAATTTTTAATTTTTTTCTGCCATATTGTGAAGCTTGGTTGTCTCT
ACCAGGTACTACCTCCTATTTACCCATAAGTATTTGGAAGGTCATCAGGATTTATGCTCA
AAAATGGAGTTTGGGGGTGAGAAGGAAGCACTTTGTTTGGAGAGGGTTTTACTGTTGAGG
CCCTGCATTAATCCCCTCTGCCACCTCCAGGAAAGCTGTGGTCACATCTGGTATAGTAGA
AAGTGCCATGGTGGCTGAGGAAGCTTGTGGGTTTATCACATTTTTATCCATGGTGGCATG
GACACCTTGTTTTTGCTTCCGAATTGCTCTTAAAGAAAAATTCTGGGGCGGATGAACCCC
ATCATCATCCAGGAAGAATATTTGCAGCACATTTTTTCTTGTCATGATGAGTTTGCTGTT
TGAGACGGTATGGTAAGAAGCTTTATAATGGCTGGCTAGTGTCATTTTCCCTCATTTAGG
CTCAACCGTGACTTTATATCTGTATACTTTATGGAAGGCCTGGAGCCTCACACTGAGGCA
GAAGAGGGAAGGGGCAAGTGCAGTTGATGGTGGCAGCTAAGTGGGAGAGAAAGTCAGCGA
AGACAATTATTTATTCAAGACCTTTACAAAGGGAGCAGCCCCACTTGTTTGCATGTTGAT
TGAACCATACCTTAGTGTCCAGTTGCTTGAGGCTTGCAGCAGCATCTTTATGCTCTTCAA
AGTGAGTGCTGCCATTGGTAGCAAGGTCTTATGGATGCCCTTGCTAGGCCCATTTCCTTC
TTTGTTATTCCAAGTATACTTCTAATGAATCAGAACCTGCCTCTTTTTTTTTTCTTTTT
TTTTTTTTTGAGATGGAGTCTTACTCTGTCGCCCAGGCTGGAGTGCAGTGGCACAATCT
CAGCTCACTGCAAGCTCTGCCTCCTGGGTTCGTGCCATTCTCCTGCCTAAGCCTCCCGAG
TAGCTGGGACTACAGGCGCCCACCACCACGCCCGGCTAATTTTTGTATTTTCTGTAGAG
ATGGGGTTTCACTGAGTTAGCCAGGATGGTCTCGATCTCCTGACCTTGTGATCTGCCCGC
CTCAGCCTCCCAAAGTGCTGGGATTACAGGTGTGAGCCACCACGCCTGGCCTGAACCTGC
CTTTTAACAAGACCCCAAGGTGATTCAAGGCACATCAAAGTTTAAGAAGCATAGATTTAC
ATTATATTCTGTCTATCCCTGCACATCTCACATGGTTATTCAGCCTAATGTCCGTGTGAG
TCAGTCTTCCTCTTTCTTTTCATGCCTTCCATGGATTTCACCTGGTGTACTCTTGATACC
ATCTGTATTAGCCTGTTCTGACAAGGCTATAAAGAAATACCGGAGACTGGGTAATTTATA
AAGGGAAGAGGTTTAAATAACTCAAAGTTCTGCGTGGCTGGGGAGGCCTCAGGAAACTTA
CAATCATGGCAAAAGGGGAAGCAGGCACCTTCTTCACAAGGCAGCAGGAGAGAGAGTGTG
AGCGTGTGAAGGAGGAACTGTCAAACACTTATAAAACCATCAGATCTCATGAGAACTCAT
TCACTATCATGAGAACAACATGTGGGAGACCCCCACCTCCATGATCCAATCACCTTCCAC
```

FIGURE 4 (Continued)

```
CAGGTCACCTCCCTTGACACATGGAGATTATGGGGATTACAATTCAAGATGAGATTTGGG
TGGGGACACTGCCAAACCATATCACCATCCTAGTACTGGCTGCAGCTTCCTTTAATTACT
GGATGAAGAAACACAATCTTTTGATCAACTAGCATTTCCCTGAAGCACTTGTAAACAATT
CCATAAAAATCCTGAGATAGGTACCTATTTGTGTTACTCTTGAACTTTCCCCAGCCTCC
TCCTCCCCATCCCTGTCTTCCCACAGCTCAATACTTCCACCTTCCATTGTTCAGTACCCC
GCTGTGACTCCTGCCTGTGCTGAGTTGCATCTATGATTGACTCTCATTAGATGTGAGCTC
CTTGAGGGAAGGGTCTTACATCATCCATTTTTATACCTTGATTCCCACCCCTGGACCTAA
CACAGGTCCTTGGACATAGTAAATATTTGCAGAATTTAATTAAGTTATTGAGTCACATTG
GAAATAATTTCAGAAGATACCAAATGCCTTTTCTTTTTTTTTTCCACATGCCATTTGTT
CTCGTACCACTAAGACCCTAAGACTTTTATTTTGTTGATATCAAGTGGTATAAATATTAA
CAAACATTGTATTATATATCATAATTTTAACTCTGAAGTTTTTAATTTATAGAACAAAAG
TTAATATTTCTCTACCAAAATAAATGTCATAGACTGAGGAAAGAATTTTGTTAATTTGGT
CATACCAAAAATATTTAACATTAATTTCTCTCCTCAACTTCTGACTCTGCTGCTCCTTAA
CTCTGTAACCATGACTTACCTGTCAAAGCCAAAACTCTTTTGAGCATTTCATGAGAAAAT
CTATAAAGAGTATATAGCCTACAATAATAGCTAACATGTATTAGCTGTACTTACAGTGTG
AGCCAGGTACTTTTTATTCTAAGTACTTTACATATAGTCTCATTTTAAAATCTCCTAATG
ACTCCATGAGGTTGATATTTGTTCTTCCCATTGTTATAGGTGAGGAAACAGAGGCACAG
GCTACAGGGTATTTTGTCCAAGATAACACAGCTAATAAAGTGGTGAGGCCAAGATTTGAA
CAGTCTCTTCTTAAAGAGCCTGCCTCCTGAAGGGTTACTGATGAATTCCTTTCTTCCTTC
AAAATGCTTCATGTGATTTAACATGCCTTATTTCATTGTGTATATTAAAGGCCCTTTGTT
TATACATTACTCTCATCTATATTTCCCCATTTGGCCAATGCATTGTATAAATTAGGTGAT
CTGTAAATGATTGTTGGCTAATTGATCCTATGTGCATACATGGGAATACTTGGAAAAGCA
ATGATTGTTTTAATATAACAAGTTCTTGATGTAGCAAGATTGTTCCTATACATTGTGGAA
CTCTCAATTTTAATATTTACTGACTCCATTATCCATCTTAAAATGGGCATATCGGAAAGG
GTAAGGAATAAATAATTGATGGTGGTGTCACACATCTAGTAATATGATAGTTGAGCTAAT
ATGAATTGGTTCTCCCACCATCTCAAACACAAAGAAATATAAAAGTCCCCTCCAGACCAA
TGCAGAGCCAAACCCAAACTCAAAAGCAATAAAGGAAATGCCCTTGTGCCAGAAATAAAA
AGGGAACTCAAAGCCAGAAGTATAAACAAGATCTGGTGCTAAGGTCTAGACCTGTCTTAA
TCTGTTTTGTGTGGCTGTAATAGAAGACCTGAGACTGGGTAACTTATAAAGAAAAGATGT
TTATTTAGGTCACAGCTCTGTAAGTTGGGAAGTTCAAGGGCATGGCCCTGGCTTCTGGTG
AAGACTTTCGAGCTGCATCAAAATATGATAGAGAAAGTCATCTCATCTTGGGCCATGTGT
ATATAATTTAATTTTAATAACTAATATAAAATTATTGTTAAAATATGGTAGAGAAGATCA
AAGGGGAAGCAGATCTGTACAAAGAGGAAAAACCCGAGGGGTATCCTGGCTTTATAACAA
CCCACTCTTGAGTATACTAATCCATTCCCATGAGAACTAATCCAGTCCTGCCAGAGTGAG
AACTCGCTACTGCAAGAATAGCACCAAACTATTCATGAGGGATCCAGCTCATGACCCCAA
GGGCTCCCACTGGGCCCTGCCTTCCAATACTGCCACAGTGGGGATGAAATTTCAGCATGA
GTTTTGCTGAGGACAAACCAACCATAGCAAGACCCACTTACAGGCTTTAATAATGGGAGA
TAGGGGTCTTAATATCCACATGGGGAAAAGTGATATGATCTTGGCCCACGTGAGTGAAGG
AGTCTAAACGAAACCTTGACATAAAGTCTGGAACCACAAAATTTGGCCCTGCCCTTGGAA
ACAAGAGCAGAGAAATTCTACCTAGTGACTAAGGAAAACCTTAAGAAAGTTTGCCATTTG
TCCATGGCTAAAATAAGAGGTTAAGAGGGTACCCATGAGAAGATTAAAATCCAGATTTAT
ACTTCCCTCAGTGCATCATCTAAATTTACACCACTGTGTAATGCCGATTTATCAAGCTGA
AAAATTAATATGAAAACTGTCCTGGAGGACTTGAAACTCCTAAGTCCCCAGAAAAAATAA
GTAGCCTGTAGGTAGACTTTCACAACTCAGAAAAAAGCCAACCCCCTCCTCAAAAGACAA
GCCTATGATCAAAAATTACAAATTACACAGGAAAAGACCCAGTAGGAGAATAGGTATCCC
CCAAACTGGAGATGATAGAACAGTCTGAAATAATATATACTAAATATGTTTAGAATAACT
AAAGAAAACAGGTGGAATAGAAACTAGATAATAGAAAATGATAGTGTGAAAAGGATAC
TGTAAGTTCTAGAAATGAAACTTAGAGTGGAATTAAAAATTCAGTGAATGAATTAAACAT
CCAGTAAATGCAACTGATGTAAGGACTGGAAACTGCAAAATAGGTGTGAGAAAATCAGT
CAATGCATCACAGAGAGATAAAAAATGGGGAATATATAAAAACCCTCCAAGGACCCATAG
ATTTGGAAACTGAAACTCATATTTTTTCAAAGAATTTACAGTTCAAAGAAAAAAATCACA
ACATAGATTTATAAGATATTTAGAACTAAACAAAAGTAAAAATACCATATAATAATTCAC
AGGACATCAACACAGAATTTAGAAGGAAATGTCTTATATGCATATACTGAAAAACAAAAA
CAAAGCTATAATTCCAGCACTTTGGGAGGCCGAAGCAGGAGGGTCAGTTGAGGCCAAGAG
TTTGAGACCAGCCTAGGCAACACAGTGAGACCCTGTCTCTACAACAAAACAAAACAACAA
```

FIGURE 4 (Continued)

```
CAAAAAAACTCACAAAGATAATGATAATGAGCTAAGCGATCAACTCCAAAAGGGAGAAAA
ATAACATAGTAAACCTTTAAAAATTAGATGGAAAGAATTTATTAGATAAGAGCAGAATTT
AGACATATAGAAAACAAAATAGGGAATGTGATATGGAATACTGAACAGCACTTTGAATGA
ACTGGATCTACTTGTATTAATATTAATAAATCTCAAAAACACAAAAGAATTTCAAAAACA
CAAGGCAAGAGAATACATCCAGACTGATACCATGTGAGTTAGATTTTTCAAGCACAAACT
GACGTGAGTAGTAGATGTATAAAGGCATGGACAAAAAGTAGGCTCAAATTAAGTGATTAT
CTAATCTATCTAAGAGAAGATGGAATTGGGGAGGATGCAATGGACCCTCAACCATAATGT
TTTATTTGGAAAAAAAGATCTGTGGAGGATTTGTTCAGTCTGCGTGGTGGATGTATACAT
GTTTATGTATTTTTACTTTTCATTGAAACATTTCAGAATACTCTTTCAAAGAATCAATAA
TTCAGATTCTGTATACTGAATAGAATTCTAACAAAATTACAATTAAGAAATAAAGTTAAT
GCCAGTGTTGCATGAGGTTTTTACTCATGTGGTTTGGTTGTAGTAAGGGATCTACAATAG
TTGTAGTAGGCAGTTCTGAGACGGCACCCAAGATTGCTACTTCTTGGCAAACATACCCTG
CATAATCCCCTTACTTTAAGTGTGGATATGATGGGATTTCACATTCATAATTAGATTACA
TTCTTTGGCAAAGGTAAAGAGACTTTTGCAAATGTAATTAAAGTCCCTAATCAGTTGATT
TTGAGTTAATCAAAACAGATGATCCTGGGTAGGCCTGACTTAATAAAGTGGAAGCCCTTA
AAGAGACTGGGCCCATCCTGCTGACTCTGAAGAGGGAAGCCACTGTGTTGTCAGAGGGCC
ACATGGCAAGGAACAGTAGGACTTGCAGGAGCCGAGAGGAGCCCCTGTTGACAGCCAGTA
AGAAATCCTACAACTACCAGGAAGTGAATCCTGAGAACAGCATCATGAGCCTGGAAGAGA
ACCCTAAGCTCCAGGAAGGAATACAGCCTAATTGACACCTTACTGAAGCCTTGTGAGACC
CTGAGCAGAGGACTCAGTGTAGCTGTGCTCAGACTCCTGATCCATGGAAATTTTGAAATA
TTACCCGTGTGTTGTTTTAAGCTACTAAATTTGTGGTGATTTGTTACACAGCAATAGAAA
ACTAATGCAGTAGCTCTATCTACCCTGTTGTATGAAAGCAGTTTGTAAATTGACATGCTA
TATAAACAGTGCTGGTTTTGTTATGGCATTGATTATTCACATTTTATCTGAGTACTATGA
TCAATACACTAGACTGTTATGGTATACTACATTTGCCATTCTGCTATACCTTCTCTTAGA
GCACAATTTTGATGGAGATAATCAAACCAGGTTCTCATTTTAGATAAAATTTCCACAAAA
GATCTACAGAAATTGTTTCTAAGCTTATATTACAAAAATGGCAGCACCTATCCAATGCTA
ATGTCTATGCGAACATCTCTATTATATGGAGTTTGAGTTTTGAGACCATTTTCTTACCGT
TTTGAAGCCATACTATGGGGCTCACTTCACTGATCTAGTAGATGTTCTGGGTATCTGTCA
TGGCAAAGTGGTAAGTCTTCTGAAAAGAAGTGGCATCTCAACTTGAACTTTAGAAAATGC
AAGAAATAAAACCCTCCTGAAGTAAGACCAGGAGCACATCAGAAGACTCCCTTATTGGGG
TCACAAACTAAGAACGAAAGAATACCCACCTCTTGTTACTCAGCTTATTCTGTGCATGTT
ATCCTCTGTGTTTATTTCCCTCTCGTCACCCCCTAGTTTTTAGTAAAGTCTCATTTAAAC
CTTCTAGTGTAGCTTCTGTTATGCCAGGGATATTAGGAGCATGGACACTTTGATGCATAC
CACGATGCGGTGATGACAGTGCTAATTGATCAGAGTCTCCCCAAGGGAAAGACATCTGCA
GGAACAAGACACAAAACTGTACAGCCCACCTCCCCTTCTCACAAGAAGATACTTCCTGCA
TGGAAAATCTTGGAGGACTGGAGTTTGATTTTATTAAAAATGCAAGTTAGGAGGTGGGCA
CAGTGGCTCATGCCTGTAATCCCAGCACTTTGGGAGGCCGAGGCAGGCAGATCACGGGGT
CAGGAGATCAGGACCATCCTGGCTAACATGGTGAAACCCCGTCTCTACTAAAAATACAAA
AACAAAATTAGCTGGGCATGGTGGCCGGTGCCTGTAGTCCCAGCTACTCGGGAGACTGAG
GCAGGAGAATGGCGTGAACCCGGGAGGCGGAGGTTGCAGTGAGCCAAGATCACGCCACTG
CACTCCAGCCTGGGAGACAGAGCAGGACTCCGTCTCAAAAAACAAACAAACAAAAAAATG
CAAGTTAGATTTTCTTATAGTTTGAGAGTATTCTGGTTTAAGAAGGTGGGAAGAAGTAAA
ATTGGTTGAGGATCTAAGGTATAAAGAGATGATACCAGAGGTTTGATAAATTGAGCCCTA
ACCTTAACAGTACATGCTTCTCAGTCTACATTCCGAGTTGGCTGTAATATATGCGGCCTC
ATCCACTCTTACCTTTCTTTGTGACACTGATACCCTTATCAACACACTTCATCCACGTCT
CTTTCTTGTGCTCTATACACACATATCCGTGTCTTCATTAAGCATCTTCCCCTCAGTGTC
CCATCCAAAACTGAACTCATCATCTTTAGAACTATCCATATTACCCACTTTGGTAGGTAT
CACCATCCACCCTGTTACCCAAGCTAGAAAACAAGAACCCCAGAACTTCACTTTCTTCCT
CATCTCTACTGCCTTCCACCTTCAGACATATAATTTATCACCAAATACTAACTCGTCCAC
CTCCTAAATTTGTTCCCCTTCTCCACTCTTTAACACCGCTCACCTTGGATCACAGCAGCC
ACTTACAGGATTCGCACACTGCTTTCTAATGCAAAACTCCTTCCAATGAAGGAGTAAATC
CTCCAGAGGCTTCCCACTGCCTTCAGGATCAGCTTCAAATCCTTAGCTTGGCGTATGGGA
TCCTTCACCACCTGCTTCTTCTTACTTGTGCAGTTACGTACATCTACCTAATTATGGGCC
ACACTGAATTGCTTGAAGCTGTTTAAATGTGCCAAGATATCCCAGATTTCTGACCTTTAA
GCCTTTGCAGTAGTCTTACGAATTCATACTCGTCCTTTCCCAGACAAATGTCTCTACTCT
```

FIGURE 4 (Continued)

```
TTTGATGAAACTGTACTGTCTTCCATCCTTAAGGGCAGGGGACATGCATCCAGCTGTCTT
TGTAGTCACACAGTGTGCCATGATGCCTATTTCTGTAGGTGCTCAATAAGTGTTTGATGT
GTATTTATTAGGATAATATACCTATGTATGAGTGAACAAATGAATATGCAGATGAATGAA
TAAGTGTAAGGAGGAATGAAGGATGAATTAGATAATTAAAAGCCTCTGCCATCAGTCAAA
ATGAAACTTTTTTTGTGTGTGTGTGTGTTGTAGAGATGGTGTCTCATTATGTTGCCCA
GGCTGATCTCAAATTCCTGGGCTCCCACCTTGGCTTCACAAAGTACTGGAATTACAGGTG
TGAGCCACCATACCTGGACTCATTTTTAAAATATATATATACTTGATTACTTCACCACAA
TAGTGTCCTTTTGCTCATGGCCCATGGGCCTAGTCCCTTTTAGAGTTCTCAGTCACCTGT
AAGATACATGCCTTGAATGCTACCAGGTGATAAATTTGAGTTGGACAATGAAGAAAATAT
TGTACATGTATTTTCTTATTTATTTAGACCAAATAGGCTGAGAGAGTAACTTGAATATTT
AAGAGCTTCCTTAAAATGCACCATAAATAATGGAAAGTGAATGACTTGATTACTTCCCTT
ATTTTTCTCTTATTTTTATTTGGGTTGATAGGAAGGAGGAGGTTTGTGGAGGGGGAGAAA
ATATAAAACAGTGGAACATGCAAAAGAGGGCCCAATTCTTCCCTTTCTCTCAATTTCCA
TGATATAACTAACTCTGATCTCTCATGGTGGGCAATGGAATATTGTGGATAAAGTCTGGA
TAACTGAATTGTCAAAACCCTCCAATATGGACCACTAATTAAAGCACTGAAAGCACAACT
AAGTGTACTCAGTATGTTAATGATGCAGAATACAATGTAACCTTTGATTCAGGAGCGGCT
TCAAGATCCAAGCGTCCTGGGAGAAGCAGCAATCCCTCTTCCTGGGCGCAGAGATGCTGG
TTTAACACAGTCATGTGTCAGAGAAAACTAGTTTTTCCTGCAGGCCCAAATCCTACCCTA
GAGAAACCCATTAGACCTTTACCAAAATCAACTTTTCTTCTGAGTCAGACCGAATTCTTA
ATTGTAGGTGATAGACCAAAAGGGAAAGATGACTCAATGTAAATAATCGTTGCTATTGAC
AAAACAGTGCAAACCACATTTCCTGTTGATGGTGGAGTCACCCATGACGGAAAACATTTT
TATTGCTTTAATAACACAATTATATTATTTTTTAACTCTTCCCCTTCAAATCCTCTAGCA
CTTAATATAGTGCTTGGGATATATTTGGATATTAATAAATGCAAAAGTGTTATTGCCTCT
TTTTGAATTAACATACTACAAAGAATGTGTTTACTGTACTTTCTTACCTTAAAACTTAAA
CCTAAAAATGTATGCTAATATGAACCTTTGCTTGACATTTCATGCTTGCCTCTTTGGTCG
CTAGGAAAAGTCAGCAACATTCAGCAAAACTGTCAAGGATTGGAGCATTTAATAGTTGGC
TGATGGTCCACAGGCAAGTCCATCCAAACAGCCAAAGTTGTATTACTCAGTGTTTTTAAA
AGATGAAGATTTGGGGTGGAGCCAAGATGGCCAAATAGGAAGAGCTCCAGTCTACAGCTC
CCAGCGTGAGTGACTCAGAAGATGGGTGATTTCTGCATTTCCAACTGAGATACCAGGTTC
ATCTCACTGGGGAGTGTCGGAAAGTGGGTGCAGGACAGTGGGTGCAGTGCACCGTGCGTG
AGCCGAAGCAGGGCGAGGCATCGCCTCACCCGGGAAGCACAAGGGGTCAGGGAATTCCCT
TTCCTAGTCAAAGAAAGGGGTGACAGATGGCACCTGGAAAATCGGGTCACTCCCACCCTA
ATATTGCACTTTTCCAACGGTCTTAGCAAATGGTACACTGGGAGATTATATCCTGCGCCT
GGCTCAGAGGGTCCTACGCCCGCAGAGACTCACTCATTGCTAGCACAGCAGTCTGAGATC
AAACTGCAAGGCAGCAGCGAGACTGGGGGAGGGGCGCCCATCACTGTCCAGGCTTGAGTA
GGTAAACAAAGCAGCCGGGAAGCTCGAACTGGGTGGAGCCCACTGCCCCTCAAGGAGGCC
TGCCTGCCTCTGTACACTCCACCTCTAGGGGCAGGGCAGTGCCAAACAAAGGCAGCAGA
ATCCTCTGCAGACTTAAATGTCTCTGTCTGACAGCCTTGGAGAGAATAGTGGTTCTCCCA
GCACACAGCTGGACATCTGAGAACAGGCAGACAGCCTCCTCAAGTGGGTCCCTGACCCCC
GAGTAGCCTAACTGGGAGGCACCCCCCAGTAGGGGCAGACTGACACCTCACATGGCAGGG
TAACCCTCTGAGACAAAATTTCCAGAGAAATGATCAGGAAGCAACATCTGCTGTTCACCA
ATATCCACTGTTCTGCAGTCTCCGCTGCTGATACACAGGCAAAGAGGGTCTGGAGTGGAC
CTCAAGCAAACTCCAACAGACCTGCAGCTGAGGGTCCTGACCGTTAGAAGGAAAACTAAC
AAACAGAAAGGACATCCACACCAAAACCCCATCTGTACATCACCATCATCAAAGACCAAA
GGTAGATAAAACCACAAAGATGGGGAAAAAACAGAGCAGAAAAACTGGAAACTCTAAAAA
TCAGAGCGCCTCTCCTCCTCCAAAGGAACGCAGCTCCTTACCAGCAATGGAACAAAGCTG
GAGGGAGAATGAGAATGACGTTGACGAGTTGAGAGAAGAAGGCTTCAGATGATCAAACTA
CTCTGAGCTAAAGGAGGAAGTTCGAACCCAAGGCTAAGAAGTTAAAAACCTTGAAAAAAA
AATTAGACGAATGGCTAACTAGAATAACCAATGCAGAGAAGTCCTTAAAGGACCTGATGA
AGCTGAAAACCAAGGCACGAGAACTACGTGACAAATGCACAAGCCTCAGTAGCCGATTCA
ATCAACTGGAATAAAGGGTATCAGTGATGGAAGATGAAATGAATGAAATGAAGTGAGAAG
AGAAGTTTAGAGAAAAAAGAATAAAAAGAAATGAACAAAGCCTCCAAGAAATATGGGACT
ATGTGAAAAGACCAAATCTACATCTGATTGTTGTACCTGAAAGTGATGGGGAGAAAGGAA
CCAAGTTGGAAAACACTCTGCAGAATATTATCCAGGAGAACTTCCCCAACCCAGCAAGTC
AGGCCAACATTCAAATTCAGGAAATACAGAGAACGCCACAAAGATACTCCTCGAGAAGAG
```

FIGURE 4 (Continued)

```
CAACTCCAACACACATAATTGTCAGATTCACCAAAGTTGCAATGAAGGAAAAAATGTTAA
GGGCAGCCAGAGAGAAAGGTCGGGTTACCCACAAAGGGAAGCCCATCAGACTAACAGCTG
ATCTCTCGGCAGAAACTCTACAAGCCAGAAGAGAGTGGGGGCCAATATGCAACATTCTTA
TAGAAAAGAATTTTCAACCCAGAATTTCATATCCAGCCAAACTAAGCTTCATAAGTGAAG
GAGAAATAAAATACTTTACAGACAAGCAAATGCTGAGAGATTTTGTCACCACTAGGCCTG
CCTTACAAGAGCTCCTGAAAGAAGCACTAAACATGGAAAGGAAAAACCGGTGCCAGCCAC
TGCAAAAACACACCAAATTGTAAAGACCAGAGAGGCTAGGAAGAAACTGCATCAACTAAC
GAGCAAAATAACCAGCTAAGATCATAATGGCAGGATCAAATTCACACATAGCAATATTAA
CCTTAAATGTAAATGGGCTAAATGCTCCAATTAAAAGACACAGACTGGCAAATTGGATAA
AGAGTCAAGACCCATCAGTGTGCTGTATTCAGGAAACCCATCTCATGGGCAGAGACACAA
ATAGGCTCAAAATAAAGGGATGGAGGAAGATCTACCAAGCAAATGGAAAACAAAAAAAGG
CAGGGGTTGCAATCCTAGTCTCGGATAAAACAGACTTTAAACCAACAAAGATCAAAAGAG
ACAAAGAAGGCCATTACATAATGGTAAAGGGATCAATTCAACAAGAAGAGCTAACTATCC
TAAATATATATGCACCCAATACAGGAGCACCCAGATTCATAAAGCAAATCCTTAGAGACC
TAGAAAGAGACTTAGACTCCTACACAATAATAATGGGAGACTTTAACACCCCACTGTCAA
CATTAGACAGATCAACGAGACAGAAAGTTAACAAGGATATCCAGGAATTGAACTCAGCTC
TGCACCAAGCAGACCTAACAGACATCTACAGAACTCTCCTCCCCAAATCAACAGAATATA
CATTCTTCTCAGCACCACACCTATTCCAAAATTGACCACTTAGTTGGAAGTAAAGCACTC
CTCAGCAAATGTAAAAGAACAGAAATTATAACAAACTGTCTCTCAGACCACAGTGCAATC
AAACTAGAACTCAGGATTGAGAAACTCACTCAAAACCACTCAACTACATGGAAACTGAAC
AACCTGCTCCTGAATGACTACTGGGTACATAACGAAATGAAGGCAGAAATAAAGATGTTC
TTTGAAACCAATGAGAACAAAGACACAACACACCAGAATCTCTGGGACACGTTCAAAGCA
GTGTGTAGAGGGAAATTTATACCACTAAATGCCCACAACAGAAAGCAGGAAAGATCTAAA
ACTGACACCCTAACATCACAATTAAAAGAACTAGAGAGGCAAGAGCAAACACATTCAAAA
GCTAGCAGAAGGCAAGAAATAACTAAGATCAGAGCAGAACTGAAGGAAATAGAGACACAA
AAAAACCCTTCAAAAAATCAATGAATCCAGGAGCTGGTTTTTTGAAAAGATCAACAAAAT
TGATAGACTGCTAGCAAGAGTAATAAAGAAGAAAAGAGAGAAGAATCAAACAGATGCAAT
TAAAAAATGATAAAGGGGATATCACCACTGATCCCACAGAAATACAGACTACCATCAGAG
AATACTATAAACACCTCTACACAAATAAACCAGAAAATCTAGAAGAAATGGATAAATTCC
TGGACACATACACCCTCCCAAGACTAAACCAGCAAGAAGTTGAATCTCTGAATAGACCAA
TAACAGGCTCTGAAATTGAGGCAATAATTAATAGCTTACCAACCAAAAAAAGTCCAGGAC
CAGATGGATTCACAGCCGAATTCTACCAGAGGTACAAGGAGGTGCTGGTACCATTCCTTC
TGAAACTATTCCAATCAATAGAAAAGAGGGAATCCTCCCTAACTCATGAGGCCAGCATC
ATCCTGCTACCAAAGCCTGGCAGAGACACAACAAAGAAAGAGAATTTTAGACCAATATCC
CTGATGAACATCGATGCAAAAATCCTCAGTAAAATACTGGCAAACCAAATCCAGCAGCAC
ATCAAGAAGCTTATCCACCATGATCTAGTGGGATTCATCCCTGGGATGCAAGGCTGGTTC
AACATATGCAAATCAATAAACATAATCCAGCATATAAACAGAACCAACAACAAAAACCAT
ATGATTATCTTAATAGATGCAGAAAAGGCCTTTGACAAAATTCAACAACCCTTCATTCTA
AAAACTCTCAATAAATTAGGTATTGATGGGACGTATCTCAAAATAATAAGAGCTATCTAT
GACAAACCCACAGCCAATATCATACTGAATGGGCAAAAATTGGAAGCATTCCCTTTGAAA
ATTGGCACAAGACAGAGATGACCTCTCTCACCACTCCTATTCAACATAGTGTTGGAAGTT
CTGGCCAGGGCAATCAGGCTGGAGAAGGAAATAAAGGGGATTCAATTAGGAAAAGAGAAG
TCAAATTGTCCCTGTTTGCAGAAGACATGATTGTGTATCTAGAAAACCCCATTGTCTCAG
CCCAAAATCTCCTTAGGCTGATAGGCAACTTCAGCAAAGTCTCAGGATACAAAATCAATG
TGCAAAAAATCACAAGCATTCTTATACACCAATAACAGACAAACAGAGAGCCAAATCATG
AGTGAACTCCCATTCACAATTGCTTCAAAGAGAATAAAATACCTAGAAATCCAACTTATA
AGGGATGTGAAGGACCTCTTCAAGGAGAACTACAAACCACTGCTCAATGAAATAAAAGAG
GATACAAACAAATGGAAGAACATTCCATGCTCATGGGTAGGAAGAATCAATATTGTGAAA
ACGGCCATACTGCCCAAGGTAATTTATAGATTCAATGCCATCCCCATCAAGCTACCAATG
ACTTTCTTCACAGAATTGGAAAAAACTACTTTAAAGTTCATATGGAACCAAAAAAGAGCC
CACATTGCCAAGTCAATCCTAAGCCAAAAGAACAAAGCTGGAGGCATCACACTACCTGAC
TTCAAACTATACTACAAGGCTACAGTAACCAAAACAGCATGGTACTGGTGCCAAAACAGA
GATATAGACCAATGGAAAGAAATAATGCTACCTATCTACAACCATCTGATCTTTGACAAA
CCTGACAAAACAAGAAATGGGGAAAGGATTCCCTATTTAATAAATGGTGCTGGGAAAAC
TGGCTAGCCATATGTAGAAAGCTGAAACTGGATCCCTTCCTTACACCTTATACAAAAATT
```

FIGURE 4 (Continued)

```
AATACAAGATGGATGAAAGACTTAAATGTTAGACCTAAAACCATAAAAACCCTAGAAGAA
AACCTAGGCAATACCATTCAGGACATCGGCATGGGCAAGGACTTCATGTCTAAAACACCA
AAAGCAATGGCAACAAAAGCCAAAACTGACAAATGGGATCTCATTAAACCAAAGAGCTTC
TGCACAGCAAAAGAAACTGCCATCAGAGTGAATAGGCAACCTACAGAATGGGAGAAAACT
TTTGCAATCTACTCATCTCACAAAGGGCTAATACCCAGAATATACAATGAACTCAAACAA
ATCTACAAGAAAAAAAAACAGCCCCATCAAAAAGTGGGCGAAGGATATGAACAGACACTT
CTCAAAAGAAGACATTTATGCAGCCAACAGACACATGAAAAAATGCTGATCATCACTGGT
CATCAGAGAAATGCAAATCAAAACCACATTGAGATACCATCTCACACCAGTTAGAATGGC
AATCATTAAAAAGTCAGGAAACAACAGGTGCTGGAGAGGATGTGGAGAAACAGGAACACT
TTTACACTGTTGGTGGGACTGTAAACCAGTTCAACCATTGTGGAAGTCAGTGTGGCGATT
CCTCAGGGATCTTGAACTAGAAATACCATTTGACCTGGCAATCCCATTACTGGGTATATA
CCCAAAGGATTATAAATCATGCTGCCATAAAGACACATGCACATGTATGTTTATTGCAGC
ATTATTCACAATAGCAAAGACTTGCAACCAAGCCAAATGTCCAACAATGATAGACTGGAT
TAAGAAAATGTGGCACATATACACCATGGAATACTATGCAGCCATAAAAAATGATGAGTT
CATGTCCTTTGTAGGACATGTATGAAGCTGGAAACCATCATTCTCAGCAAACTATTGCA
AGGACAAAAAACCAAACACTGCATGTTCTCACTCACAGGTGGGAATTGAACAATGAGAAC
ACTTGGACACAGGAAGGGGAATATCACACACCAGGGCCTGTTGTGGAGTGGGGGGAGGAG
GGAGGGATAGCATTAGGAGATATACCTAATGTTAAATGACGAGTTGATGGGTGCAGCACA
CAAACATGGCACATGTATACACATGTAACTAACCTGCACATTGTGCACATGTACCCTAAA
ACTTAAATAATAAAAAAAAAAGATGAAGATGTTTAATGTGGGGAAATGCTTATGACTTA
ACATTAAATGAAAATTGCTTTTTAAAAAAATCACATGCGGCCGGGCGCGGTGGCTCACGC
CTGTAATCCCAGCACTTTGGGAGGCCGAGGCGGGTGGATCATGAGGTCAGGAGATCGAGA
CCATCCTGGCTAACAAGGTGAAACCCCGTCTCTACTAAAAATACAAAAAATTAGCCGGGC
GCGGTGGCGGGCGCCTGTAGTCCCAGCTACTCGGGAGGCTGAGGCAGGAGAATGGCGTGA
ACCCGGGAAGCGGAGCTTGCAGTGAGCCGAGATTGCGCCACTGCAGTCCACAGTCCGGCC
TGGGCGACAGAGCGAGACTCCGTCTCAAAAAAATAAAATAAAATAAAATAAAATAAAATA
AAAAAAAAAAAAATCACATGCTACAACATGGATGTACCTTGAAAACATGCTACGTGAAAT
AAGCCAGATACAAAAGGCTGCATCTTGTATGATTACATTTATAGGAAATGCCAGATTAGG
CAAATCCATAGAGACAGAAAAGTAGATTAGTGGTTACCAGGAGCCCTTGGGGGTAGGGAG
AAGTGGGGAGTGACTAACAGGTGTGGAATTTTGGGGGGGTAATGGAAATACTGGAACTAG
ACATTGGTGACAGTTGTACAACATTGTATGTTAAAACCATGGAATTATATACTTTAAAA
TGGTAAATTTTATGTTATATGAATTTGATCTCAAAAAAAATTTACAAAAAACTACATATA
TAGCCATTAAAAATTATGAGATATTTCAGCAGAATACAGATTGTAAATAATTTTTTAAAT
TATAAGAGATAATACAAAAGACAATTCATTTGAAATGTTTAGTTCAAGGCCTGACATATA
GTATGTGTTTAGTATATCTGAGACAGGTCTCAGTTAATTAAGAAAGCTTATTTTGCCAAA
GTTAAGGACTCACCTGTGACAGCCTCAGGAGGTCCTGAGGACATGTGCCCAAGGTGGTCA
GGGCACAGCTTGGTTTTGTACATTTTAGGGAGATATGAGATATCAATCAGTACATGTAAG
ATTTACATTGGTTCAGTCCAGAAAAGGCGTGACAACTTGAAGCAGGCAGGCAGCTTCCAG
GTGACAGTTAGGTAAGAGACAAAGGTTGCATTCTTTTGAGTTTCTGATTAGCCTTTCCAA
AGGAGGCAATGAGATATAAAATTATCTTTGAGCGGAGGGATAACTTTGAATAGAATGGGA
GGAAGATTTGCCCTAAGCAGTTGCCAGCTTGACTTTTCCCTTTAGCTTAGGGATTTTGGG
GCTCCAAGATTTATTTTCCTTTCACAGCTGCAATATATAAGGAAAAATAGAAACAATACA
ACCTTGGATGTATTTGAGTTGATTAGTTTGTGGATGAATTTTTGCATTTATTTTTATTGC
AGGCAGAGCTGCTATAATATATTGCCAGTATAGTAAATACTTTATTTAAAGGATTTGAAA
ATAAAAAATAAAAGCTTTATGGACTCCAGCATCTGTGCTTTGAGCCGGAATTCCCGTGAA
GAGCCTGTATTGGTGGAGCTACTCAGCTCTTTAGGGAGGCAGGAAGAGATGAGAAAGGGA
TACAGATTATTACAGCCTAAGGGCAGGATGGAGAAACTATCCGTCTATTTATCCACTGAA
TGCATGTAGTCATTTGTCAGTAAGTGTTCTTCTAAACTTATTTACTCATCATCAACGTTC
ATCTTAGATTAGCTCCCAAAGGGCAAAAAGACACATAATTAATTTGCTTAATGTAGTGCC
TAGCATGATGACATGGTGAGATATGTTTTAGCAATAATTAAAAATACTTTTTCCTTTGCC
AGTAATTCTTATTTAATCAAGCCAAAATTAATTTACATAGAGAACTACTCTATGGCTTTC
ATTTAAAAAAACAACAGATGATTTCAATCTCTTTTCTGCAAATACCCCAAAAGAAGAACA
ATGCTGTTTTCATAAATCTTAGTCAAATGAAACTCAGCTACTATCCCCAGGTTAATTTTA
TAACTGTAAAAAGTGTGTGTGCATAAGAACAAAGGCTGGTTAGGACCTGGAAAAAACGAG
AGAGGGAGAGATAGACTGATGTAATGATATGTGACTTTTTTGTTCTTTTCTGATTCCCAG
```

FIGURE 4 (Continued)

```
TATTGTTTCCTGAACAATATTTTTTTTATAAACTTAGCAACAAAAAACAAATCACTTCAG
AACCTCTGAGACAAGGCTGTGGACTGGCAGTTGTTTTTTGAGACAACATGGAAGAAATGA
TATTCTGTGCATCTTCTCTTTTAAACTTTCATCTTTGAACTTAAAGATGATCCCTAGCTG
AGATCATGGGTGTTTTCCTCCCATGTTTCTTTCTTTGTGTTTTACCAACTTATTTATTTA
TTTATTTTTTGAGATGGAATCTCACTCTGTCATCTAGGCTGGAGTACAGTGGCATGATCT
CGGCTCACTGCAACCTCTGCCTCCCAGGTTCAAGCGATTCTCCTGCCTCAGCCTCCTGAG
TAGCTGGGACTACAGGTACACACCACCAAGCCTGGCTAATTTTTGTATTTTTAGTAGAGA
TGGGGTTTCACCAGCTTGGCCAGGATGGTCTCAAACTCCTGACCTCGTGATCCATCTGCC
TTGGCCTCCCAAAGTGCTGGGATTACAGCCATGAGCCACTGTACCCGACCTTACCAACTT
ACTTATATTTAGCATAAAAGCTGGAGAAAGCGATAGGGACAGGAGGCAGAGAAATTCTGG
GCAGAAGAGGGCAGTCCCCAGCAAGGGCCTCACTCTGAAGCCTGGACCCATGGCCCAAAG
TGAGAACATACATTCTTGTTTTCCTGCTCAAATGTTGCCTTTTCCAAAACCACCCATGGC
CCTCCTGCCACCCATCATGTGCCCATAAAAACCCCAGTCTCCAACAGCAGAGAAAGGAGA
AGAGGAGAAGCAGCTAGACATTGGAGAGAAGCAGCTTGACTTCAAAGGGATGGCTTGACA
GTGTTACCTCAGGGAGGAGTCTGGCCAGGGATGGCCAGACTCTGGGGGAAGATTATCCCG
CTCCATCCCCTTTTCAGCTCCCCTCCATTGAAAGCCATGTTCATCAGCAATAAAATCCTC
CACATTCACCACCCTTCAATTCATTCATGTGACCTGATTATTCCTGGACACCAAACAAGA
GCTCGGGTGCCATGGGTGAGGATGCTAAAGGCTGTCACACTGACCCTGTGCTCTCGGTAG
AGAGCAACTGTCTCATGCAAAAAGGCAGAGGGCCCACTGAACTGTTGACACTTAAGCCGT
CCGTGGATGGCAAAAGCTAAAGAGCGCTGACTAAAACACATGCCCTCTGGGCCTTCAGG
GGTAATGGGCACCCACTAGACACTGCCTCAGGACTCTGCACGGAGTTCACTCCAGCTGAT
GCCCAGAAGCACTCACCCTGGCTCCTGTACCTGCTCACCTGTGGACTCCCTTCTGCAAGG
GGTGAAGTGCAACGGGTCCAAGTGAGTGGAGTTTGCCCCTGCCAGTGACAAAGCGGCCAG
CTAGATCCAGCACCCGTGCACTGCAGTTCCCACCTGCAACGGTGTCAGGGAAATTTCCTG
CTTCAAAAGCACAGGCAGCTTTCTTGGAAATGAGATAATGTGATCTCATTTTAAAGTTGA
GGACATCAAGGCTCAGAGGTGATTAGAGGCATTAGAAGGGACTTCTGAAGACAGCTAATC
TAACCCTTGAAAATAGGAGAAGTTAAAGTTATGGCCCAGGTTCCACACCTCACAATTGGT
GGAACCAGGCTTGAGCCTGCTTGCCTAATACCAGTGTCCTTCCCAAGCTTCCCAAGCATC
TGCTTGAAATTACCTGTGTCTGTGGTGGGAAGGAAGCGCAAGAATGGTGTCCTGTGTCCA
TTGCTGGGGCTTTGGGGGTCCAGGTACTTAGTTTACTTTTGAGAATTCCTTGTTGGCTCT
GCTGAAGTCCTTCCTGCTACACCGTTCAGGGAAATTGTTGATCTTGTCAACCTGAAATAA
TCAAAAGGATCAGAATCCAGTTTTAAAGAGTTTATTCAAGCAAAAAGCTGGGAATAGCCA
TCCAAGAATCATGGACTCTAGAGAAATGGGGTCAGTGCTTCGAAGTTAAAAGTTAAGTAC
TTGCTTCTATACAGCAAACAAAGAAGTTTAGTAGGATTATAATATTTTCTATACAAGCCT
GGTTTATGAGTGACAATTTAGTTCGTTTGTTTTCTTTTCCATACAGCTTGTTTTCGTTTC
CTTTCCAATTTAAAAGCAAGTATTTAACATTCCATCCTAGTTAGTGTGATAACCATGAAG
CCTTTGTGTGAAAGAGGAAAGAGGGAGGCTAGTCTATAATGAAGATCCATACTTAGAGAG
AAAGGGTCTTCCCTGGCACCCTTTAGTAATTTATAACACTTTACCAAACAATGTAGGTAA
GGAAAAGGCTAATCTATAATCAGAGAAACAAAGGTTACAGCTGCCTATTTATGTGACTCA
GGTTCCATAATCACATTCCCTTAAGGCTCAAAATAAAGTTTCAACGGCTGAGATTTTCAA
TTATTTATTTTCACAATCTTTACCTTTCTTAGTTCTGGGAGTGGCCTTACCAGGTGGGCC
TGGCCTGCGTACTCCCAGAAGGGCAGTTATTCCTAGCAGCCTTTGGCTTTGGGAACCTCT
CCATAATTCTTAATCCAGCCCAAGGTTCTGACTCTGTTAATGGGTAAAGAAAGGTTATGC
CCTATGAGACTCTGACCTCTTCTTGGGACCTGGAAAATCTTCTGGTGATTTTCCTCATCC
CGAATCTGCTGTTTCTAAACTGCTTGAGACCAAGATAAAGCACACCAATTTACAAGGCAT
AACTCCTAGGTGAGGTCATTCACTAGCCATTTCTTGTATTTGAGGGTCTCAGTGTGACAT
CCCAACTTCATTTCCAGCACTAGATTGGTATTTCTATTCTTCTTTTTAGAAAGGAAAGGA
GAGGGGAGGGAAAAGGAAAGGGAGAGACACGGAGGGAGGGAGGAAGGAAGGAAGGAATA
TTGGAGTACAATTTGTGGCACTCAATTTCAAGAACAAGCTTGATAGAAAGTTGTAATTGC
CAAATACAGTAACCTACTTGGGGTACATGTCACCTTTTATTGCTTTCAAGCTACTGTACC
TGGCAACTCTTATTTCTCCCTTTAAAAAAATCCTGTATCTGGCTAAAGGCTGAAAAATAG
CAAGTACATATCTTTCTAATGACCCTACATTAATTTAGCATAGAGATAATTAGAGGCACA
GTTAATCATTAGTAATATAAGCCCTGAGATTGGGGCACATGGGTTTCTCTTGCTATTCAA
CAGAGTCCTTGTGTGGCTAGTGTTTGAGTACAGACACATCTTTATTTTTTACATACTGAG
CTTTCTTTGACATACAAGCCAAAAATTTACTTGAAGCAACCTGAATAGTATGAGAGAGAA
```

FIGURE 4 (Continued)

```
TATTTGTTTTTTAAAGTCCTGGGAATTACAGCGTATCCTTAGGGCATAATATAGGTATGT
TCATATAGAACAGCTGAACACAGGCAGTTTATAAAGCAGGAAGTGAGCACATCGTACTTT
TTAAATTTATTTAAAATACTTTGAATTCTTGGTGTTCTTATCCATTCAAGAGTCTCTAAC
ACTAGGGTTGTAAAATAGAAACCAAATAGCATTGATAATAGAGTTTTGTTTCATCTTTGT
CTTAGCTACAATTTGGGAAATGTTTATATGTTTGTTCCAAAAATGATTTAAAATTGTGTA
TTCACAATGCAGTAGTGTGTAAACACTACTGAATCACCAGAAATGCATCCAGTAGTGCAT
GCACAAAATAGAGATCAAGGCAAAGGTAGAATAGGGAAATAAAATTAAGCTAAGGATAAG
GTTAGTATACAAAATGCATCTTGTGAGGTTCATCTATTTGGTCTACTAGTGGGCATGGGA
AGGATGCCTGAATTTAAATGAAAATTCTAGTACTGATTATAATTCACATATTCTTTCATT
GCCCTAGAGTTTTTAATTGTGCCCAAATAAGTCTTGGTATTCACAAACTAATTACTTGAG
TTTTTAGGTTCACATACCAGTGATATCCTCCTTGAATCTTTCTGCCACTTAGTCATTTTA
CTTCCAAATATCATGACATCCAACAGAGGCCGATGAAGGAAAAAAGATGCAAAAGTCATC
CCATTTATTTTCTGCCTTAAAATAAGAGTGTGTATATTGGGAGAAGGAAAGGGTAAAGC
AGTTAGATGTTATTAGAAATACTTGGAAGAGAATAGAAATAAAAATTTGTGATTTTTAGT
TATTAAAGTCATCATTAAATTGTGTTATCCATACAACTGAAGGATTTCAATATGGGCATC
TTGTTAAGGAAAAGCTTTCAGAGAATGGTAACATTTCTTAATAGTGAACATGTCCCTACA
CTCACATAATTATAAGACTTCATGTACAAGGTACTCAAAATCAGAAACTTTGTAAAAAGC
CTTTTAATCAGATAAACCTGAATATATCATTATCTAGAAATAACTGAAAAGAGTGCAAAA
CATTAGAGAACAGTCATTTGATAATATGGTAAATAAATCAATAGGCTATTATATTCCTAT
TAAAATTATAAAGTTGCATAAACAGGAAAGATTATACAAATATACCATAAAAAGTACTT
ATAATAAAAATATGAGAAAAATACAAACTGATATGTAAACTATAAAATATGTAAAATAGC
CAAGCATGGTGGTTCACACCTGTAATCCCAGCACTTTCGGAAGTCGAGGTGGGCAGATCA
CTTGAGGCCAGGAGTTCGAGACCAGCCTGGGCAACCGAATGAAACCCTCTCAAGAAAAAA
ATACAAAAATTAGCTGGACATGGTGGTGCGCATATAGTCCTAGCTACTCGGGAGGCTGAG
GTGGGAGGATCGACTGAGCCTGGAAGGTTGAGGCTGCAGTGAGCCGAGATGGTACCACTG
TACTCTAGGCTGGGTGACAGAGTGAGACCCTGTCTCAATAAAAATAATAAAATATGTAAA
ATATCTCTGCAGGTAGAAAAAGGTGGTGTGTGAATGCAAAAGAGTTATACTGGATTGACT
AAGATGATTTTTTTTCTCACAGTATTCTTTGATATTTTGTCATAATAAGTGTAATTGATA
GCGAAGAAATGACAACAAAGCTTTCATGTATAGAATACTTTTTACAGATTTACTGAATAA
TGTGTACTTTCTGTTCACTGTCTTTTAAAATATAATTTCAGTCTAGATTTTACAGACTCA
TGGGAAATGATCTAAACTATTTTTCTTGCCATTAAAATGTGCATTTGGGAGTATTTTTCC
ATAGACATAGATACAGGAGAACTCAATAATGTTCCTCTTCCTTCTTTCCAACTCTTGTTT
TCCTTAGGCATTACCACAGGAGTCTTGGTTCGAGAACACAGCAACCTCTCAACTCTAGAG
AAATTCTACTTTGCTTTTCCTGGAGAAATTCTAATGCGGATGCTGAAACTCATCATTTTG
CCATTAATTATATCCAGCATGATTACAGGTACCTTGAGAAAACAGATGTTCTCTATATTA
GTCCATTTTCATACTGCTGTAAAGAACTTCCTGAGACTAGGTAATTTATAAAGGAAAGAG
GTTTAATTGACTCACAGTTCATCCTGGCTCAGAAGGTCTCAGGAAACTCACAATCATGGC
GGAAGGCAAAGGGGAAGCAAGACAACCTCCTTCACAAGGTGGCAGGAAGGAGAAAGGCTG
GGCGAAGCAGGAAGAGCCCGTTATAAAACCATAAGATCTCGTGAGAACTCACTCACTATC
ACGAGAACAGCATGGGAGAAACTGCCACTATGATTCAATTACCTCCACCTGGTCTCTCCC
TTGACACCTGGGGATTATGGGGATTACAATTCAAGATGAGATTTGGGTGGGAACACAAAG
CCTAACCATGTCATTCTCTATGATTATTTAAAAGCTTTCACCTAAGTTGTTCTTTTCTA
ATTACGGGAAAAATTGAAATACATTAGATGTCTCTCTCTCTCTCTCTCTCTCTCTCTCTC
CACCTCTCTCCACTTGGAATGTCTATATTTGCTTCTGTGGAAACATTTTACTGTTCTCAA
CATGGCATTGCTTTGTCATATGCTGTGCCTACAGCTCTGTCCACCACTGCTCAAATCTTC
ATTTGACCAGCATGTGATGTCTTGGGAGGAAAATGTCATTTTCAAACATATAAACAAAC
GTTATCTGGGGCATGGGAAAAAAAGCATATTTGGTCACTGAAATGTCAGCTAGTGTCCT
CAGGAAAAATATAGTTGTCAATTTTGATCATGTTTTCAGCCATTCACTCATTTATTTCCC
AACTGCAGCTGTGCTGCCCCAGCCTCTCAGCAGCTGCCTTCAGGGTCTCTGCACTCCTT
ACCCACTTTCTACTCAAAGCCAGAACTTGCTATGTGTCTGCCCTGCATATTTGCTGTGGG
GACCAGCAGTCAAGTTCTGTGAGAAGGGTTTAAATATGGAAGTGCACCATATTCGAAAAG
CCTAGTATTTTTAAAACTTGTGACACAGTTGCATTTGGAAATGACTTTTCCCTTATTGAT
CATTACATTGCAGGGCTCCTTTGAAGAGGAAGCTTCCTTAGGTAGATAGAGATGAATTTG
GTTTACAAAAATGTCATTTGTCTGGCTGTGATAAGTTTCTCTGCATTGCAGTTTCTTGTA
CTTAACTCTGGCAATTAGTAAAATGTGGCATGACAGTAGCTGGTGGTGTTAGATTGAAAA
```

FIGURE 4 (Continued)

```
TCAAGGTTTTATGTAAACATGCAATTAGAAGTCGTGACATGTCCCCTTCTAGAACATTTT
TCTCCACTGCCACTGTAAAGGTCTGGGACTGGCCCTGGTAGAGTACTGGACGTTGGTGGG
GGCACGGGAGGGTGGGGGTCAGGATCTGCTGCATTCAGGGACTGCATTGCTTGAAGAGCT
GTCACATTTGGCCTTTGAATTTCCCAAATGCCAAACTCGAATTAGACTAGAGTCCCTTGG
GAGCTTTGTCCTTAAATGGTCTTGATGTTCTCGGCTTATGAGAAACCTAAAGAGAACATT
TAATTATTTTTATGAATGTATTTAATTACGTTTGGAAATGCCTGGTTCCTTTTAACCCTA
GCAACCTGATTGACACAGCCGCAGACCAATTATTTGTCCCATGTAATATTTGTTTATTTG
TTTAAATTGTCATAAGCATTTAAAATTGGAAGATTTCATGTAAATATCCAAATTGCTGG
CTTTCTCTGAAAAAAAAAATGAAGATCTGGGAACACTGGCCCAGTATTTCCACCTATCA
ACGGTGGTCTGAAACCAAGAGACAACTACTCCATTTAGCTGGAGCAAATGCATTTGAGAA
TGCCATAGTCTCCACTACTCCCGATTGCCCAGTACTTTGTCCACTTCACTCTTACGTTAC
CTGCCTGGCCGCCGTAAGGATGGCAGTTATAATCCCTTAGAATCTTCTCCATATCAAAGA
TTCTTTAAAAAAATGTTTTAAACATGGGTCTTGATATGTTGCCCAGGCTGGTCTTGAA
TTTCTAGGCTCAAGCAATCCACCCACCTCAACCTCCCAAAGTGCTGGGATTATGGGCATG
AGCCACTGCATCCAGCCCAAGATTCCTAATTTTTCTTGGGCTCCTTTGAGAATACAATG
CAAACTTTGGACTTCCTTTCGAGAAAAATCTTCACAATTGTACATATATACTATATTTG
CACGCAATTGCACAAGGTGCATAAACCACCTGATGAGCAATACTATTGAACTCATGTGTC
TATGAGGGGAAGTATAGAAGATTGATCCAAATTATGCAGCAAACCCAAAACTCGAGGTAA
AACAGGTTTTAGAAGAAAAGGTAAAAATACATGTATGAATGTCTAATTCTGTAATATCAG
ATGTTTGAAAATACATGCCACTCTTGACAGTCAATAACAAGTGAGTTTTGTTTTGGTTTG
GTTTTTTTTCTGGGAAGTATAGCCTTTGGCCAGAAGCCAGAAACAGATACTTCCTCTAGT
GAGATTTTTGCAGTCTGGATGTTTTGTGTGTTAGCTCAGCCTTGCAAATAATCTAGGAAA
ATAATTTACAACTCAGCATTCCACTGACATAGCCCAGCTACTTTTGAAGCTATAGCATGG
ATCAAGTAGTTTCTCCACTTTTCCTCCACCAAACCCCCAGCAGCCAGTCAAGAACTAGAG
GCAGCGAGCAAAACCACCACCCCATCTTTTGATTTGGAGCAATGAAATAGTCAAAGATTC
AAGGGATATGAACAAAGCAGGGTGGGGACAATGATGGCATATCCATGTTTTAAATTGTCA
GATTAGAGGGAAAAGCAACAAGACTAGTGTTGGCACAGTTATAGGAAAATAAGTTCATTC
ATACACTTTCAGTTACCTAATAAATTGGAACAAACTTTCTGGAGAACAGTTTGGAGCATG
TTCTGATCTCTTCACCCAGTAATTCTGTTTCTCAGAATTGATCATAAAGAAATAATCAGA
GATATGTTCAAACTCCTAAGTACAAGGATATTCATGGTAGCATTTTTTGTAATGGTGAT
AAATTATAAGCAACCTAAATGTATACAAATTTATATTGTATACATATGTATACAAATTTA
TCTTTTATACTATGTATACATAGTATACAAATTTTCATACTAAGCAACTATTAAAAACTT
GTCTTAGAATCATATTTAATTACATGTGGGAACATTCCCAATACAGTATAAAGTGGGAAA
ATAAAATTACACAACAGGATAGTGTATACAATCCAAATTTTATTAAAATGTATATACATT
TTTAAAAGTTGTGATCAAAACCAAAAGGTTAACATCCAGAAAGTAAGAAAACATGATCTG
TTCTGCTTTCTTTACATTTTCAACTGAACCTGTGTTTTTGTTTGGTTTGTATTTTTAATG
AAAGAGATGGGGATGGAGTCTGGCCTGAGATCCTCCAATTTTGCCTCTGGTCGCTTCTCT
GCCTCATCTCTGCTCCCTTCCCCTGCCGGCTCAGTGCCACCTTTACCTGGTACACAGCTC
CTTCCTCCAGACCCTGAAGTAGTCTTCAGCCTCCCTACCCAGAAGATGGCCGTGGAAAAC
ACACAGGAAGGGCCATTTCACATTGCAAATGCCCTCATGAATCCAGCAGGCTGGTAGCTT
AACGTATACAGTTATTAGGCCGAAGGAGGATGCAGGTGGGAAGCTGAGGAGGGTTGAATG
AGTCCCCTAAGGATACGTAAATTAGAAGCAGAAACACAGCTAGAATTCAGACCCAAGATT
AATAATCTGTGCTCCTGCATAAAGGAAACTCTCTTGCCAAATTAACAGGTAGAAAAAAAA
ATTCTGCCATCAAAGCCTCTGGTGAGATTAAAAAAATACTTTATAGCTTTTTAAAAAAC
AGGAAGAACCCCTTTTTATGTGATGATAAGGTTAAGAAGCCAAATTTACCAGGGAAATTT
GAACATAGACTGGCTGTTAGATGGTATCAATAATTTGTTAATGATTTTGTTAGAGATGAT
GATGGCATATAGTTGTATAAGAAAATGTCCTTACTTTTTAAATGCATATGGAGTTATGAA
ATGACATAATGTCTCAAATTTACTTTAAAACAGAAAAAAAAAATGGCACAGTTGATATAA
ACTCAAGACATTTTCAGAGACAATCATTGTGGGTACCAATAGAATCCTACCGATAAATTA
CATTGTGAAGAACATGCTCCCGCCCTGCTGAGGAATATCTGTGTTTGGATCTGCTAACA
TTTAGGCTTGTAAGCCGTATTTATGTCAAAGCACCAGAGAAATAACAGGAAATAGCTTAT
GAATATGCCTGAGAATTGTGGCTCTGGAAAAATCCTGGTCCAGCCAGTGAGTTTAAATTC
AGGTCACATTTTCTTTACTACTTCCCAAAATTAAACTATGATGATTGGAGCCTCCTATGA
CCAACACAGGGACAGAACAGCACCTCCAGTCCCGCTCCCAGAGGTCCCCTGAGCATCCTT
CCCGGATGCTCATAACTTTGCTCAGGAAGAGGTTGCAGCTCTTCCACTTTAGCCTCTGCC
```

FIGURE 4 (Continued)

```
ACCCCCGCCTGGGCCAGAAGCACTCCAGTGGGCACAGCTGCGCCTCCTGGTGTCTGCTGT
GGCTGCCACTACCCCGGTGACCTAAGGAGTTCCGCTCTTTGCTCCTCCATCCTAAGACAG
GAGCAGAAGCTTAATTCTCCAAAGTGCAGCTGAGACCACACTTCTACTCAGGACATAATC
TTTGCTAAAGGTAACCAAAAGCAGATGAAACACCAATGGTGACATCCAACTGCTCCCTGA
AGGGGCTCCCAGGGCCTCTTAACAGGGATGCCCCTCTGCTTAGCTGCTTGCCTCCAGGAG
GCTAGAGTTCATCTCTAAAGGTGTTCCAAGCTTTCCTGCACCCCAGATCCCAGAACCTGA
CACCAAGTTCTAAGAAGGAAAAATTCCGCTATCACACAGGCCATCCTGTCCTGACCTGGA
GTGACCTCTTCCTGGGATGCTTGCCATTGTGGAATATCCACTTCAGAGAAAACCCCCCTC
ACGGCCACAGGGGGATAGCCTTTCCTCGTGGACCCCATCAGGAGCCTTCCATAGACTCCA
TACCATAGTACCTGCTGGGTTATTGCAACCACCCTGCTTGTAGAACCTGGGAGTCTGTCC
AGGTCAGGCTGGGCCAAGTCCATGCCAGTTCCTGTGCACATTTCTTCCTCCAGAGCAAGG
AGTTGCTCATTCCTAACCCTTCCTGTGATGTCGCAGCTCTGGATTTCCTAAAAACGCCTG
CTCAAACAAGGGCACACACAGCTCCTCAAGAAACAGCACCAGTTTGCAGCTCAGTGGATG
TCAAGCCAAGCAGATATCAAGCCAAGAAAACTCCCTCCTTTCCCTCCTCTCTCCCCCAGG
CCACTGAGTGTGAGTCCTAGTACTGATTCTGCTTCCTGGACAAGTCACATTATTAAACAC
TAGACGTCAGGAGAAAATATTTGCGTTTTGTTTATCAATGACTTTCAGTTTCCACCAGAC
ACTGGTTGGGTGACTGGATTTACAATTGAGGATCTTCTCCAAAGATAAATTTAACACTCT
ACCCTTGGAAGATTTAAAAAACAAAAAATGCTCCAGACTTTTAGATGATTGTTACTCCAG
CTTTCATGTTAGGATTTCAAAATTTTTAGGGCTTGACCTCAACCATAGGATCAGAGGTTT
TCTACTACTTTTTGTTGGGAAAGGGTGGGAAGACAGGGTCTCATTCTATGGCCCAAGCTG
GAATGCAGTGGTACCAGTATAGCTCACTGTAGTCTTGAACTCCTGGACTCAAGCCATCCT
TCCACCTAAGCCTTCCTAGTGGCTGGGACTACGGGTGGCCCACACCACCATGCCTGGCTA
ATTCTTACTTTTGTCGCGATAGGGTCTTGATATATTGCCAGGGCTGGTCTCAAACTCCTG
GCCTCAAGTGAGCCTCCCACCTTGGCTTCCCAAACTGCTGTGATTACAGGAATGAGCCAC
CACACCTGCCCTACTTTTTAACCAAGTAAAAAAGTTTAAAGCCTTATAAAACCTTAGGTA
TATTCAGTATTTATTAAACAACAGCCAGATGTAGAATGCATATGTGAGTTGGTTGCCTTT
CAAGCAAGGATTTTTCTATGAAGGGCCCAATAGTAAATATTCTAGGTTTTACAGGTCCTG
TGTATTTTGCCCAACTACCCAACTCTGTTTGTCATGGGAAAGCAGCCACAGACCGTATGT
AAATGATTGAGGGTGACTGTGTGCCAATGAAACATTCATTTACAAAAACAGGAGGCCAGC
CAGGAGCTGACCCCTGCCCAGCTAGACTCTGACACTCCAGATGCAATCTAGTTGAGGTTG
AATCCAGGTAACAAAATAAACTACCACATCAGGCAAGGAGTATGAATGCACTGAAGAGAC
TGAAGAATAGAGGGTGAGCAGAATAAAGTGCAGTTGGTGATAGTTTTAGAGCACCTTATT
TGTAAACTCAGGCTTTACAGCAGATGACACACTTAAATCTTTGGGGCTGAGGAAGGCTTT
TTTTTAAAGGCTATGTATTCATTTACTCAGAGGCAGCTGTGTATCTGGAAACAATCCCAC
ATCCTCCTATGAAAAGAACCATGCCACGTGCCTCCCCGAGACAAGGTTCAGTTTTATTCA
GCTAACATTTGTTAACTCCAGCTGCATGAAAACAGACTAACAGAAAACCAGGTATAAGAG
GGTGAGGCCCTACCACTCACATGGTCATGGAGCTGAGGTCATCTGATAGTCAGGTCCAGG
AGTCCCTCGTTAGCAAGAATTGCAAGACTTGAAGACGCATATCACTTTGTTGTACAACTT
GCTATTAAATGTAAGCTACTGTTCATAAACATAGGTGGCTAAGAGCATTTAATGTCAATT
TTAGCTACGAGGGAGGAGTATGCATTCTTTTCTTGAAACATTGGTGGTCCATTATACAGT
TTAGTTTCTATGAAAATTGCCATTCAAGGTGGTTTATAAACTTAAAACTCCAGGCAGGAA
GACAAGTTTGTTGCCTAAGACTGTACAGTCTGAGAGTGAACTTCTTGCCTCATTTGCAAC
ATCTGGAACCAGTGGGCTCTTCATGCACTTTAAGTGCTCCTTTCCCTAAGATTATCAAGA
AATTTGTGTTGAGTTAGAATACAGCTGTTGAAGCCAAAGGACTTATTGTATCAATTTGAT
TTCTGAAATGCCTGGCCTCCAAAGACAAAACGACCACATAGTGTATAAGGAAGAGCTCCC
ATAATGAACATGCCATTTGCAAGTAATAAAATGAATAGTGGCAAGAGATAAATATGCCCT
GCTTTAGTCTTTCCTGAGACAGTGAAGCCCAGAGAATCAACCATGCATGAGCCTTCTTTC
TGACTAAACAGGTATTAGACTTGTTCATAGCTCTGTTCAGCTGTAAGATAACCTGATTTG
ATTACTTAAAAAGGGATTCTAAGGACCTTCTATATATTGGAGGCATGGACCTGGAAGACC
ATTCGTTCATTTATTTATTTATTCATTCTATCTTTAATGAGCCAGGCTCTGCTAGACACA
CAAGGTGTAAAATTAAGTCTTATCTCAGCAAGAAAGAGTACATTACAATGCTGTGTGATA
AGCACTTTCTGGGAATGAGGTCAGTGCAGGGGACATTGGAAGGAGCCATTTTGAAGGAAG
CATAGAAATCAAGTGAAAGGAAGAGGGTGGGTATTCCAGGCAAGAGAAAATAGCATCTTT
GTCCTCCCAAAATAGCATCTTGGGAGGACAGTGAGACTTGAAGTGCGATGCTGGAAACGT
GGGCAAGAGGAATGGGATGGAAAGGGGGAGCACAAGGGTTTACTGGCCTCGTGTGCCTTG
```

FIGURE 4 (Continued)

```
CCAAGGGGACTGGACTTGAGCCTGCAGGCGAGGGAAGCAATTCTAGCAGTGACTCCCACC
TGTGCCATTCTCTACAGAGGGACACCTGAATAAGTATCCATCCTAGAGGGGCAAGAGAGT
CCAGTGGTTAAGAGTACAGACAGGAGCCACACTGCCTGGGTTTGAATCCTGGTTCTGCCA
TGGATTAGCTGTGAAACCTTGGATTTTACTTAACTTGTCCTCAGCTTTAAAATATGGATA
ATAATAATGTTTCATAGAACATCTAGAATGCCATACAATTTTTTTACTTACTCTTTTTTG
TCTGAGACCTTCAGAAGTTCCTATAAAGTACCTGAACTGGCAGCAGAATCTACAGGGCCA
ATATCAGAATTGAGCTACGCAGATATGAACACACTGAATGCATTCATTCTGGAAATGAGA
ACAATATAAAAAGACTTGCTCTGCCATCAGTTTGTAAAGTTCACCAGCATGTAAGAAGCT
TTTGCCTAGAAGTCCGAGATACCAATTTTATGGATAAAGAGAAGCAAAGAGACAGCTCAG
TCATATTTAGGTTGTGGCAAAAACCCAGAAAAGTCTCACTGAGCCATTAGCTAGCTGCTG
CTGTCAGAGCATTCATATGGACTTTGGAAAAGAACAGTTGAGTTCCTCAGATTCTTTGGG
GTATATTTAATGCTTTTACTGGACAATAAGTTCAGGGAGTCAAAAAGTTCATGGAGTCTT
CTGAAAAACTGGTCCTAACTACAAATACCACCGTGTTCCATAGTAATGAAAAAAATGTTA
AAACAGCTCCTGGACTGCTGAAACCAGGACACAGCCCACCGCTTCTTTTTTTTTTTTTTT
TTTTTGACAGAGTCTCACTGTGTTGCCCAGGCTGGAGTGCAGTGGTGCGATCTCAGCTC
ACTTGCAACCTCCACCTCCTGGGTTCAAGCGATTCTCCTGCCTCAGCCTCCCAAGTAGCT
GGGACTATAGGTGTGTGCCACCACCACCGGCTAATTTTTGTATTTTTAGTAGAGATGAGG
TTACACCATGTTGGCCAGGCTGGTCTTGAACTCCTGACCTCAAGTGATCCACTTGCCTCA
GCCTCCCAAAGTGCTGGGATTACAGGCATGAACCACTGCACCTGGAGAGCCCACTGCTTC
TTGATGCATGTTTTGAACTTCAAATGTGGACCAGCTGACAGAGGCTTCAAGGGGACCTTT
AGCTGATTCTGCTCAAGGACCAGTTTATTTTGTTAACATCACCAAATAGCCTAGAGTGGT
GATATTACCTATTTTAAGAGAGTTCTTCATGTCTCTAAGAAAAGTAGATGTCATAGGTGA
TGCATGCACAGAAAGATTTTGCATGCTCCTCTTTGCCTCTTCCTTTCCCTTTGAACATCC
AGGGAGTACTAATCAAGGCTGCAGAGATTTCCCTATGCCCTGGATTAACAAAGTAAGATC
ATATCCTGCCTTGTTTCTCTGGGGAATAAAAGAAACATTTTGGAATTTAAAAATCATGA
ACCTGTTTATTTAATCCTCATAGCAGCCCTATGAAGTCATCAAGTAGGTGGGACCTTAAC
TCCATCTTTAGAGATAAGGAAACAGGAGGTTGAAGACAGATTAAGCCACTTTTTCAAGAT
CACACAGATCATAAGGGCAGCAGCTGGAACTGGCAAGTTTTGTTCTGGCAACACTCTGCT
GCCAAGGGGCCAGAGCCTGGGAGAGGGATCCAGGGCAGTCAGCCATACTTAAATACCTGT
TAGTCATTCAATCAGCATGTTTACTGAGCATCTCCTATGTGCTGGGCACTGAGTATACAT
TCGTGAACAAGCAGATAGCTAGGTCTCCTGCCTTCATGGAGCTTAAAACCTAGCAAGAAA
GAGATATAAAATAATGAACCAATGATAAAAATTGTTGAGATATGATATGCACAGGATGCC
AAGCAAGGAAATCAGGACACCCTGGTTTAGGGTGGATAATCAGGGAAGGATTCTGAGGAA
AGGACTTAAAAGCCAAATGAAGAGTGAGGAAGAGCACTCCAGGCAGAGGGAAGAGCCTGT
GCAAAGGCCTTGGGGTGGGAAGGAGCTTGGTCTGTTCCAGAAGAGGCTGGAGGAGGGGAT
GAGACAGGAAGATGGCACAAAGAGGGGCTGGAGAGGCAGGCAGGTGCCTCCCCTGCAAGG
CCTGTTGGCCAAGGTAAGGATTTTTTCTTTTTATCTTCAGTGCCATTGAAGGGTTATCCT
GATGTATAAAATCACCTGATTTATGTTTTTAAAGGATCTCTTTAGTGACCGTGTAATGAA
GGAATGAATGAGGGAGGGAATGAATGAATCAGTTAATGCTTGTTGAATACCTTCCATCTG
CTCAGTGATGCACATCATCTTTATCATTTATTCAGTAATCATGCAGGCTATTTACTAAGA
ACACACTGTGTTCTGGGCACTGTACTAGGCCTGTTATAGACATTATTTCTAATCCTCACA
ACAGCTACGCAAGCTGAGGTTGTTCACTTTGTTCCTCACAATTAACCTAAAGGCGATAGA
GGCATTTCAGATCCTCCAATTTATAGATGGAGAAGCTGAGTCTGGGAGGAGGCTGGGATT
TGAGCCCAGTCTGTCCCACCAAAGCCCATGCCTTCTCTCTGCACAGGTGGCCTCTCTGCC
GGTGACAGAGACAGGAGTCATCCACATGGCGAGTTTTAACTCCTATGCAACAATGAGTTT
CTTGGATGTGGTGTCCACTTATAATGGCATAACACCACCAAATGTCAGACCTAAAAGAAC
TTCCAATAAGGGGTTGAATTTTGATACCTTAACAGCAATGTGGAGAGATTGTCACGAAAG
CTTTGTTCTCAGTGGGTGGTTGCTTAATCAGAGAGCTCTAGGAGGAGTCTTTTGCCCTCA
GATGTTTATTTTTAAAACATGCTATTGTTTAGCCAGGCAACTGCTTCCTTTGGAGTGTTT
TTGTAAAAAGTTCAGATGATTACTGCTTTGGCTGGGAGCCAACACCCTTGCTCATCAGAG
CCTTCTCCTGAGGTGAAAAAAGCAAATAAATGCCTTTACCTAAAATAAAGAGCTAGCAGG
TGCCCCTGACTTCCAAGGACAACCGGGGATTTTATCCCTGTTTCTAGGCCACAGCCGAGC
CTCAAAACTGTCCCAGGTTCTAATGGATAACCCTGGGTTCACAGGGAACTGGAATCGTGC
TCTTCTTTTTCTGCCCAATTCAGGTGCCACCTGTTCCATCAAGCCTCTCCTGCTCATCTC
AATCTGGTGACAGTTCAGGCTCCTCTGAAAGCCCACAGTAACTGGTCTCCGCACCAGGGC
```

FIGURE 4 (Continued)

```
TTCACAAAACATCTAGTTTTTAAACTGGATGGAGCAAATCCAGTTGTTAAAATTTCTGAT
CTGTTACAGATCAATAACCTTCGTAAACTATAGTTAGAGCAAATTACTAGAAAAGTTATA
TTAAAAATAGACATACAAAATACTAGCCCTATTTTTTTTTTTTTGAGATGGAGTTTCA
CTCCTGTTGCCCAGGCTGAAGTGCAGTGGCATGATATCGGCTCACTGCAACCTCCACCTC
CCAGGTTCAAGAGATTCTCCTGCCTCAGCCTCCTGAGTAGCTGGGATTGCAGGTGCACAC
CATCACACCCAGCAAATTTGTGTGTGTGTGGTTTTGTTTTTGTTTTTTGTTTTTTA
AGTAGAGATGGGGTTTCACCATGTTGGCCAGGCTGGTCTCAAACTCCTGACCTCAGGTGA
TCCACCTGCCTGGGCCTCCCAAAGTGCTGGGATTACCGGCGTGAGCCACTACGCCCCGCC
CCTATCTTTTATTATTACATTCAACAGAAATAAAGTTACTGTCCAATTACTATAAACATT
TTAAATACTCACTGTTGATTTCTGTGCAGATGCCATCACACCTGCTTAGTTCATTCTCAT
TTATCACCCCCTATAGGACAGCTTTCAACTCCCAGGAGAAACGAGTTCTGATAGTGAACT
GTAAAGAGAGGGGGTCCTTCAGACCTCGCCAGCCACCAAAGATGGCCTGAGAGCAAGAAA
CCCGGGGGTCCATTGAGAATAAAAACTCAGAACTAAAGGGCAAATGAGGTTTTACTTGTT
TGGGACTAAGTTGGGCCTGATCTTCGACGTCAACGCCAGTTAAGAGTCTAATGCCTGGAT
TCTCATTCTCACAGTCAACATTCATTGCGCTAGACCACAAGTTCTCACCAAGACAATATC
GTCCCCAAGGCAGCAAAAGCTGTTTTTATTTGGTGGTGGTGAGTTGGGGGAGAAAATCTT
ACTCTTTTTATGTAAAAAAACACATGTATCATTTACTATATAACCAGATATACAGTTTGC
GGTTTTAGAATTTCAGAGGGGTGGTGATTAGGAAAACGGCTTTGGGGGGTGGTTTTGCAC
AACAACAACAACAATAAAACAAGGTTGAAAAAGACTGAGATGTTACATGTGTTCCCCTGT
GGAGTCTTTTATGGCTGAAAAGTGTTCTCGTTGGCTGCCCTGGGAACCAAACTAAACCAC
CATGTATAAGCGGTTTCTAAGGGGACTACCTGCTGAGGTCCAAGTTTCGGACCCAGAAAT
GGATCTTTGAAATGGGGTCATTTGTAAGCAGACGATTACTTGCAAAAATGCAGCTCTTTC
TGTCATGTGGAAAGCTTCAAGTACAAACATTCGTAGAGCACCTTATTTAAGGCACTGGGG
GCCCAGTGAAGAATAAGCTTCAGGCCTTACAGCCATATGATCAGTGCAGTGATGGAACTA
CGTGCCAGGAGATTTGCGCGTAGCATCTTCCTTTCCCCTGCCCATGCTTGCAAGGCAAAG
AGCTTTTCCTGAATTTGATAATGGAGTTAAGCTATAGTTTGTTCATTCGACATTGTCGAG
CACCCACTAAATGCTAAACACTGGTAGGGTCTAGAGAGATTGGGCTGTCCAATATGATAG
CCATTAGCCACGTGTGGCTACTTAAATTGAGATTAATTAAAACTGGCCAGGTGTGGTGGC
TCACACCAATAATCCTAGCAATTTGGGAGGCCGAGGTGGGAGGATCGCTGGAGCTCAGGA
GTTCAAGACCAGCCTGGGCAACATAGTGAGACCTCATCTCTACAATTAAAAAAAAAATT
AAAATAGATTAATTAAAATGAAAACTCAGTTTGTCAGTCACACTAGCCACTTTCCAAGTG
CTTGCTAGCCATATGCACTTTGTGGCTACTGCAGGGGACAGCACAAAAACAGAACGTTTC
TATCATCAGGAAGCTCTACTGGGCAGCGCTAGTCTAGAATTTTGTAGCACATGGATAGAG
CCAATATGGAATAGTGGTTAAGAATATGGCCTTTGAGGTAAAATGTAGATTGAGATCCCA
GCTCTACCACTCACCTTACCAGCTTTATGATCGTATGGTACTTAGCCTTTCTGAGCTATA
GTTTTGTCCTCTGTAAAATGGGGGTAATAATGCCCGCCTCCTTGGGTTGTAATGAGAATT
AAAGATGATGCATTAACATGCAGTCAATATAGTGTTTATTGTCATCATTATTATTTGTAT
TATGATTATCATCCTCATCATTATTGACATTACTCGCAGATGGGGTGTTTACAACCATCC
AGACAGATATTTTATGGTCATTAAGTTCTGTAATGTTCCTATTTATAGAGGTTTTCAAAG
ATTAGGCTGTTTCCCTGTATCTGTTCTCTCCCTCATGGTGGTCACCACCCTTATCCCCA
ACAATGCATTATAAATCATCCAACAGCCTGGACTTGGGGGCCAGCTCTGCCCCCATGTTG
ATGACTAGAGAGGTAGAGGGTAACTATAGAGTGGTAACTATACAGAGGTAGAGGTAACTA
TACAGTGTAGAGAAGTATAATCGTTGATTTGTGTAAATATCTGATATATCCGGGAAATTG
GTAGGATGGAGGTGGATTAGAGGAATGGGAAACAAAGACCCGTGCTGAAAGTTACTACAA
GATAGTTGCTGTGCTCCAGGACAGAGGGGAAATTGGATGACTACTTGGGGATGTATTTGT
TTAAGATATTTTCACCAAGATCTCATTATTATCAAGCCTTTTATTGCCAGCTGAGTCCTG
GAGTACAAGCAGAGGCACCAGCCCATGGCCAAATCATTAAGACAAATTAAGACATATTAA
CATATGCTGGGAACAATTATCCACATAGATTTAATTTGTTTCACTGCTGGAAGAAAATCC
TGAGAGAGTACCAAACACATCCCCGAGAACAGCTCTGTAACTACTCTGTGACTCTCACTT
GTCAGCACTTCAGGGGCTGGAATCTGCTTAAACTGGACATCTACCAAAGAAGGACGACAT
ATCTGAAAATAGATCCCATATTAGGGCTACAGATGAGTTACTTGGAGTCTGTTAAGGTGG
TGATTCTTTTTGTTTCTTTTTAACCTATGCATCTTAGAAATAATTATTACAGTTATCAAA
ACAATATACCAAGCTCTAAAATGAAACAGGCACATATTTTATAATCATATAATATACTTA
GCAAGCTTACATATTTGTATTATGATTTGCTCTTTCTTTAAGAGACCTAAACTAAATATG
AGATAGTGAACTTGTTTCTGAATTTTGGCCTTCAATCTCTCTTGACTTTTTTGTTGTTGC
```

FIGURE 4 (Continued)

```
TGTTGTCCCTTGCCTAATTGTTATCTTTCATTGTCTTACTGGGAGGAAAAGAAAGACTCT
TCAACACAGCAAACTGCATTTTTCTCAAATCGAATAGAATCTATCATCAAGATTATTCTA
GAATGTGACTATTGCAGTATGCCCATTATATGGCAATTGCACAATCTTTTCTCAGTGGTT
GATGAATGGCGCCTTAACAACATCCTGGGGTAGCTGCTACAGAGGCCAGAGCACCTTCTC
TCAAAATATTAACTTCCAAAGGAGCAATCAACAGCCAGAGAAATGGTGTGTTTAGAGTGA
GAAATGACTTGTTCTGTCATCATAATGGTGATCACTTCCTTGCAGATTTTCTTCCTGTAC
ATCAAATATGTATGATTATATATGAGAAGCATAAACCCCCAGTCACTTAAAAAAAATGGA
TAGGCCTTTTAGTGTGGGAAATGAACATAAAAGTTACCTATGCATGCTGATAGCCATACA
GGTTTACTGCCTTTCCCTTGGGGTTGCCTTGTGACAACCTCTTCCTTTTTCCTGCTACCC
TGTACCTTAGGCTTTGCAAATGGTTATGGGACAACTCATGCGTGTTAATATGCAAAATC
ATTTTCTATAATGCTCCTTTGACTCAAAATATGACCCTCATTTTGGAAATCAGGCTTGGT
AGTGTCTGAAACCTCCAATGACAGCTTGCCGAAAGATGATTCAGTTGTTTCTCAACTTGG
CCCATTCCCCACGTCCAAGTCCAATTGGAGAACGGCTTTTGACTCCGTTTATATGAGCAT
CTTTGATAGAGAGCAAAGGTTTCTGGCAAGGCGGGATGCCTGCCTTCCACCTCTAATCCA
GCTGTCCTTGACACTCCAGACAGCCCTTTCAAATCTGGGCAACACTTAGTCATCTTACTG
GTAGCCAAGGACCATTTGAAGTGAGATCTAACAATATGATCGTAAGTCTCTGACATTACC
TGTGCCCTGGGAAATTATTTATTAATATCTTTCCTTTTTCAAATAGAAATTTTAAGATGT
CTCACAATAAAAGCTATACACAATAAGGTTGTTTACACAGAAGCAATTTGAAAATCATGA
AAAGAGGAAGGAAACACACTAACCAGAATGGATAATGACATTACTGTGAATGTGGCCCCG
GGACCATTTAAAGATCCAGCAATAAGTGGATCATTAAATACATTCTGGTACAGCCACATG
ACAGATTACTGAGCCATTAAAATTATCCTCAGGGTGAGTTTGTAACAATGTGGGAAAATG
CTTACAACTATAATATTAAGAAGAAGAGAGAGGGTTAGAAACTATAAAATTCTCCCAGCT
GTTTACAAAAAATTGAGAAAAATATTAGAAGAAAATCACCAGAATATTAACTTGGTTGAT
GAGATGATGTGATTTTTGTTGTCATCTTTACCTTTTCTCCTTTTTCAGATAGTTGTAATG
AATATATATTACTTTTATAATTGTATATAAACATTATTTTTTCCAGTTAAGCCTAAGCTT
CCTGACAGAAAAGGCAGAAAGGAAAACTATCATGAGTTACATGATTCTCAAGTGTTAAAA
AAAAAAAAAATCTCAGGCAGGACATGATGACTCACACCTGTAATCCCAGCACTTTGGGAG
GCCAAGGTTGTGGATCACCTGAGGTCAGGAGTTCGAGACAAGCCTGGCCAACATGGTGGA
ACCTCATCTCTACTAACAATACAAAAATTAGCTGGGTGTGGTGGTGTGCACCTGTAATCC
CAGCTACTCGGGAAGCTGAGGAAGGAGAATCGCTTGAACCCAGGAGATGGAGGTTGTAAT
GAGCCGAGATCACACCATTGCACTCCAGCCTGGGTGACAGAGTAAGACTCTGTCTCAAAA
CAAACAAACAAACAAACAACAACAACAACAAACGATCTCAGTTCTTTGAGATAAATTTTT
CCTAGATAACTGAATTCCAAAGGAGGTTTATCACAAGGGATGTTGAATGATATAATACAA
ATCTTGGTAAAGTTCTTAGTGCAAATGTGGGACAGGGACTCCTTATGATTATTTCCTGAC
CAACTCCAGGAAGATCTGAAGGCAGGACACTCCTGGAGGTGAAGGCTGTGGGAAGCTGCC
TGCAGGGGAACTTGCACCTGACTGGGCTTCCCTCTCTTAAATCTGTTTGGAATTTTGAAG
TGTTGCTTTTGCCCATTGCATGTTATTGCCCATTGTCTGTAGATGAGAACGCCTCTCAGC
TCTTTATTTCACAACCTGAGGATTAAATCGCGGGTCCTGGAAACCTGTCTTTTAAAATTA
ATGTAATTTGATTTCTGTCTCCCCTTCAGGTGTTGCTGCACTGGATTCCAACGTATCCGG
AAAAATTGGTCTGCGCGCTGTCGTGTATTATTTCTGTACCACTCTCATTGCTGTTATTCT
AGGTAATACTTATTTCTGAATCCTTACTACTTTATGTAATGGTGATTTTTTCATTCGAAA
AGTAGTTGGTGGCCAGATGCGGTGGCTCAGGCCTGTAATCTCAGAAATCTGGGAGGCTGA
TGTGGGCAGATCCCTTGAGGTCAGGGGTTTGAGACCAGCCTGGCCAACATGAAAACCCGT
TTCTACCAAAAATACAAAAATATTAGCCGGGTATGGTAACATGCGCCTGTAGTCCCAGCT
ACTTGGGAGGCTGAGGCAGGAGAATCACTTGAACCTGGCAGACAGACTTCAAAGGAAAAA
CTTTATGGTACTTTGACAATACTACTTTCTGATTTTAAAAAATTGTATGTTAAGAAAAGC
TCAACTACTTTTTAAAATATGTATTTTTTAATTAAAAAGAGACGTGGGGAGTCTTCTAT
GTTGCCCAGGCTGGTCTTGAACTCTTGGGCTCAAGGGATCTGCCTGCCTCAGCCTCCCAA
AGTGCTGGAATTACCGGCATGAGCCACTGTGCCTGGCCCTAACTACTTTTTTTTTTTTTT
TTTTTTTCAAGAGGGAGTCTCACTCTTGTCACCCAGGCTAGAGTGCAGTGGCATGATCT
CGGCTCACTGCAACCTCTGCCTCCTGGGTTCAAATGATTCTCCTGCCTCAGCCTCCCGAG
TAGCTGGGATTACAGGTGCACACCACCATGCCCAGCTAATTTTGTATTTTTAAATAGA
GACAGGGTTTCACCATGTTGGCCAGGCTGGTCTTGAACTCCTGACCTCAGGTGATCTACC
TGCCTTGGCCTCCCAAAGTGCTGGGATTACAGGTGTGAGCCACCATGCCCAGCCACTTAC
ATAATTCTTAAAGTGGATGATTGGTCTATAATAGTGGAGTTGAGTATAATTATAAAATAT
```

FIGURE 4 (Continued)

```
TTCCAGAAATATAGCATTTTAGTGCATTTCACGTAGTAACAAGAGCTAACAGCTAATAGA
TCCTTGTTAAGGATAAATCCCACTTGTAAGAGGGAGAAAATTCTAATAAGGGAGGAGCTG
CTCTTATACCCTTAGCATAGTTTTTTGAAGAATGCTTGGTCTTTGTAACCCTGAGTGACA
TTTTAAGAAGAATGCCCAATTCCCACCTATGAGTGAGAATATGTGGTGTTTGGTTTTTTG
TTCTTGCAATAGTTTACTGAGAATGATGATTTCCAATTTCAACCATGTCCCTACAAAGGA
CATGAACTCATCATTTTTATGGCTGCATAGTATTCCATGGTGTATATGTGCCACATTTTC
TTAATCCAGTCTATCATTGTTGGACATTTGGGTTGGTTCCAAGTCTTTGCTATTGTGAAT
AATGCCGCAATAAACATACGTGTGCATGTGTCTTTATAGCAGCATGATTTATAGTCCTTT
AGATCACATGGACACAGGAAGGGGAACATCACACTCTGGGGACTGTTGTGGGGTGGGGGG
AGGGGAGAGGGATAGCATTGGGAGATATACCTAATGCTAGATGATGAGTTAGTGGGTGCA
GCGCACCAGCATGGCACATGTATACATATGTAACTAACCTGCACAATGTGCACATATACC
CTAAAACTTAAAGTATAATAATAAAAGAAAAAAAAGAGAGAGAGAGAAAAAAAAAAAAG
AAGAATGCCCAGAGGGGGAAGACAGAAGGAGCATATACTCAGATGTGGCAGCAGCTCGGC
CCTTGTAGCCCTGCTTCAATGAGCTGATAAGAAGGGGTGGGATGTGGTGAGGCTTTAGTG
GTATTAGGCCAAGGGACCCAGGAGGGCTTGAACTGTACCATAAAACAAAACCACATCATC
TCATGAGTTTCCTGAGGAAGACAGACACAGAGAAAAATAGCAATGAGAATCAAGATACT
GCTCTCTTATTAGCTGGAGGCGTATAGCCCTTCTACAACCCTGAGAGAGGAAAAGAGTGG
GCCATGCCCAGTCATGGCCCCTTATTGCCCAGGAGTTCCTCCCATTAGCAAAATGGACCC
ATTCAGCATCCCAGAGCCCTACCCCCTGGATTACCATTGCCTCTTCTTGAGGGAGGAGCA
ATAAAGAGCATGAGGACCTTTTTCTTCTTCACTTCCCTCCAGTCAAACACCCTCCAATGT
CTTGGTCTCTTCTACAGCCTCCCATCTTGGCTTGGATACTCAAGTGACAGGAACCCATTA
CTTCCCAAGGCCACAATGATGCTGTCAGATGCTCTGCCATGTAGACAGTTCTTCCTTACA
GAGAGATGAACCTTCTCTCCCTATAAATCCCATCTATTTGTCCTCATTCCACCCCCGGAA
CAGCATTTTCCTACATGACTGCTTTCTAGATACTTGAAGACCTACGGTATGGAAGGAAGG
CAAGGCTTGTTTTGTATGATCCTCAGGAGAATAACCAGCATCTGGGTAAAAGTTGCAGAA
AGACATCAGATGCATTCTCTGGGCTAGAAAATGGATCATCCTTACCCTAACACCTTCCTA
GGCTGGTCTCATAAGTTCAAGAAAAGAATATTCTCATCAGCAGGTGTTTCCAGAAGCAA
TTCTGGGATGCAGCCCCTTCATTTAAAACACACATACACACACACAGACGCACACGCA
CGCACGCAAGCACATGGAGTTCTTTCTGCTTACTCATTTAAATGGAAGAGTAATTAAGGT
GGCTGCTGAGGTTCCAGAGGAGGCTCAGCATTTTGGCTGGACCTCAGGGTCCTCCCCATC
ACACTATTGCCTGGTACAACCATGCCCATTGTTCTAAAGGTGCCAGCTGTGCCAGGTGCC
CTGGAAGGTTCCTAATGCTCTGTGGACGCTGTTCTTGGCCACAGGTATTGTGCTGGTGGT
GAGCATCAAGCCTGGTGTCACCCAGAAAGTGGGTGAAATTGCGAGGACAGGCAGCACCCC
TGAAGTCAGTACGGTGGATGCCATGTTAGATCTCATCAGGTGAGTGTTTTGCCACAAGGT
GGCTTCAAGGGCATGCGGATAGCAGCACAAGGCCTTGTATGTGGTTTAATATTCTGCTGT
TACTGTATTGAAATTTTTAATAACTTTTGAATTATTGTGCACTTTCATTTTGCCCAGGAA
CCCACAAATTACATAGCCAGTACTGTTTGCCAAGTCTTGGTTCCAAGAGGGAAGGGAAGA
AACAGGCTTCCGCATCAGGATTTAGGATGAACAGAGATGCAGCTACATGTTCCAGAGAGA
TGCTGGGATGGATTGGTAGTCAGTTCTGAAGCGCACTTAGAAAAATACATCTTTTAATTG
TACAGGAGAAACTCTCTTATCTAAAGCAACCAGAGGGGTAAATAGGTCAGTCAATAAAAA
ATACCAGTTAAAGCAGAGACTCATAAAAAAAGACATAAGATACACATTACAATTTTGTTT
TCACTTAAAACTTAGTGCATTTATTCACCAATTGTTTGACATAAAGCTAAGGTCTTTTCT
TCAAGTTTGTTAGCTCATGGTAATTTCTTACGGGTTCTGTTGCATATACAGCCCTTATAA
ATATATCATCTGCAATTTCCAGGTAAAGTTTCTATAGAACAGAGCACCAAAACTTTTAGA
CATTGCAAAGAAAGCTAAGTGCAAATCTTTCCAGTTTTTCTTTTAATTTCAATAATCTT
CCCATACCTAATCTAACCATAAAAATTTTAGTCACTGGCCTTTATTGAGTTTCCAGGTAT
GTGGCTTAGATTTTATAGAAACCATACCTTCTTTTATGCTCATATTTCACTGGTTTACA
TAATATGAAATGCAGTAATTATGATGATATTTGCAACTGGTATAAAGAATTTGGGAACAA
ATAAAATGAACCCTTGGTAAGTGTATTAGTCCATTTTCACACTGCTATAAAGAACTACCT
GGGACTGGGTAATTTATAACGGGAAGAGGCTTAATTAAGTCACAGTTCCTCACGGCTGGG
GAGGCCTCAAGAAACTTACAATCATGGCAGAAGGCAAAGGGAAGCAAGGCACATCTTAC
ATGGCTGCAGGAGAGAGAGCAAGGGCGAAGGGAGAAGTGCCACACACTTTCTAACAACCA
GATCTTGTGAGAACTCACTCATGATCATGAGAATAGCATGGGAGAAACCACCCCCCATGA
TCCAATCACCTCCCACAAGGCCCCTCCCCTGACATGTGGGGATTACAATTTGACATGAGA
TTTGGGTGGGGACACAGAGCCAAACCATATCAGTAAGCATACAACCTCATTGATGAAAAC
```

FIGURE 4 (Continued)

```
AGAAGTGTTCAGAATATTAAAGAATAAATAGTCTCTTGACTGTGAGTGTCCATTTCACCA
AGGAGCGTAAGCATGTCAGTTACTCAGTGAATCAATTAAGTGATGGTTGATTACAGAGCT
TTCTATACTTGGGTGAAGCTCAGCAGGAAAAAGAAATCTCAATACAAGGAAGTATTACG
CAAAGCAGGGGCCAGAAGAGAAACCAGAGTACTAGTTTTATGTTATACTAATTTCTACCA
ATATATTAGGTATGACAAAACAATACTTTTTGCCCTAACATAATACTGCCTTTTATGTCT
CCAACAGGAATATGTTCCCTGAGAATCTTGTCCAGGCCTGTTTTCAGCAGGTAATATTAA
TTACTTGTGCCCTTAACTTGCTACCCTCTTCCCATTATCAATTAAAAATGTTTTTTTCTG
CTGTGACTCAAGAAATGGAATTAGCCCCGTGAAAATGGCAGCAGGAAGTAAACCTGTGAC
TGGCCAAGTTTAAGGTGATGTCTCTGTTTTGTATGCAGCCTTTCTGGCTCACAGTAAGGT
GCATGTCACAATTTACACTGCTTCCTTTTCCTTTATGCTTTTTCCCCCAAAAAGGCTCAA
ATGGTACAAATCAGAAATCTGTCAAATAATGAGTATTTTAAAATGTGGCCTCCAGTACCT
ATTTTTGGAGAACCATAGTATATTTGTACTGAAGTTTAAACTTTCTGCAGAAAAAAGGTA
GCTCTCTATCTCCTCTTTGCTTTTCCTCTGGTATTAGAACCCAGGATCTAACCCTCATGG
TGTGGTCCACATCTGGGTTCAGTCTTCTCCTTAATCATTGTGTCCCAGAGAGGCGTGGAA
GCTCACACCTGTAATCCCAGCACTTTGGGAGGCCAAGGTGGGCAGATCCCTTGAGCTCAG
GAGTTCCAGACTAGCCTGGGCAACATGGCAAGACCATGTCTCTAAAAAGAAATAATTTAA
AAAAAAATATAAAAAATCGTTGTATCCCCATTGCTGGAGCTCTACAATGCAGTGTAACAA
AGCCATGATTTTTTTTTCTGTAGGAAAATTGAACAATCTCTTCACTCCATTTACTTCAAG
CCTTTCCCTCCTATTTATCTATGTGCTTTAAGACAGCTGAGTCCATCACAAACTGCTGTA
TTCATTCACATAAGTTACATGAACACAGACTTCTGTGTATACCAACAAAAATGGCAACTC
TGTTGCTCTCTGCCGGCCTCCACGAGGGACAGAACCTCCTCTATTACAGGGGGCCTTTGC
AGATCAGTCACAGTGGTTGTTTGTAAGGTTCTCAGTGTTGGCAGAGCCTGGTAGTGGGGG
ACATTTATGCCTGGTGTAATAATATACTCACTCTTTCTTAAATCCCCATGTGGAAGCTCC
ACAGAACCAAACAGGGCTGAAAGAAGAGAATTCAACTGCAGTCTCACTCACTGAATAGCC
CCAAGGGGACTGTTGATTTTGGAACAACCATATCGTTAAACCTTTCTTGATGCTTATTAA
AGTTGTAGTGATGTTATCAAAGTAATGAAGTGTGTTTGCTCAGATTAAAAATCATTTATT
AATTAATAAAAACAAAAATGATTGACAGGAATCCTTACAGAGTCTGTCTCTGACAGCACC
TGCAGATCAAGCCTGTACTTTCTTTTGTATTATTCTTCTATCAACTTGTCGTTTATTGTG
AAAGTGAAGGAACATTTTGACATAATTGAATGGTGATCGTGGGAGTCAGGGGTTTAAATT
TCTGCCTCGCTTTTAGTTCCAAAACCTGATGGGAGGTACCGTTGACAACTGGAGCCAACA
GAGGCATTGGATGTAGATCCCTTCAGTGGCACTGTTTGGCCAAAATAACATGTTCCTGTG
ATTTAGTCTCAAAAGCTTAAAAAAAATTCTTTTTTTGTTTGCTTGTCCTTGATTTTCTCC
AACATGCAGTACAAAACTAAGCGTGAAGAAGTGAAGCCTCCCAGCGATCCAGAGATGAAC
ATGACAGAAGAGTCCTTCACAGCTGTCATGACAACTGCAATTTCCAAGGTACCATTCTTA
TTTCCTGTTCCTCTTCCCCAGGAGACAGGCACTGAGTCATGACTGAGCAGGAAATACAAT
CAATCCTCGTCATTCACAGAATCGCATTTGCAAATTCACCTACTTGCTAAAATTTATGTG
TGACCCCAAAATCCATACTTAAGGGGCTTTCATGGTCATCATCTCGCACACAAAGAGCGG
CAAAATATTTGAGTCACCCGACAGGCACGTTCCCAGCTAAGGTGAAAAAGGCTGTGCTCT
GCTTTCTTGCTTTGATTCTCATGCTGGAAACAAGTGTCCCTTTTGCAGTGTGTTTAGTGT
CATATTTTTTGCATTTTTGTGATTTTTCTTGCTGATTTCGCTGTTTGAAATGGACCAAGG
TGGGGTTCAGTGACTCATGTCTGTAATCCCAGCATGCTGGGATGCCGAGGCGGGAGGATC
GCTTGAGCCCAGGAGTTCCAGACCAGTCTGCGCAACATAGTGACACCTCACCTCTACAAA
AAATGAAAAATAGCCGGGTGTGATGGTGCACACCTATTGTCCCAGCTACTCGGGAGGCTG
AAGTGGGAGGATTGCTTGTTCCAGGGAATTCAAGGCTGCAGTGAGCCATGATTGAATCAT
TGCACTTCAGCCTGGGTAGCAGACTGAGACCCTGTCTCAAAAAAAAAAAAAAGGACCAG
GCTGGGCATGGTGGCTCACACTTGTAATCTCAGTACTTTGGGAGGCCAAGACAGGTGGAT
CGCTTGAAACCAGGAGTTTGAGACCGGCCTGGGAAATATAGTGAGACCCCATATGCACAA
AACATTTTAATATTACCCAGGTGTGGTGGCACATGCCTGTAGTCCCAGATACTTGAGAGG
CTGAGGCAGGAGGATCGTTTGAGCTATGATTGCACCACTGCACTCAGCCTGGGTGACAGA
GCAAGACTCTTGTTTCAAAAAAAAAAAAAAAAACATACACACAAAAAAGCATCATATTGA
AGTGGTCTCCAGTGTTCCTAAGCACAAGAAGACTGTGATGTGCCTTAGGGAGAAAATTTG
TGCTTTAGATAAGCTTCATTCAGGCATGAGTTATAGTGCTGTTGGCTGTGAGGTCAGTAT
TAATAAATTAACAATCTATATGAAACAAGGTGTCTTTAAAAGAAACACATACAACAATGT
TATATATTGATTGTTTGCTGAAAAGGATGTGTCCAAGGTTCCCAGAAACTTAACCCTGTA
TTTCCCCCAGGAGCAACGGTTCAGTATTTGCTAATTCAGTGTTCATGAGCACTTTATAGA
```

FIGURE 4 (Continued)

```
ACATAACTACCAGGAATAGAGAGAGTCGACCACAAAGAGCAAAAAAAGAGCCCTGTTGCC
TCTACCTCTCTGGGTCTGCTTACAGTAGAGCTGGCCATCTCTAGAAACTGCTATAGATTT
GTCAGGTACATAAGCATGCAATGCAGGCCCACAATTCCTAGTCTGAATCTCTCTGCCCAG
ATGTAATTCAGAGTTCAGAGTTTCTCAGACTTTAGAAAGGCCATGTGGTGTATATACTGC
ATATTATGCAACCTTTATAAGTGGGATGGGCAACAACATGCCAGAATCAACCACATCAAT
GTTTTTATAACAAACTCATAAATATTCTGCCAAGGAGAGAAATGGACCCTTAGTAGCCAG
TAGCCTCATCTCAGTTTAGGATGGGATTTGCTGCCAAAAGAGTTTGCTATAAACTTATCA
ATAAAATCAACATGCTTTGAGAGCTTTTGGGATTTCAGAATTGGAGATCAGAATGTGTGG
GCCTGCATTGGTACCTCTGTAAGCCTGTAGCAGATTTCTCCCGAATGTTCTCTCAACTTC
ACACAGGAAGGAATGATTTAAGGAGAAAAGGAGTGTTCATTAGACTTAAGAATTCAAATT
AAATAAACCACCGTTGGCTCCCTGCTTCCTACTGCAGAAAGCCTTAACTCCTCTGGCTGA
GTTCAGAGGCCCTGCATGACCTGGCTTCTCTAGTTTTCACAGCTTACTTCCAGTGGGC
ACCTCTCTTCTTTCCAGATTCACCTCCTCCATCACTCCTTATTCCTGCCTTTTGATGTTG
TTCCACAAATACTTTCTGAGCACCCTCTATACCCCAGGCCCTGCTGGGCATTGGGATTAT
AATGGTGAAAAGACAGATGCCAGGCCTCTGTCCTCACACAAAGAATGATGAGTATTATAA
TCAGGAAGAATGGGATGTTTGGGAGGCATTCAGCAAGGGATGTTAAATTAGTCTGGAGGC
CATAATGAATGAGCAAGAATTATTCAAGCAGGGTGCAAAGGCCCAGTGCATGATCGTTTT
TGCCTTTGCTTGCCATCTTTCTGAAACATGCTTTTTCTCCTGGCTGCTGATTCCTCAGCC
CTAGCTTTCCCTAACCTTGAAACCCACATTCATGTCCCACTCTTCATATGACGCTTGTAT
CTCATAGTTTGGGCGCACAATTAATTACATACCTTCCTGCTATTATTGGCTCATGCTTCT
CACAGTCAGTCTTGTCTCTCCAGCTGAATCTTAAGACCTTATGCTATAGCCAGTGCAGTA
ATACTCTAGCTTTTCCCTAAATATATGTTTGATCATAAGTAAGAAATGACTGGTAGCCCA
GTGGGTCCTCAACATAATTTTTTTTTTTTGAGATGGAGTCTGACTCTATCGCCCAGGCT
GGAGTGCAGTGGCGTGACCTTGGCTCACTGCAGCCTCCGCCTCCTGGGTTCAAGCAATTT
TCTGCCTCAGCCTCCCAAGCAGCTGGGATTACAGGCACGTGCCACAATGCCTGGCTAATT
TTTGTATTTTTAGTAGAGACGGGGTTTCACCATGTTGGCCAGGCTGGTCTTGAACTCCTA
ACATCAGGTGATCCACCTGCCTCAGCCTCCCAAAATGCTGGGATTACAGGTGTGAGCCAC
CGCACCCAGCTAACATAATTCTTTATAAACATAGTTGGCACCACTCAGTTATCTCTCTGT
AAATCTCAGGCTATTTTTACCCAGGATAAAGTGAAGAAATTAAGCCAGGCATGGTGGCAT
GCCCCCGTAGACCCAGCTACTTGGGAGGCTGAGGTGAGAGGATCACTTGAGCCCTCCTTT
GAGGAGTTTGAGGCTGCAGTGAGCTATGATCATGCCACTGCACCCCAGCCTGGACAACAT
GAGACCCTGTCTGTTTAAAAAAAAAAAAAAAGGTAAAAACATGATTCACAGTAGTAGGTAT
TTGGCTAATTTTTATATGTCTAAAATCCTACCAATGATAGACTGGATAAAGAAAATGTGT
ACATATATACCATGGAATGCTATGCTGCCATTTAAAAAGAACAAGATCATGTCCTTTGTA
AGGGACACGGATGGAGCTAGAGGCCATTATCCTTAGCCAACTAACACAGGAACAGAAAAC
CAAATACTGCCTGTTCTTTCTTATAAGTGGGAGCTAAATGATGAGAACACATGGACACAT
AGAGGGGAACAACACACACTGGGGCCTATCAGAGGGTAGAGGGTGGGAGGAGGGAGAGGA
TCAGGAAAAATAATTAATGGATACTAGGCTTAATACCTGGGTGATAAAATAATCTATACA
ACAAACCCCATGACACCCTGTACATCCTGCACCACATGTACCCCTGAATGTAAAAGTTTT
TTTAAAAAAATCCTGGCTGGGCACAGTGGCTCACACCTGTAATCCCAGCACTTTGAGAGG
CTGAGGTGGGCGGATCACCTGAGGTCAGGAGTTCGAGACCACCCTGGCCAACACGGCGAA
ACCCTGTCTCTACTAAAAATACAAAAAATTAATTGGGTGTGGGGGCGGATGCCTGTAATC
CCAGCTACTAGGGAGGCTGAGGCAGGAGAATTGCTTGAACCCGGGAGGTGGAGGTTGCAG
TGAACTGAGATACCACCACTGCACTCCAGCCTGGGTAACAGAGCGAGACTCCATCTCAGA
AAAAATAAATAAATAAATAAATAATCCTATTGGTCATCCAAGACCGCAGGCATAAA
GAGTGTTACTGTGCTTCATTATCAGGGTAAAACAGAAGGTAAAATGTCCTAAAAGTGTTC
ACACTGGTAAGTATTCTGTACTTCCTGCATTATTAATTCCTGTGTTTTTTAAGCAGACT
CCAAATGTAGCTAGCAGTTAAAATGACCCTGAAAAGTGCCTTCAATCTAAAATTCATAAT
AAAAATATAAACCATTCCAGAATAAGAAATCTTTATAAGAAATATTCAAATATGGACTTG
TTGAAAGAAGAGAAAGCATTTTAACTTCGGGGAGCAAGGGTAAAGTTTGTTACATGCATA
GGTGTTTTATTATTGTTTTATATTTTCTATAGTTTTGTTGACTCTGCCTGGGAGATCA
CCAGTTTATTATGTTTGGTCATTGTATCTTCTCATTTCTGGACCTGTGCTTTCTAACAAG
ATTATAATCGTGCATCAATATGTTTTCTTGGTTTTGATCCACAGAACAAAACAAAGGAAT
ACAAAATTGTTGGCATGTATTCAGATGGCATAAACGTCCTGGGCTTGATTGTCTTTTGCC
TTGTCTTTGGACTTGTCATTGGAAAAATGGGAGAAAAGGGACAAATTCTGGTGGATTTCT
```

FIGURE 4 (Continued)

```
TCAATGCTTTGAGTGATGCAACCATGAAAATCGTTCAGATCATCATGTGGTGAGCAGACA
CTGTTTAATGTCATTTTGCTTCCCCTGACAATTCTGTCTCCTCAAAATTAGAAAGAAGAG
GTTTTATGTTTGTCAACTGATGAAGCTAGAGAAGTTGGACATTTAATATTGAACCACCAG
AGTATTTTGTGGGGGCTTTTGTTGCTGTTCTTTGTTTTTGTTTTAGAGGCAGAGTCTCAC
TCTGTCACCCCAGGGTGGAGTGCAGTGGTGCAATCTCGGCTCACTGCAGCCTCAACTTCC
TGTGCTCAAGCGATCCTCCCGTCTCAGCTACCTGAGTAGCTGGGACTATAGGCATGTACC
ACCATGCCCAGCTATTTTTTGTATTTTTTGTAGAGACAGGGTTTTGCCATGTTGCCCAG
GCTGATCTCAAACTCCTAGGCTCAAGCAATCTACCCACTTCATCCTCCCAAAATGCTGGA
ATTACAGGCATTAGCCACCACACCCAGCCACCACTAGAGTATTAAATAATTCCACATATT
ACCCAGGAGTTAGTTCATGAACAGAAGTCTAGCTATCAACCATTGTCTTTTCCCTCAAAG
CCTTGGGAGATCATCTTGCACTCAACCAGCCTTCGTGTAAGAAGTAATTCTTTAAAAAAT
GATTTGAAGGATTTCACTGTACATGAGAACACAAAGTGCTTTCCCTATTGCACCCCATGC
AAAAGTGAGTTTCAAAATATTTATAACTGGCACTGCATGGGCACTAACCCATCTGAATGA
AAGCTACCATCCGTGAGCATACCAGTGACACCATTTCAGTGTCTGTCCTCTCCCTGAAAA
TGCCAAAAAGTCCACCTTTCTTAGGATGCATCTGTCTCGCTTACCTCATATTTAATTTGT
TCAACATTATTTAATCCAAAGTGTAGATACTGACAGTGATGTAAAGGGTTCAGTAAAAAT
GGCAAGGCAGGTCACTTAATACTGCAGAAACCTCAGCTTCATCATCTGTTAAAAAGGATA
ATAAAAGCTACCCCCAGGGATAGGAGAAGTACATTAAATGAAATGATGCATGTAAAATAC
TTTCCCTCATGCAAGATACAACGATAGCTCCACAAATAGAGCTATTATGATCACTTCCAG
TACTAATACTATCGCCTCTATTGCTGATACCTGGGAAACAGATGACCGTGGCTAGAAAGA
GCCATATTTGGCAGTGAGGGTCAAGCTCAAGTGAGATCTGCAGATAGGACAATCAGCAGG
ATATATATGCACTAGGAACACGGCATGAGGTGCGCACCCATCTAACCACATGTTCTTGCC
AAGTTTGCAAACTACCCTATGGTAGTTTGGATGGGTAGAATTTAAGGTGCACACAGGTAC
TAAAAACTAGAGCCAATATTGTTCACCCAGGACTTGAAACAACTCTTAGCTTCAATTCCC
ATCCTGTGCTCCACCAAGTGTGCATGCCAAGCTGAGGGTGCCCACACTGGAGTGTTCCTT
CCCCACCAACCTAGCATGAGAAAGCACTTGATGACGGAATCACGCCTCTGTTGTGCTTCC
TTTCCAGTTATATGCCACTAGGTATTTTGTTCCTGATTGCTGGGAAGATCATAGAAGTTG
AAGACTGGGAAATATTCCGCAAGCTGGGCCTTTACATGGCCACAGTCCTGACTGGGTATG
TCAGACTCAAGAGAAGAGACAGAAACCTCCTTTGATCTAATAGGATGGCCGCTGAGAGGT
TGGGTTTCAGTTGGTTAAAACTGGCTTCTGCCCTATGTGCTGGGAAAGATAGGGTTCAGA
GATAAGACAGCAGGGGGAGGAGGGCTGCCCTTTAACAGCTGTACTGTAGGTGGATCATGC
TGTGCTAATTGTCAGCTCTTGGCAGAACAGCCTGGACCAGGCTTTGTCACTGCCTTTATT
GGTTATGTTAAAATAATTTTTTACAACAAGAGAGAAACCCACTCGTAGCCTCCCTTGGCT
CTCTCCTGGCCTTCATTTCCTTAAGAATGTAAACTAGCCAAGCAAGCAAGAATAGCCTCC
ATGTACCCTGAACCTGAAAGAAATTAGCAAGGGCCTAAATGAAATCAGACTTGAGCAAGT
AGGAGCAGGATGGCTGTTGGTTCAAACACTGTTGCTGGGGCTGTTAACCACCACCATGTC
CTGCAGCATCAGAGTGTCAGAGAGGGTGCCAGGAGAATCTTGAGGCTGGGAGGAATTGTG
TGGGCCTTTTTGGAAGCCATTAAACAGGAAGGCAGCAGGGGTTGGGTAGTTTCCATATTT
ATTACAGCCTAGCTACTGTTTCCTTGAGAAAAGATGAGGTGGGATAAGTTATGAATGGTG
CCCCTGGACACCTAGACAGGGGCAGAATATGTCACATACCCTAAGAAATACAGACTAAGG
GAATAAATAAATATCATTGATTTGACTCTCACAAGTCAATACCTACAAACACCCAACTTG
AGCAATGAACTCACCTATTGGAACTTGATCGTATTGGAGATTTCCAACACAGCGCATTTG
GTTCTTAATCTGTGTTTGCCAAAAACACAGCCCTGCCAGCCAACACAGAGGCAGATTTGG
TCCCTACAGTGTGAGGCCCCTGGCGCTAAGGGAGGTGGGACCTCCAATTCACTGGAGGCC
ACCCTGCTGTAGGGCTGCTGAAACAGGCAGTGCCAGGGATCGTGTCTCAGCAGTGACGTG
GCTGGGGTGTATGAGCTGAGCCATTTCATAACCGAGTTCTGCTGGTTTCTATTCTCTTAC
CCCAGCTAGGTGTCTAACAGGAAACTAAAAGTCAGTTCCTCATGGTTTTTAGCTACAAGC
TCTCTATCAAGAAGATCCTCTCGCCAGAACTCCAGGATCTATATTTTTGATGGCCATTTC
CTATTTCAAACACACATAACTGATCTGTAAACTCTAAGCTGCCAGTTACATATATATCTA
TCTGTGAAATGAGTCTCATTTCTTAAGCCTCCTAGTTCATGTAACCTGTGTATTTCCATG
TGAAACAATGAACAGTTTGAGAAGGCAGGAATAACAAAGAAAGAAATAATCCTAAAGTAT
GGCTGTGGAAGAGCTGAGACTTTTTCCTTACTGTAACTCTGACTTCCCTCTTAGACAGT
GGGCGCCACCAGCAAGACAGCAGCTTGGTGCAGGGAATGGAGTGGGTGAGGACTGAGCGC
TGTGATAAGGGGTATAATGAGGTATAAGGTAGTGGTGACATACAGGGTGCCAAGGAAGGA
AGGCTCAGCCCTACCTGAGGAAGTGAGGGAAGGCTTCCTGGAGGAAGGGGGATGCCTATC
```

FIGURE 4 (Continued)

```
TGAGTCTTAAGAGGAGAAGAACTGAGCAGCAACAGAAGGAAAAAAGGGCACTTTTGTGCA
TGTGGCAGGAATAGCACACACAGGGGTGTGGCAGCATGATATAATTCTGTTCTGTGAAGC
CTTGAATTTGGATTCAGCTACTGGCTTTGTCATTAACTCTGACAAGATGCTTCATGTGCT
GAGAGAGCCTCTAAACCCTCATACATGGAATGGGACGTATATTCCTGCCCTACTCCCATT
TCTTATTGGGCCATTATGAAAGTCAAACAATTTTATAAATTAAAAAGATGTTTGATAAAA
GGATTAAGTGTGGGGAGGTGGTATTATCTTTGAAACTTTAATTTCTCTTTCTTGTTTACA
GGCTTGCAATCCACTCCATTGTAATTCTCCCGCTGATATATTTCATAGTCGTACGAAAGA
ACCCTTTCCGATTTGCCATGGGAATGGCCCAGGCTCTCCTGACAGCTCTCATGATCTCTT
CCAGGTAAACAGAAGAGGGGTTTCTGGAAGAAGCCTCCAGGCTCAACGTTATCAACTCTC
ACCTCACTTTACAAAACAGACTCCAGCTTGCGGTTTTTGTAGCTGTCTTTGAGAAATGAC
CTCCGTATTCTCGGCCCCTGGCCCTGAACACATTGCTTCATGCTGTTGCATATTCCTGC
TCTCTTGGCATGACCTGCAGCTCAGGAAGGGGTTATGGAATAACTGGGAGCAGTGGTGGG
CACAGCACCTTCTGATTCCTGGACCTGCCTAAAGGGCTAGCATGATTTGGATCCTTTGTT
TCATTTTGTTTTGTTATTTTCTTTACTTTTCTCGACAAGATTACCTAAAAGGACCCTTTG
TTTACTTTTTGGAAGACAGGCATGTCTTCAGGCAGGGACTAAGGTCCAGCATTTCTAGAC
ATAAGTTCCTTTCTATTTTTATCACACAGTTCAGCAACACTGCCTGTCACCTTCCGCTGT
GCTGAAGAAAATAACCAGGTGGACAAGAGGATCACTCGATTCGTGTTACCCGTTGGTGCA
ACAATCAACATGGATGGGACTGCGCTCTATGAAGCAGTGGCAGCGGTGTTTATTGCACAG
TTGAATGACCTGGACTTGGGCATTGGGCAGATCATCACCATCAGGTGGGGCATGGTGTCA
CATTCATTGTCATCACTGATACAGGGATTACCGCCAGTAAAAATTGTCCATGAAGGGACA
CCAAGAATGTCGCAGTGATGAATTCTTTTTCTTGATCTATAAAGTCCCTTCCCAAGATTA
AATACGACTATATCCTGGTATGCAAGATTTCTGCTTCGGGGTCTGGGTAGCCAAAGCCAT
CACTCTGTGCTCAGTTTACTGAAGCCAGTAGGATCTAGGCACAGGCTAGCACAAAGACTC
AAGGCTGAGTAAGGGCCAGTCCCTGCTTTCAAACTATCCCTGCTAGATGGGCATGCACAT
ATCCAAATGAATGCTGAAGACCATGATGAGGGATGTAAGAGAACTCTGTATGGTGTTCAC
AGAGGACTCCAGAGAGGGAAGGCTGGTTCTAGCTGGGAAGGTGAACGATGGCTTCCCAG
AGGAGGGGAACATTTAGCTGAATCTTAGAAGAATAGGAATTTAGCAGGCAAAAGAAAAGC
TAGGAGCATTTGGAGTGGCAGAAATAGCTTGTGATGCAGCCATGGGCTAGTTACAGCATA
CAGATTTCTTGCTATGGCTGGCATAAAGGATACATAAACATTCCTTTATGTTTAAACGAA
TGAGGAGGCAGGGGTCATGTCATGAAAGGTTTTGTACGAAGAGCTTGTGGAAAGCTCTTA
GATGCTTTGTCATATTATGGACAGATTTGCATTTTATGTATTTATTTATTTTTTGAGATG
GAGTTTTGCTCTGTCGCCCAGGCTGGAGTGCAGTGGCACAATCTCGGCTCACCACAACCT
CCGCCTCCAGGGTTCAAGCAATTCTCCTGCCTCAGCCTCCTGAGTAGCTGGGACTACAGG
CGTGCACCACCACACCTGGCTAATTTTTGAATTTTTAGTAGAGATGGGGTTTCACCATGTT
GGCCAGGCTGGTCTTGAACTCCTGACCTCAGGTGATTTGCCCACCTCAGACTCCCAAAGT
GCCGGGATTATAGGTGTGAGCCACCACGCCCGGCAGATTTGCATTTTACAAAGATAAGCA
GCAATATGGAAGATATATTGGATGGGAGCAGGGACCAAATCTAGGAAACCAGTTAGGAGA
CCACTGCAGAAGTCCAGGCAGGGTATTAGAAGGCACTGACACTGAGGTTGGAGAAGAGCT
AATGAATTGAAGAAGCATCAGCTGGATTCAGGGTGAAAGGCGAGGGAATGCCAGGATGAC
TCCCAGGATTGGCAGATGATTCTAAATTGGTGGGTGGGGCTTACCAGAACAGGAACGAGT
GTAAGAGAAGCACATATAGGTGGGAAAGATAAATAGTAAATACTTTTTGACAGATTGAAT
TTGAAATGCCTTTAAGACTTCCAGTTGCACATATGCAATGAGAAATATAGGTCTGGCTGC
AGATACAGACATCAGGAACATGGCTTAATAATGGTCTTCAAATGTGTAAGTCACAAGTT
ATTGCTTGTATTGGAATCGCGGCTACATCATGATTAGCTGTGATCTTGGGCAAGTGACTT
GAATTTTTAAACTTCTGTTTTCTCATCTGTAAAATGAATAATAGTACCTACAACTTATTC
AAGTAGTGGCAATTAAGTAATATGCATATAAAATGTTTATAACTGTGCCTATGTAGTGAG
TACTCAGTGAATGTTGAAAATGGATGACATGACGTAGGGAGAGTTTGCAGAGAAGAGAAG
GAGATTAAGGACTGAGGCTTGGAAAAATCCTAATACTAGAAGCAGGTAGAGAAGGGAAAA
CCCAAGAGGGAGAGGGAGAAGGACAGAGAGATGGGAGGGAAGCCAGTAAACCTTGGTATC
ATGGAAACCCAGAAAAGAGAGATTTTCAAGGGTGAAATGGTCCACAGAGTCAGAAGCTGC
AGAGAATTCTAGTGAAATGAGGATAGACATTGTCTGCCCAAGTAGATGGTAGAACTGTCA
TTAGTGGATTTTGCCAGATTTGTTTCTCTAGGACAGCACTATTCAATATGGTAACCACTA
GCCATGTGGCCCACTGAATTGGATAGCACAGACACAGAATAGTTTCATCATTGCAGAAAG
TTCTTTTGGACAGCACTATGTTAGAGTGATAGGCTGGGATTAGAGTTAACCTGAAGACTT
TTGTTCAGTTTAGAATGGAAGTTTAAGACTAAACTGGTCCCTAGGCCTGCTCAAGGTTGA
```

FIGURE 4 (Continued)

```
ATCTGAACTTTTTAGAGTTAATTCATTCTTGTGTCCCAGCCTAAACATAAATTCTAGGGA
TAAAATCAGAGTTTGTTAACTAACAATGTTCTAATACAATGCATTTTTTAAATCCTCCCC
AACCCTAAATCGCAAAGTATTTCTGTTGGCTGAAGACAAGTGCAAAATACACCATTTGGC
ACACCAGCTGGGGAACTATCCCAATGCTGTGTAATCTATAAAAAGTGTTAGCGGCTAAAG
AAGCCTGTGCCAAAGAGATTGAGCAAAGTCCTGTAATTATAACAGCAGAGGGTATGTCAA
AATTGAAACCTTGAATCATGCCTGAAAAAGTTTCTGCTCCACAACCACCCCTGTGCTTCC
AACAGTTGTTACTTTTACATTTCCAAGGGTTTTTTCCCACTTCCCTCACCCTGGGCTGTG
GAACCCAGTCTTCACTGAACTGATTTCCAAGGAGTGGTTTATGAAGTGCCTATTCTTTTG
TGTATTTGACACTTTGTGATGAAATCCCTCCCTCTTTTTTGGTTGTAAGTTTTCTAGATC
TTTCTAATCATTTTTTAATCTCACTGCCAGAGGAATGAACTCTGGGCCTAGAAGCTAAA
TAGTCAATTCTCATTAAAGCCTCTCCGGCTACCTCTGGTATATTCTTAAATCAGATTTGC
TGAAAACTACTGGCCCAGAGCCAATAACAACTGTGAGGCCCAAAGTAATCATTGGCTTAA
AATTAAAAATCCTCACTGGCTCTACATGGAAAATAATAAAAGTTGGTTTTGCTTGACAGT
TACCATTATAGTTCATGTGACTAATGGTTAAAGAGATTTTTAGACCCAAAGTATATTTCT
GTGGACTGGACATCAAAGAAACATAGGTACCATCTACCCAAAACATACCCTTTTGTGGCT
TTATCATAATACTCAAAGGTTACAACGGATTGAAAATTGTGTGAGAATATGTGTCAAAAT
GGAAAAAAAAAGGATAAATTGTCTTATAAAAATAATTAGGGCCGGAAGCGATGGCTCAGA
CCTGTAATCCCAGCACTTTGGGAGACCTAAGTGGGTGAATCACTTGAGTCCAGGAGTTCG
AGACAAGCCTGGGCAAAATGGCAAAACCCCATGTTTACCAAAAATATTCTAAAAAAGAAA
AATTAGCCAGGCATGGTGGCATGTGCCTGTAGTCCCAGCTACTCAGGAGGCTGAAGTGGG
CAGACTGCTTGAGCCCAGGAGGCAGAGGTTGCAGTGAACTGAGATGGCGCCACTGCACTC
TAGCCTAGGCAACAGAGTGAGATTCCATCTCAAAGAAAAGAAAGAAAGAAAGAAAGAGAG
AAAAGAAAAGAAAGAAAGAAAAGTAAAGCTAATTATACAGCAGGGCGCAGAGGCTCACA
CCTGTAATATCAGCACTTTAAGAGGCCAAGGCGGGCGGATCACTTTAGCCCAGGAGTTTG
AGACCAGCCTGAGCAACAAGGCGAGGCCCCGTCTCTACAAAAAATACAAAAATTAGCCAG
GTGTTATGGAGTGCATCTGTGGTCTCAGCTACTCAGGAGGCTGAGGCAAGAAGATCGCTT
GAGCCCAATAGGTGGAGGCTGCAGTGAGCTGTGATCATGCCACTGAACTCCAGCCTGGGC
AACAGAGTGAGACCTTGTCTCTGGAAAAAAAAAAAATATATATGTGTGTGTGTGTGTGTG
TGTGTGTGTGTGTGTGTGTGTGTGTGTGTGTATAAGGAATAAAGAAGAAAGACAATTG
TAGGATTTGGGGCCTAGAAAGAGCTGAGAGAAAAAAAAAGTAGCAGTAGTAATAGTAGTA
GTAGTAGTTGTTGTAATAGTTGTTGTTTTGGTTGCTGCAGTAGCAGTAGTAATAATACCA
GTGGCAGCAGCGACAGCAGCAATAGAGGAAGCATTAGCAGCAACTGCTGTTGTTGCAGAA
GTAGCAGCAGAAATGGCACGTTTTAATCTTTTTGTTTGTTTTTGTTTTATTTTACTTT
AAGCTCTGGGATACGTGTGCAGAACATGCAGGTTTGTTACATAGGTATACGTGTGGAAAT
GGCATGTTTTTAAGCATCTACTATACAAGTGCTATCCCAGATGCCTTACGTGTATTAACC
TCATTTAATCTTCCCAGCAGCTTGCAGTAGACATACTGTCCCCATCTTACAGGCAAGGAA
TTGAGATTCAGAGAAGTAACTTGCCTGAAGAAATGCCATCAGTAAAATGGTAGAGCCCAA
AGTACATCACCCAGGTGTGTCTGACACTAAAACCTGTGTTCCCTCCAAGTCACAAGCCAT
CCTTCAACCTGTTTAGAGAGCCAAGTCCAATGGCCGGTCCTAAAACTAGGACCTCAGTGT
GAGGAAAGAACTTTGTACCACTGATATTTATGTTTTCTTCTGTGGAAATCCTCTAACTCA
AAGTAGAATATGTTCAAGCAGCAGGAATAGGTTTTTATATTATTTTCTCCCATCTGAAGG
TTCATAGTTCTGAGTTTCAGACCAATGCCAGTCAAACAGCAGTAGTCTGGTAAGCAAGGT
CAAGGCTCAAGGACAGAGTTTTCTTTGACTAAATGAATTTTGAGTTTCAAGCCCAGCCTC
AGGCTATAGAGACATGGATTACTGTGACACGTCAGGGTTTCCAAGAGGGATCAGCTGGCA
TGGACACAAATCACTTCTGACAAAGAAAACCTGTTGATGCATTCCATTTAAATTTTTTTC
AACCAGCATTAAAATAAACTTGGGCTTTCCAAAGAGTACTTAGGTCAGAAGAGATCCAAA
GGGTTATAGAGGCCAGAAACCTTTGAGACTGAGGCCTGAAACCTTTAGAGTAATTGGTAC
AGCCCCAGAAATCTCTAATTTACTATAATTTGGTGGTCAAAACCACTGAATGAAAATACA
CTTGTCAAAAAACTCTGGCCTGTGTTTGACTGTACCCTCAAATGCTTTCTGCAACACCTC
AGTAGGCAGATGAATGGGCAGTAGAATCAGCTTCCTAAGAACTCTGGCTTTTTTAGCCC
CAAAGAATATGAATGTGTGGATAGAATCAGGGATTCTTCCAGTTTAAATTGCCAATTTTT
ACATTTTCACCTTTCAACACAGTGGAACCCGGGCAACAGTTCAGGCCTTGGCCCAAGGGC
AAGGACTTGTCTCCAGAAAGCACTGTAGGTGTGGCCTCCAGCTTATCCAAGTCAAGGGAT
TTTTCAGGGCATGTTGAACCCTTGTTTCCTTCAGAATGATCCAATTAAAATAAGGAAGAT
GTTGCTGATAAAGAGACTGCACATTACAAAGAAAAAAATCCCTACTGCCTCAGCTGATCT
```

FIGURE 4 (Continued)

```
TACCAAGAGGGATCTTTTTAAATACCTGGTAATAAAGTTCACCTGGCTGCCCCTCCTGGA
TTCCAGATCTTTCTTTCCCACAAAGTGCATCTACTGGCAAAAAGGAGCAGTCAGGAGTAA
ATGCTTGTACCTTGGACAGGATCAGCTATTTCTCAATTCAGTGCCCTGAAGAGCAGTTCC
CAGAGGTAAAGAGTCCTGTGATGTCAAGAGAGTGCATAAAGCCTGCTTAACCATTGTCTC
ATTCCTTTGCCTTCACCTGAAATGCCCTTGCCCATCTGCCCCTACAACTATCCTTCTGTC
CATCCTTCAGGGCAACTTAAATTCCTGCCATATATTAGGTGCTCAGTAAATTATTGGGTG
GTGAGTAGATGGAACAAGGGAGTAGGAAGGCAGGTGCAGAGGTACCTGGCACTTATTTAG
GATGAGTGTATGTATACATAGATGAGTACACGAAGCCTCCTATTAACACCCCATTTAGTA
AACTCCTGCTTTCCTCTTGAGTATCTCTCTTACTTATTTTTGGTGCCACTTATGCAGTT
CTTCCTTGCATTAGAGTGATGTGCCATATCTCCGTCTGCAAGGAGATGGCATCATACCCC
TCATAGTCCCCCTCCCCCCACAGCTCTAATCCTGTAATGAGGCAGAGCTGGGCTCAGCA
AGTCACAGATTCTAACTACCCAATTTAGGGACACAGCAGTAATAGCCATCGGGACTAAGC
GGGAGTAACCATTTCAGGCCAGGGCTTTAACGGGAGAGGTAAGTGTCTAACTCCTTTCCT
GCTGGTATGTTTCTGCAGTATCACGGCCACATCTGCCAGCATCGGAGCTGCTGGCGTGCC
CCAGGCTGGCCTGGTGACCATGGTGATTGTGCTGAGTGCCGTGGGCCTGCCCGCCGAGGA
TGTCACCCTGATCATTGCTGTCGACTGGCTCCTGTGAGTTGGAATAAATGCACTGCCTTA
GCTGGATGTGCAGGCGGGCTTCCCAGCCTCGCAGGCGCTGCAGTCTGTCATCATTCTCTC
CTCAGATTGCCTAATGAGCCACCTGTTGCTGCTTTAATTTTCCTCTGACCAGGCCATCTG
ATAACATGCCTAAAAATTAACTCCTCATAACGTGGAGCAGTGATTTTAAAAAGCCGGTGA
GCTCCATTAGCTCATTATACCTGGTAACACTCAAGCTTAGGAGCTGGGTGTGGGACAGAG
ATAAACACAGAACAAGGTGAGAAGCCAGGCAGGGCCCCAGAGCCATCCTGACCTATCCCA
GCCCTGGTTCAGCATCATAGGCTCAGAACCACCTAGTTCAAAATCAGTCCGTCTTCCTAA
GCATCTTCCGAACCATCAGGGACAGTGGCACAAGCACTTGGGTTTGAATCTCCGTCCTGT
GTCTTACCAGCTTCTTGACCTCGAGCAAGTTTCCTTAACCTGAGGCCCAGTTGCATAATC
TGTGAGATGGGAAAAAATCTGCCTATGTCATTGGGTTGTTTTAAGGACTGAGTGAGCTCA
TGTGAGTGGAGCATCTAGAACAGCGTTTGGCAGCCCATACATGCTCAATAAATGGCAAGT
TTTATTGTTATGATTAGAATGAGTTGGACCATTCAGGCCCCAATCAACAACACTTCTCTC
TCTCTCTCTCTCTCTCTCTCACACACACACACACACACACACACATATGGAA
TACAGCAGAACATCTGGGTGAGAAAGTACCTTCAGTGACCCTCAAGGTTAAAGTTAGAAC
CAGCCTGGCTCCAAGCTTTACCCTTGATGCCCACTTCTGTGCATGGATCTTACAGCATTT
AGGTCTGGCTCTGTCCCCTGGCATTGCAGGTAAGTATTGCTCCACATGGAGCCTTTGCTC
AGAACCAGCTCAGGCTCACTGGGGAGTCCAGTGCTATGTACTGTAGTTTGCAGGTGACAG
ATGAGATGGAAAGGGAAGCAGAGACATCCTATTGGGCTTGAAAACACAGATTCACATTTC
AAATGGCAAAAGCCCCTGCACCTGGCTTGGAAGCTGTGCCATGAGGTGGCCCCTCAGTAG
CTAACTGGGCTATAGGCCCAAATGAGGTGGCACCCTTCTTGCAAAGATATCCTATCATTG
AGTCAAGATTTGGTTCTTTCTAGTGATGCTGGTGGATTTGCATTTTTCTCCTTTCCCTGA
GTCTTCCTGGAACCAGTTACCTTCCCTGCCAAGATACCCAGATGAGTCAAAGGTCCAATT
GGAGGTATGGGATAAAAAGACACTAGGGCCAGTTCAATCCCTGGACTTGTTCTAAATAAC
AGAAGGGCATCCAGGGTGGTCATGTGTAAGCATTGTCAGCCTTTTCTGTTCTGCAGGTGT
AGTTTTCACAAGATTCCCCCTGCATGCAGTTCCTGTCAACAAAGTGCCAGTATCAAAATG
GATCCTCTCCTCTGCAGTGTGCCTTCTCTACCTGTCTTCCTGCCACCAGTCTCTTCCCCA
GGCTCTCTGGAAATTAAGACTGGATGAGGGTGGCCCACAGAGAAATCCATTCCTGGGCTG
ACCTGTGTTTTCTGACCCCGTGCTCTGCACCATGCCTCCTGGTTTGCTCATAAGTAGAGT
GACCTAGATTGGTAAATAAACAAGTACACCATGGACCTGAACAAACACATACATACCCCA
CATGCACATGGTACATACTCCACCCACAAAACACCCAAGTTCTCTGACCTTTGCCCAAAG
AGAGCCCACAATGGCATTTGCATTGAATCTAGAAAATCCCAAGATAGAGGTTAGGGCTGA
AAAACTTACTGAATTCTGAACCTCCCTCAGTCCCCCAAAAAATATCTGGAACGACTCTAT
TCATGTTTCTTTGGGAGAAGAGGAAGGAATTTAGGGAGACTTAGGGGAGTCATTGCTACT
TTGGGGGAGCTCATGCTGTGCCTTTATGAACAACCCCAGGCCTGTGAGGAGCCTTCAGTC
AGTCAGCCATGAGGACAGCACTTTCTGCACTTACTGAAATCTAAACTGAACATGTCAGGT
CCTTGCATCTCTCCAGTGATGAAGGAAAATGAAATCTGGGCCTCCTGTCTGACTCCTCCC
GTCTCTCCCCAGGGACCGGTTCAGGACCATGGTCAACGTCCTTGGTGATGCTTTTGGGAC
GGGCATTGTGGAAAAGCTCTCCAAGAAGGAGCTGGAGCAGATGGATGTTTCATCTGAAGT
CAACATTGTGAATCCCTTTGCCTTGGAATCCACAATCCTTGACAACGAAGACTCAGACAC
CAAGAAGTCTTATGTCAATGGAGGCTTTGCAGTAGACAAGTCTGACACCATCTCATTCAC
```

FIGURE 4 (Continued)

```
CCAGACCTCACAGTTCTAGGGCCCCTGGCTGCAGATGACTGGAAACAAGGAAGGACATTT
CCGTGAGAGTCATCTCAAACACTGCTTAAGGAAAAGAGAAACACTAATGGCCAAGTGTAC
ATTTGATTTGATATACAGACCTCCAGATTATTTTCTATATTTGGATTCACAGCCTTTGCG
CTCTGGGTTTTGGGATTTGGGTGTGGGGTAAGTTGAAGGGAAATCAATTTAAAGGAAAGT
TCTATTATCTGGGTTTTAGAAATTCTATAAGAGACAAAGTTTGGAAGTACATAAAGTAAT
AACTGTTAGAATTAGGTAATGGATATGAAAGAGAAAATGCTTTCTCATGCATAGACAAGT
GTTTTGGGTTTTTAAAAAAAATATTCTGTCATTGGTTACAAATTTTTACTCAGGCTTTCT
ATTGGCATGGATTTCCTTTGACCTCTCACTTTTTTATAAATTATAATGCATCTAAACCAC
CTGTCCCCAGTTAATGTGCCAAAATGTCAATTTTTAACTTATCTCCAGCCAATTTCAAAG
AAAACAGACCAGCATAGTTCTGCAATAACAGTTTTAAGATGGGCATAGGGTTTGGAAGAA
AGGGAGAAGGATTCTTTTTTCAATGTACTGTATTGGGACGCTGGTAACTGTTAACCCAGT
GTTCAGCATAGAGCTATATATATATATATATGTATATATTTATTATTTTCATATAATTTG
CCAGACAGAGATCAGAATTGAACCGTCAATGTGAAATAAAGAGTTCTCCTTGTACTTGAA
TAATAACCACGATTCCAACCCAGGTCTGCTTTGGGGCTTATCAGAACTCCTTTCTAAGGA
GCACTAGAATGAGAAATCATGTTGTTCGATCGTTTCACATCTGTATATCAGCTCTAAAGC
AGAGATGTATTATGGTGATACTCCAAGGTGGCATAGCCATTCATTTACAACTTCCAGATT
TGAGCTGCCTGGAGGGAATCCATATCAGCTCTGCATAAGATTATATACAAAGCTGTCACT
CACAAAAGGCTGGATGTGCTTTCATCCAACTGGAAGGCTTTATTCTTCCAAGTTCATTCA
TACTCAAAGAGGCCAGTACTTTGCCATCCTTGCACTTCTGTTATCAGGGCCCAAATAACA
GTGGCAAGCTACCAACTAAGTTGTATTTTAATAAAGATTCCATGGGTTGAACAAGCCACG
TTGCAGAAAAAGAGCTTCCCCTAACCTGGGTTGTTGCAGAGTAAATCCCACGACATAAGC
TGGTATCA
S (pos 4576808)
TGGTTCGGGGGAAATAGTTCCATTCTATGACTCTTGTCTCCTCCTCCAGGA
GGACTGTTCTAACTAGTAATCTTGGCCCTATTCATTACATCCTCTGCTTGTCATTCTGCT
AATTTATGAAGATAGTTTATTATAGTCTGTACTTCAGTTCTCATCTTGTAAATAATGCTT
AACATAAACTTGTACTTACACTGAAATCCAAAATAGTCATGTTTCTGCAGTATTCTGTAG
CCAACTTAAACCTGTGCTTTCATGTTTAAGAAATGAGAAATTGTGCCAAAGATAGCAGAA
GAGTAGATAAGTGCTCAGTATTGACGACCTACATCTGAAATCTACAACATAATGATACTG
AATTGTTATGTAAACATCATAAATAGTAAATAATGATTCAATGTGAATTTTAAAATGCAA
ATATTGCTATTGTTTATAGGAAATAAATCTAAATATAAATG
```

SLC1A1 MARKER FOR ANXIETY DISORDER

This application claims the benefit of provisional application 60/731,472 filed Oct. 31, 2005, the entire content of which is expressly incorporated herein by reference thereto.

FIELD OF INVENTION

The present invention relates to a diagnostic or a treatment for an anxiety disorder. More particularly, the present invention relates to association of a genetic marker with an anxiety disorder.

BACKGROUND OF THE INVENTION

Anxiety disorders are typically characterized by an exaggerated, recurrent or inappropriate apprehension, uncertainty, anxiety, or fear. They are classified according to the severity and duration of their symptoms and specific affective characteristics. Some categories are: (1) generalized anxiety disorder (GAD); (2) obsessive-compulsive disorder (OCD); (3) panic disorder; (4) post traumatic stress disorder (PTSD); (5) social anxiety disorder (social phobia); (6) specific phobia; and (7) separation anxiety disorder. Current treatment for most anxiety disorders may involve a combination of psyco-social treatment with antidepressant medication. Psycho-social treatments used in the treatment of anxiety disorders include, for example, cognitive behavioral therapy (CBT), exposure therapy, anxiety management and relaxation therapies, or psychotherapy. Drugs used to treat anxiety disorders include, for example, selective serotonin reuptake inhibitors (SSRIs), tricyclic antidepressants, benzodiazepines, beta blockers, or monoamine oxidase inhibitors (MAOIs).

Anxiety disorders may develop from a complex set of risk factors, including genetics, brain chemistry, personality, and life events. A combination of factors may underlie a given anxiety disorder. For example, while trauma itself acts as a trigger for post traumatic stress disorder, genetic factors may predispose some individuals toward being more or less susceptible to developing the full-blown disorder. Genetic factors have been suggested to play a role in several other anxiety disorders, including for example, obsessive-compulsive disorder (OCD).

OCD is a neuropsychiatric condition affecting an estimated 1 to 3% of the population worldwide. It is associated with significant morbidity, as reflected in its ranking by the World Health Organization as one of the 10 most disabling medical conditions. Large, controlled family studies have indicated significant familial aggregation of OCD, with a meta-analysis indicating an aggregate risk of 8.3% compared with the general population prevalence of approximately 2%, resulting in an odds ratio of 4 for first degree relatives of OCD probands. Twin studies in OCD suggest increased concordance in monozygotic twin pairs (80-87%) compared with dizygotic twin pairs (47-50%). Taken together, the family studies and twin studies indicate that genetic determinants may play a significant role in the etiology of OCD.

Molecular genetic studies in OCD have been largely based on a candidate gene approach, in which variants (polymorphisms) of candidate genes are genotyped in a population of affected probands and either population or family-based controls. Candidate genes may be selected based either on location within a linkage region identified in a whole genome scan, or the presumed role of the gene in pathogenesis. In the only published genome scan based on OCD probands, a region of suggestive linkage (LOD=2.25) was found in chromosome 9p24 based on seven multigenerational large pedigrees in which there was a pediatric proband with OCD (Hanna G L, Veenstra-VanderWeele J, Cox N.J. et al. Genome-wide linkage analysis of families with obsessive-compulsive disorder ascertained through pediatric probands. Am J Med Genet 2002;114:541-52), a linkage finding which was subsequently replicated in a study by Willour and colleagues (Willour V L, Yao Shugart Y, Samuels J et al. Replication study supports evidence for linkage to 9p24 in obsessive-compulsive disorder. Am J Hum Genet 2004;75:508-13).

Within the 9p24 region of 7.5 MB only one gene has been shown to be expressed in brain, the neuronal glutamate transporter gene SLC1A1 (OMIM #133550), which codes for the neuronal glutamate transporter excitatory amino acid carrier 1 (EAAT3/EAAC1). This gene is highly expressed within cerebral cortex, striatum, and thalamus, brain regions which are connected in functional cortico-striatal-thalamic circuits (CSTC's) implicated in OCD (Bronstein Y, Cummings J. Neurochemistry of frontal-subcortical circuits. In: Lichter D, Cummings J, eds. Frontal-subcortical circuits in psychiatric and neurological disorders. New York: Guilford Press; 2001:59-91).

SLC1A1 is a strong functional candidate gene for OCD given the mounting evidence for a role of altered glutamate neurotransmission within CSTC's in the pathogenesis of OCD. However, genetic association studies between OCD and SLC1A1 and the surrounding genetic region have produced mixed findings. Veenstra-Vanderweele and colleagues (Veenstra-VanderWeele J, Kim S J, Gonen D, Hanna G L, Leventhal B L, Cook E H, Jr. Genomic organization of the SLC1A1/EAAC1 gene and mutation screening in early-onset obsessive-compulsive disorder. Mol Psychiatry 2001; 6:160-7) failed to find any evidence for biased transmission in a family-based association analysis of a haplotype consisting of two intronic SNPs in intron 3 of SLC1A1 (p=0.42). Willour and colleagues (Willour et al, supra.) found modest associations between two microsatellite markers flanking SLC1A1, GATA62F03 (p=0.02) and D9S288 (p=0.05). Accordingly, association between SLC1A1 and OCD is still not clear.

Similarly, genetic markers for other anxiety disorders have yet to be clearly established.

According to the Anxiety Disorders Association of America (ADAA; www.adaa.org) anxiety disorders may be the most common psychiatric illnesses affecting both children and adults. 19 million adult Americans are estimated suffer from anxiety disorders. However, only about one-third of those suffering from an anxiety disorder are properly diagnosed and receive treatment.

Accordingly, there is a need for diagnostics or treatments pertaining to anxiety disorders. Furthermore, there is a need to further clarify an association between anxiety disorders and SCLA1A or SCLA1A variants.

SUMMARY OF THE INVENTION

The present invention relates to a diagnostic or a treatment for an anxiety disorder. More particularly, the present invention relates to association of a genetic marker with an anxiety disorder.

The invention provides an improved method of diagnosing an anxiety disorder or identifying a risk of developing an anxiety disorder based on testing of the SLC1A1 gene, SLC1A1 gene variants, or related gene products.

In general, the invention provides a method of diagnosing or identifying susceptibility of a subject to an anxiety disorder which comprises testing a sample obtained from the subject for the presence of a polymorphism or haplotype in the SLC1A1 gene, wherein the presence of the polymorphism or haplotype that the patient is susceptible to an anxiety disorder.

In one embodiment, the sample obtained from the subject is tested for the presence of a polymorphism in Intron 10 of the SLC1A1 gene, wherein the presence of allele G of the A/G polymorphism rs301434 indicates that the patient is susceptible to an anxiety disorder.

In another embodiment, the sample obtained from the subject is tested for the presence of a polymorphism in Intron 10 of the SLC1A1 gene, wherein the presence of allele A of A/G polymorphism rs301435 indicates that the patient is susceptible to an anxiety disorder.

In yet another embodiment, the sample obtained from the subject is tested for the presence of a polymorphism in the 3' untranslated region of the SLC1A1 gene, wherein the presence of allele C of C/G polymorphism rs3087879 indicates that the patient is susceptible to an anxiety disorder.

In a further embodiment, the sample obtained from the subject is tested for the presence of a haplotype in the SLC1A1 gene, wherein the combined presence allele G of the A/G polymorphism rs301434 and allele C of C/G polymorphism rs3087879 indicates that the patient is susceptible to an anxiety disorder.

In a preferred embodiment, the presence of a particular allele at the polymorphic site as provided by rs301434, rs301435 or rs308787 is determined in relation to the nucleotide sequence of about 15 nucleotides upstream and about 15 nucleotide downstream of the polymorphic site. However, the present invention also contemplates that the presence of a particular allele may be determined in relation to a the nucleotide sequence comprising about 20, 25, 30, 50 or more nucleotides upstream (or any number therein between) and 20, 25, 30, 50 or more nucleotides downstream (or any number therein between) of the polymorphic site as provided by rs301434, rs301435 or rs308787, respectively.

In these embodiments, the sample is blood and the anxiety disorder is obsessive-compulsive disorder. The obsessive-compulsive disorder typically comprises aggressive obsessions, checking compulsions, symmetry obsessions, ordering compulsions, counting compulsions, repeating compulsions or a combination thereof. The step of testing preferably comprises DNA extraction and PCR analysis.

The present invention also provides a method for identifying a compound that is capable of modulating expression of an SLC1A1 sequence that is at least 80% identical to SEQ ID NO:3 comprising contacting the SLC1A1 sequence with a compound; and determining whether the compound is capable of modulating the stability of the SLC1A1 sequence.

The present invention also provides a method for identifying a compound that is capable of modulating glutamate uptake by an EAAC1 protein that is at least 80% identical to the amino acid sequence encoded by SEQ ID NO:3 comprising contacting the EAAC1 protein with a compound; and determining whether the compound is capable of modulating glutamate uptake.

The present invention also provides a method of screening for a compound that is capable of modulating expression of an SLC1A1 sequence that is at least 80% identical to SEQ ID NO:3, comprising (a) contacting a cell comprising the SLC1A1 sequence with a compound; (b) determining a response; and (c) comparing the response of step b) to a control response as determined in the absence of the compound.

The present invention also provides a method of screening for a compound that is capable of modulating activity of an EAAC1 protein that is at least 80% identical to the amino acid sequence encoded by SEQ ID NO:3, comprising (a) contacting a cell comprising the EAAC1 sequence with a compound; (b) determining a response; and (c) comparing the response of step b) to a control response as determined in the absence of the compound.

The present invention also provides a method of treating an anxiety disorder in a subject, the method comprising administering to the subject, a therapeutically effective amount of an SLC1A1 sequence that is at least 80% identical to SEQ ID NO:3.

The present invention also provides a method of diagnosing or identifying susceptibility of a subject to an anxiety disorder such as obsessive compulsive disorder that comprises aggressive obsessions, checking compulsions, symmetry obsessions, ordering compulsions, counting compulsions, repeating compulsions or a combination thereof, the method comprising testing a sample obtained from the subject for the presence of a polymorphism in Intron 10 of the SLC1A1 gene, wherein the presence of allele G of the A/G polymorphism rs301434 indicates that the subject is susceptible to an anxiety disorder such as obsessive compulsive disorder that comprises aggressive obsessions, checking compulsions, symmetry obsessions, ordering compulsions, counting compulsions, repeating compulsions or a combination thereof.

The present invention also provides a method of diagnosing or identifying susceptibility of a subject to an anxiety disorder, for example, but not limited to, obsessive compulsive disorder that comprises symmetry obsessions, ordering compulsions, counting compulsions, repeating compulsions or a combination thereof, the method comprising testing a sample obtained from the subject for the presence of a polymorphism in Intron 10 of the SLC1A1 gene, wherein the presence of allele A of A/G polymorphism rs301435 indicates that the subject is susceptible to an anxiety disorder such as obsessive compulsive disorder that comprises symmetry obsessions, ordering compulsions, counting compulsions, repeating compulsions or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a portion of the SLC1A1 nucleotide sequence (SEQ ID NO:1) that comprises SNP7 (rs301434) in accordance with an embodiment of the present invention;

FIG. 2 shows a portion of the SLC1A1 nucleotide sequence (SEQ ID NO:2) that comprises SNP8 (rs301435) in accordance with a further embodiment of the present invention;

FIG. 3 shows the SLC1A1 cDNA nucleotide sequence (SEQ ID NO:3) that comprises SNP9 (rs3087879) in accordance with a further embodiment of the present invention;

FIG. 4 shows the genomic SLC1A1 nucleotide sequence in accordance with a further embodiment of the present invention.

DETAILED DESCRIPTION OF THE PREFERRED EMBODIMENTS

The present invention relates to a diagnostic or a treatment for an anxiety disorder. More particularly, the present invention relates to association of a genetic marker with an anxiety disorder.

The following description is of a preferred embodiment.

The present invention provides a genetic marker that may be used to diagnose an anxiety disorder or identify a susceptibility to an anxiety disorder. As described in more detail below, specific polymorphisms in the SLC1A1 gene may be used as an indicator of an anxiety disorder, for example, but not limited to obsessive-compulsive disorder (OCD). Additionally, altered levels of SLC1A1 mRNA or altered levels of EAAT3/EAAC1 protein may be used as an indicator of an anxiety disorder, for example, but not limited to OCD.

In certain examples of the present invention a subject's SLC1A1 gene or related gene products is assayed or tested to diagnose an anxiety disorder or identify a susceptibility to an anxiety disorder. Examples of an anxiety disorder include, without limitation, (1) generalized anxiety disorder (GAD), (2) obsessive-compulsive disorder (OCD), (3) panic disorder, (4) post traumatic stress disorder (PTSD), (5) social anxiety disorder (social phobia), (6) specific phobia, and (7) separation anxiety disorder. In certain examples, specific polymorphisms in the SLC1A1 gene are used as an indicator of an anxiety disorder. In other examples, altered levels of SLC1A1 mRNA are used as an indicator. In still other examples, altered levels of EAAT3/EAAC1 protein are used as an indicator.

In a further embodiment of the present invention, which is not meant to be consider limiting, a subject's SLC1A1 gene or related gene products is assayed or tested to diagnose an anxiety disorder or identify susceptibility of a subject to an anxiety disorder that has specific symptoms. For example, but not wishing to be limiting, a subject may be tested to identify susceptibility to obsessive compulsive disorder that comprises aggressive obsessions, checking compulsions, symmetry obsessions, ordering compulsions, counting compulsions, repeating compulsions or a combination thereof.

The results of assaying the SCL1A1 gene or related gene products may be used alone or in conjunction with other clinical tests, for example, personality test, neurocognitive testing, or magnetic resonance imaging analysis. In one example, a susceptibility to OCD can be identified by assaying for a polymorphism in the 3' UTR of the SLC1A1 gene. In another example, results of a clinical psychiatric test, such as without limitation Y-BOCS (Goodman, W K, Price L H, et al. The Yale-Brown Obsessive Compulsive Scale (Y-BOCS): Part 1. Development, use and reliability. Arch Gen Psychiatry. 1989; 46:1006-1011 Diagnostic and Statistical Manual of Mental Disorders, Fourth Edition. Washington, D.C. American Psychiatric Association, 1994), SCID (Structured Clinical Interview for DSM-IV), or FIGS (Family Interview for Genetic Studies), may be considered in conjunction with the results of assaying for a SCL1A1 polymorphism or results of determining levels of SLC1A1 mRNA or EAAT3/EAAC1 protein.

Any tissue sample may be used for genotyping SLC1A1 polymorphisms, or for determining levels of SLC1A1 gene products, including but not limited to, blood, saliva, spinal fluid, brain biopsy, cultured cells, stool, urine, autopsy samples, or frozen sections taken for histologic purposes. Such samples are typically obtained from a mammal, for example, a primate, such as a chimpanzee or human; cow; dog; cat; a rodent. In certain examples, blood is obtained from a subject for assaying with respect to SLC1A1 polymorphisms. In an example, venous blood is obtained from a subject using standard venipuncture techniques.

Certain examples of the present invention pertain to use of SLC1A1 gene or related gene products for diagnosing an anxiety disorder or identifying a susceptibility to an anxiety disorder. In one example, diagnosis involves testing a sample obtained from a subject for the presence of a polymorphism in the SLC1A1 gene. In another example, diagnosis can involve determining the level of a SLC1A1 mRNA or EAAT3/EAAC1 protein in a subject and then comparing the level to a baseline level or range in a control sample. Typically, a control sample is a healthy control not suffering from an anxiety disorder or under the effects of medication or other drugs or not having an SLC1A1 polymorphism that is indicative of an anxiety disorder. Examples of suitable sample types are, without limitation, blood, saliva, spinal fluid, brain biopsy, cultured cells, stool, urine, autopsy samples, or frozen sections taken for histologic purposes.

Variation of levels of a polypeptide or polynucleotide of the invention from the baseline level or range may indicate an anxiety disorder or a susceptibility to an anxiety disorder. Any convenient method may be used for assaying or testing the SLC1A1 gene or its related gene products, including without limitation, SNPs or haplotypes associated with the SLC1A1 gene, SLC1A1 mRNA, and EAAT3/EAAC1 protein.

Standard techniques used to determine expression levels of SLC1A1 mRNA may include, without limitation, Northern analysis, or quantitative PCR.

Levels of EAAT3/EAAC 1 protein may also be measured using any variety of techniques known to the skilled person, for example without limitation, ELISA, immunodiffusion, immunohistochemical assays, or other methods that are known to one of skill in the art.

The genes provided herein also can be used to develop probe sets for PCR and chip assays.

Single nucleotide polymorphism (SNP) analysis is useful for detecting differences between alleles of the SLC1A1 gene. Various real-time PCR methods can be used to detect SNPs, including, e.g., Taqman or molecular beacon-based assays (U.S. Pat. Nos. 5,210,015; 5,487,972; and PCT WO 95/13399) are useful to monitor for the presence of absence of a SNP. Many other SNP detection methods are known in the art, including, without limitation., DNA sequencing, sequencing by hybridization, dot blotting, oligonucleotide array (DNA Chip) hybridization analysis.

Applied Biosystems, Inc (Foster City, Calif.) has developed several aspects of SNP genotyping technology. In one well used protocol PCR amplification of a desired SNP region is conducted using targeting primers, including two allele-specific fluorogenic probes, each consisting of a different fluorescent reporter dye and a fluorescent quencher. Prior to PCR, proximity of the quencher to the fluorphore causes fluorescence resonance energy transfer (FRET), reducing the fluorescence from the reporter dye. During PCR, the 5' nuclease activity of Taq digests the allele-specific probe bound to the region of the SNP, releasing the fluorescent dye from the quencher and allowing generation of a fluorescence signal.

The method of obtaining a sample and analyzing its DNA or protein levels is not critical to the present invention and any methods may be used (e.g. Ausubel, et al. (eds), 1989, *Current Protocols in Molecular Biology*, Green Publishing Associates, Inc., and John Wiley & Sons, Inc., New York, at p. 2.10.3, or Maniatis et al., in Molecular Cloning (A Laboratory Manual), Cold Spring Harbor Laboratory, 1982, p. 387-389). For example, which is not to be considered limiting in any manner, DNA may be extracted using a non-enzymatic high-salt procedure. Alternatively, the DNA may be analyzed in situ. Other methods of DNA or protein analysis that are known to persons skilled in the art may also be used.

Several scientific collaborations have attempted to identify and/or classify SNPs for genomes of several species including *Homo sapiens, Arabidopsis thaliana, Caenorhabditis elegans, Ficedula albicollis, Ficedula hypoleuca, Gallus gallus, Mus musculus, Pan troglodytes, Plasmodium falciparum*, and *Rattus norvegicus*. For example, the HapMap project attempts to determine the common patterns of human DNA sequence variation (haplotypes). SNP genotypes, recombination rates and other types of information may be browsed at or downloaded from the HapMap website (www.hapmap.org). SNPs are typically identified by location within a nucleotide sequence, or by a database assigned reference SNP ID number ("rs" number). In addition to HapMap, SNPs may be searched using various other resources. For example, individual rs numbers of the SNPs that are known to be located in a sequence of interest may be obtained by conducting a Blast search at the UCSC Genome Bioinformatics Web Page (www.genome.ucsc.edu). Conversely, sequence and scientific literature information associated with a given rs number may be obtained by searching the dbSNP of the Entrez SNP search option provided by the NCBI web page (www.ncbi.nlm.nih.gov).

With reference to examples pertaining to assaying SLC1A1 polymorphisms, examples of single nuclear polymorphism (SNP) indicators are at chromosome 9p24 at position 4572082A/G (rs301434) located in Intron 10, at position 4572843A/G (rs301435) located in Intron 10, or at postion 4576808C/G (rs3087879; position 3065 of SLC1A1 cDNA shown in FIG. 3) located in the 3' UTR of SLC1A 1.

In a preferred embodiment, the presence of a particular allele at the polymorphic site as provided by rs301434, rs301435 or rs308787 is determined in relation to the adjacent nucleotide sequence upstream and downstream from the polymorphic site, for example, but not limited to, about 15 nucleotides upstream and about 15 nucleotide downstream of the polymorphic site. However, the present invention also contemplates that the presence of a particular allele may be determined in relation to a the nucleotide sequence comprising about 20, 25, 30, 50 or more nucleotides upstream (or any number therein between) and about 20, 25, 30, 50 or more nucleotides downstream (or any number therein between) of the polymorphic site as provided by rs301434, rs301435 or rs308787, respectively. Other means and methods of comparing nucleotide sequences to determine if a particular polymorphism or group of polymorphisms is present in a subject, as would be known to a person of skill in the art may be employed in the practice of the present invention.

Polymorphisms may be genotyped using conventional techniques. For example, PCR using primers incorporating fluorescent probes is one suitable technique. For example, which is not to be considered limiting, primers may be derived from the following sequences GGATAAGCTGGAGGCCACACCTACA[A/G]TGCTTTCTGGAGACAAGTCC TTGCC (SNP7; rs301434; SEQ ID NO:5);

-continued

TTAGAGCTGTGGGGGGAGGGGGACT[A/G]TGAGGGGTATGATGCCATCT CCTTG (SNP8; rs301435; SEQ ID NO:6)

AATCCCACGACATAAGCTGGTATCA[C/G]TGGTTCGGGGGAAATAGTTC CATTC (SNP9; rs3087879; SEQ ID NO:7).

A sample from a subject can be assayed for comparing or quantifying SLC1A1 mRNA levels, EAAT3/EAAC1 protein, or both SLC1A1 mRNA levels and EAAT3/EAAC1 protein levels. Samples may be obtained from a variety of nervous system tissue, for example but not limited to, brain tissue. Examples of brain tissue that may be used include cerebral cortex, striatum, and thalamus.

The subject may be a human or an animal subject. For example, other mammals that may be tested include, but are not limited to a dog, cat, horse, mouse, rat, or cow.

In certain examples of the present invention, an SLC1A1 sequence comprising an SNP or a haplotype that is associated with an anxiety disorder is used in an assay to identify a compound that can modulate the level or activity of SLC1A1 mRNA or its protein product. Any type of compound may be tested in these assays including, without limitation, naturally occurring or synthetic compounds, protein, antibody, oligopeptide of less than about 100 amino acids in length, peptidomimetic, small organic molecule, polysaccharide, lipid, fatty acid, polynucleotide, RNAi, polynucleotide, antisense RNA, and ribozyme. Assays that may be used to identify a compound are well known to those skilled in the art. For example, compounds may be tested in a neuronal cell culture expressing a SLC1A1 sequence comprising an SNP associated with an anxiety disorder to determine whether the compound modulates glutamate uptake or any other function of SLC1A1 gene or its related gene products. While assays involving cell culture may typically use neuronal cell lines or neuronal explants, other cell types may also be used including, without limitation, HeLa cells, CHO cells or stem cells. In another example, an assay is designed to determine whether a compound can modulate SLC1A1 mRNA stability either within a cell or in solution. In another example, compounds are tested in an animal model for an anxiety disorder where the SLC1A1 gene has benn manipulated to comprise a SNP or haplotype that is associated with an anxiety disorder. In yet another example, compounds are designed or their effect is predicted in silico with available computer software.

In some examples of the present invention, cells comprising a SLC1A1 sequences or EAAT3/EAAC1 sequences may be used to identify compounds with therapeutic potential for treating an anxiety disorder. In one example, a SLC1A1 nucleotide sequence as set forth in SEQ ID NO:3 or the EAAT3/EAAC1 amino acid sequence encoded by SEQ ID NO:3 may be used for screening compounds. In another example, compounds are screened by contacting a cell that comprises the SLC1A1 sequence as set forth in SEQ ID NO:4. In other examples, a variant of an SLC1A1 nucleotide sequence or an EAAT3/EAAC1 amino acid sequence can be used to screen for therapeutic compounds or to prepare a therapeutic compound. A variant will be substantially identical to a SLC1A1 nucleotide sequence or an EAAT3/EAAC1 amino acid sequence. The term "substantially identical" is used to describe similarity of sequences. For example, nucleotide sequences or polypeptide sequences that are greater than about 70%, about 80%, about 90% identical to the SLC1A1 coding sequence or the encoded polypeptide, respectively, are contemplated.

To determine whether a nucleic acid exhibits similarity with the sequences presented herein, oligonucleotide alignment algorithms may be used, for example, but not limited to a BLAST (GenBank, using default parameters: Program: blastn; Database: nr; Expect 10; filter: default; Alignment: pairwise; Query genetic Codes: Standard(1)), BLAST2 (EMBL using default parameters: Matrix BLOSUM62; Filter: default, echofilter: on, Expect:10, cutoff: default; Strand: both; Descriptions: 50, Alignments: 50), or FASTA, search, using default parameters. Polypeptide alignment algorithms are also available, for example, without limitation, BLAST 2 Sequences (using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. for at least 1 hour. Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

In testing compounds, the SLC1A1 gene or its related products may be analyzed or quantified according to standard techniques. For example without limitation, expression levels of SLC1A1 mRNA may be measured using Northern analysis or quantitative PCR. Levels of EAAT3/EAAC1 protein may also be measured using standard techniques, for example without limitation, ELISA, immunodiffusion, or other methods that are known to one of skill in the art.

Compounds that are found to affect level or activity of SLC1A1 gene or its related gene products may be used to treat an anxiety disorder in a subject in need of such treatment. Treatments may include pharmaceuticals, gene therapy, antibody therapy, and any other form of therapy known to the skilled person.

The present invention provides a method of diagnosing or identifying susceptibility of a subject to an anxiety disorder comprising:

testing a sample obtained from the subject for the presence of a polymorphism in Intron 10 of the SLC1A1 gene, wherein the presence of allele G of the A/G polymorphism rs301434 indicates that the patient is susceptible to an anxiety disorder.

The present invention also provides a method of diagnosing or identifying susceptibility of a subject to an anxiety disorder comprising:

testing a sample obtained from the subject for the presence of a polymorphism in Intron 10 of the SLC1A1 gene, wherein the presence of allele A of A/G polymorphism rs301435 indicates that the patient is susceptible to an anxiety disorder.

The present invention further provides a method of diagnosing or identifying susceptibility of a subject to an anxiety disorder comprising:

testing a sample obtained from the subject for the presence of a haplotype in the SLC1A1 gene, wherein the combined presence of allele G of the A/G polymorphism rs301434 and allele C of C/G polymorphism rs3087879 indicates that the patient is susceptible to a anxiety disorder.

The present invention also provides a method of diagnosing or identifying susceptibility of a subject to an anxiety disorder such as obsessive compulsive disorder that comprises aggressive obsessions, checking compulsions, symmetry obsessions, ordering compulsions, counting compulsions, repeating compulsions or a combination thereof, the method comprising:

testing a sample obtained from the subject for the presence of a polymorphism in Intron 10 of the SLC1A1 gene, wherein the presence of allele G of the A/G polymorphism rs301434 indicates that the subject is susceptible to an anxiety disorder such as obsessive compulsive disorder that comprises aggressive obsessions, checking compulsions, symmetry obsessions, ordering compulsions, counting compulsions, repeating compulsions or a combination thereof.

The present invention also provides a method of diagnosing or identifying susceptibility of a subject to an anxiety disorder, for example, but not limited to, obsessive compulsive disorder that comprises symmetry obsessions, ordering compulsions, counting compulsions, repeating compulsions or a combination thereof, the method comprising:

testing a sample obtained from the subject for the presence of a polymorphism in Intron 10 of the SLC1A1 gene, wherein the presence of allele A of A/G polymorphism rs301435 indicates that the subject is susceptible to an anxiety disorder such as obsessive compulsive disorder that comprises symmetry obsessions, ordering compulsions, counting compulsions, repeating compulsions or a combination thereof.

The present invention will be further illustrated in the following examples.

EXAMPLES

Example 1

Genotyping of Living Subjects for Possible Association Between SLC1A1 and OCD

The SLC1A1 gene is highly expressed within cerebral cortex, striatum, and thalamus, brain regions which are connected in functional cortico-striatal-thalamic circuits (CSTC's) implicated in OCD (Bronstein Y, Cummings J. Neurochemistry of frontal-subcortical circuits. In: Lichter D, Cummings J, eds. Frontal-subcortical circuits in psychiatric and neurological disorders. New York: Guilford Press; 2001:59-91)

SLC1A1 is a strong functional candidate gene for OCD given the mounting evidence for a role of altered glutamate neurotransmission within CSTC's in the pathogenesis of OCD. Indirect support for this hypothesis is provided by an animal model in which transgenic mice with increased cortico-striatal glutamate output exhibit a phenotype reminiscent of OCD and "OCD spectrum" disorders including generalized behavioral perseveration, compulsive leaping, grooming-associated pulling and biting of skin and hair (similar to trichotillomania), and tics (Nordstrom E J, Burton F H. A transgenic model of comorbid Tourette's syndrome and obsessive-compulsive disorder circuitry. Mol Psychiatry 2002;7:617-25). More direct support for the role of glutamate in OCD is provided by recent investigation using proton magnetic resonance spectroscopy (1-H MRS) suggesting a pharmacologically reversible glutamatergically mediated thalomocortical-striatal dysfunction in OCD (Rosenberg D, MacMaster F, Keshavan M, et al. Decrease in caudate glutamatergic concentrations in pediatric obsessive-compulsive disorder patients taking paroxetine. J Am Acad Child Adolesc Psychiatry 2000;39:1096-1103. Rosenberg D R, Mirza Y, Russell A et al. Reduced anterior cingulate glutamatergic concentrations in childhood OCD and major depression versus healthy controls. J Am Acad Child Adolesc Psychiatry 2004;43:1146-53). In addition to its effects on glutamate levels, EAAT3/EAAC1 and other glutamate transporters are crucial for GABA uptake into neurons. Loss of GABA uptake through either knockdown of SLC1A1 in adult mice or application of glutamate transporter antagonists (Mathews G C, Diamond J S. Neuronal glutamate uptake Contributes to GABA synthesis and inhibitory synaptic strength. J Neurosci 2003;23:2040-8.21) produces demonstrable effects on GABAergic transmission. This glutamate-GABA interaction has potential implications for OCD given the that the gamma-amino-butyric acid type B receptor 1 (GABBR1) gene may be a susceptibility factor in this disorder (Zai G, Arnold P, Burroughs E, et al. Evidence for the gamma-amino-butyric acid type B receptor 1 (GABBR1) gene as a susceptibility factor in obsessive-compulsive disorder. Am J Med Genet B Neuropsychiatr Genet 2005;134:25-9).

Sample Characteristics and Clinical Assessment:

The study was approved by the Research Ethics Board of the Centre for Addiction and Mental Health, Toronto where the research was conducted. After complete description of the study to participants, written informed consent was obtained.

157 probands (138 adults 18 years of age or over, 19 children or adolescents) were recruited from consecutive referrals to the Anxiety Disorders Clinic and the Children's Mood and Anxiety Disorders Service at the Centre for Addiction and Mental Health, Toronto, Ontario, Canada. Families were included in the study only if both biological parents and/or or at least one sibling were willing to participate in the study. Relatives who agreed to participate were assessed using the same methods. Relatives were deemed affected if they met full DSM-IV criteria for OCD, consistent with the narrow phenotype model which produced the strongest linkage findings for 9p24.

All participants were assessed using age-appropriate versions of the Structured Clinical Interview for DSM-IV (SCID), and probands and affected relatives were assessed using age-appropriate versions of the Yale-Brown Obsessive Compulsive Scale (YBOCS). Lifetime severity of symptoms was estimated using highest known lifetime YBOCS score, a retrospective estimate of the time when the most severe OCD symptoms were experienced for two or more consecutive weeks.

Instruments were administered by trained interviewers blind to the genotypes of the probands, and then reviewed by psychiatrists experienced in the diagnosis and treatment of OCD and related conditions to ensure diagnostic accuracy using DSM-IV criteria. Only probands with a confirmed diagnosis of OCD were included. Exclusion criteria included lifetime history of neurologic or metabolic diseases, bipolar disorder, psychotic disorder, or substance dependence.

Genotyping:

Using a non-enzymatic, high salt extraction method genomic DNA was extracted from 20 mL of venous whole blood of OCD probands and family members. Initially, six informative single nucleotide polymorphisms (SNP's) spanning SLC1A1 were selected, based on information derived from the International HapMap project (www.hapmap.org) with the aid of Haploview 3.2 (Barrett J C, Fry B, Mailer J, Daly M J. Haploview: analysis and visualization of LD and haplotype maps. Bioinformatics 2005;21:263-5). The reference sequence numbers and locations of these six SNP's were as follows: SNP1 (rsl980943, Intron 1), SNP2 (rs3780415, Intron 2), SNP3 (rs7856209, Exon 4), SNP4 (rs3780412, Intron 7), SNP5 (rs301430, Exon 10), and SNP7 (rs301434, Intron 10). To narrow down the association signal indicated by initial positive findings at SNP7, the following three additional SNP's were also genotyped: SNP 6 (rs301979, Intron 10) and SNP8 (rs301435, Intron 10) and SNP9 (rs3087879, 3'-untranslated region).

Genotyping was performed using Assays-on-Demand and standard TaqMan methods on the Applied Biosystems (ABI) 7000 sequence detection instrument (Applied Biosystems Inc., Foster City, Calif.), with DNA concentrations of 20 ng/uL. Statistical Analysis: Association between the nine selected polymorphisms of the SLC1A1 gene and OCD was tested using two complementary methods: 1) the Family Based Association Test (FBAT) and the 2) Transmission Disequilibrium Test (TDT) (Spielman R S, McGinnis R E, Ewens W J. Transmission test for linkage disequilibrium: the insulin gene region and insulin-dependent diabetes mellitus (IDDM). Am J Hum Genet 1993;52:506-16) as implemented in the Haploview 3.2 program. FBAT is a unified approach to family-based association testing which was used because it enables analysis of a variety of family structures, both qualitative and quantitative traits, and different models of inheritance using the same framework. The version of FBAT used in this study, version 1.5.5, is available on the world wide web (www.biostat.harvard.edu/~fbat).

Single locus and haplotype analyses were performed in FBAT based on the categorical phenotype of OCD diagnosis and the quantitative phenotype of highest known lifetime YBOCS score. The models of inheritance that were examined are based on the number of copies of an allele required for increased susceptibility and included the additive, dominant and recessive models, defined as follows: 1) additive—one or two copies of a risk allele increases the likelihood of possessing a trait in an additive fashion (i.e. risk with 2 alleles>1 allele>0 alleles), 2) dominant—one or two copies of an allele is associated with an equal likelihood of having a trait, and 3) recessive—two copies of an allele are necessary to increase the likelihood of having a trait. All three models were examined because segregation analyses indicate that OCD is likely due to at least one gene of major effect on a polygenic background, with the mode of inheritance unclear.

Prior to haplotype testing, the Tagger subroutine on Haploview 3.2 was implemented to select tag SNPs. Tag SNPs are SNPs which predict the variation in other SNPs within the same haplotype block with a high degree of certainty. To minimize the redundancy resulting from testing highly correlated SNPs and the potential loss of power resulting from testing multiple low-frequency haplotypes, only haplotypes consisting of tag SNPs within the same haplotype block were tested. As a further check against multiple testing, a two-stage procedure was employed when using the HBAT routine of FBAT: 1) the omnibus test was performed followed by 2) testing individual haplotypes if the omnibus test was statistically significant.

All tests were performed based on the compound null hypothesis of no linkage and no association between the phenotype and the genetic variant. The asymptotic variance option was used in FBAT for calculation of z-scores from which the p values were derived, with a set to 0.05. Because construction of the standardized z score is based on a normal approximation, analyses in which there were less than 10 informative families were excluded from consideration in order to minimize violation of normality due to small sample sizes. A secondary FBAT analyses was performed based on 1) presence of an affected proband and/or sibling with early onset of symptoms (less than 15 years of age), and 2) gender of the proband. Data was split according to gender with the aid of the PedSplit program (Lanktree M B, VanderBeek L, Macciardi F M, Kennedy J L. PedSplit: pedigree management for stratified analysis. Bioinformatics 2004;20:2315-6).

Genetic associations were also tested using the TDT option as implemented in Haploview. In contrast to FBAT, only complete trios (including transmissions to affected siblings) are analyzed in this version of TDT. However, Haploview was used in addition to FBAT as this program includes an option for permutation testing for both single markers and haplotypes. Single marker and haplotypes within blocks were tested for 100000 permutations, resulting in a corrected p value based on the number of permutations in which the chi square value exceeded the observed chi square. Linkage disequilibrium information was obtained from Haploview, including D' values and the haplotype block structure. Hardy-Weinberg equilibrium was also analyzed using the Haploview program.

Results:

A total of 476 individuals in 157 families were genotyped. There were 157 probands (97 females and 60 males) and 49 affected relatives (including 34 females and 15 males) in our sample, for a total of 206 affected individuals. A total of 270 unaffected family members were genotyped. Family structures were varied and included: 72 simple proband-parent trios, 39 sibships containing a proband plus one or more siblings (19 containing at least 1 affected individual), 21 nuclear families with a parent-proband trio plus one or more siblings (4 containing at least 1 affected individual), and 25 sibships plus one parent (5 containing at least affected sibling). The ethnic background of the families was 96% Caucasian.

TABLE 1

D' values between nine polymorphisms on SLC1A1

|      | SNP1 | SNP2 | SNP3  | SNP4 | SNP5 | SNP6 | SNP7 | SNP8 |
|------|------|------|-------|------|------|------|------|------|
| SNP2 | 0.17 |      |       |      |      |      |      |      |
| SNP3 | 0.14 | 0.25 |       |      |      |      |      |      |
| SNP4 | 0.14 | 0.25 | 0.99* |      |      |      |      |      |
| SNP5 | 0.04 | 0.03 | 0.56  | 0.46 |      |      |      |      |
| SNP6 | 0.33 | 0.24 | 0.86  | 0.81 | 0.12 |      |      |      |
| SNP7 | 0.22 | 0.01 | 0.38  | 0.39 | 0.00 | 0.67 |      |      |
| SNP8 | 0.23 | 0.02 | 0.39  | 0.40 | 0.02 | 0.66 | 1.00 |      |
| SNP9 | 0.17 | 0.09 | 0.57  | 0.60 | 0.79 | 0.83 | 0.96 | 0.98 |

*Bolded values indicate haplotype blocks

Genotype frequencies in offspring did not differ significantly from Hardy-Weinberg equilibrium for any of the 9 SNPs. The degree of linkage disequilibrium between the 9 polymorphisms is depicted using D' values in Table 1. The highest D' values were between SNPs 3 and 4 (d'=0.99), and between SNPs 7, 8 and 9 (d'=0.96 to 1.00). Analysis using Haploview 3.2 indicated that these two clusters of SNPs constitute two distinct haplotype blocks. However, results from running the Tagger subroutine indicated that SNP3 adequately covered the allelic variation in Block 1, and that SNP7 and SNP9 were tag SNPs for Block 2. Therefore, haplotype analyses were only performed using combinations of SNP7 and SNP9.

The results of FBAT single-locus analyses are shown in Tables 2 for the additive model. There was a significant association with OCD diagnosis for SNP7 (rs301434), SNP8 (rs301435) and SNP9 (rs3087879). The most highly significant association was with SNP7, with increased transmission of allele G under the additive model (z=3.39, p=0.0007). Increased transmission of allele G was also found under the recessive model (z=3.68, p=0.0002); whereas significantly decreased transmission of allele A was seen under the additive (z=−3.39, p=0.0007) and dominant (z=−3.58, p=0.0002) models.

TABLE 2

Results of the FBAT Analysis of SLC1A1 Polymorphisms: Additive Model

| Polymorphism | Allele (frequency) | Families[a] | S[b] | E (S)[c] | Z score[d] | P value[e] |
|---|---|---|---|---|---|---|
| SNP1 | C (0.64) | 77 | 102.0 | 99.5 | 0.48 | 0.63 |
| (rs1980943) | T (0.36) | 77 | 70.0 | 72.5 | −0.48 | 0.63 |
| SNP2 | A (0.57) | 84 | 100.0 | 104.0 | −0.74 | 0.46 |
| (rs3780415) | G (0.43) | 84 | 86.0 | 82.0 | 0.74 | 0.46 |
| SNP3 | C (0.58) | 88 | 107.0 | 107.0 | −0.00 | 1.00 |
| (rs7856209) | T (0.42) | 88 | 87.0 | 87.0 | 0.00 | 1.00 |
| SNP4 | A (0.45) | 91 | 107.0 | 105.0 | 0.26 | 0.80 |
| (rs3780412) | G (0.55) | 91 | 95.0 | 96.5 | −0.26 | 0.80 |
| SNP5 | A (0.74) | 76 | 106.0 | 104.0 | 0.41 | 0.68 |
| (rs301430) | G (0.26) | 76 | 56.0 | 58.0 | −0.41 | 0.68 |
| SNP6 | C (0.39) | 71 | 73.0 | 69.5 | 0.69 | 0.49 |
| (rs301979) | G (0.61) | 71 | 87.0 | 90.5 | −0.69 | 0.49 |
| SNP7 | A (0.43) | 84 | 66.0 | 84.0 | −3.39 | 0.0007* |
| (rs301434) | G (0.57) | 84 | 114.0 | 96.0 | 3.39 | 0.0007* |
| SNP8 | A (0.54) | 79 | 105.0 | 87.5 | 3.32 | 0.0009* |
| (rs301435) | G (0.46) | 79 | 65.0 | 82.5 | −3.32 | 0.0009* |
| SNP9 | C (0.65) | 76 | 115.0 | 101.0 | 2.74 | 0.006* |
| (rs3087879) | G (0.35) | 76 | 51.0 | 65.0 | −2.74 | 0.006* |

[a]Number of informative families (i.e. families with a non-zero contribution to the test statistic) Analyses not performed if <10 informative families;
[b]Test statistic for observed number of alleles;
[c]Expected value of S under null hypothesis;
[d]z = (S − E(S))/root(var(S));
[e]Two tailed.
*Results significant at p < .05).

Omnibus haplotype testing for SNP7 and SNP9 (Block 2) indicated that this haplotype block was significantly associated with OCD. With respect to individual haplotypes, increased transmission of G-C was found under both the additive (z=3.43, p=0.0006) and recessive (z=3.53, p=0.0004) models; whereas there was a weaker yet still statistically significant association with decreased transmission of the A-G haplotype under the additive (z=−2.23, p=0.03) and dominant (z=−2.03, p=0.04) models (Table 3).

TABLE 3

HBAT Analysis of SNP7 and SNP9

| Model of Inheritance | Haplotype (frequency) | Families[a] | S[b] | E (S)[c] | Z score[d] | P value[e] |
|---|---|---|---|---|---|---|
| Additive | G-C (0.52) | 77.0 | 142.8 | 124.4 | 3.43 | 0.0006* |
| | A-G (0.34) | 71.0 | 76.8 | 88.2 | -2.23 | 0.03* |
| | A-C (0.12) | 40.0 | 24.2 | 29.6 | -1.65 | 0.10 |
| Omnibus test: $\chi^2 = 13.8$ (3 df, p = 0.003*) | | | | | | |
| Dominant | G-C (0.52) | 45.9 | 97.8 | 91.8 | 1.87 | 0.06 |
| | A-G (0.34) | 57.9 | 63.8 | 71.6 | -2.03 | 0.04* |
| | A-C (0.12) | 38.0 | 24.2 | 28.2 | -1.31 | 0.19 |
| Omnibus test: chisq = 8.12 (3 df, p = 0.04) | | | | | | |
| Recessive | G-C (0.52) | 47.0 | 45.0 | 32.6 | 3.53 | 0.0004* |
| | A-G (0.34) | 26.0 | 13.0 | 16.7 | -1.43 | 0.15 |
| Omnibus test: $\chi^2 = 13.0$ (2 df, p = 0.001*) | | | | | | |

[a],[b],[c],[d],[e],*footnotes same as for Table 2

Analysis of the quantitative trait of highest lifetime symptom severity (total YBOCS score) under the additive model also resulted in a statistically significant association with SNP7 (allele G, z=2.58, p=0.01). Furthermore, omnibus testing using HBAT resulted in a statistically significant association for this block. Lifetime YBOCS scores were associated with increased transmission of the G-C haplotype under the additive (z=2.81, p=0.005) and dominant (z=2.26, p=0.02) models; whereas decreased transmission of the A-C haplotype was found under both the additive (z=-2.36, p=0.02) and dominant (z=-2.07, p=0.04).

Secondary analyses were performed on the subsets of families in which the probands had an age of symptom onset known to be less than 15 years of age (early onset) or greater than or equal to 15 years of age (late onset). Reliable age of onset data was available on 116 of 158 nuclear families (77 early onset, 42 late onset). Analysis of the families containing offspring with early onset symptoms resulted in a positive association with the SNP7-G allele on FBAT analysis (z=2.46, p=0.01), whereas analysis of families without early onset offspring resulted in no statistically significant findings.

Separate analyses of transmissions to male (83 families) and female (118 families) probands or sibs were also performed. As shown in Table 4, these analyses revealed an association with OCD diagnosis for SNP7 (z=3.1, p=0.002), SNP8 (z=3.24, p=0.001) and SNP9 (z=3.1, p=0.002) in families of male affected offspring (under the additive model). Haplotype testing of transmissions to male offspring resulted in a significant result for omnibus testing of the SNP7-SNP9 block, with increased transmission of G-C (z=3.29, p=0.001) and decreased transmission of A-G (z=-3.14, p=0.002) to male offspring. There was a trend towards increased transmission of SNP7 and the G-C haplotype (z=1.66, p=0.10) (z=-1.65, p=0.099) to female offspring, but no statistically significant single locus or haplotypic associations.

TABLE 4

HBAT Analysis of Haplotype Block 2: Males and Female Offspring: Additive Model

| Sex | Haplotype (frequency) | Families[a] | S[b] | E (S)[c] | Z score[d] | P value[e] |
|---|---|---|---|---|---|---|
| Male | G-C (0.56) | 22.0 | 42.0 | 34.0 | 3.29 | 0.001* |
| | A-G (0.29) | 20.0 | 13.0 | 20.0 | -3.14 | 0.002* |
| | A-G (0.14) | 15.0 | 7.0 | 8.0 | -0.51 | 0.61 |
| Omnibus test: $\chi^2 = 12.6$ (3 df, p = 0.006*) | | | | | | |
| Female | G-C (0.52) | 47.0 | 80.9 | 73.7 | 1.66 | 0.10 |
| | A-G (0.38) | 45.0 | 53.9 | 56.4 | -0.58 | 0.56 |
| | A-C (0.10) | 20.0 | 13.1 | 16.3 | -1.34 | 0.17 |
| Omnibus test: $\chi^2 = 6.07$ (3 df, p = 0.10) | | | | | | |

[a],[b],[c],[d],[e],*footnotes same as for Table 2

Finally, TDT analysis was performed using Haploview followed by permutation testing. Results from the whole sample and analysis of transmissions to male offspring are reported in Table 5. For the whole sample, the strongest result was for the SNP7-SNP9 haplotype block, in which only 510 out of 100000 permutations of the data resulted in a $\chi^2$ value greater than the observed $\chi^2$ of 12.60 (p=0.005), and for SNP7 ($\chi^2$=10.49, p=0.006). For transmissions to males, empirical p values were statistically significant for SNP7 (chi square=10.31, p=0.01), the C-G haplotype ($\chi^2$=9.39, p=0.02), and SNP9 (chi square=8.76, p=0.03).

TABLE 5

Permutation Testing of SLC1A1 Polymorphisms: Results After 100000 Permutations

| Sample | Polymorphism or Haplotype | $\chi^2$ (from TDT)[a] | Permutation P value[b] |
|---|---|---|---|
| Whole sample | G-C (Block 2) | 12.60 | 0.005 |
| | SNP7 (rs301434) | 12.04 | 0.006 |
| | A-C (Block 2) | 5.63 | 0.19 |
| | SNP9 (rs3087879) | 5.19 | 0.22 |
| | A-G (Block 2) | 4.35 | 0.32 |
| Male Offspring | SNP7 (rs301434) | 10.31 | 0.01 |
| | G-C (Block 2) | 9.39 | 0.02 |
| | SNP9 (rs3087879) | 8.76 | 0.03 |
| | A-G (Block 2) | 7.22 | 0.05 |

[a]TDT = Transmission Disequilibrium Test
[b]Empirical p value based on number of times chi square values exceed observed $\chi^2$ in 100000 permutations. All other results were not statistically significant based on corrected p values < .05.

Example 1, thus, shows a significant association between three tightly linked polymorphisms lying within the same haplotype block of SLC1A1 and OCD. Furthermore, a common haplotype (C-G) of Tag SNPs (SNPs 7 and 9) in this block was also positively associated with OCD diagnosis under the additive and recessive models of inheritance in FBAT. When tested using TDT as implemented in Haploview, the association with the G-C haplotype and SNP7 (rs301434) remained highly significant even after correction from permutation testing was applied. This haplotype also appeared to be associated with the quantitative score of lifetime symptom severity in OCD-affected individuals.

Gregory Hanna and colleagues have recently found evidence of association to rs3780412 and rs301430 in an independent sample of families derived from early onset probands. Although association with these two SNPs was not replicated in this study, it is interesting to note that rs301430 is in modest linkage disequilibrium with SNP9 (D'=0.79), lying within the haplotype block associated with OCD in this study.

The fact that the most significant haplotype association was only found under the additive and recessive models is contrary to expectation based on linkage findings in 9p24, in which findings were found only under the dominant model. It should also be noted that as expected there was an increased number of informative families under the additive model as opposed the dominant/recessive models of inheritance, resulting in more statistical power based on additive assumptions. The authors of the FBAT program have noted that an assumption of an additive model is appropriate under most circumstances unless there is very compelling evidence for a dominant/recessive model (personal communication, N. Laird, FBAT course, January 2005), and results shown here are consistent with this.

Another finding from this study, not predicted a priori, was that the association between the G-C haplotype and OCD was more significant in transmissions to male, than female, offspring. This finding occurred despite the smaller sample size of transmissions to male compared with female OCD-affected offspring. This finding is consistent with sex-specific genetic effects for complex behavioral traits reported in humans and model organisms (Anholt R R, Mackay T F. Quantitative genetic analyses of complex behaviours in *Drosophila*. Nat Rev Genet 2004; 5:838-49) and also are consistent with evidence of gender dimorphism of clinical features of OCD (Zohar J, Gross-Isseroff R, Hermesh H, Weizman A. Is there sexual dimorphism in obsessive-compulsive disorder? Neurosci Biobehav Rev 1999;23:845-9). For example, males are believed to have an earlier onset of OCD and a higher likelihood of having comorbid tics or prominent symmetry/ordering symptoms. Furthermore, a segregation analysis of OCD found significant differences in the inheritance of OCD (Nestadt G, Lan T, Samuels J et al. Complex segregation analysis provides compelling evidence for a major gene underlying obsessive-compulsive disorder and for heterogeneity by sex. Am J Hum Genet 2000;67:1611-6).

Secondary analysis of transmissions to early versus late onset probands indicated a weak association within only the early onset group, which was not significant following permutation testing using the Haploview program. However, interpretation of these findings is limited both by the missing age-of-onset data in 26% of our families and the relatively small number of families with only late-onset offspring.

SNP9 is located in the 3'-untranslated region of the gene, a location that is known (Conne B, Stutz A, Vassalli J D. The 3' untranslated region of messenger RNA: A molecular 'hotspot' for pathology? Nat Med 2000;6:637-41) to produce changes in messenger RNA (mRNA) processing and thereby may affect the quantity of the EAAC1 protein. Further genotyping of additional polymorphisms in the 3'-UTR region may uncover other association signals. Additionally, further association SNPs may be located in either Exon 11 or 12 which appear to lie within the same haplotype block according to the HapMap data. However, no SNPs in the coding regions of Exons 11 or 12 are available in public databases and none were identified when SLC1A1 was sequenced in seven OCD subjects (Veenstra-VanderWeele J, Kim S J, Gonen D, et al. Genomic organization of the SLC1A1/EAAC1 gene and mutation screening in early-onset obsessive-compulsive disorder. Mol Psychiatry 2001; 6:160-7).

In summary, a positive association was found between the neuronal glutamate transporter gene SLC1A1 and OCD, a finding which remained statistically significant even after permutation testing. This association was statistically significant in transmissions to male offspring. The likelihood that variation within SLC1A1 affects risk for OCD is enhanced given the putative role of glutamate in OCD pathogenesis based on preclinical, neuroimaging and candidate gene studies.

Example 2

Treatment of an Anxiety Disorder

EAAT3 (EAAC 1) protein encoded by SLC1A1 may represent an important functional candidate gene in OCD studies. EAAT3 is one of five sodium-dependent glutamate transporters (GluTs), but is the the only glutamate transporter located primarily on post-synaptic neuronal membranes, where it is most concentrated in the perisynaptic region and in dendritic spines. By virtue of this localization in close proximity to post-synaptic glutamate receptors, EAAT3 may act to fine-tune glutamate concentrations near post-synaptic neurotransmitters. Furthermore, EAAT3 may facilitate more efficient neurotransmission through preventing glutamate from spilling over to neighbouring synapses. This model is given added plausibility by the high expression of SLC1A1 in areas of the brain implicated in the pathogenesis of OCD, including the cerebral cortex, striatum, and thalamus.

Knockout of the SLC1A1 gene in mice produces dicarboxylic aciduria due to its effects on renal tubules. The only apparent neurological abnormality in the SLC1A1-null mouse is reduced open-field activity (Peghini et al., 1997), a behavioral abnormality which has been used as a rodent model for fearfulness (Talbot et al., 1999). This observation has interesting implications for OCD given the prominent anxiety typically seen in the disorder.

Treatment Considerations:

Given the hyperactive cortico-striatal glutamatergic neurotransmission model, variants in SLC1A1 could lead to altered glutamatergic neurotransmission and associated vulnerability to developing OCD symptoms. One possible mechanism would be decreased levels of the EAAT3 protein leading to decreased neuronal glutamate uptake.

A recent open-label trial of riluzole suggests that modulation of glutamatergic neurotransmission may have therapeutic benefits in OCD (Coric et al., 2005). Riluzole reduces glutamate neurotransmission in a variety of ways, most directly through inhibiting glutamate release. Topiramate, which inhibits glutamate action at AMPA/kainate receptors, was found to be effective in the treatment of OCD in an open trial of augmentation of serotonin reuptake inhibitors (Van Amerigen et al., 2005). Lamotrigine, an anticonvulsant which blocks glutamate release, was found not to be effective in a small study of eight treatment-refractory OCD patients, (Kumar & Khanna, 2000). This drug warrants further study given the methodological limitations of the study including small sample size and low doses of lamotrigine compared with trials in other psychiatric disorders.

In a putative mouse model of OCD, a metabotropic glutamate receptor antagonist was found to be effective in reducing compulsive marble-burying (Shimizaki et al., 2004). A recent review also suggested agents modifying metabotropic glutamate receptors may be effective in treatment of anxiety disorders including OCD (Marino & Conn, 2002). In contrast the NMDA antagonist MK-801, which indirectly stimulates cortico-striatal glutamate release, was noted to increase compulsive behaviours in a transgenic mouse model of OCD (McGrath et al., 2000).

Possible changes in mRNA function may be predicted "in silico" based on the variants that have been found to be associated with OCD. The less common variant of SNP 9 (rs3087879) produced a significant change in predicted mRNA secondary structure. This may have an effect on mRNA stability and/or translational efficiency. In vitro experiments can be carried out to confirm this result.

The SLC1A1 gene, or its related gene products may be a target for therapy in OCD and other anxiety disorders. Standard assays may be used to identify compounds that modulate SLC1A1 function, and suitable medicaments comprising these compounds may be prepared for use in treating an anxiety disorder.

Example 3

Using Symptom Subtypes to Investigate SLC1A1 in OCD

Like all complex genetic disorders, OCD is believed to be a highly heterogeneous disorder and phenotypic heterogeneity of OCD greatly complicates the search for susceptibility genes (46). Phenotypic heterogeneity has begun to be addressed through examination of specific factors generated by analyses of the Yale-Brown Obsessive Compulsive Scale (28). Although there have been minor differences with regard to the symptoms contained in each factor, multiple factor analyses of adult samples have consistently identified three to five symptom dimensions, which have been associated with distinct neurobiological profiles and differential treatment response (reviewed in (44)). There is also evidence that symptom dimensions are quite temporally stable, with changes in symptoms typically occurring within rather than between dimensions (48). It has recently been demonstrated that the factor structure of children with OCD based on the Children's Yale-Brown Obsessive Compulsive Scale (CY-BOCS; (29)) scale is remarkably similar to that in adults (49).

Family and segregation analyses have demonstrated that OCD symptom dimensions have distinct genetic correlates and patterns of inheritance (34, 50-55). In a genome scan of 77 sib pairs affected with Tourette's Syndrome (TS), the phenotype of hoarding was linked with the chromosomal regions 4q (in close proximity to a region previously linked to TS), 15q, and 17q (56). These results strongly suggest that classifying subjects according to symptom type is a useful strategy for gene localization in association and linkage studies of OCD.

This study was performed to determine if SLC1A1 polymorphisms associated with OCD were also associated with specific OCD symptom subgroups.

Methods:

Sample Characteristics and Clinical Assessment:

The study was approved by the Research Ethics Board of the Centre for Addiction and Mental Health, Toronto where the research was conducted. After complete description of the study to participants, written informed consent was obtained. The sample consisted of 160 nuclear families of OCD probands and their relatives collected from two outpatient clinics at the Centre for Addiction and Mental Health: the Anxiety Disorders Clinic and the Children's Mood and Anxiety Disorders Service. The sample was essentially the same as that described in Example 1 with three additional families.

All probands and affected relatives were assessed using age-appropriate versions of the Yale-Brown Obsessive Compulsive Scale (YBOCS) (28, 29). The YBOCS symptom was used to determine lifetime history of symptoms within the four symptom dimensions first identified by Leckman and colleagues (57) and subsequently confirmed by our group (34) using factor analytic methods. Affected individuals were coded as to whether they endorsed target symptoms within the following symptom dimensions: 1) Factor 1 (aggressive, sexual, religious and somatic obsessions; checking compulsions), 2) Factor 2 (symmetry obsessions; repeating, counting and ordering compulsions), 3) Factor 3 (Contamination obsessions, washing compulsions), 4) Factor 4 (Hoarding obsessions and compulsions. All assessment materials were reviewed by psychiatrists experienced in the diagnosis and treatment of OCD and related conditions to ensure diagnostic accuracy.

Genotyping:

Genotyping methods are as described previously in Example 1. We studied the same nine single nucleotide polymorphisms (SNPs) described previously for association with symptom subgroups: SNPI (rsl980943, Intron 1), SNP2 (rs3780415, Intron 2), SNP3 (rs7856209, Exon 4), SNP4 (rs3780412, Intron 7), SNP5 (rs301430, Exon 10), SNP 6 (rs301979, Intron 10), SNP7 (rs301434, Intron 10), SNP8 (rs301435, Intron 10) and SNP9 (rs3087879, 3'-untranslated region).

Statistical Analysis:

We tested for association using the Family Based Association Test (FBAT). FBAT is a unified approach to family-based association testing which enables analysis of various family structures, qualitative and quantitative traits, and different models of inheritance using the same framework (33). The version of FBAT used in this study, version 1.7.2, is available on the world wide web (www.biostat.harvard.edu/~fbat). Single locus and analyses were based on the categorical phenotype of OCD diagnosis and the quantitative phenotype of highest known lifetime YBOCS score. Additive, dominant and recessive models of inheritance were examined.

All tests were performed based on the compound null hypothesis of no linkage and no association between the phenotype and the genetic variant. The $\alpha$ threshold was set to 0.01 based on a Bonferroni correction for the five phenotypes assessed in this and the previous study (phenotypes including OCD diagnosis and the four symptom factors). Because construction of the standardized z score is based on a normal approximation, analyses in which there were less than 10 informative families were excluded from consideration in order to minimize violation of normality due to small sample sizes. Only the additive model of inheritance was used given our earlier results of association between SLC1A1 variation and OCD diagnosis that was strongest under the additive model (59).

Results:

Demographic information regarding the sample is described in detail in Example 1 and Arnold et al (59). Out of 152 participants for whom we had information regarding target symptoms, the proportion of individuals endorsing target symptoms within the four symptom dimensions was as follows : Factor 1 (Obsessions/checking, 71.4%), Factor 2 (Symmetry/ordering, 54.6%), Factor 3 (Contamination/cleaning, 48.0%), Factor 4 (Hoarding, 17.1%). Categorization into symptom dimensions did not significantly differ between male and female participants (Factor 1 $\chi2=0.14$, p=0.71; Factor 2 $\chi2=0.03$, p=0.87; Factor 3 $\chi2=0.43$, p=0.51; Factor 4 $\chi2=0.12$, p=.73).

Genotype frequencies did not significantly differ from Hardy-Weinberg equilibrium for any of the nine polymorphisms tested. Previous linkage disequilibrium analysis revealed that the highest D' values were between SNPs 3 and 4 (d'=0.99), and between SNPs 7, 8 and 9 (d'=0.96 to 1.00).

Results for analysis of the nine selected polymorphisms for their association with the four symptom subtypes are summarized in Tables 6 to 9:

TABLE 6

FBAT Analysis of Obsessions/Checking and SLC1A1 Polymorphisms

| Polymorphism | Allele (frequency) | Families[a] | Z score[b] | P value[c] |
|---|---|---|---|---|
| SNP1 (rs1980943) | C (0.64) | 42 | 0.09 | 0.93 |
|  | T (0.36) | 42 | −0.09 | 0.93 |
| SNP2 (rs3780415) | A (0.55) | 55 | −0.32 | 0.75 |
|  | G (0.45) | 55 | 0.32 | 0.75 |
| SNP3 (rs7856209) | C (0.55) | 54 | −0.46 | 0.65 |
|  | T (0.45) | 54 | 0.46 | 0.65 |
| SNP4 (rs3780412) | A (0.53) | 53 | −0.50 | 0.62 |
|  | G (0.47) | 53 | 0.50 | 0.62 |
| SNP5 (rs301430) | A (0.71) | 47 | −0.65 | 0.52 |
|  | G (0.29) | 47 | 0.65 | 0.52 |
| SNP6 (rs301979) | C (0.30) | 39 | 1.37 | 0.17 |
|  | G (0.70) | 39 | −1.37 | 0.17 |
| SNP7 (rs301434) | A (0.47) | 46 | −2.62 | 0.009* |
|  | G (0.53) | 46 | 2.62 | 0.009* |
| SNP8 (rs301435) | A (0.51) | 40 | 2.12 | 0.03 |
|  | G (0.49) | 40 | −2.12 | 0.03 |
| SNP9 (rs3087879) | C (0.63) | 47 | 2.19 | 0.03 |
|  | G (0.37) | 47 | −2.29 | 0.03 |

[a]Number of informative families (i.e. families with a non-zero contribution to the test statistic) Analyses not performed if <10 informative families;
[b]z = (S − E(S))/√(var(S)), where S = Test statistic for observed number of alleles;
[c]Two tailed.
*Results significant at p < .01).

TABLE 7

FBAT Analysis of Symmetry/Ordering and SLC1A1 Polymorphisms

| Polymorphism | Allele (frequency) | Families[a] | Z score[b] | P value[c] |
|---|---|---|---|---|
| SNP1 (rs1980943) | C (0.63) | 34 | −0.38 | 0.71 |
|  | T (0.37) | 34 | 0.38 | 0.71 |
| SNP2 (rs3780415) | A (0.55) | 42 | 0.00 | 1.00 |
|  | G (0.45) | 42 | 0.00 | 1.00 |
| SNP3 (rs7856209) | C (0.56) | 49 | 0.29 | 0.77 |
|  | T (0.44) | 49 | −0.29 | 0.77 |
| SNP4 (rs3780412) | A (0.54) | 50 | 0.55 | 0.58 |
|  | G (0.46) | 50 | −0.55 | 0.58 |
| SNP5 (rs301430) | A (0.73) | 37 | −0.73 | 0.46 |
|  | G (0.27) | 37 | 0.73 | 0.46 |
| SNP6 (rs301979) | C (0.32) | 29 | 2.05 | 0.04 |
|  | G (0.68) | 29 | −2.05 | 0.04 |
| SNP7 (rs301434) | A (0.48) | 41 | −3.78 | 0.0002* |
|  | G (0.52) | 41 | 3.78 | 0.0002* |
| SNP8 (rs301435) | A (0.51) | 36 | 3.16 | 0.001* |
|  | G (0.49) | 36 | −3.16 | 0.001* |
| SNP9 (rs3087879) | C (0.63) | 36 | 2.29 | 0.02 |
|  | G (0.37) | 36 | −2.29 | 0.02 |

[a]Number of informative families (i.e. families with a non-zero contribution to the test statistic) Analyses not performed if <10 informative families;
[b]z = (S − E(S))/√(var(S)), where S = Test statistic for observed number of alleles;
[c]Two tailed.
*Results significant at p < .01).

TABLE 8

FBAT Analysis of Contamination/Cleaning and SLC1A1 Polymorphisms

| Polymorphism | Allele (frequency) | Families[a] | Z score[b] | P value[c] |
|---|---|---|---|---|
| SNP1 (rs1980943) | C (0.63) | 31 | 0.16 | 0.87 |
|  | T (0.37) | 31 | −0.16 | 0.87 |
| SNP2 (rs3780415) | A (0.55) | 40 | 0.23 | 0.82 |
|  | G (0.45) | 40 | −0.23 | 0.82 |
| SNP3 (rs7856209) | C (0.56) | 41 | −1.17 | 0.24 |
|  | T (0.44) | 41 | 1.17 | 0.24 |
| SNP4 (rs3780412) | A (0.54) | 38 | −1.76 | 0.08 |
|  | G (0.46) | 38 | 1.76 | 0.08 |
| SNP5 (rs301430) | A (0.73) | 32 | 1.46 | 0.14 |
|  | G (0.27) | 32 | −1.46 | 0.14 |
| SNP6 (rs301979) | C (0.32) | 31 | 0.90 | 0.37 |
|  | G (0.68) | 31 | −0.90 | 0.37 |
| SNP7 (rs301434) | A (0.48) | 36 | −1.31 | 0.19 |
|  | G (0.52) | 36 | 1.31 | 0.19 |
| SNP8 (rs301435) | A (0.51) | 33 | 1.11 | 0.27 |
|  | G (0.49) | 33 | −1.11 | 0.27 |
| SNP9 (rs3087879) | C (0.63) | 32 | −0.15 | 0.88 |
|  | G (0.37) | 32 | 0.15 | 0.88 |

[a]Number of informative families (i.e. families with a non-zero contribution to the test statistic) Analyses not performed if <10 informative families;
[b]z = (S − E(S))/√(var(S)), where S = Test statistic for observed number of alleles;
[c]Two tailed.
*Results significant at p < .01).

TABLE 9

FBAT Analysis of Hoarding and SLC1A1 Polymorphisms

| Polymorphism | Allele (frequency) | Families[a] | Z score[b] | P value[c] |
|---|---|---|---|---|
| SNP1 (rs1980943) | C (0.63) | 11 | −1.42 | 0.16 |
|  | T (0.37) | 11 | 1.42 | 0.16 |
| SNP2 (rs3780415) | A (0.55) | 13 | −1.14 | 0.26 |
|  | G (0.45) | 13 | 1.14 | 0.26 |
| SNP3 (rs7856209) | C (0.56) | 13 | −1.00 | 0.32 |
|  | T (0.44) | 13 | 1.00 | 0.32 |
| SNP4 (rs3780412) | A (0.54) | 13 | −0.80 | 0.42 |
|  | G (0.46) | 13 | 0.80 | 0.42 |
| SNP5 (rs301430) | A (0.73) | 12 | −1.09 | 0.28 |
|  | G (0.27) | 12 | 1.09 | 0.28 |
| SNP6 (rs301979) | C (0.32) | 10 | −1.36 | 0.17 |
|  | G (0.68) | 10 | 1.36 | 0.17 |
| SNP7 (rs301434) | A (0.48) | 14 | 0.89 | 0.37 |
|  | G (0.52) | 14 | −0.89 | 0.37 |
| SNP8 (rs301435) | A (0.51) | 14 | −0.89 | 0.37 |
|  | G (0.49) | 14 | 0.89 | 0.37 |
| SNP9 (rs3087879) | C (0.63) | 13 | −1.22 | 0.22 |
|  | G (0.37) | 13 | 1.22 | 0.22 |

[a]Number of informative families (i.e. families with a non-zero contribution to the test statistic) Analyses not performed if <10 informative families;
[b]z = (S − E(S))/√(var(S)), where S = Test statistic for observed number of alleles;
[c]Two tailed.
*Results significant at p < .01).

The rs301434 variant, previously associated with OCD diagnosis, was found to be associated with Obsessions/checking (p=0.009) and Symmetry/ordering (p=0.0002). Another statistically significant association found, after correction for multiple phenotypes tested, was for rs301435, which is in complete linkage disequilibrium with rs301434.

All references are hereby incorporated by reference.

REFERENCES

1. Rasmussen S A, Eisen J L. The epidemiology and differential diagnosis of obsessive compulsive disorder. J Clin Psychiatry 1994;55:5-10; discussion 11-4.
2. Murray C, Lopez A. Global burden of disease: a comprehensive assessment of mortality and morbidity from diseases, injuries and risk factors in 1990 and projected to 2020. 1 vol: Harvard: WHO; 1996.
3. Nestadt G, Samuels J, Riddle M et al. A family study of obsessive-compulsive disorder. Arch Gen Psychiatry 2000;57:358-363.
4. Pauls D, Alsobrook J, Goodman W, Rasmussen S, Leckman J. A family study of obsessive-compulsive disorder. Am J Psychiatry 1995;152:76-84.
5. Hettema J M, Neale M C, Kendler K S. A review and meta-analysis of the genetic epidemiology of anxiety disorders. Am J Psychiatry 2001;158:1568-78.
6. Carey G, Gottesman I. Twin and family studies of anxiety, phobic and obsessive disorders. In: Klein D, Rabkin J, eds. Anxiety: new research and changing concepts. New York: Raven Press; 1981.
7. Inouye E. Similar and dissimilar manifestations of obsessive-compulsive neurosis in monozygotic twins. Am J Psychiatry 1965;121:1171-1175.
8. Hanna G L, Veenstra-VanderWeele J, Cox N J et al. Genome-wide linkage analysis of families with obsessive-compulsive disorder ascertained through pediatric probands. Am J Med Genet 2002;114:541-52.
9. Willour V L, Yao Shugart Y, Samuels J et al. Replication study supports evidence for linkage to 9p24 in obsessive-compulsive disorder. Am J Hum Genet 2004;75:508-13.
10. Kanai Y, Hediger M A. The glutamate/neutral amino acid transporter family SLC1: molecular, physiological and pharmacological aspects. Pflugers Arch 2004;447:469-79.
11. Bronstein Y, Cummings J. Neurochemistry of frontal-subcortical circuits. In: Lichter D, Cummings J, eds. Frontal-subcortical circuits in psychiatric and neurological disorders. New York: Guilford Press; 2001:59-91.
12. Shigeri Y, Seal R P, Shimamoto K. Molecular pharmacology of glutamate transporters, EAATs and VGLUTs. Brain Res Brain Res Rev 2004;45:250-65.
13. Huang Y H, Bergles D E. Glutamate transporters bring competition to the synapse. Curr Opin Neurobiol 200;14:346-52.
14. Rosenberg D, Keshavan M. Toward a neurodevelopmental model of obsessive-compulsive disorder. Biol Psychiatry 1998;43:623-640.
15. Phillips K A. The obsessive-compulsive spectrums. Psychiatr Clin North Am 2002;25:791-809.
16. Nordstrom E J, Burton F H. A transgenic model of comorbid Tourette's syndrome and obsessive-compulsive disorder circuitry. Mol Psychiatry 2002;7:617-25.
17. Rosenberg D, MacMaster F, Keshavan M, Fitzgerald K, Stewart C, Moore G. Decrease in caudate glutamatergic concentrations in pediatric obsessive-compulsive disorder patients taking paroxetine. J Am Acad Child Adolesc Psychiatry 2000;39:1096-1103.
18. Rosenberg D R, Mirza Y, Russell A et al. Reduced anterior cingulate glutamatergic concentrations in childhood OCD and major depression versus healthy controls. J Am Acad Child Adolesc Psychiatry 2004;43:1146-53.
19. Sepkuty J P, Cohen A S, Eccles C et al. A neuronal glutamate transporter contributes to neurotransmitter GABA synthesis and epilepsy. J Neurosci 2002;22:6372-9.
20. Mathews G C, Diamond J S. Neuronal glutamate uptake Contributes to GABA synthesis and inhibitory synaptic strength. J Neurosci 2003;23:2040-8.
21. Zai G, Arnold P, Burroughs E, Barr C L, Richter M A, Kennedy J L. Evidence for the gamma-amino-butyric acid type B receptor 1 (GABBR1) gene as a susceptibility factor in obsessive-compulsive disorder. Am J Med Genet B Neuropsychiatr Genet 2005;134:25-9.
22. Veenstra-VanderWeele J, Kim S J, Gonen D, Hanna G L, Leventhal B L, Cook E H, Jr. Genomic organization of the SLC1A1/EAAC1 gene and mutation screening in early-onset obsessive-compulsive disorder. Mol Psychiatry 2001;6:160-7.
23. International HapMap Consorium. The International HapMap Project. Nature 2003;426:789-96.
24. Arnold P D, Rosenberg D R, Mundo E, Tharmalingam S, Kennedy J L, Richter M A. Association of a glutamate (NMDA) subunit receptor gene (GRIN2B) with obsessive-compulsive disorder: a preliminary study. Psychopharmacology (Berl) 2004;174:530-8.
25. Delorme R, Krebs M O, Chabane N et al. Frequency and transmission of glutamate receptors GRIK2 and GRIK3 polymorphisms in patients with obsessive compulsive disorder. Neuroreport 2004;15:699-702.
26. First M, Spitzer R, Gibbon M, Williams J. Structured Clinical Interview for DSM-IV Axis I Disorders, Patient Edition. (SCID-I/P, version 2.0). New York: Biometrics Research, New York State Psychiatric Institute; 1996.
27. Hien D, Matzner F, First M, Spitzer R, Williams J, Gibbon M. Structured interview for DSM-IV childhood diagnoses (KID SCID). Unpublished manuscript 1999.
28. Goodman W, Price L, Rasmussen S et al. The Yale-Brown Obsessive-Compulsive Scale: I. Development, use, and reliability. Arch Gen Psychiatry 1989;46:1006-1011.
29. Scahill L, Riddle M A, McSwiggin-Hardin M et al. Children's Yale-Brown Obsessive Compulsive Scale: reliability and validity. J Am Acad Child Adolesc Psychiatry 1997;36:844-52.
30. Lahiri D, Nurnberger J. A rapid no-enzymatic method for the preparation of HMW DNA from blood for RFLP analysis. Nucl Acids Res 1991;19:5444.
31. Barrett J C, Fry B, Maller J, Daly M J. Haploview: analysis and visualization of LD and haplotype maps. Bioinformatics 2005;21:263-5.
32. Spielman R S, McGinnis R E, Ewens W J. Transmission test for linkage disequilibrium: the insulin gene region and insulin-dependent diabetes mellitus (IDDM). Am J Hum Genet 1993;52:506-16.
33. Laird N, Horvath S, Xu X. Implementing a unified approach to family based tests of association. Genetic Epi 2000;19:S36-S42.
34. Alsobrook J, Leckman J, Goodman W, Rasmussen S, Pauls D. Segregation analysis of obsessive-compulsive disorder using symptom-based factor scores. Am J Med Genet (Neuropsychiatric Genetics) 1999;88:669-675.
35. Cavallini M C, Pasquale L, Bellodi L, Smeraldi E. Complex segregation analysis for obsessive compulsive disorder and related disorders. Am J Med Genet 1999;88:38-43.
36. Nicolini H, Hanna G, Baxter L, Schwartz J, Weissbacker K, Spence M. Segregation analysis of obsessive compulsive and associated disorders. Ursus Medicus 1991;1:25-28.
37. Stram D O. Tag SNP selection for association studies. Genet Epidemiol 2004;27:365-74.

38. Lanktree M B, VanderBeek L, Macciardi F M, Kennedy J L. PedSplit: pedigree management for stratified analysis. Bioinformatics 2004;20:2315-6.
39. Anholt R R, Mackay T F. Quantitative genetic analyses of complex behaviours in *Drosophila*. Nat Rev Genet 2004; 5:838-49.
40. Zohar J, Gross-Isseroff R, Hermesh H, Weizman A. Is there sexual dimorphism in obsessive-compulsive disorder? Neurosci Biobehav Rev 1999;23:845-9.
41. Nestadt G, Lan T, Samuels J et al. Complex segregation analysis provides compelling evidence for a major gene underlying obsessive-compulsive disorder and for heterogeneity by sex. Am J Hum Genet 2000;67:1611-6.
42. Chabane N, Delorme R, Millet B, Mouren M C, Leboyer M, Pauls D. Early-onset obsessive-compulsive disorder: a subgroup with a specific clinical and familial pattern? J Child Psychol Psychiatry 2005;46:881-887.
43. Conne B, Stutz A, Vassalli J D. The 3' untranslated region of messenger RNA: A molecular 'hotspot' for pathology? Nat Med 2000;6:637-41.
44. Mataix-Cols D, Rosario-Campos M C, Leckman J F. A multidimensional model of obsessive-compulsive disorder. Am J Psychiatry 2005;162:228-38.
45. Gottesman, II, Gould T D. The endophenotype concept in psychiatry: etymology and strategic intentions. Am J Psychiatry 2003;160:636-45.
46. Miguel E C, Leckman J F, Rauch S et al. Obsessive-compulsive disorder phenotypes: implications for genetic studies. Mol Psychiatry 2005;10:258-75.
47. Rosenberg D R, Hanna G L. Genetic and imaging strategies in obsessive-compulsive disorder: potential implications for treatment development. Biol Psychiatry 2000;48:1210-22.
48. Rufer M, Grothusen A, Mass R, Peter H, Hand I: Temporal stability of symptom dimensions in adult patients with obsessive-compulsive disorder. J Affect Disord 2005; 88(1):99-102.
49. Stewart S: Obsessive compulsive disorder (OCD) phenotypes in pediatric OCD, in American Academy of Child and Adolescent Psychiatry/Canadian Academy of Child and Adolescent Psychiatry Joint Annual Meeting. Toronto, ON, Canada, 2005, p 56.
50. Leckman J F, Pauls D L, Zhang H, Rosario-Campos M C, Katsovich L, Kidd K K, Pakstis A J, Alsobrook J P, Robertson M M, McMahon W M, Walkup J T, van de Wetering B J, King R A, Cohen D J: Obsessive-compulsive symptom dimensions in affected sibling pairs diagnosed with Gilles de la Tourette syndrome. Am J Med Genet B Neuropsychiatr Genet 2003; 116(1):60-8.
51. Denys D, de Geus F, van Megen H J, Westenberg H G: Symptom dimensions in obsessive-compulsive disorder: factor analysis on a clinician-rated scale and a self-report measure. Psychopathology 2004; 37(4):181-9.
52. Richter M A, Summerfeldt L J, Swinson R P, Kennedy J L: Symptom Subtypes and Family History in OCD. Presented as part of a symposium: "Models for Subtyping OCD" (Dr. Michele Pato, chair), in Annual meeting of the American Psychiatric Association. Chicago, Ill., 2000.
53. Hanna G L, Fischer D J, Chadha K R, Himle J A, Van Etten M: Familial and sporadic subtypes of early-onset Obsessive-Compulsive disorder. Biol Psychiatry 2005; 57(8):895-900.
54. Bhattacharyya S, Prasanna C L, Khanna S, Janardhan Reddy Y C, Sheshadri S: A family genetic study of clinical subtypes of obsessive-compulsive disorder. Psychiatr Genet 2005; 15(3):175-80.
55. Bienvenu O J, Samuels J F, Riddle M A, Hoehn-Saric R, Liang K Y, Cullen B A, Grados M A, Nestadt G: The relationship of obsessive-compulsive disorder to possible spectrum disorders: results from a family study. Biol Psychiatry 2000; 48(4):287-93.
56. Zhang H, Leckman J F, Pauls D L, Tsai C P, Kidd K K, Campos M R: Genomewide scan of hoarding in sib pairs in which both sibs have Gilles de la Tourette syndrome. Am J Hum Genet 2002; 70(4):896-904.
57. Leckman J F, Grice D E, Boardman J, Zhang H, Vitale A, Bondi C, Alsobrook J, Peterson B S, Cohen D J, Rasmussen S A, Goodman W K, McDougle C J, Pauls D L: Symptoms of obsessive-compulsive disorder. Am J Psychiatry 1997; 154(7):911-7.
58. Summerfeldt L J, Richter M A, Antony M M, Swinson R P: Symptom structure in obsessive-compulsive disorder: a confirmatory factor-analytic study. Behav Res Ther 1999; 37(4):297-311.
59. Arnold P D, Sicard T, Burroughs E, Richter M A, Kennedy J L: Glutamate transporter gene SLC1A1 associated with obsessive-compulsive disorder. Arch Gen Psychiatry 2006; 63(7):769-76.

The present invention has been described with regard to one or more embodiments. However, it will be apparent to persons skilled in the art that a number of variations and modifications can be made without departing from the scope of the invention as defined in the claims.

What is claimed is:

1. A method of diagnosing or identifying susceptibility of a subject to an anxiety disorder which comprises testing a sample obtained from the subject for the presence of a polymorphism or haplotype in Intron 10 of the SLC1A1 gene, wherein the presence of allele G of the A/G polymorphism rs301434 indicates that the subject is susceptible to an anxiety disorder.

2. The method of claim 1, wherein the sample is blood.

3. The method of claim 1, wherein the anxiety disorder is obsessive-compulsive disorder.

4. The method of claim 3, wherein the obsessive-compulsive disorder comprises aggressive obsessions, checking compulsions, symmetry obsessions, ordering compulsions, counting compulsions, repeating compulsions or a combination thereof.

5. The method of claim 1, wherein the step of testing comprises DNA extraction and PCR analysis.

6. A method of diagnosing or identifying susceptibility of a subject to an anxiety disorder which comprises testing a sample obtained from the subject for the presence of a polymorphism or haplotype in the SCL1A1 gene, wherein the presence of allele A of A/G polymorphism rs301435 indicates that the subject is susceptible to an anxiety disorder.

7. The method of claim 6, wherein the sample is blood.

8. The method of claim 6, wherein the anxiety disorder is obsessive-compulsive disorder.

9. The method of claim 8, wherein the obsessive-compulsive disorder comprises aggressive obsessions, checking compulsions, symmetry obsessions, ordering compulsions, counting compulsions, repeating compulsions or a combination thereof.

10. The method of claim 6, wherein the step of testing comprises DNA extraction and PCR analysis.

11. A method of diagnosing or identifying susceptibility of a subject to an anxiety disorder which comprises testing a sample obtained from the subject for the presence of a polymorphism or haplotype in the SCL1A1 gene, wherein the presence of allele C of C/G polymorphism rs3087879 indicates that the subject is susceptible to an anxiety disorder.

12. The method of claim 11, wherein the sample is blood.

13. The method of claim 11, wherein the anxiety disorder is obsessive-compulsive disorder.

14. The method of claim 13, wherein the obsessive-compulsive disorder comprises aggressive obsessions, checking compulsions, symmetry obsessions, ordering compulsions, counting compulsions, repeating compulsions or a combination thereof.

15. The method of claim 11, wherein the step of testing comprises DNA extraction and PCR analysis.

16. A method of diagnosing or identifying susceptibility of a subject to an anxiety disorder which comprises testing a sample obtained from the subject for the presence of a polymorphism or haplotype in the SCL1A1 gene, wherein the combined presence of allele G of the A/G polymorphism rs301434 and allele C of C/G polymorphism rs3087879 indicates that the subject is susceptible to an anxiety disorder.

17. The method of claim 16, wherein the sample is blood.

18. The method of claim 16, wherein the anxiety disorder is obsessive-compulsive disorder.

19. The method of claim 18, wherein the obsessive-compulsive disorder comprises aggressive obsessions, checking compulsions, symmetry obsessions, ordering compulsions, counting compulsions, repeating compulsions or a combination thereof.

20. The method of claim 16, wherein the step of testing comprises DNA extraction and PCR analysis.

* * * * *

SEQUENCE LISTING

```
<160> NUMBER OF SEQ ID NOS: 7

<210> SEQ ID NO 1
<211> LENGTH: 651
<212> TYPE: DNA
<213> ORGANISM: Artificial Sequence
<220> FEATURE:
<223> OTHER INFORMATION: primer
<220> FEATURE:
<221> NAME/KEY: Misc_feature
<222> LOCATION: (326)..(326)
<223> OTHER INFORMATION: R = A or G

<400> SEQUENCE: 1
cagggcactg aattgagaaa tagctgatcc tgtccaaggt acaagcattt actcctgact      60
```

```
gctccttttt gccagtagat gcactttgtg ggaaagaaag atctggaatc caggaggggc    120
agccaggtga actttattac caggtattta aaaagatccc tcttggtaag atcagctgag    180
gcagtaggga ttttttcttt tgtaatgtgc agtctcttta tcagcaacat cttccttatt    240
ttaattggat cattctgaag gaaacaaggg ttcaacatgc cctgaaaaat cccttgactt    300
ggataagctg gaggccacac ctacartgct ttctggagac aagtccttgc ccttgggcca    360
aggcctgaac tgttgcccgg ttccactgt gttgaaggt gaaatgtaa aaattggcaa      420 tttaaactgg aagaatccct gattctatcc acacattcat attctttggg gctaaaaaaa    480
gccagagttc ttaggaagct gattctactg cccattcatc tgcctactga ggtgttgcag    540
aaagcatttg agggtacagt caaacacagg ccagagtttt ttgacaagtg tattttcatt    600
cagtggtttt gaccaccaaa ttatagtaaa ttagagattt ctggggctgt a             651

<210> SEQ ID NO 2
<211> LENGTH: 651
<212> TYPE: DNA
<213> ORGANISM: Artificial Sequence
<220> FEATURE:
<223> OTHER INFORMATION: primer
<220> FEATURE:
<221> NAME/KEY: Misc_feature
<222> LOCATION: (326)..(326)
<223> OTHER INFORMATION: R = A or G

<400> SEQUENCE: 2
gccagtcgac agcaatgatc agggtgacat cctcggcggg caggcccacg gcactcagca     60
caatcaccat ggtcaccagg ccagcctggg gcacgccagc agctccgatg ctggcagatg    120
tggccgtgat actgcagaaa cataccagca ggaaggagt tagacactta cctctcccgt     180
taaagccctg gcctgaaatg gttactcccg cttagtcccg atggctatta ctgctgtgtc    240
cctaaattgg gtagttagaa tctgtgactt gctgagcccc agctctgcct cattacagga    300
ttagagctgt gggggaggg ggactrtgag gggtatgatg ccatctcctt gcagacggag     360
atatggcaca tcactctaat gcaaggaaga actgcataag tggcaccaaa aaataagtaa    420
gagagatact caagaggaaa gcaggagttt actaaatggg gtgttaatag gaggcttcgt    480
gtactcatct atgtatacat acactcatcc taaataagtg ccaggtacct ctgcacctgc    540
cttcctactc ccttgttcca tctactcacc acccaataat ttactgagca cctaatatat    600
ggcaggaatt taagttgccc tgaaggatgg acagaaggat agttgtaggg g             651

<210> SEQ ID NO 3
<211> LENGTH: 3533
<212> TYPE: DNA
<213> ORGANISM: Homo sapiens

<400> SEQUENCE: 3
agcggaggag ccgggcgcgc ctgccacgca aaactaccgg gctggcaggg cggcgggcgc     60
ggtgcgcgat cccgggtggc ggcggcaacg gcggtggtga cggcggcgac tgcagcggcc    120
ggctctcacc tctcccctgt gcacccgcat ctcgccgcgc cgccgagcag ccagcagtcc    180
ccgggtcgcc cagcccacgc gcgcacggcc gagcccagcg cacaatagcg cgacagcca     240 tggggaaacc ggcgaggaaa ggatgcgagt ggaagcgctt cctgaagaat aactgggtgt    300
tgctgtccac cgtggccgcg gtggtgctag gcattaccac aggagtcttg gttcgagaac    360
acagcaacct ctcaactcta gagaaattct actttgcttt tcctgagaa attctaatgc     420
```

```
ggatgctgaa actcatcatt ttgccattaa ttatatccag catgattaca ggtgttgctg      480
cactggattc caacgtatcc ggaaaaattg gtgtgcgcgc tgtcgtgtat tatttctgta      540
ccactctcat tgctgttatt ctaggtattg tgctggtggt gagcatcaag cctggtgtca      600
cccagaaagt gggtgaaatt gcgaggacag gcagcacccc tgaagtcagt acggtggatg      660
ccatgttaga tctcatcagg aatatgttcc ctgagaatct tgtccaggcc tgttttcagc      720
agtacaaaac taagcgtgaa gaagtgaagc ctcccagcga tccagagatg aacatgacag      780
aagagtcctt cacagctgtc atgacaactg caatttccaa gaacaaaaca aaggaataca      840
aaattgttgg catgtattca gatggcataa acgtcctggg cttgattgtc ttttgccttg      900
tctttggact tgtcattgga aaaatgggag aaaagggaca aattctggtg gatttcttca      960
atgctttgag tgatgcaacc atgaaaatcg ttcagatcat catgtgttat atgccactag     1020
gtattttgtt cctgattgct gggaagatca tagaagttga agactgggaa atattccgca     1080
agctgggcct ttacatggcc acagtcctga ctgggcttgc aatccactcc attgtaattc     1140
tcccgctgat atatttcata gtcgtacgaa agaacccttt ccgatttgcc atgggaatgg     1200
cccaggctct cctgacagct ctcatgatct cttccagttc agcaacactg cctgtcacct     1260
tccgctgtgc tgaagaaaat aaccaggtgg acaagaggat cactcgattc gtgttacccg     1320
ttggtgcaac aatcaacatg gatgggactg cgctctatga agcagtggca gcggtgttta     1380
ttgcacagtt gaatgacctg gacttgggca ttgggcagat catcaccatc agtatcacgg     1440
ccacatctgc cagcatcgga gctgctggcg tgccccaggc tggcctggtg accatggtga     1500
ttgtgctgag tgccgtgggc ctgcccgccg aggatgtcac cctgatcatt gctgtcgact     1560
ggctcctgga ccggttcagg accatggtca acgtccttgg tgatgctttt gggacgggca     1620
ttgtggaaaa gctctccaag aaggagctgg agcagatgga tgtttcatct gaagtcaaca     1680
ttgtgaatcc ctttgccttg gaatccacaa tccttgacaa cgaagactca gacaccaaga     1740
agtcttatgt caatggaggc tttgcagtag acaagtctga caccatctca ttcacccaga     1800
cctcacagtt ctagggcccc tggctgcaga tgactggaaa caaggaagga catttccgtg     1860
agagtcatct caaacactgc ttaaggaaaa gagaaacact aatggccaag tgtacatttg     1920
atttgatata cagacctcca gattattttc tatatttgga ttcacagcct ttgcgctctg     1980
ggttttggga tttgggtgtg gggtaagttg aagggaaatc aatttaaagg aaagttctat     2040
tatctgggtt ttagaaattc tataagagac aaagtttgga agtacataaa gtaataactg     2100
ttagaattag gtaatggata tgaaagagaa atgctttct catgcataga caagtgtttt     2160 gggttttttaa aaaaaatatt ctgtcattgg ttacaaattt ttactcaggc tttctattgg     2220
catggatttc ctttgacctc tcactttttt ataaattata atgcatctaa accacctgtc     2280
cccagttaat gtgccaaaat gtcaatttt aacttatctc cagccaattt caaagaaaac      2340
agaccagcat agttctgcaa taacagtttt aagatgggca tagggtttgg aagaaagaga     2400
gaaggattct ttttcaatg tactgtattg ggacgctggt aactgttaac ccagtgttca      2460
gcatagagct atatatatat atatatgtat atatttatta ttttcatata atttgccaga     2520
cagagatcag aattgaaccg tcaatgtgaa ataaagagtt ctccttgtac ttgaataata     2580
accacgattc caacccaggt ctgctttggg gcttatcaga actcctttct aaggagcact     2640
agaatgagaa atcatgttgt tcgatcgttt cacatctgta tatcagctct aaagcagaga     2700
tgtattatgg tgatactcca aggtggcata gccattcatt tacaacttcc agatttgagc     2760
tgcctggagg gaatccatat cagctctgca taagattata tacaaagctg tcactcacaa     2820
```

| | |
|---|---:|
| aaggctggat gtgctttcat ccaactggaa ggctttattc ttccaagttc attcatactc | 2880 |
| aaagaggcca gtactttgcc atccttgcac tttctgttat cagggcccaa ataacagtgg | 2940 |
| caagctacca actaagttgt attttaataa agattccatg ggttgaacaa gccacgttgc | 3000 |
| agaaaaagag cttcccctaa cctgggttgt tgcagagtaa atcccacgac ataagctggt | 3060 |
| atcactggtt cggggaaat agttccattc tatgactctt gtctcctcct ccaggaggac | 3120 |
| tgttctaact agtaatcttg gccctattca ttacatcctc tgcttgtcat tctgctaatt | 3180 |
| tatgaagata gtttattata gtctgtactt cagttctcat cttgtaaata atgcttaaca | 3240 |
| taaacttgta cttacactga atccaaaat agtcatgttt ctgcagtatt ctgtagccaa | 3300 |
| cttaaacctg tgctttcatg tttaagaaat gagaaattgt gccaaagata gcagaagagt | 3360 |
| agataagtgc tcagtattga cgacctacat ctgaaatcta aacataatg atactgaatt | 3420 |
| gttatgtaaa catcataaat agtaaataat gattcaatgt gaattttaaa atgcaaatat | 3480 |
| tgctattgtt tataggaaat aaatctaaat ataaacgaaa aaaaaaaaa aaa | 3533 |

<210> SEQ ID NO 4
<211> LENGTH: 96821
<212> TYPE: DNA
<213> ORGANISM: Homo sapiens
<220> FEATURE:
<221> NAME/KEY: Misc_feature
<222> LOCATION: (96369)..(96369)
<223> OTHER INFORMATION: S = C or G

<400> SEQUENCE: 4

| | |
|---|---:|
| agcaggagga gccgggcgcg cctgccacgc aaaactaccg ggctggcagg gcggcgggcg | 60 |
| cggtgcgcga tcccgggtgg cggcggcaac ggcggtggtg acggcggcga ctgcagcggc | 120 |
| cggctctcac ctctcccctg tgcacccgca tctcgccgcg ccgccgagca gccagcagtc | 180 |
| cccgggtcgc ccagcccacg cgcgcacggc cgagcccagc gcacaatagc ggcgacagcc | 240 |
| atggggaaac cggcgaggaa aggatgcgag tggaagcgct tcctgaagaa taactgggtg | 300 |
| ttgctgtcca ccgtggccgc ggtggtgcta ggtgagcggc gcggcgggtg ggcgatgcgc | 360 |
| gcaccctcac gcgctctctg cgcccaggcc gcgtgcggct gagggtgggc ttggcgctgg | 420 |
| cgcactccat gcagggtccc tcgatgcccc tcggccttta gctcgggcc cctgcgggg | 480 |
| gctttccccc aagcgctcta attactgcac accaagaaca aagctcctct gggactccca | 540 |
| tttgagtgct ccttgagctg ctggttcctg ctctacccaa aatgatcaaa ggggcttggg | 600 |
| ggtagaaagg gaagcaagta gctcttggtt ctgctcgttt gaaaacaggg ttcgatttt | 660 |
| ttctttgtta atcccgcacc gtatctcccc ctatcaccgc caccttcctc accccacacc | 720 |
| cccagcctcg ctgcgcgggc agagattgag tgtggattac agttctcagt cgaattggaa | 780 |
| gaggcaccct ggcctccggg atgggccgga cccttagggg agggaggctg agaacgctgt | 840 |
| cgccgctcat cctgggcagt gcgtggaaag gtgccttccc acgcggcgag cgccgactgc | 900 |
| ctgcacccgg gctctgaaaa gctgccagat tcgtgcctga attctgggat gtgccactgt | 960 |
| ggcccgcggg aggtcaccgg ggaagagagc taagagaact cagccgtctc ttctcctgcc | 1020 |
| ttccttgctc tccacgttgt ttttgtattt aagataatgt ttaagccatc cttgcctgtt | 1080 |
| tttaaacaag ggtgtattta agtgatccac ccctcacaga tcactggacc aggtggatgt | 1140 |
| ctgagccatt gctcagaggt atgagttatt cctatttaga ttctgatttt ttaccaaggt | 1200 |
| tgtgtgtttc tagctccggc ccggggatgc acttccttgg gattagcgcc atatctgtcg | 1260 |

```
ccttcccagt gatagctcct cagcaggtga gggctgttgc accctctgag gaatgtggat    1320
tcctcggcag gctccacctt ccccttggaa actgcagctg tgtttgctga aaaggcaagt    1380
ggggacagct tgtttcctcc caacctcagg taccttcctc tccaactgct gctcctaaat    1440
ctcagaatat atggtgttgc ttgcttctcc tccgaaccgc cccctcccct cagggtgggg    1500
atagggcatg gaaatggcct ttggaagtta atgggattct tggggtcaga ttggattctc    1560
cagaaccttg gggaaaggaa agtcaggttt ctagtaaata ataacatcc tggaatggcc     1620 ctagcagagg ctatttgtag gaggaaagga gagaagtaca gaagcaaatc ttgactattt    1680
cccccaagaa gtgccaagtg ttttggaac ttttttttt cggttttgaa cattttaag      1740 ggaaagttta tcctactcta ccatatttaa atagcatacg ctacaagaa cgacttgatt     1800 tcctttaggc caaagagaag atggccctt gtttgttttc ctagtgataa gagtcgagga    1860
ttaattgtta aatctctttt tgaagactga gagatgccag gcaaggtgg ctcatgccta    1920 taacccagt tactcgggag gctgaggcag gagaattgct tgaacccaga aggcagaggt     1980
tgaagtcagc caagattgtg ccactgcact cccgcctggg tgacagagca agaatccacc    2040
aaaaaaaaaa aaaaaaaag gaaaggact tttagagggc caggcacggt gactcacacc     2100
tataatccca atattttggg aggccaagga aggaggattg cttgagccca ggagttggag    2160
accagcctgg gcaacatggc aaaatgccat ctctacaaaa aagtacaaaa attagcgtgg    2220
tggtgcacat ctgtagtcct agctactcag gagactgagg tgggaggatc acctgagccc    2280
agggaggtcg aggctgcagt gagccgtgat cgtgactctg cactccagcc tgggcaacaa    2340
gaatgagacc ttgtctaaaa agaaaaaaaa aaaagacttt gcaggataaa cattggcttg    2400
agtctccctc ctgattccct gtggaagtgg agttatcctg ccttttcagc atggggctct    2460
ccagagatac tcacttgcta cccaagtgtt gcacaccact cgtcagcatg cgattcactg    2520
gagactggtt tggagaaggt tttaagcaat tgttccctgg cctttggaat cagttgcgtg    2580
aataagaaga agtacatgct cattttgcag acatggcctt tggtctcaga tgggcacttt    2640
cctccaattt taatgtctgt gagccccaag agcttagttt gagtactttt ctccagaaag    2700
gaaagtcacc acttaaaaat caagtgccca gctgaaatct tcctagatat tgttccttc    2760 agatggcaac aaagggcagt cctgcttctg gtctgagaag tctcaaacct agaccacccc    2820
cgatatgccc attaacaggg gtccttttct tgtcctttt cttcagagta ctgggcctga    2880
gtggaaactc atacttgttt gtgtagtctg taagggctga tttgtttaat tgacagtgaa    2940
attccagtga cttataacag tggcactgag tctattcata aacccttgct agataatgat    3000
agtaagagct tattttataa ctgccttaac tgatccagaa aaatcgcaag agctctaatg    3060
cagcctccct tttggacttt tcagcatgtg gaacttaaag aagaaaaaaa actgtgaaat    3120
ttattaacta tcatgacaaa acatcttctt ctgattatag ccgttcaaat gtttggtccc    3180
tgaccaggtg cagtggctca gacttgtaat cctaggactt tggaaggcca aggtaggagg    3240
aatgagtgag ttcaggagtt tgagaccagc ctgatctcat ctctatttct aaaaaaaata    3300
atttaaagaa ataataatgc aatgaaatgt tcagtcacta ctataattca gtagccctaa    3360
tactttgaaa tatttgatta tagaaataag aggcaaagat ttttatgagc cagcttaaag    3420
cctgattttt caagatacag cacatgaggg gaaatgtaat aagggtcatc tttattaggt    3480
gtggaagttc actctttca tggacaagga aatgctaaga actaaacatt tctcaaattc      3540
ttgttcacaa gatgaaggga ttcaatagtt aggtgaccat cttttaaat ttctgcgaca     3600 ccctacatgg tcctgaaaat agtatcttgg attttcacag gaaaatcctc tgctaaaata    3660
```

```
ccactagaaa cactttcacg gctttcatta caattcttat aggcttattc tctgcttcca   3720
tagaatggta gaatgagcac agagcctgga gtgaagagtc cttgggattt gaattctggt   3780
actatcaagc tctatcatgc aggcaaactg tgtatttccc tacaagcctc aatttcctca   3840
tctggaaatt ggagatatta cttattactt cgtttgttat tagaggtgtg aaagatactc   3900
agttgtgtgg ctggcatata ttcagcactc aatagttgtt attttaaggt aaatctgaat   3960
aatttgatta tgagaaaatt aatattttct tatgaaataa attctctcat agtatgtctc   4020
tttctgtgtc ctgcttagtg tcccgcctat aatttagggt gactcaagtg ttttgatgac   4080
ctgctctgtc tgagctaata actgtccctg tagtattatt catttcttta aagaggaaat   4140
ggaaagaatg aatcatttat ttttgtgccc caccggctaa tcctcaattc atttaaatat   4200
aatatttaaa tatataattt atataaatat aatttaagta tgtaaattct gaaggaaggt   4260
tttatgctct aagtgggaat tctgtccaag cagaattact gagtgagaat tctgccagcc   4320
ttctaatgcg ggtcatccaa taatgattat atagtatatg atgttgttaa ggcacttctt   4380
atatcctcac cctattcaca ataataacc taatctttct ctccagacca gttatgccat   4440
tacttctgtc atttgaaaaa tctgtgattt caacttagag ctattcagaa aaagcaatag   4500
gtattggcat ttacatgaca gagctggcaa gcttattcat tctaaattgt tttctttgga   4560
gcgctaagga agcaatcatg catagattct gattccatta tctaaaatca gaaacagctc   4620
cttcatggtc ttagcaatac ccttgcccag cctcgtgtct ctaccctgga gctcatgtag   4680
cgtgcatctg gcagtgctaa tttgagacgt ggcataggct ttcccgcttt gtctgtgaag   4740
cccctgagga cagggcccag cggcggttca cgctggttcc aggcccagcc cctcacctgc   4800
atagaacctt ggctcagcag tgtttaggaa tatccctgta ataatcaaca cttaagccat   4860
tcattcattt aacagatatg tatcagaccc ccactgtgca ccagggattg ttctacagcc   4920
gggtcacaca gcatgtcctc atgggactta atgttcaagt agagagaggt agaccataaa   4980
tagaatacat aggtaaccta ctgtatagag catgttagat gagaatagtg ttctggagta   5040
gtatagagca gggagtgggc tggcaaggtg gggggttgca attttaaaca gggtgacagg   5100
ggaggccata ctgagaaggt gacagttgaa tcaagacgga ggagaggtga aggaacaagt   5160
tgcacaggta tctggggagc atcctagttt gtgtgagaaa catcaaggag tagaatgagg   5220
gagggaaaga gtaggaggag atgaagtgga ggtgaggctg ggggcagagc aatagggtgg   5280
ttcaggtcca aggtccagga aaggggaaat gggtgcctca gctgagcagc caggagtgga   5340
acagaatgaa aagacagctg cttgaggtta acctgcaggg cttggctgga tttggtccaa   5400
gggagaaggc agtggctatc tccagcaaaa cagagagtcc tggaaggggc accgacttgg   5460
aaaagaacat ggcatgttcc acggtggacg tgttgagttt gaggagccag aagggtgttt   5520
gggtaaaggt aggcagcaaa cacctggcta agtgagtctg gtgctcagga gacaaatgtg   5580
gagtggagtg tcgacttaag acagcatgtc agggacctgg ttaaggcttt gggaatgaat   5640
gaacctatcc tgggagaaaa gggagaagag aagaccaaag acagagttct ggacaacccc   5700
aacattggag gtctgggaag agaaggggcc cacaggagaa accggacgtg gtgtgataga   5760
aattaagaac aggaacagtg atgggtgaga ggctcggggg caggagtgag agggtctgag   5820
gaggaagttc aacagcgttg gggatacaaa ggacagggat gtgaccttct gggctttat   5880
ttggaggcac ttaggtgtga agaattcag agaaagtgga agtcacgttt aagatccaga   5940
gagtattttt ctttctttttt ttaagagaca gggtctcgtt ttgttgccca ggctggtctt   6000
```

-continued

```
gaatgcctgg cttcaagctg tcctcctgcc tcagcctccc aaagtgctag gattacaagt    6060
gcaagccact gcactcagcc ttgttttgtt ttgtttttgt ttgtttttg ttttttaagg     6120 agacttgagt ctgactgaac ctgaagagaa gtgatcatta aaataaaaa tgcagctgag     6180 catggtgact catgtctgta atcccagcac tttgggaggt gaaggtggga ggactgcttg    6240
aggctaggag ttcaagacca gcctgggcaa cacagcagga cccctgtctc tgcaaaataa    6300
aaattaaatt agccaggcac gatggtgcgt gcctgtggcc ccaactactc aagaggctga    6360
tgtgggaaga tcacatgagg ccaggagttc aggctgcag ggagcttgat cacatcattg     6420
tacactccag ctgaggtgac agtgcaagat cctgtctctg aaaataata ataataaatg     6480 cagaagagag agaaaataat gaatgctgtt gggtggagtg aggcctggga cagtagaaga    6540
cagtgtgaaa tggagggacc tagttgggga ttggccagaa acgggactt tatactcctg     6600 agatggaagg gaggagttaa gggtgaagca ttgtattcct ttcctgtggc tgccctaaca    6660
aattaccaca aaccgggtgg ttttaaaaaa cagaaatttt tttttgagac ttaggtgtat    6720
ccattactct gtgccaagaa ctgttctgag tgctatatag gtattaaatg atttaatctt    6780
tccatcaagc atattttcag gaaacagagg cacagagaat taagaaactt gcccaaggtc    6840
gagggcagag ccgggattca aaccctggaa gtctggctct agagcctctg cttctaacca    6900
ctatcctctc ccgctgctgt gtgatattat taccctatat tctgatgttt ctgcctccct    6960
caccaattca ggaaccctaa gggaaggacg tttgtgttgc tcttctctgt gcccatagta    7020
cctatcacat tgcacagtag ggtgaataca tttgttgaat tgctgagcca tttatgaccc    7080
agagagttag taaaatgttg tccttgtttg tcaagggaac aaatgagcct aaagcttaaa    7140
tcaaactcta ttacctccat aaattctcct ctgcctgttt cagcccccctc tgatctatgt   7200 cagcaacata gattaacact tgatgaatct atataaaatat caagcatgtt gatcttttct   7260
ttctcaaaac tagattacag accccttgag gtccctctta ttacatttca caggcactaa    7320
aaaataaaat gaggccataa agtaatgaga ctgactctta actgtttttt taattttaa    7380 aaaagtatat ctgataccta tactctctga gtctttgttt cttattaaca agaaagggac    7440
ttagattagc tgggagagca aagaagattc tattcatgca tctattacca cttataggta    7500
gtggactatc tggtatgatc tttattgaaa aagagttgaa aacaaaagtc tgaaattgat     7560
tactgctgtc tggcactggc ttaggatcag gaactagtgg tatgcgtgct gagtaattgt     7620
tgacttgggt tataaaacct ctgagagtcc ttctagcttt aagaaccttt agctttatga     7680
ctgtatattc attcctcagt tcattgctgg gagccagagg aactcttctg taaggagcta    7740 aggggggttca aagggcatta caagatgata aaatgaccta gacattgagt caactgttct    7800
gtgtttgaac tgctgatcag tgacataggg ataatcatgt aaattgtata tggggctatt     7860
accatggtaa tatgttctat gtcagtatta ttagatggtt tattacaaca gtaatagaag    7920
gtctaatata tgtatgtttt tggactttat atgtctctaa tttaaaatat ttgcaaagta    7980
cacaatactc caaaaacact aaataaaata atagtttctt caaaatgaca ggaatagcct    8040
agttcctata tcctcaaaac cagtgatttc cacaacaata atcagtttga cataggggaaa   8100 acaaaaaaaa gcatagttat tcatatataa tggggacttt tgctttcaat gaggaatata    8160
gctttatgtt tatgtatttc tgaaaagtga tgaaaacaga caaggttgct agtttagtca    8220
tatatattta atttgtatta atatatttat tccatagcat gccacagaca tgacaatatt    8280
agcaaaataa tgagcactac taattagttt ccataatatt ttctagaaat ttgggagttg    8340
ctagtgagtt aagttcatct gcaaaaaaat atatatatat gtgtgtgtgt gtgtatatat    8400
```

```
atgatattgc ttatactttc tctaaaatac tgagagatat gtggtctctg tctctgtata    8460
tattacatgt atacatacat atacatatgt atgtattata tacataatat atacatatat    8520
attatatatg tatatataat cttatatatt atatataaga ttatatatta tatatatata    8580
agattacata ttatatatgt atatatatat cttttttttt tttgagaaca agtctcactc    8640
tgtcacctag gctggagtgc agtggcacga tcttggctca ctgcaaccc tgcctcccag     8700 gttcaagcga ttcttctgcc ttagcctccc gagtagctgg gattacaggt gcccaccacc    8760
acacccagcg aattttttgta ttttttagtag agacaaagtt tcaccatgtt ggccaggctg   8820
gtctcgaact cctgacctca ggtgatccac ccacgttggc ctcccaaagt gctgggatta    8880
caggcatgag tcacgggcc cagccatata ttatgtatct ccatctatct tatctcctta    8940
gttaagtacc ttagagaaga gatccttctg gcctcgccaa agttctacat attaaagaat    9000
taggaaaaga aactgggctt tgaatgctta tgcctggtgt tttcattttt gcaactaaat    9060
cagaatcaga tttgaagcat cactgaaatg attctgattt ttggttgttc tatgcaaggt    9120
atatatgact caagtctatc aaaactccaa caaaatgatc taaacacaaa attataaaat    9180
gaatctttaa aatgatttta catattagac tctgcacatg caggttggta tatacaatct    9240
taatgcctcc tatgaggaag actgaatata aattgctagt ggttggcaaa tattgaatat    9300
cttgttagat gttgcttaat ttaagatacg gtgttttatt tagtacagta aaactacaaa    9360
attgaagttg ctcacctgtt aaaaatttga gcactgggca taagaaataa agaaagcttc    9420
aaatgaaaac acgctgtgta gaaaattttt gtgtgcaaat tcaggatgtg gtggagctca    9480
ggtgggtaaa gcctgggtta tgtcagacaa ggtaggatta ggaatcagtt gttagagagc    9540
atgtatgcat gtgagagcac ttgcttataa agagagaaag ctttccacat taattgcttg    9600
tgagaaattg tgattacctt taacagagcc gagactgaaa ataactgtcc tagggagtcc    9660
gtgacacact ggcctggtgc cagggaagct gtgttcgcct gaggtattgc aaatttcccg    9720
tgtcgctgga gatttggggt cacagatgct gtgacaactc aagcactctc gaagaaaatg    9780 aactcattt agatgacatt gagtggcccg tttaaactcc ccatagcagt gtctattaaa    9840
gtagaaagtg tttttaaatgg ccttttctat tttgtttgtt ttattttgag acagagtctc    9900
actctgtcac ccaggctgga gtgcagtagt gcgatctcgg ctactgcaac ctccacctcc    9960
caggttcaaa caattctcct gcctcagcct cccgggtagc tggcagtaca ggtgcctgcc   10020
accacaactg gctaatattt tctatatgtt tagtagagac ggggtttcac catgctggcc   10080
aagctgctct cgaactgtta actgcaggta gtctgcccgc ctcggcctcc caaagtgctg   10140
ggattacagg tgtgagccac tgcactgcgc ccaagaaact gatttagaaa gagttaatac   10200
attatacttg ctgaggaaca gccccaaact gcaacaaaga gtactctgtt gtaattagta   10260
cagcccacag taacacctct gttaatagaa aggaagtgtt tcagtgactc actctttttc   10320
agaaatttta ctactttact ttgaaaatta tctgctgact gcctgttccg ttaccaaagg   10380
tagaatattt cctttccaat aaatagtcct atactttctg ggatggacag atctcatccc   10440
agctcacaga tgcttcatgt tcctctccca ggcccagcct cggctatgtg agctccgggc   10500
agcggttccc actcagccaa gacagggagg gatacagtgc cctgttctct accactaatc   10560
cccagaccca gccctgagaa gataagacgt cccaccagtc ctgcactcat gctgaggtca   10620
ccactcccga gcccttcttt agtctcagag tccctaaccg tgtccaacac aggacaattg   10680
tcacagcaga tctccgcatg tctaggaagg ctcttgatag tagaaagtgt tttaaatggc   10740
```

```
cttttctatt ttgttttgtt ttgagacaga gtctcactcc gtcacccagg ctggagtgta   10800
gtagtgtgat ctcggcaact gcaacctcca cctcccaggt tcaaacaatt ttcctgctat   10860
catcatgtga ctctctgctt ggtctgcatg ttgaagcaat agcagacttt gggactggaa   10920
cttggcttcg gaaacaccct cagagagggt ccacatggcc acatggtgtg tttattctta   10980
taatctctct gagacaacta tttgggtata acacttccag atgtagttaa aactacagca   11040
ctttggccag gtacggtgct cacgcctgta atcccagaac tttgggaggc cgaggtgggc   11100
agatcacctg aggtcaggag ttcaagacca gcctgaccaa catggagaaa ccccatctct   11160
actaaaaata caaaattagc caggtatggt ggtgcatgcc tgtaatccca gctactgggg   11220
aggctgaggc aggagaattg cttgaaccct ggaggcagag gtcgcagtga gccgagatca   11280
cgccattgca ctccagcctg gcaatgaga gctaaactcc atctccaaaa caaacaaaa   11340 caaacaaaa caagaaaac tacagcactt actcaaccaa gggggaaatc cttataggag   11400
agagcttagg tgagaatgta caattatttt tctaccattg ttctattgct taagagttac   11460
ctcgttacta ataattcagt aaggaattaa gtcaacataa aaaaatgcac catcaccaga   11520
aatgcctaaa ctacagagag cctaatctct gagcctctcc ccattactgg aaaataaact   11580
gatactgttc aacttctgtg ggtatctcaa agacttgttt tctgagccac ttagcaggtt   11640
tcatttaaga tttccccaaa ttatgggcca ggcacagtgg ctcacatctg taattctagc   11700
actttgggag gccaaggcat acagatggct tgagcccagg agtccaagac cagcctgggc   11760
aacatggtga cacctcatct ctacaaataa tacaaaaatt aaccaggtgt ggtgggtcac   11820
gcctgtagtc ccagctactc aggggggctga ggtgagagga tcacttgagc ccgggaggtt   11880
gagtctgcag tgagccaaga tcacaccaca gcactcctgc ccgggtgata gaatgagacc   11940
ctgtctccag aaaaaaaaaa aaaaaaaaa aaaaagattc cctgaagtat gagacattga   12000
gagagaaagt gagagtgaca tattttctcc cttgaaaagt tctctttggc taaccaaccc   12060
taatatcaat atttattgag aatttaccac gagttttatg tacatttatc tcccatttga   12120
ccctcagtac aatgagttag ggggttccca ttttaccaga tgaggaaact gaaatttaca   12180
aggcttaggt catgtagctg agcacacaga gctaggatta gcacccagga ctgtctgatt   12240
ccaaagctta ggttactaat tattaatcat taagcaagtc ttcttccttc ctagtaaacc   12300
ttgatacacc tacacctaat tggtagttag aaccatactt ggagacaggc ttctttcttg   12360
caaagtggcc aaataaagcc tattctcctc cttcttgctt catcctttct cagtcttgta   12420
gctcatcttt attgcgtgtg gttagtcctt tccgctacgc ttctcctaca taaaccttct   12480
gtttgagctt gaattctagt gaaactcatc tagttgcttt cccagaactg ttgtactttc   12540
atgccctaat ccttttgctc aaatgtttca ctcactgtta tcctgcctat ccttgaagat   12600
ggatttaatt accacttta tgttgtagac ttctctgact gcagttggag ataatctccc   12660
ttctctacat tcttaacccT tgatttatat gcataaatta tcaccattag caccaccatt   12720
cccacgtctg ttctgtggca gacatcactg attacagtac tcttcactac tgagctctgt   12780
catggcctca gaatcctcga aactttgctc caggcaacca ctgttaatca aacagaattg   12840
gtgcctaaga tgaaaagtat tgtttgttgc tgggaaaagt ttattcattt ggcaatcaat   12900
taggaactga atttaaattg agcaagtact gatgttactg ataagagaag cagagtcaaa   12960
gtctgtattt tgtcctctca gtccattggt ggcaatacat ccacaatcac taacatgatc   13020
ctgagtgtgg taaatgctgc aaggaggctg cagcatgctg tgggccttca agaaggtgc   13080 aactgggaaa gttcctggag gaggccataa ttggaatggc cttgagcagg tgtggtagga   13140
```

```
tttctgggct tgaagactgg aacgagcaag tctgtataaa ggtgatgata cacataagga   13200
gggcttatca tctcttaggt tcaatttcag tattacatgg aactataatt taatatatgt   13260
gttgctgtgc tttcgcactt tttcttacct gtttcctaag gacaagaatg caatactaca   13320
caggtctgtc acatcatagc atccagcatt gtacttactt cacaggaggt gcccccagat   13380
atatctgact gattacaacc ttcttcactg aagaattaaa acaggtaaat ctttgatgaa   13440
ccaatcccat tgatccccta gaagcccact cagttgtatg agttttttgag tgaagaccat   13500 gaggaactct tatgctagcc taagtcatcc caaacatact taactcctgg aatggggacc   13560
ccagaagaag agcaagtctg gttgctaaca gttttgaagc cattttattg tgagcactgc   13620
atgaccctga agctcccaga ctggagagca tctctgtacc ctaaggaaga tctgatcttc   13680
tcaagaaacc agcaccagaa cccacctgat ctccagataa ttctctgggc taattagaga   13740
aaatggaaga tccatctctt tttccataat tgggctacag cttggcactg aatcaaccct   13800
ggatggtaga gccttttcag ctacggtatt tagcaactct tacaccattc attgaattta   13860
tttctggatt ttccccctcc aagtgtcctt tcacatcctt atccaaattc tgcccacttc   13920
tctccctgtc tggagattat ttctatgata agaaattaat tagcctgtct gtactacctg   13980
ttccaggaga cttgaacaa ctgcgtgggt aaacactaga tgtggtcacc aaagagtcgg   14040
aaaataagtt tttactttt cattagcaaa agttaattgt caaccaggag atgtaacagg   14100
cttgctccat ttctgctgcc gcttcttgga tttctttctt gcatgtggag aatttcctga   14160
ggtttcacca gactgaagag attctgagtt cttgaagtga tggagataaa gatcttgttg   14220
tcataaaaca gcaaagagca ctgtgattgg gtttgaaaga tttttgattg tgttatggac   14280
agtgctctta ctggttttta aaagttgat gttttcttct gtgtaaattt aaataatttc   14340
tttaaaggca gtaagctttt atatttaata taccttcac tgtgcaatca caacaggaag   14400
attttctaaa ttagacatct ttaccttgaa gaagaaactt gtctgtttca gtgtctttt   14460 gtagcaagat tgaccaaaac aagtggtaaa taagtctgta atatttaact gtcatgaaat   14520
acctttgcta ataaggaaat ggcctcggtt tggattaggt ggagtttcgt gtgtgcgatg   14580
tgggggtgta tgtgtacata tatttctttt tttttttttt ttttgagat acagcctcac   14640 tatgtcgccc aggctggagt gcagcggcat gatcttggct cactgcaacc tccgcctccc   14700
aggttcaagc gattctcctg cctcagcctc ccaagtagct gggattacag atgtgcaaca   14760
ccatgcctag ctaattttt tgtatttta ataaagatgg ggtttcacca tgttggccag   14820
gctggtcttg aacttctgac ctcaggtgat ccacctgcct tggcctccca aagagctggg   14880
attacagggg tgagccaccg cacccggccc atatttcctt tttttatact ggatagcaat   14940
atagggtctt gtctttcacc ttttaagttc acagaacagt ttgtcctgac cacacataag   15000
ttaccagtat aatgttttat gaaggtttag aaatgagctc ccagaaaaat aatattttaa   15060
tatctacaaa taaataatct gaggatgttt ctcaattcag catcaatgct gggttgtgcc   15120
ttgtggattt ccattggctc tacgtgcaaa agattaagtt agttagaatg aggaagacat   15180
ttttaattac tgtgaaattc tttgttgttg ttgttgttgt ttttcttttt gttttgggaa   15240
ggtgtctcac actgttaccc aggctggagg gcagtggcat gatcttggct cacttcaacc   15300
ttcacctcct gggttcaagc aattctgctg cctcagcctc ccgagtagct gggattatag   15360
gcatgtgcca ccacgcccag ctaattttg tactttagt ttgggatg gagagtctct   15420 gtcacccaga atggagtgca gtggcaccaa ctcagctcac tgcaacctcc gccttccgag   15480
```

```
ttcaagcgat tctcctgcct cagcttccca agtagctggg attacaggtg cccaccacca   15540
cgcctggcta attttttgtat gtttttagta gagagggggg ttcaccatgt tggccaggct   15600
ggtcttgaac tcctgacctc aagtgatcca ctcacctctg cctcccaaat tgctgggatt   15660
acaggctcct gccgtctgac ttaattttg tactttagt agagacgggg tttcgccatg    15720
ttagccaggc tggtctagaa ctcatgacct taagtgatcc acctgcctca gcctcccaaa   15780
gtgctgggat tacaggcatg agccatcatg cccggccaaa ttactatgaa attctatcct   15840
gccagtgctt tagaataact tgcattttaa agtacatttg cacattttac atataatgct   15900
atatggttgt gtttgggctt tgtgtacaga tgacttttgt tattaagtgg aaaaggcctg   15960
aaatatgctg ttctatgtta agtaaattga tataacctaa gaaaagatct tgttgccaat   16020
tcagaaacca taaccttaaa tagcatgcct gggtctcctc tgtatctggt ttaacatctg   16080
cattgaatat tggtattttc caataatctc caactagctt atttattttg aaaaaaaaaa   16140
atagaaatct acgtctactt tgcttaagt ggaaatactt gagtaatgct tggttgcttt    16200
tttaacctca agtcagtaac tgtgaaagac tggacttact gcacctaaga tctagaaccc   16260
tgaagttatc taattggtgc tcatcactga gcttgtgtag gcttcctgaa gcctattcag   16320
ggccctgtgt actagggaaa agggttggca gatcacagtg tgtggagtat gcagccagta   16380
attctttctt agattctctc tcccctctta gaacctcccc tcatttccca gggaacatct   16440
gttttccatg agggcagtac taaggggggct gaagattccc acagacatat aataaaaggt   16500
tccaagagta ggctggcggc agtggctcac gcctgtaatc ccagcacttc gggaggccga   16560
ggtgtgtgaa tcactaggtc aggaaatgga gaccatcctg gataacatgg tgaaaccccc   16620
tctctattaa aaatacaaaa aaaaattagc tgagcgtggt ggtgggcacc tgtagtccca   16680
gccacttggg aggttgaggc aggagaatgg cgtgaacccg ggaggtggac cttgcaagtg   16740
agccaaagtg gcgccactgc actccagcct gggtgacaca gcaagactct gtctcaaaaa   16800
agaaaaaaaa aaatagattc caagagtaaa caaaatcctc aagtgttact gtgcaaagat   16860
tatactcacc atgtttgatt ttttttggtct ctggtggtca tcccagatgc attcacagtc   16920
atttctggac ctttaatgta atccactgtt gttattaaat gagctgatcc acatggagtt   16980
actttttgaa atcatgaagt tccttatgaa tgtttgttat tgtgtcttaa attctttaaa   17040
ttcttaaaat atgtcttaac tcacttaaag ataaaagtaa atgtttctgt ggtccttctg   17100
ggagtgggga aagttacaac tccacaaatg ttaagagaga agggtgaaca gttagcagtc   17160
aggcagcatg gttgggagtc atgaggaaga gcattcaaga tgacacaagt tttgtaagca   17220
gacctaagga acgggctgaa gaatgttgtg gagacccagg tacttcgact tagcattctg   17280
agttcagagt tcgcccagga gttccaggct tgtggcaggt ttagaaaatc caggatgatc   17340
ggccaccttc tttctcccag aggtcgatct gatcttaagt tgtacctgac taaaacctgc   17400
tgcaggagag atggtcagat tttatttaca cacaggagaa tggcttccta agattgtgta   17460
gtgaaccaag aaggtgttta caggcatgtg aaactggcta ttgtaaagag gcagtgatct   17520
gggacacgtg atgttagtta aagtggagga aaaggtgtac ccttcaagca gaggattcca   17580
gggcctctcc aaaccgtaca agtctgagcc aagggacaga aattccatca gtggcttgga   17640
agccaaatat ttgccctgat actgaggaag ggaaagagtg gaacgtgacc gtgggataga   17700
taagggtct tcacaggaat gcaaacaaga tgataggtag aatcacccat gagattagca   17760
aacaaatcac tttaagagga aaaagtagaa ataagagag tcaaccacag gtagaaaatg   17820
caagactttg gaatccacaa gtcatagata tgtatctcgg gaaataatcc aagcacacat   17880
```

```
gcatggtact gatacacctg tgggagagtg agagtctggt tgtcccgaga ctgatagatt  17940
cacccacctg ctgggctcta agccagttgg atatttgctc gagagactag attcctgtgg  18000
gctggtccta actttcccaa ctaagctcac cctcacttga gcccaaagga ctcctaagac  18060
tccatcccca ggaggcatcc ccaggtgagg agctgggcac ttgaattgtc atgtgtacag  18120
caccatagcc attgtaaaag gagaacatct cacaagtcag gagttactgg agagactgtt  18180
tatgacacac ttctgggttc gatggccctg agacaataaa ttcatccaca ttcctgtggc  18240
ccagttttca tgctttgctc atgacatcct ccctcagtga ttttctcctg cctttcataa  18300
tcaggtttga tgagcaaagg ttagaaagtg cagtggcttc ctgggcatgt gcattaaata  18360
gcaattaaaa tgcagtcctg gttcggctca atgcagcagg tgtcaatcaa acacctacag  18420
tgtgtcaagc ttgatgccgg ggcggtgggg tacaggaatg agcagacaaa tgcttctgcc  18480
ttgggagctt gagatgaaag ggaaggagag cacgaattag acctgtttga gggggtaata  18540
gaaattcaga taaaactgag tagggtccag aggagagatt ctttccacct gagaagacag  18600
cctaggaaag gctttctgga ggaggtggct ttttaactag gctttaaggg gtgggtagga  18660
gtttattagg cagagatagt ggcaaagggc tttcaaggga gggcgatctg tgtgaacaag  18720
agtgtgaaag caaaaaagca tgtaaacaaa aaagcatgga gcatctttaa gaaatagcaa  18780
ggagtttgct gtgactggat ctgctgggat tgggggtga aaggacatg caggcctgta  18840
ttggttaggg acctggcagg aagcagactc aaaagagttt cactgagcag aattgaatca  18900
agggactatt tatagagttc agcagggtaa aaggaatcag caagggatgg tgaggcaccc  18960
agggatgaat aactgggaag ctattagctc atctaggcct gaacagacaa gagagggtga  19020
tggggtttcc acagtacagt gagggctgag ttgtggcagg gaaccaaaag gcagggccta  19080
tgtggctgca gaagaacagg ggaagggagg gcgggagaaa ataaaaaaaa aaacccaacc  19140
tctgtctctt tctaccatta agatctacag ctactgcctc tcatttgcta aacccagcca  19200
aaaccagagg caaggaaccc tggatcagcc ctcccagtgc acagagcagg acaaagaaag  19260
acagagggtg aatcggaggg caaatggaga gtgactagca cagagccata tggcatgagg  19320
tgccatgctg aaaggttttc tcgggacatc aagaagtgtt gaaaagatac aaagtctagg  19380
aatgatggca gggaaattat tatttatttta ctgagatgga atcttgctct gtcccccagg  19440
ctggagtgca gtggtatgat ctcagctcac tgcaacctct gcctcccagg ttcaagcaat  19500
tctcttgcct cggccttcca agtagctggg attacaggca tgtgccacca tgcctggcta  19560
attttttcat ttttagtaga aatggggttt gctgtgttg gccaggctgg tttcaaactc  19620
ctgacctcaa gtgatccgcc caccttggcc tcccaaagtg ctgggattac aggcatgagc  19680
cactacgccc agtctatttt gataacatct ggtgatactg gtggctgttg cttaagggca  19740
ttatgggaaa tgagaggtaa gaatggcttc cacagcctct agctatatac cagcaggacc  19800
atctcctgct gttcacacaa gcctagccct aggcctctac atctagaaag cattgcccgt  19860
gcatctacca gcctttcttc catgcaagga gggcaaatgt ggctggcgga gaaggcacct  19920
agaataccag tggcagcttc tctgtctccc cactataatt taggactctt ctaattgtaa  19980
gcaacagaaa atccagttca aacaggctta atccagaaag gtgtaaggag gcgggggtga  20040
catataaaat ttatggctca gataccataa gagtctagaa acagtacctg gcttccagta  20100
caggggttta atatcatctg gacctgttgt ctccttacat acagtctctt tacacctgtg  20160
tcattttcac tcccaagcaa gactcttccc tggtgttgat acagctgcca gcacaggtca  20220
```

```
aggtttcttt ttcccagttc cacacccagc aggagagata aagtttctga tccctattag   20280
ttcaaacaag actccatggc cttagcctta ggctaactca gccctgagtc agagctccat   20340
tcctcaatat agtcttggga ccaaaggaac atggtgatct gattggctag accagggtcc   20400
ctccctcatc ctaccatgtt cccccaagct tctggactac ttagggcttc agctccaccg   20460
taaacaaatt gagagttaga aggtatgctg ttcactgcag ggacaaggga tactgtccct   20520
tagcaagagc aacagacctg cctttatct gttatgttct tgagctattt cctgaaagca   20580
atcaatacaa cactcataag ttaaattta ttgaattcat agttacaaaa gccaggaagt   20640
cgtttagtta ttaaccacat ggtttgaaat tgatggaatt gagacagaaa tcactttaaa   20700
aactgagaga gggtgtcata gtctgttctg ctgctgtaa caacatccca cagactacgt   20760
agcttataaa aacagacat ttatttctta tagttctgga ggccaggatg tccaagatca   20820
aggtgccatt agattccgtg tctgctgagg gcccacctcc tggctcatga atgatgcctt   20880
ctagctgttt cctcacacag tggaagtggc aaggcagctc tctgggactc tttcaaaaag   20940
gcactaatcc cattcaggag ggctctcccc tcacgaccta atcacctctc aagggcccca   21000
ccttctaaca ccatcacatt gatgattagg tttcaaaata tgaatttgaa ggaggacata   21060
cacattcata ccatagcaga ggagaagaaa aattaagcat gttttgcctt aaactcttaa   21120
gaattctaca cacacacaca cacacacaca cacacacaca ctacactaca ctacagctta   21180
tatttaatgc tgaaagtctg aatgctttcc ccctaagagc aggaataagg caaaggtgtc   21240
cattctcacc atttcttttg aatatctcac tggaaacctg gccagtgca acagggcaag   21300
aaaaagaaat aaaaggcatt ttgaaaagaa agaaacaaaa ctgtccctat tcacagatgg   21360
catgattttc tacacaggaa atcccaagaa attacaaaat aaattttaag actaataagt   21420
gatttagca gggctgcaag atacaaggtt aacacacaaa aatcacttgt tatttctata   21480
tgttaacaat gtacaactga aaatggaaat ttaaatacat tgtgtgacat agctccaaaa   21540
ggtaaggatt aggtatgtaa caaaatatat ataggatcta tactctgaca attataaaac   21600
actgatgaaa gaaatcaatg aatgccaaag taaatggaga gacataagtt gttcatggat   21660
tggatgactc aacatagtaa tgatgtcagt tctcccataa ttgatgtata gatttaatgc   21720
aattctgatc taaatcccag cagggatttt tgtagatata ccagacaagc tgattctaaa   21780
attcatatgg aggcagggtg cggtggctca cacctgtaat cccagcactt tgggaggctg   21840
aggtgggcag attgcttgag ctcaggaatt gaacaccatc ttgggcaacg tggcaaaact   21900
ctacaaaaaa atacaaaact tagccaggca tggtggcatg cgcctgtagt cccagctact   21960
tggtaggctg aggtgggagg attgcttgag cccgggagat tgaagctgca gcgagccatg   22020
atcacgccac tgcactcaag cctgggtgac agagtgagat cctgtctcca aaaaaaacaa   22080
acaacaaata aaactcatat ggaaagataa aggcattaga agagctaaaa taattatgaa   22140
aaagaagaaa gttggaggaa tcatcctatc ttatttcaat atggttttca agatatcaag   22200
tgtaatattg gtgaaaaggt agacatggca aaaactgcaa ttacttttgc accaacctaa   22260
tagatgaatg aagcagaaca gagattccag aaatagaccc atagaaatat gcccagttgg   22320
tcttttttat tttttttaa attgagacag gtctcactc tgtctcccag gttggagtgc   22380
agcagcatga ttgtagctca ttgcagcctt gaactcctgg gctcaagaag tcctcctgct   22440
tcagactctc aaagtgctga gattgcaggt gtgagccact gtacctggcc ctccaattga   22500
tttttgacaa aggtgcaaaa gctattcaaa gagcaaagga tagtctttcc aacaaatggt   22560
attggaacaa ctagacatca tatgcagaaa aaaaaatgaa cctcaaccta aaatcacatt   22620
```

-continued

```
acattcaaaa attaactcca aaaggaaaag agtaagatat aagactttta gaagaaaaca   22680
taggggtaaa atctacatga gctggagtta ggcaaagaga tctagatgcc aaagcacaat   22740
tcataaaaga aaaaaattgg taagttggac tttaacaaat aaatctcttt ctctccaaaa   22800
ggcacttaag agaatgaaca aacaagctac agactgggag aaaagaattg cagatcatat   22860
atccaacttg tctaaatttg tatccagaat atatagagaa actctcaaaa ctaagtaata   22920
agaaaacaaa tgatcaaact ttaaaaatag gcaaaacctg aacagacact tcaccgaaga   22980
gggtatactg atggcaaata aacacatgaa aaaatattca gcatcgttgg ccgttaggga   23040
aaagtgaatt aaaaccacaa taagatgcca gtaaatacct attagagtgg ctaaaaaaaa   23100
atacaacacc aagtgctgat gaggatgtgg agcaactggt actattaaac actgctgata   23160
tgggaatata aaatggtaca gccactctaa aaaacaattt ggcactttct tatcacctta   23220
aatacagctt tatgatatgg cacagcagtc ccactcctgt gtataggtcc tagagaaagg   23280
aaaacatgtt cacacaaaaa tctgtatgtg agtgtttata gcagcactct gcataatcaa   23340
tcaaaatggg agacgagtca aatattcttc aataagtaaa taaactactg tctatccata   23400
aaacgtgatc tattcagcaa gagaaaggaa cataccattg atacgtacaa aactcagatg   23460
aatcttagag gcattatagt cagtgaaaaa accagtctca caacttacat agaatatgat   23520
tccatctgca tgatagcctc aaaaagacaa aaccatagtg gtggaaaaca gactagtggt   23580
tgctagaggt taggaatgga gaaaggtgtg actagaaaga tacagcatga gagagctctt   23640
tggcgtgatg gagctgttct atattctaat tttgatggtg gctataagaa ttttaacatg   23700
ttaaccatag aactgtacac taaaatagtc aattttattg tatgatcaac acatgtacac   23760 acacataaa acatgccctt aagagtcagt tggtgcatac atgtccagca tttgcaagag    23820
agggtctgtg tttactggtg gggaattcct gttttctact gagttctcat ccctgaaaag   23880
agcaaaacct tgagtggcct gatgctgccg taattcccat tgaggatatc tgacctaatt   23940
gttttgggta ttgttgggca tggaaggttc actaacatct taagataaca ttcacacggc   24000
cagccagagc ctccctggtt atctggcttg gggacgcaca tgtcacatgg atcttggagg   24060
aggttgggaa ggctttccaa atacacttgg gctgagtttt gaagtcactg aaatggtaat   24120
cagataaatg agagagcaga gggagcaata aataaaggct caaagacatg agcgcagggc   24180
agaactgaca cagtgggcat ggttggggtt ggggctgggg ctagggtggg tcagagagct   24240
tgcatgccac cctatgttag gggaccactg aaggggcttt aagctggaga gtgactccgc   24300
cagatttgca tcctggaaag atagctctga cttagtttgc agaatgaact ggcagagaca   24360
agattgtatg cagaaagagt tttaggaagt tgatgaagta gccttggtga gaaatgcagc   24420
ggacctgaac caagacagtg tcagaggcca tcactcactt tacattacat tacattactt   24480
tacattacag tgtaaaggcc atcactcact tgtcttctga ctgggctggc aggattcaag   24540 cagccgggc tcctgtatcc cttttctcgc tgactctctc tctcctcttc tctttctctc    24600
tctctctccc ccaaccccca cccccactat actccctctt gctctggttt tcccatgttg   24660
cctctccagc atggcagctt caaggcagct ggacttctta catgatgctt cagggcttca   24720
aagtgagtgt cccaagaaga aaactaatca gatgctggcc tcttctaacc tatctcagat   24780
ttcacatagc ctcactactg ctgcattttg tctatcaagg tgatcacgaa ggccaaccca   24840
gcttcaagag acagggacag agcctccatt ttctgatggg aagagtatca gatattctat   24900
aggcctattt ttaaagtacc aggggaccca gaatgaaaag tctgaggttt tctgaaggga   24960
```

-continued

```
ggatagatac gtttattttt cctttgttgg gtctcatgtg caggtatcca ggtagagtcc    25020
cagcaggtaa ttgtatattg agtttgtcac tggggaaaca gcatgaggca acagatagag    25080
atggaaatgg aagctataaa aacagatggg atccctgtgg gagagtgtgc tgcccaagaa    25140
gagggtggaa gacaaaccct tgatgaacat caacaatgtc aaaggtggag agatgagaac    25200
ttatccagct ggctgagttc ctctagacat ccaactggtt ttcactccta gagtactgca    25260
gtctgagact tctctgggat tcagtattct cttggtaaaa gagtcatctt tccagcagga    25320
ctgaacccct tgcttgcccag atcaagggtc ctcttccacc tctcacagct ggctgctgag    25380
tcagaacctc ctaccttcct cccaaggcca ggctgtgttg tggagccttc tgtcctgtgt    25440
gtttccagta tgggacaagg cactagatcc tccaccctct tcccagttag ctatgttccc    25500
tggagtaaaa gagtctttga acaagttgtt aggaaagttt ctcctcttca accacttcaa    25560
aatgtccttt tgagtgtaag ccacatccaa ataattagtc ttcagttcca gatcctgtta    25620
gagagccaca ctggtacagg agctttcctg attcctcttt tgtgagttgc cataaagaaa    25680
gaggaaatga cctataatct atgaaagagc caggttctaa aacagatcat tctgacttca    25740
gagctcagcc cttcacccta ggcatccctc caagagacac cagcatgaac ttacccagaa    25800
cgggcctgaa catttgaaca actgaacaca atacacccca gctggctcct ggcagattgc    25860
actccagtgt ggtgagttta atttgagcaa gcagttgaaa taaaacaggg ctggctgtgg    25920
ggatgtggca gagccagaat ggcttctctt gatctttttt ttctctctgg gaaacaagat    25980
gaattaatga actgattcat actcccttt acccaaagtc tgaaataaac cacccttatc    26040
atctcatcaa acctttaccc gacccaaact atggatctgg gattcttact cttctcttgc    26100
cttcaatcta tcccactcct gatgaagttc cttcccaact tccaatccca tgggcttcac    26160
tttcctgcct ataaacagct gtcaactgcc tgatttccct atgctaatcc attctacaca    26220
ttttaaccag gcttttctcc aatctaggct ggcttttaca caaacatgtt caatggctat    26280
tcattatcct taaaaactaa tctttgtata ttatagttta acacacggtt tatctcatt    26340 tatcctcaca atgaacccat tatatggaag ggaacttagg gtcagagaag tataaattct    26400
cctccctggc attcaagggc tttcatggtg tgccccaagt gatttcctag tcttggtttt    26460
ctaaaccacc cctcaagcac cagccaaact actgactgaa cacactctta tcacctcttt    26520
atggaagaaa cagaactttg gtgtccaaca gaactggata tcgaagctgg ccatgtgact    26580
ttggacaagt ttcctaacct gtgttacatt attatctta tctgtaaata acaggctttt    26640
tagatcagat gattaaataa aataacgtat tataaaagtg tttgggcctt aggcacctga    26700
cacgttaatt tcttcttccc ctgcccctct gtctttaggt gttctctcca ctctccaccg    26760
tcctcaatag tccccgccta gtgaattcct tctcactctc acatccaagg ttcatctaaa    26820
attctttctt aatctcacct agtgtgaatt tcaagggtag ctctgaactc ctacaacttt    26880
ggggtggccg ttcctataga ctagcttgtt ctcttgtctt ctgtcttgtc ctgcctacta    26940
gaatacaatt tctcagtggc aggagcagcg tcctctcttt gacctcacaa catagcacct    27000
ctgtggtgct ggcacgaaga agtcatccag aaaacatttg taagattgac tcaagaccac    27060
gggaggcttc ttgtgttcca cgtgctgatt tcctgattgc tgtgatattt gctttcggct    27120
gaacactggt caccttccct cttctgttat tgtgtaccag aatgaaagat gacagccagg    27180
aggaagtttg cttgcagagg tatgtgggct gagctcacaa aatttaacaa ttgttttag    27240 cttttgttca cattttaaaa attgggtggt ctcacacaaa gacctagatt tttagtttct    27300 cttttaaaaat tcaggagaaa aggccaccat ggaccctcac tttcatgtga tggggcttgg    27360
```

```
gcagagacat caagaccacc acagacccat gggcctgctt ccctcacttc tgccctgatc    27420
cctgtagcct tgtacgtttg cagtctttga tgtcaactga aaattgttga aatgtatttc    27480
aaccctatct ttaagaatga agttgtagcc gagcacggtg gctcacgcct gtaatcccag    27540
cactttggga ggctgagaca ggtggatcac ttgaggtcag gagttcaaga ccagcctggc    27600
caacatgggg aaactccatc tctactaaaa ataaataata aaaaaactta gccaagcatg    27660
gtggtgggtg cctgtaatcc cagctactca ggaggctgag gcaggagaat tgctgaacct    27720
gggaggcaga ggttgcagtg agccgagatc tcaccattgc actccagcct aggtgaaaga    27780
gcgatattcc acctcaaaaa aaaaaaaaaa aaaaaaaaa gaatgaagtc cttactttt     27840 ttttgattt aggacagatg accaaggagg tgttacttcc ttgagtggtg aaaaggttct    27900
tctactgcat ggggtttttt gtggttttgt ttttttttg tttttgagat aaggtctcac    27960
tctgtcaccc aggctggagt gcagtggcat gatctcagct cactgaagcc tcagcagcct    28020
gagctcaagc gatcatccca ctttagcttc cctaatagct gggattacac acgtgggcca    28080
ctgcgcctgg cctacagtat ggttttaaa tatctttgtg ctctccctct gtagacatct    28140
ttcatttgct tagaatctgt ggtgatggag gcctcatgcc ctattccaac tccagctgcc    28200
tgtcaatgta gtgtctgtag cttctttcac atggagaagc tatcagtccc attctgtcca    28260
tcaaggtaga gtgaaaata tcaggtcact ctgctgcctc taccacctt cagcactgat     28320 ggctccactc cctgagggga gaggcacaag tgacagggaa ggaagaaaga agaagaattt    28380
tctcactttg tgatttattg catttaattc tcaccctgag tctgagttgg gtatcattcc    28440
ttcttgactt atagcaaaat caaggcacat agaggctgtc ctttatgctc catcccaaag    28500
ctagaaaata aatgatgagt ggtttgggcc cggttgtgtc taattgtgtc atgtttttc     28560 actattctgt ctgccttagg gtctccaacc cctttcagct gtatttataa gactgatgtt    28620
tgcagaactg tttattagtt tgcaggactg tttattagac aactacaaac ggagctgaaa    28680
taaaactttg gtttctgttt gctctaaaga gaagtttctg ttcaatcctc cactgggagt    28740
gtgtctttag gcctctaaat tttataccat aactatttgt ataatttgaa tggtctccaa    28800
tgaaatggat acaaataata ataaatacat tctaaaatag caataatgca tgacattggt    28860
ttagatcaca gtgtttccta tgtacatttt ctctttgggt tcacccaaca ttctcgagat    28920
accctcactc aagtttttag ataaagcaat caaaaagcaa gaggatttaa atgacatagg    28980
taagtatgca tgtggtagaa atggaattag aatccagatt cttagctcct cttttcatta    29040
tctgatcctg cttggttttt actcacacca ggcaataatt ttgaaagctc tgctctctct    29100
acttgtgata ttattatctg ttgttattat tcaatcataa atatttattg agccttcctg    29160
caggccaagg gcagggctaa gtcctgtgca ttcattattt cacttaatgc tcaggacagc    29220
catatgacat aggtactctt ctcatttctc tttaactgat gaggatacag aggcttagag    29280
ggattcagta acttatgtaa ggtcacactg ctagtaactg gtaggacata ctcaactcca    29340
gataggtgac tcatggaaat ttctgctgtg tcttacatct tcacctagat tgtaaaccac    29400
atggggaccc ggaccacatg tcctccacag agcttagcaa agtggttgta tgcacaggta    29460
tgcaagtcat taattaatga cagttgattt tttctcggcc attagctttt attttacttt    29520
atctataggg attttcagat cacactgttc tcaaaataat cctggttttc tgttggctgt    29580
tttgatttat ctttagacac tgtaattgaa aattaagctc ttaagcatct cctttacagg    29640
ctatgttcca caatctgtaa tcacaacttt tctttaaatt gatcatcatc ttttgagctg    29700
```

```
ttaataaaca tgtctggctt catttgggtt ttcaaattgt tatttccaga cggtgagact   29760
ttcagatctg ataggctcac acacatcctg ccaagtggaa gtttgagcaa aatgtcacat   29820
cttttggcaat atttgtgcta ttagtatgat gattaaagga aaaagaaaag tttcactgtg   29880
atgtcagcag ctttcccacc tcatgaaaaa gccatcaaat tatcaaccaa tcaaaattaa   29940
atgaatccca tttaattta ttattatcta tttttcttt ttccccgttt taaaaatgaa     30000
tttggttcat ttgctttctg cttctggatt tgcctgttct ggacatttca tataaatgga   30060
atcatataat acatggactt ttgtgactgg cttcttggc ttgtttcact tagtgtaatg    30120
ttttcaaggc tcatccatac cacagcatgc agcagtgctt tattccttt tatggctgaa    30180
tattattcca ttggatagag atacaatatt ttgtttatcc aataataaat tgggcactta   30240
gattgttttc acatttggct attaggaata atgttgttgt gaacatttct tgtacagttt   30300
ttgtgtaagg acatgttttc aattccagag gctatatatc taggcatgca attgctgggt   30360
cacatggtaa ctctatgttt aattttgag gaactgccaa acagtcttcc acagaggctg    30420
caacatttta cattctcacc aaaaaggcaa aaagattcca gtttctccac atcctcacca   30480
acatatatca ttttctctt tttgtgtttt taaaaatag ccattctaat gagtacaaag     30540
taacatctta ttgtggtttt gatttatatt tccctaatga ctaataatat tcgacatctt   30600
tttatatgct tactgtccat ttgtatatct tcattggaga aatgtctatt caaatatttt   30660
gtctatttt aacaatttgg ttgtcttttc attgttgagt tgtaagaatt ctttatgtat    30720
tctagaccct taccagatac ataatttgca cacttctctt ttttgaataa attgcaaagc   30780
aacattttc aaaaaaattt ttaattttt tctgccatat tgtgaagctt ggttgtctct     30840
accaggtact acctcctatt tacccataag tatttggaag gtcatcagga tttatgctca   30900
aaaatggagt ttggggtga aaggaagca ctttgtttgg agagggtttt actgttgagg     30960
ccctgcatta atccccctctg ccacctccag gaaagctgtg gtcacatctg gtatagtaga  31020
aagtgccatg gtggctgagg aagcttgtgg gtttatcaca ttttatcca tggtggcatg    31080
gacaccttgt ttttgcttcc gaattgctct taaagaaaaa ttctggggcg gatgaacccc   31140
atcatcatcc aggaagaata tttgcagcac attttttctt gtcatgatga gtttgctgtt   31200
tgagacggta tggtaagaag ctttataatg gctggctagt gtcatttttcc ctcatttagg  31260
ctcaaccgtg actttatatc tgtatacttt atggaaggcc tggagcctca cactgaggca   31320
gaagagggaa ggggcaagtg cagttgatgg tggcagctaa gtgggagaga aagtcagcga   31380
agacaattat ttattcaaga cctttacaaa gggagcagcc ccacttgttt gcatgttgat   31440
tgaaccatac cttagtgtcc agttgcttga ggcttgcagc agcatcttta tgctcttcaa   31500
agtgagtgct gccattggta gcaaggtctt atggatgccc ttgctaggcc catttccttc   31560
tttgttattc caagtatact tctaatgaat cagaacctgc ctcttttttt ttttcttttt   31620
ttttttttt gagatggagt cttactctgt cgcccaggct ggagtgcagt ggcacaatct    31680
cagctcactg caagctctgc ctcctgggtt cgtgccattc tcctgcctaa gcctcccgag   31740
tagctgggac tacaggcgcc caccaccacg cccggctaat ttttttgtatt ttctgtagag  31800
atggggtttc actgagttag ccaggatggt ctcgatctcc tgaccttgtg atctgcccgc   31860
ctcagcctcc caaagtgctg ggattacagg tgtgagccac cacgcctggc ctgaacctgc   31920
ctttttaacaa gaccccaagg tgattcaagg cacatcaaag tttaagaagc atagatttac   31980
attatattct gtctatccct gcacatctca catggttatt cagcctaatg tccgtgtgag   32040
tcagtcttcc tctttctttt catgccttcc atggatttca cctggtgtac tcttgatacc   32100
```

```
atctgtatta gcctgttctg acaaggctat aaagaaatac cggagactgg gtaatttata   32160
aagggaagag gtttaaataa ctcaaagttc tgcgtggctg gggaggcctc aggaaactta   32220
caatcatggc aaaaggggaa gcaggcacct tcttcacaag gcagcaggag agagagtgtg   32280
agcgtgtgaa ggaggaactg tcaaacactt ataaaaccat cagatctcat gagaactcat   32340
tcactatcat gagaacaaca tgtgggagac ccccacctcc atgatccaat caccttccac   32400
caggtcacct cccttgacac atggagatta tggggattac aattcaagat gagatttggg   32460
tggggacact gccaaaccat atcaccatcc tagtactggc tgcagcttcc tttaattact   32520
ggatgaagaa acacaatctt ttgatcaact agcatttccc tgaagcactt gtaaacaatt   32580
ccataaaaat cctgagatag gtacctattt gtgtttactc ttgaactttc cccagcctcc   32640
tcctccccat ccctgtcttc ccacagctca atacttccac cttccattgt tcagtacccc   32700
gctgtgactc ctgcctgtgc tgagttgcat ctatgattga ctctcattag atgtgagctc   32760
cttgagggaa gggtcttaca tcatccattt ttataccttg attcccaccc ctggacctaa   32820
cacaggtcct tggacatagt aaatatttgc agaatttaat taagttattg agtcacattg   32880
gaaataattt cagaagatac caaatgcctt ttcttttttt ttttccacat gccatttgtt   32940
ctcgtaccac taagacccta agacttttat tttgttgata tcaagtggta taaatattaa   33000
caaacattgt attatatatc ataattttaa ctctgaagtt tttaatttat agaacaaaag   33060
ttaatatttc tctaccaaaa taaatgtcat agactgagga agaattttg ttaatttggt    33120
cataccaaaa atatttaaca ttaatttctc tcctcaactt ctgactctgc tgctccttaa   33180
ctctgtaacc atgacttacc tgtcaaagcc aaaactcttt tgagcatttc atgagaaaat   33240
ctataaagag tatatagcct acaataatag ctaacatgta ttagctgtac ttacagtgtg   33300
agccaggtac tttttattct aagtacttta catatagtct cattttaaaa tctcctaatg   33360
actccatgag gttgatattt tgttcttccc attgttatag gtgaggaaac agaggcacag   33420
gctacagggt attttgtcca agataacaca gctaataaag tggtgaggcc aagatttgaa   33480
cagtctcttc ttaaagagcc tgcctcctga agggttactg atgaattcct ttcttccttc   33540
aaaatgcttc atgtgattta acatgcctta tttcattgtg tatattaaag gccctttgtt   33600
tatacattac tctcatctat atttccccat ttggccaatg cattgtataa attaggtgat   33660
ctgtaaatga ttgttggcta attgatccta tgtgcataca tgggaatact tggaaaagca   33720
atgattgttt taatataaca agttcttgat gtagcaagat tgttcctata cattgtgaa    33780
ctctcaattt taatatttac tgactccatt atccatctta aaatgggcat atcggaaagg   33840
gtaaggaata aataattgat ggtggtgtca cacatctagt aatatgatag ttgagctaat   33900
atgaattggt tctcccacca tctcaaacac aaagaaatat aaaagtcccc tccagaccaa   33960
tgcagagcca aacccaaact caaaagcaat aaaggaaatg cccttgtgcc agaaataaaa   34020
agggaactca aagccagaag tataaacaag atctggtgct aaggtctaga cctgtcttaa   34080
tctgttttgt gtggctgtaa tagaagacct gagactgggt aacttataaa gaaaagatgt   34140
ttatttaggt cacagctctg taagttggga agttcaaggg catggccctg gcttctggtg   34200
aagactttcg agctgcatca aaatatgata gagaaagtca tctcatcttg gccatgtgt    34260
atataatttta atttaataa ctaatataaa attattgtta aaatatggta gagaagatca   34320
aaggggaagc agatctgtac aaagaggaaa aacccgaggg gtatcctggc tttataacaa   34380
cccactcttg agtatactaa tccattccca tgagaactaa tccagtcctg ccagagtgag   34440
```

```
aactcgctac tgcaagaata gcaccaaact attcatgagg gatccagctc atgaccccaa    34500
gggctcccac tgggccctgc cttccaatac tgccacagtg gggatgaaat ttcagcatga    34560
gttttgctga ggacaaacca accatagcaa gacccactta caggctttaa taatgggaga    34620
taggggtctt aatatccaca tggggaaaag tgatatgatc ttggcccacg tgagtgaagg    34680
agtctaaacg aaaccttgac ataaagtctg gaaccacaaa atttggccct gcccttggaa    34740
acaagagcag agaaattcta cctagtgact aaggaaaacc ttaagaaagt ttgccatttg    34800
tccatggcta aaataagagg ttaagagggt acccatgaga agattaaaat ccagatttat    34860
acttccctca gtgcatcatc taaatttaca ccactgtgta atgccgattt atcaagctga    34920
aaaattaata tgaaaactgt cctggaggac ttgaaactcc taagtcccca gaaaaaataa    34980
gtagcctgta ggtagacttt cacaactcag aaaaaagcca acccctcct caaaagacaa     35040
gcctatgatc aaaaattaca aattacacag gaaaagaccc agtaggagaa taggtatccc    35100
ccaaactgga gatgatagaa cagtctgaaa taatatatac taaatatgtt tagaataact    35160
aaagaaaaac aggtggaata gaaactagat aatagaaaaa tgatagtgtg aaaaggatac    35220
tgtaagttct agaaatgaaa cttagagtgg aattaaaaat tcagtgaatg aattaaacat    35280
ccagtaaatg caactgatgt aaggactgga aactgcaaaa taggtgtgag aaaaatcagt    35340
caatgcatca cagagagata aaaaatgggg aatatataaa aaccctccaa ggacccatag    35400
atttggaaac tgaaactcat attttttcaa agaatttaca gttcaaagaa aaaaatcaca    35460
acatagattt ataagatatt tagaactaaa caaaagtaaa aataccatat aataattcac    35520
aggacatcaa cacagaattt agaaggaaat gtcttatatg catatactga aaaacaaaaa    35580
caaagctata attccagcac tttgggaggc cgaagcagga gggtcagttg aggccaagag    35640
tttgagacca gcctaggcaa cacagtgaga ccctgtctct acaacaaaac aaaacaacaa    35700
caaaaaaact cacaaagata atgataatga gctaagcgat caactccaaa agggagaaaa    35760
ataacatagt aaacctttaa aaattagatg gaaagaattt attagataag agcagaattt    35820
agacatatag aaaacaaaat agggaatgtg atatggaata ctgaacagca ctttgaatga    35880
actggatcta cttgtattaa tattaataaa tctcaaaaac acaaagaat tcaaaaaca     35940
caaggcaaga gaatacatcc agactgatac catgtgagtt agattttca agcacaaact    36000
gacgtgagta gtagatgtat aaaggcatgg acaaaaagta ggctcaaatt aagtgattat    36060
ctaatctatc taagagaaga tggaattggg gaggatgcaa tggaccctca accataatgt    36120
tttatttgga aaaaaagatc tgtggaggat ttgttcagtc tgcgtggtgg atgtatacat    36180
gtttatgtat ttttactttt cattgaaaca tttcagaata ctctttcaaa gaatcaataa    36240
ttcagattct gtatactgaa tagaattcta acaaaattac aattaagaaa taagttaat     36300
gccagtgttg catgaggttt ttactcatgt ggtttggttg tagtaaggga tctacaatag    36360
ttgtagtagg cagttctgag acggcaccca agattgctac ttcttggcaa acatacccg     36420
cataatcccc ttactttaag tgtggatatg atgggatttc acattcataa ttagattaca    36480
ttctttggca aaggtaaaga gacttttgca aatgtaatta aagtccctaa tcagttgatt    36540
ttgagttaat caaaacagat gatcctgggt aggcctgact taataaagtg gaagccctta    36600
aagagactgg gccatcctg ctgactctga gagggaagc cactgtgttg tcagagggcc      36660
acatggcaag gaacagtagg acttgcagga gccgagagga gcccctgttg acagccagta    36720
agaaatccta caactaccag gaagtgaatc ctgagaacag catcatgagc ctggaagaga    36780
accctaagct ccaggaagga atacagccta attgacacct tactgaagcc ttgtgagacc    36840
```

```
ctgagcagag gactcagtgt agctgtgctc agactcctga tccatggaaa ttttgaaata   36900
ttacccgtgt gttgttttaa gctactaaat ttgtggtgat ttgttacaca gcaatagaaa   36960
actaatgcag tagctctatc taccctgttg tatgaaagca gtttgtaaat tgacatgcta   37020
tataaacagt gctggttttg ttatggcatt gattattcac attttatctg agtactatga   37080
tcaatacact agactgttat ggtatactac atttgccatt ctgctatacc ttctcttaga   37140
gcacaatttt gatggagata atcaaaccag gttctcattt tagataaaat ttccacaaaa   37200
gatctacaga aattgtttct aagcttatat tacaaaaatg gcagcaccta tccaatgcta   37260
atgtctatgc gaacatctct attatatgga gtttgagttt tgagaccatt ttcttaccgt   37320
tttgaagcca tactatgggg ctcacttcac tgatctagta gatgttctgg gtatctgtca   37380
tggcaaagtg gtaagtcttc tgaaaagaag tggcatctca acttgaactt tagaaaatgc   37440
aagaaataaa accctcctga agtaagacca ggagcacatc agaagactcc cttattgggg   37500
tcacaaacta agaacgaaag aatacccacc tcttgttact cagcttattc tgtgcatgtt   37560
atcctctgtg tttatttccc tctcgtcacc ccctagtttt tagtaaagtc tcatttaaac   37620
cttctagtgt agcttctgtt atgccaggga tattaggagc atggacactt tgatgcatac   37680
cacgatgcgg tgatgacagt gctaattgat cagagtctcc ccaagggaaa gacatctgca   37740
ggaacaagac acaaaactgt acagcccacc tccccttctc acaagaagat acttcctgca   37800
tggaaaatct tggaggactg gagtttgatt ttattaaaaa tgcaagttag gaggtgggca   37860
cagtggctca tgcctgtaat cccagcactt tgggaggccg aggcaggcag atcacggggt   37920
caggagatca ggaccatcct ggctaacatg gtgaaacccc gtctctacta aaaatacaaa   37980
aacaaaatta gctgggcatg gtggccggtg cctgtagtcc cagctactcg ggagactgag   38040
gcaggagaat ggcgtgaacc cgggaggcgg aggttgcagt gagccaagat cacgccactg   38100
cactccagcc tgggagacag agcaggactc cgtctcaaaa aacaaacaaa caaaaaaatg   38160
caagttagat tttcttatag tttgagagta ttctggttta agaaggtggg aagaagtaaa   38220
attggttgag gatctaaggt ataaagagat gataccagag gtttgataaa ttgagcccta   38280
accttaacag tacatgcttc tcagtctaca ttccgagttg gctgtaatat atgcggcctc   38340
atccactctt acctttcttt gtgacactga taccttatc aacacacttc atccacgtct   38400 cttcttgtg ctctatacac acatatccgt gtcttcatta agcatcttcc cctcagtgtc   38460
ccatccaaaa ctgaactcat catctttaga actatccata ttacccactt tggtaggtat   38520
caccatccac cctgttaccc aagctagaaa acaagaaccc cagaacttca ctttcttcct   38580
catctctact gccttccacc ttcagacata taatttatca ccaaatacta actcgtccac   38640
ctcctaaatt tgttcccctt ctccactctt taacaccgct caccttggat cacagcagcc   38700
acttacagga ttcgcacact gctttctaat gcaaaactcc ttccaatgaa ggagtaaatc   38760
ctccagaggc ttcccactgc cttcaggatc agcttcaaat ccttagcttg gcgtatggga   38820
tccttcacca cctgcttctt cttacttgtg cagttacgta catctaccta attatgggcc   38880
acactgaatt gcttgaagct gtttaaatgt gccaagatat cccagatttc tgacctttaa   38940
gcctttgcag tagtcttacg aattcatact cgtcctttcc cagacaaatg tctctactct   39000
tttgatgaaa ctgtactgtc ttccatcctt aagggcaggg gacatgcatc cagctgtctt   39060
tgtagtcaca cagtgtgcca tgatgcctat ttctgtaggt gctcaataag tgtttgatgt   39120
gtatttatta ggataatata cctatgtatg agtgaacaaa tgaatatgca gatgaatgaa   39180
```

```
taagtgtaag gaggaatgaa ggatgaatta gataattaaa agcctctgcc atcagtcaaa    39240
atgaaacttt ttttgtgtgt gtgtgtgtgt tgtagagatg gtgtctcatt atgttgccca    39300
ggctgatctc aaattcctgg gctcccacct tggcttcaca aagtactgga attacaggtg    39360
tgagccacca tacctggact cattttttaaa atatatatat acttgattac ttcaccacaa   39420
tagtgtcctt ttgctcatgg cccatgggcc tagtcccttt tagagttctc agtcacctgt    39480
aagatacatg ccttgaatgc taccaggtga taaatttgag ttggacaatg aagaaaatat    39540
tgtacatgta ttttcttatt tatttagacc aaataggctg agagagtaac ttgaatattt    39600
aagagcttcc ttaaaatgca ccataaataa tggaaagtga atgacttgat tacttcccctt   39660 attttttctct tatttttatt tgggttgata ggaaggagga ggtttgtgga gggggagaaa   39720
atataaaaca gtggaacatg caaaaagagg gcccaattct tcccttctct tcaatttcca    39780
tgatataact aactctgatc tctcatggtg ggcaatggaa tattgtggat aaagtctgga    39840
taactgaatt gtcaaaaccc tccaatatgg accactaatt aaagcactga aagcacaact    39900
aagtgtactc agtatgttaa tgatgcagaa tacaatgtaa cctttgattc aggagcggct    39960
tcaagatcca agcgtcctgg gagaagcagc aatccctctt cctgggcgca gagatgctgg    40020
tttaacacag tcatgtgtca gagaaaacta gttttttcctg caggcccaaa tcctacccta   40080
gagaaaccca ttagaccttt accaaaatca acttttcttc tgagtcagac cgaattctta    40140
attgtaggtg atagaccaaa agggaaagat gactcaatgt aaataatcgt tgctattgac    40200
aaaacagtgc aaaccacatt tcctgttgat ggtggagtca cccatgacgg aaaacatttt    40260
tattgcttta ataacacaat tatattattt tttaactctt ccccttcaaa tcctctagca    40320
cttaatatag tgcttgggat atatttggat attaataaat gcaaaagtgt tattgcctct    40380
ttttgaatta acatactaca aagaatgtgt ttactgtact ttcttacctt aaaacttaaa    40440
cctaaaaatg tatgctaata tgaacctttg cttgacattt catgcttgcc tctttggtcg    40500
ctaggaaaag tcagcaacat tcagcaaaac tgtcaaggat tggagcattt aatagttggc    40560
tgatggtcca caggcaagtc catccaaaca gccaaagttg tattactcag tgtttttaaa   40620
agatgaagat ttggggtgga gccaagatgg ccaaatagga agagctccag tctacagctc    40680
ccagcgtgag tgactcagaa gatgggtgat ttctgcattt ccaactgaga taccaggttc    40740
atctcactgg ggagtgtcgg aaagtgggtg caggacagtg ggtgcagtgc accgtgcgtg    40800
agccgaagca gggcgaggca tcgcctcacc cgggaagcac aagggtcag ggaattccct     40860 ttcctagtca agaaagggg tgacagatgg cacctgaaa atcgggtcac tcccacccta     40920
atattgcact tttccaacgg tcttagcaaa tggtacactg ggagattata tcctgcgcct    40980
ggctcagagg gtcctacgcc cgcagagact cactcattgc tagcacagca gtctgagatc    41040
aaactgcaag gcagcagcga gactggggga ggggcgccca tcactgtcca ggcttgagta    41100
ggtaaacaaa gcagccggga agctcgaact gggtggagcc cactgcccct caaggaggcc    41160
tgcctgcctc tgtacactcc acctctaggg gcagggcagt gccaaacaaa aggcagcaga   41220
atcctctgca gacttaaatg tctctgtctg acagccttgg agagaatagt ggttctccca    41280
gcacacagct ggacatctga gaacaggcag acagcctcct caagtgggtc cctgaccccc    41340
gagtagccta actgggaggc accccccagt agggcagac tgcacctca catggcaggg     41400 taaccctctg agacaaaatt tccagagaaa tgatcaggaa gcaacatctg ctgttcacca    41460
atatccactt ttctgcagtc tccgctgctg atacacaggc aaagagggtc tggagtggac    41520
ctcaagcaaa ctccaacaga cctgcagctg agggtcctga ccgttagaag gaaaactaac    41580
```

```
aaacagaaag gacatccaca ccaaaacccc atctgtacat caccatcatc aaagaccaaa   41640
ggtagataaa accacaaaga tggggaaaaa acagagcaga aaaactggaa actctaaaaa   41700
tcagagcgcc tctcctcctc caaaggaacg cagctcctta ccagcaatgg aacaaagctg   41760
gagggagaat gagaatgacg ttgacgagtt gagagaagaa ggcttcagat gatcaaacta   41820
ctctgagcta aaggaggaag ttcgaaccca aggctaagaa gttaaaaacc ttgaaaaaaa   41880
aattagacga atggctaact agaataacca atgcagagaa gtccttaaag gacctgatga   41940
agctgaaaac caaggcacga gaactacgtg acaaatgcac aagcctcagt agccgattca   42000
atcaactgga ataaagggta tcagtgatgg aagatgaaat gaatgaaatg aagtgagaag   42060
agaagtttag agaaaaaaga ataaaaagaa atgaacaaag cctccaagaa atatgggact   42120
atgtgaaaag accaaatcta catctgattg ttgtacctga aagtgatggg gagaaaggaa   42180
ccaagttgga aaacactctg cagaatatta tccaggagaa cttccccaac ccagcaagtc   42240
aggccaacat tcaaattcag gaaatacaga gaacgccaca aagatactcc tcgagaagag   42300
caactccaac acacataatt gtcagattca ccaaagttgc aatgaaggaa aaaatgttaa   42360
gggcagccag agagaaaggt cgggttaccc acaaagggaa gcccatcaga ctaacagctg   42420
atctctcggc agaaactcta caagccagaa gagagtgggg gccaatatgc aacattctta   42480
tagaaaagaa ttttcaaccc agaatttcat atccagccaa actaagcttc ataagtgaag   42540
gagaaataaa atactttaca gacaagcaaa tgctgagaga ttttgtcacc actaggcctg   42600
ccttacaaga gctcctgaaa gaagcactaa acatggaaag gaaaaaccgg tgccagccac   42660
tgcaaaaaca caccaaattg taaagaccag agaggctagg aagaaactgc atcaactaac   42720
gagcaaaata accagctaag atcataatgg caggatcaaa ttcacacata gcaatattaa   42780
ccttaaatgt aaatgggcta aatgctccaa ttaaaagaca cagactggca aattggataa   42840
agagtcaaga cccatcagtg tgctgtattc aggaaaccca tctcatgggc agagacacaa   42900
ataggctcaa aataaaggga tggaggaaga tctaccaagc aaatggaaaa caaaaaaagg   42960
caggggttgc aatcctagtc tcggataaaa cagactttaa accaacaaag atcaaaagag   43020
acaaagaagg ccattacata atggtaaagg gatcaattca acaagaagag ctaactatcc   43080
taaatatata tgcacccaat acaggagcac ccagattcat aaagcaaatc cttagagacc   43140
tagaaagaga cttagactcc tacacaataa taatgggaga ctttaacacc ccactgtcaa   43200
cattagacag atcaacgaga cagaaagtta acaaggatat ccaggaattg aactcagctc   43260
tgcaccaagc agacctaaca gacatctaca gaactctcct ccccaaatca acagaatata   43320
cattcttctc agcaccacac ctattccaaa attgaccact tagttggaag taaagcactc   43380
ctcagcaaat gtaaaagaac agaaattata acaaactgtc tctcagacca cagtgcaatc   43440
aaactagaac tcaggattga gaaactcact caaaaccact caactacatg gaaactgaac   43500
aacctgctcc tgaatgacta ctgggtacat aacgaaatga aggcagaaat aaagatgttc   43560
tttgaaacca atgagaacaa agacacaaca caccagaatc tctgggacac gttcaaagca   43620
gtgtgtagag ggaaatttat accactaaat gcccacaaca gaaagcagga agatctaaa   43680 actgacaccc taacatcaca attaaaagaa ctagagaggc aagagcaaac acattcaaaa   43740
gctagcagaa ggcaagaaat aactaagatc agagcagaac tgaaggaaat agagacacaa   43800 aaaaacccctt caaaaaatca atgaatccag gagctggttt tttgaaaaga tcaacaaaat   43860
tgatagactg ctagcaagag taataaagaa gaaaagagag aagaatcaaa cagatgcaat   43920
```

```
taaaaaatga taaaggggat atcaccactg atcccacaga aatacagact accatcagag    43980
aatactataa acacctctac acaaataaac cagaaaatct agaagaaatg gataaattcc    44040
tggacacata caccctccca agactaaacc agcaagaagt tgaatctctg aatagaccaa    44100
taacaggctc tgaaattgag gcaataatta atagcttacc aaccaaaaaa agtccaggac    44160
cagatggatt cacagccgaa ttctaccaga ggtacaagga ggtgctggta ccattccttc    44220
tgaaactatt ccaatcaata gaaaagagg gaatcctccc taactcatga ggccagcatc    44280
atcctgctac caaagcctgg cagagacaca acaaagaaag agaattttag accaatatcc    44340
ctgatgaaca tcgatgcaaa aatcctcagt aaaatactgg caaaccaaat ccagcagcac    44400
atcaagaagc ttatccacca tgatctagtg ggattcatcc ctgggatgca aggctggttc    44460
aacatatgca aatcaataaa cataatccag catataaaca gaaccaacaa caaaaaccat    44520
atgattatct aatagatgc agaaaaggcc tttgacaaaa ttcaacaacc cttcattcta    44580
aaaactctca ataaattagg tattgatggg acgtatctca aaataataag agctatctat    44640
gacaaaccca cagccaatat catactgaat gggcaaaaat tggaagcatt cccttttgaaa    44700
attggcacaa gacagagatg acctctctca ccactcctat tcaacatagt gttggaagtt    44760
ctggccaggg caatcaggct ggagaaggaa ataaagggga ttcaattagg aaaagagaag    44820
tcaaattgtc cctgtttgca gaagacatga ttgtgtatct agaaaacccc attgtctcag    44880
cccaaaatct ccttaggctg ataggcaact tcagcaaagt ctcaggatac aaaatcaatg    44940
tgcaaaaaat cacaagcatt cttatacacc aataacagac aaacagagag ccaaatcatg    45000
agtgaactcc cattcacaat tgcttcaaag agaataaaat acctagaaat ccaacttata    45060
agggatgtga aggacctctt caaggagaac tacaaaccac tgctcaatga aataaaagag    45120
gatacaaaca aatggaagaa cattccatgc tcatgggtag gaagaatcaa tattgtgaaa    45180
acggccatac tgcccaaggt aattatag ttcaatgcca tccccatcaa gctaccaatg    45240
actttcttca cagaattgga aaaaactact ttaaagttca tatggaacca aaaaagagcc    45300
cacattgcca agtcaatcct aagccaaaag aacaaagctg gaggcatcac actacctgac    45360
ttcaaactat actacaaggc tacagtaacc aaaacagcat ggtactggtg ccaaaacaga    45420
gatatagacc aatggaaaga aataatgcta cctatctaca accatctgat ctttgacaaa    45480
cctgacaaaa acaagaaatg gggaaaggat tccctatttta ataaatggtg ctgggaaaac    45540
tggctagcca tatgtagaaa gctgaaactg gatcccttcc ttacaccttta tacaaaaatt    45600
aatacaagat ggatgaaaga cttaaatgtt agacctaaaa ccataaaaac cctagaagaa    45660
aacctaggca ataccattca ggacatcggc atgggcaagg acttcatgtc taaaacacca    45720
aaagcaatgg caacaaaagc caaaactgac aaatgggatc tcattaaacc aaagagcttc    45780
tgcacagcaa agaaactgc catcagagtg aataggcaac ctacagaatg ggagaaaact    45840
tttgcaatct actcatctca caagggcta atacccagaa tatacaatga actcaaacaa    45900
atctacaaga aaaaaaaaca gccccatcaa aaagtgggcg aaggatatga acagacactt    45960
ctcaaaagaa gacatttatg cagccaacag acacatgaaa aaatgctgat catcactggt    46020
catcagagaa atgcaaatca aaaccacatt gagataccat ctcacaccag ttagaatggc    46080
aatcattaaa aagtcaggaa acaacaggtg ctggagagga tgtggagaaa caggaacact    46140
tttacactgt tggtgggact gtaaaccagt tcaaccattg tggaagtcag tgtggcgatt    46200
cctcagggat cttgaactag aaataccatt tgacctggca atcccattac tgggtatata    46260
cccaaaggat tataaatcat gctgccataa agacacatgc acatgtatgt ttattgcagc    46320
```

```
attattcaca atagcaaaga cttgcaacca agccaaatgt ccaacaatga tagactggat   46380
taagaaaatg tggcacatat acaccatgga atactatgca gccataaaaa atgatgagtt   46440
catgtccttt gtagggacat gtatgaagct ggaaaccatc attctcagca aactattgca   46500
aggacaaaaa accaaacact gcatgttctc actcacaggt gggaattgaa caatgagaac   46560
acttggacac aggaagggga atatcacaca ccagggcctg ttgtggagtg ggggaggag   46620 ggagggatag cattaggaga tatacctaat gttaaatgac gagttgatgg gtgcagcaca   46680
caaacatggc acatgtatac acatgtaact aacctgcaca ttgtgcacat gtaccctaaa   46740
acttaaataa taaaaaaaaa agatgaagat gtttaatgtg ggggaaatgc ttatgactta   46800
acattaaatg aaaattgctt tttaaaaaaa tcacatgcgg ccgggcgcgg tggctcacgc   46860
ctgtaatccc agcactttgg gaggccgagg cgggtggatc atgaggtcag gagatcgaga   46920
ccatcctggc taacaaggtg aaaccccgtc tctactaaaa atacaaaaaa ttagccgggc   46980
gcggtggcgg gcgcctgtag tcccagctac tcgggaggct gaggcaggag aatggcgtga   47040
acccgggaag cggagcttgc agtgagccga gattgcgcca ctgcagtcca cagtccggcc   47100
tgggcgacag agcgagactc cgtctcaaaa aaataaaata aaataaaata aaataaaata   47160
aaaaaaaaaa aaatcacatg ctacaacatg gatgtacctt gaaaacatgc tacgtgaaat   47220
aagccagata caaaaggctg catcttgtat gattacatt ataggaaatg ccagattagg   47280
caaatccata gagacagaaa agtagattag tggttaccag gagcccttgg gggtagggag   47340
aagtggggag tgactaacag gtgtggaatt ttggggggt aatggaaata ctggaactag   47400
acattggtga cagttgtaca acattgtatg ttaaaaacca tggaattata tactttaaaa   47460
tggtaaattt tatgttatat gaatttgatc tcaaaaaaaa tttacaaaaa actacatata   47520
tagccattaa aaattatgag atatttcagc agaatacaga ttgtaaataa ttttttaaat   47580
tataagagat aatacaaaag acaattcatt tgaaatgttt agttcaaggc ctgacatata   47640
gtatgtgttt agtatatctg agacaggtct cagttaatta agaaagctta ttttgccaaa   47700
gttaaggact cacctgtgac agcctcagga ggtcctgagg acatgtgccc aaggtggtca   47760
gggcacagct tggttttgta catttaggg agatatgaga tatcaatcag tacatgtaag   47820
atttacattg gttcagtcca gaaaaggcgt gacaacttga agcaggcagg cagcttccag   47880
gtgacagtta ggtaagagac aaaggttgca ttcttttgag tttctgatta gcctttccaa   47940
aggaggcaat gagatataaa attatctttg agcggaggga taactttgaa tagaatggga   48000
ggaagatttg ccctaagcag ttgccagctt gacttttccc tttagcttag ggattttggg   48060
gctccaagat ttatttttcct ttcacagctg caatatataa ggaaaaatag aaacaataca   48120
accttggatg tatttgagtt gattagtttg tggatgaatt tttgcattta ttttttattgc   48180 aggcagagct gctataatat attgccagta tagtaaatac tttattttaaa ggatttgaaa   48240 ataaaaaata aaagctttat ggactccagc atctgtgctt tgagccggaa ttcccgtgaa   48300
gagcctgtat tggtggagct actcagctct ttagggaggc aggaagagat gagaaaggga   48360
tacagattat tacagcctaa gggcaggatg gagaaactat ccgtctattt atccactgaa   48420
tgcatgtagt catttgtcag taagtgttct tctaaactta tttactcatc atcaacgttc   48480
atcttagatt agctcccaaa gggcaaaaag acacataatt aatttgctta atgtagtgcc   48540
tagcatgatg acatggtgag atatgtttta gcaataatta aaaatacttt ttcctttgcc   48600
agtaattctt atttaatcaa gccaaaatta atttacatag agaactactc tatggctttc   48660
```

| | |
|---|---|
| atttaaaaaa acaacagatg atttcaatct cttttctgca aataccccaa aagaagaaca | 48720 |
| atgctgtttt cataaatctt agtcaaatga aactcagcta ctatccccag gttaatttta | 48780 |
| taactgtaaa aagtgtgtgt gcataagaac aaaggctggt taggacctgg aaaaaacgag | 48840 |
| agagggagag atagactgat gtaatgatat gtgacttttt tgttcttttc tgattcccag | 48900 |
| tattgtttcc tgaacaatat tttttttata aacttagcaa caaaaaacaa atcacttcag | 48960 |
| aacctctgag acaaggctgt ggactggcag ttgttttttg agacaacatg gaagaaatga | 49020 |
| tattctgtgc atcttctctt ttaaactttc atctttgaac ttaaagatga tccctagctg | 49080 |
| agatcatggg tgttttcctc ccatgtttct ttctttgtgt tttaccaact tatttattta | 49140 |
| tttattttt gagatggaat ctcactctgt catctaggct ggagtacagt ggcatgatct | 49200 |
| cggctcactg caacctctgc ctcccaggtt caagcgattc tcctgcctca gcctcctgag | 49260 |
| tagctgggac tacaggtaca caccaccaag cctggctaat ttttgtattt ttagtagaga | 49320 |
| tggggtttca ccagcttggc caggatggtc tcaaactcct gacctcgtga tccatctgcc | 49380 |
| ttggcctccc aaagtgctgg gattacagcc atgagccact gtacccgacc ttaccaactt | 49440 |
| acttatattt agcataaaag ctggagaaag cgatagggac aggaggcaga gaaattctgg | 49500 |
| gcagaagagg gcagtcccca gcaagggcct cactctgaag cctggaccca tggcccaaag | 49560 |
| tgagaacata cattcttgtt ttcctgctca aatgttgcct tttccaaaac cacccatggc | 49620 |
| cctcctgcca cccatcatgt gcccataaaa accccagtct ccaacagcag agaaaggaga | 49680 |
| agaggagaag cagctagaca ttggagagaa gcagcttgac ttcaaaggga tggcttgaca | 49740 |
| gtgttacctc agggaggagt ctggccaggg atggccagac tctgggggaa gattatcccg | 49800 |
| ctccatcccc ttttcagctc ccctccattg aaagccatgt tcatcagcaa taaaatcctc | 49860 |
| cacattcacc acccttcaat tcattcatgt gacctgatta ttcctggaca ccaaacaaga | 49920 |
| gctcgggtgc catgggtgag gatgctaaag gctgtcacac tgaccctgtg ctctcggtag | 49980 |
| agagcaactg tctcatgcaa aaaggcagag ggcccactga actgttgaca cttaagccgt | 50040 |
| ccgtggatgg caaaagctaa aagagcgctg actaaaacac atgccctctg ggccttcagg | 50100 |
| ggtaatgggc acccactaga cactgcctca ggactctgca cggagttcac tccagctgat | 50160 |
| gcccagaagc actcaccctg gctcctgtac ctgctcacct gtggactccc ttctgcaagg | 50220 |
| ggtgaagtgc aacgggtcca agtgagtgga gtttgcccct gccagtgaca aagcggccag | 50280 |
| ctagatccag cacccgtgca ctgcagttcc cacctgcaac ggtgtcaggg aaatttcctg | 50340 |
| cttcaaaagc acaggcagct ttcttggaaa tgagataatg tgatctcatt ttaaagttga | 50400 |
| ggacatcaag gctcagaggt gattagaggc attagaaggg acttctgaag acagctaatc | 50460 |
| taacccttga aaataggaga agttaaagtt atggcccagg ttccacacct cacaattggt | 50520 |
| ggaaccaggc ttgagcctgc ttgcctaata ccagtgtcct tcccaagctt cccaagcatc | 50580 |
| tgcttgaaat tacctgtgtc tgtggtggga aggaagcgca agaatggtgt cctgtgtcca | 50640 |
| ttgctggggc tttggggggtc caggtactta gtttactttt gagaattcct tgttggctct | 50700 |
| gctgaagtcc ttcctgctac accgttcagg gaaattgttg atcttgtcaa cctgaaataa | 50760 |
| tcaaaaggat cagaatccag ttttaaagag tttattcaag caaaaagctg gaatagcca | 50820 |
| tccaagaatc atggactcta gagaaatggg gtcagtgctt cgaagttaaa agttaagtac | 50880 |
| ttgcttctat acagcaaaca aagaagttta gtaggattat aatattttct atacaagcct | 50940 |
| ggtttatgag tgacaatttta gttcgttgt tttcttttcc atacagcttg ttttcgtttc | 51000 |
| ctttccaatt taaaagcaag tatttaacat tccatcctag ttagtgtgat aaccatgaag | 51060 |

```
cctttgtgtg aaagaggaaa gagggaggct agtctataat gaagatccat acttagagag   51120
aaagggtctt ccctggcacc ctttagtaat ttataacact ttaccaaaca atgtaggtaa   51180
ggaaaaggct aatctataat cagagaaaca aaggttacag ctgcctattt atgtgactca   51240
ggttccataa tcacattccc ttaaggctca aaataaagtt tcaacggctg agattttcaa   51300
ttatttattt tcacaatctt tacctttctt agttctggga gtggccttac caggtgggcc   51360
tggcctgcgt actcccagaa gggcagttat tcctagcagc ctttggcttt gggaacctct   51420
ccataattct taatccagcc caaggttctg actctgttaa tgggtaaaga aaggttatgc   51480
cctatgagac tctgacctct tcttgggacc tggaaaatct tctggtgatt ttcctcatcc   51540
cgaatctgct gtttctaaac tgcttgagac caagataaag cacaccaatt tacaaggcat   51600
aactcctagg tgaggtcatt cactagccat ttcttgtatt tgagggtctc agtgtgacat   51660
cccaacttca tttccagcac tagattggta tttctattct tcttttttaga aaggaaagga   51720
gaggggaggg gaaaaggaaa gggagagaca cggagggagg gaggaaggaa ggaaggaata   51780
ttggagtaca atttgtggca ctcaatttca agaacaagct tgatagaaag ttgtaattgc   51840
caaatacagt aacctacttg gggtacatgt caccttttat tgctttcaag ctactgtacc   51900
tggcaactct tatttctccc tttaaaaaaa tcctgtatct ggctaaaggc tgaaaaatag   51960
caagtacata tctttctaat gaccctacat taatttagca tagagataat tagaggcaca   52020
gttaatcatt agtaatataa gccctgagat tggggcacat gggtttctct tgctattcaa   52080
cagagtcctt gtgtggctag tgtttgagta cagacacatc tttatttttt acatactgag   52140
ctttctttga catacaagcc aaaaatttac ttgaagcaac ctgaatagta tgagagagaa   52200
tatttgtttt ttaaagtcct gggaattaca gcgtatcctt agggcataat ataggtatgt   52260
tcatatagaa cagctgaaca caggcagttt ataaagcagg aagtgagcac atcgtacttt   52320
ttaaatttat ttaaaatact ttgaattctt ggtgttctta tccattcaag agtctctaac   52380
actagggttg taaaatagaa accaaatagc attgataata gagttttgtt tcatctttgt   52440
cttagctaca atttgggaaa tgtttatatg tttgttccaa aaatgattta aaattgtgta   52500
ttcacaatgc agtagtgtgt aaacactact gaatcaccag aaatgcatcc agtagtgcat   52560
gcacaaaata gagatcaagg caaggtaga atagggaaat aaaattaagc taaggataag   52620
gttagtatac aaaatgcatc ttgtgaggtt catctatttg gtctactagt gggcatggga   52680
aggatgcctg aatttaaatg aaaattctag tactgattat aattcacata ttctttcatt   52740
gccctagagt ttttaattgt gcccaaataa gtcttggtat tcacaaacta attacttgag   52800
tttttaggtt cacataccag tgatatcctc cttgaatctt tctgccactt agtcatttta   52860
cttccaaata tcatgacatc aacagaggc cgatgaagga aaaagatgc aaaagtcatc   52920
ccatttattt ttctgcctta aaataagagt gtgtatattg ggagaaggaa agggtaaagc   52980
agttagatgt tattagaaat acttggaaga gaatagaaat aaaaatttgt gatttttagt   53040
tattaaagtc atcattaaat tgtgttatcc atacaactga aggatttcaa tatgggcatc   53100
ttgttaagga aaagctttca gagaatggta acatttctta atagtgaaca tgtccctaca   53160
ctcacataat tataagactt catgtacaag gtactcaaaa tcagaaactt tgtaaaaagc   53220
cttttaatca gataaacctg aatatatcat tatctagaaa taactgaaaa gagtgcaaaa   53280
cattagagaa cagtcatttg ataatatggt aaataaatca ataggctatt atattcctat   53340
taaaattata aagttgcat aaacaggaaa gattatacaa atataccata aaaagtactt   53400
```

```
ataataaaaa tatgagaaaa atacaaactg atatgtaaac tataaaatat gtaaaatagc   53460
caagcatggt ggttcacacc tgtaatccca gcactttcgg aagtcgaggt gggcagatca   53520
cttgaggcca ggagttcgag accagcctgg gcaaccgaat gaaaccctct caagaaaaaa   53580
atacaaaaat tagctgggaca tggtggtgcg catatagtcc tagctactcg ggaggctgag   53640
gtgggaggat cgactgagcc tggaaggttg aggctgcagt gagccgagat ggtaccactg   53700
tactctaggc tgggtgacag agtgagaccc tgtctcaata aaataataa aatatgtaaa   53760
atatctctgc aggtagaaaa aggtggtgtg tgaatgcaaa agagttatac tggattgact   53820
aagatgattt tttttctcac agtattcttt gatattttgt cataataagt gtaattgata   53880
gcgaagaaat gacaacaaag cttttcatgta tagaatactt tttacagatt tactgaataa   53940
tgtgtacttt ctgttcactg tcttttaaaa tataatttca gtctagattt tacagactca   54000
tgggaaatga tctaaactat ttttcttgcc attaaaatgt gcatttggga gtattttcc    54060
atagacatag atacaggaga actcaataat gttcctcttc cttctttcca actcttgttt   54120
tccttaggca ttaccacagg agtcttggtt cgagaacaca gcaacctctc aactctagag   54180
aaattctact ttgcttttcc tggagaaatt ctaatgcgga tgctgaaact catcattttg   54240
ccattaatta tatccagcat gattacaggt accttgagaa aacagatgtt ctctatatta   54300
gtccatttc atactgctgt aaagaacttc ctgagactag gtaatttata aaggaaagag   54360
gtttaattga ctcacagttc atcctggctc agaaggtctc aggaaactca caatcatggc   54420
ggaaggcaaa ggggaagcaa gacaacctcc ttcacaaggt ggcaggaagg agaaaggctg   54480
ggcgaagcag gaagagcccg ttataaaacc ataagatctc gtgagaactc actcactatc   54540
acgagaacag catgggagaa actgccacta tgattcaatt acctccacct ggtctctccc   54600
ttgacacctg gggattatgg ggattacaat tcaagatgag atttgggtgg gaacacaaag   54660
cctaaccatg tcattctcta tgattattta aaaagctttc acctaagttg ttcttttcta   54720
attacgggaa aaattgaaat acattagatg tctctctctc tctctctctc tctctctctc   54780
cacctctctc cacttggaat gtctatattt gcttctgtgg aaacatttta ctgttctcaa   54840
catggcattg ctttgtcata tgctgtgcct acagctctgt ccaccactgc tcaaatcttc   54900
atttgaccag catgtgatgt cttgggagga aaatgtcatt ttcaaacata taaacaaaac   54960
gttatctggg gcatgggaaa aaaaagcata tttggtcact gaaatgtcag ctagtgtcct   55020
caggaaaaat atagttgtca attttgatca tgttttcagc cattcactca tttatttccc   55080
aactgcagct gtgctgcccc cagcctctca gcagctgcct tcagggtctc tgcactcctt   55140
acccactttc tactcaaagc cagaacttgc tatgtgtctg ccctgcatat ttgctgtggg   55200
gaccagcagt caagttctgt gagaagggtt taaatatgga agtgcaccat attcgaaaag   55260
cctagtattt ttaaaacttg tgacacagtt gcatttggaa atgacttttc ccttattgat   55320
cattacattg cagggctcct ttgaagagga agcttcctta ggtagataga gatgaatttg   55380
gtttacaaaa atgtcatttg tctggctgtg ataagtttct ctgcattgca gtttcttgta   55440
cttaactctg gcaattagta aaatgtggca tgacagtagc tggtggtgtt agattgaaaa   55500
tcaaggtttt atgtaaacat gcaattagaa gtcgtgacat gtccccttct agaacatttt   55560
tctccactgc cactgtaaag gtctgggact ggcctggta gagtactgga cgttggtggg    55620
ggcacgggag ggtgggggtc aggatctgct gcattcaggg actgcattgc ttgaagagct   55680
gtcacatttg gcctttgaat ttcccaaatg ccaaactcga attagactag agtcccttgg   55740
gagctttgtc cttaaatggt cttgatgttc tcggcttatg agaaacctaa agagaacatt   55800
```

```
taattattt  tatgaatgta  tttaattacg  tttggaaatg  cctggttcct  tttaaccta     55860 gcaacctgat  tgacacagcc  gcagaccaat  tatttgtccc  atgtaatatt  tgtttatttg   55920
tttaaattgt  cataagcatt  taaaattgga  aagatttcat  gtaaatatcc  aaattgctgg   55980
ctttctctga  aaaaaaaaaa  tgaagatctg  ggaacactgg  cccagtattt  ccacctatca   56040
acggtggtct  gaaaccaaga  gacaactact  ccatttagct  ggagcaaatg  catttgagaa   56100
tgccatagtc  tccactactc  ccgattgccc  agtactttgt  ccacttcact  cttacgttac   56160
ctgcctggcc  gccgtaagga  tggcagttat  aatcccttag  aatcttctcc  atatcaaaga   56220
ttctttaaaa  aaatgttttt  aaacatgggg  tcttgatatg  ttgcccaggc  tggtcttgaa   56280
tttctaggct  caagcaatcc  acccacctca  acctcccaaa  gtgctgggat  tatgggcatg   56340
agccactgca  tccagcccaa  gattcctaat  tttttcttgg  gctcctttga  aatacaatg    56400 caaactttgg  acttcctttc  gagaaaaatc  ttcacaattg  tacatatata  ctatattttg   56460
cacgcaattg  cacaaggtgc  ataaaccacc  tgatgagcaa  tactattgaa  ctcatgtgtc   56520
tatgagggga  agtatagaag  attgatccaa  attatgcagc  aaacccaaaa  ctcgaggtaa   56580
aacaggtttt  agaagaaaag  gtaaaaatac  atgtatgaat  gtctaattct  gtaatatcag   56640
atgtttgaaa  atacatgcca  ctcttgacag  tcaataacaa  gtgagttttg  ttttggtttg   56700 gtttttttc   tgggaagtat  agcctttggc  cagaagccag  aaacagatac  ttcctctagt   56760 gagattttg   cagtctggat  gttttgtgtg  ttagctcagc  cttgcaaata  atctaggaaa   56820
ataatttaca  actcagcatt  ccactgacat  agcccagcta  cttttgaagc  tatagcatgg   56880
atcaagtagt  ttctccactt  ttcctccacc  aaaccccag   cagccagtca  agaactagag   56940
gcagcgagca  aaaccaccac  cccatctttt  gatttggagc  aatgaaatag  tcaaagattc   57000
aagggatatg  aacaaagcag  ggtggggaca  atgatggcat  atccatgttt  taaattgtca   57060
gattagaggg  aaaagcaaca  agactagtgt  tggcacagtt  ataggaaaat  aagttcattc   57120
atacactttc  agttacctaa  taaattggaa  caaactttct  ggagaacagt  ttggagcatg   57180
ttctgatctc  ttcacccagt  aattctgttt  ctcagaattg  atcataaaga  aataatcaga   57240
gatatgttca  aactcctaag  tacaaggata  ttcatggtag  cattttttg   taatggtgat   57300 aaattataag  caacctaaat  gtatacaaat  ttatattgta  tacatatgta  tacaaattta   57360
tcttttatac  tatgtataca  tagtatacaa  attttcatac  taagcaacta  ttaaaaactt   57420
gtcttagaat  catatttaat  tacatgtggg  aacattccca  atacagtata  aagtgggaaa   57480
ataaaattac  acaacaggat  agtgtataca  atccaaattt  tattaaaatg  tatatacatt   57540
tttaaaagtt  gtgatcaaaa  ccaaaaggtt  aacatccaga  aagtaagaaa  acatgatctg   57600
ttctgctttc  tttacatttt  caactgaacc  tgtgtttttg  tttggtttgt  atttttaatg   57660
aaagagatgg  ggatggagtc  tggcctgaga  tcctccaatt  ttgcctctgg  tcgcttctct   57720
gcctcatctc  tgctcccttc  ccctgccggc  tcagtgccac  ctttacctgg  tacacagctc   57780
cttcctccag  accctgaagt  agtcttcagc  ctccctaccc  agaagatggc  cgtggaaaac   57840
acacaggaag  ggccatttca  cattgcaaat  gccctcatga  atccagcagg  ctggtagctt   57900
aacgtataca  gttattaggc  cgaaggagga  tgcaggtggg  aagctgagga  gggttgaatg   57960
agtcccctaa  ggatacgtaa  attagaagca  gaaacacagc  tagaattcag  acccaagatt   58020
aataatctgt  gctcctgcat  aaaggaaact  ctccttgcca  attaacaggt  agaaaaaaaa   58080
attctgccat  caaagcctct  ggtgagatta  aaaaaatact  ttatagcttt  tttaaaaaac   58140
```

```
aggaagaacc cctttttatg tgatgataag gttaagaagc caaatttacc agggaaattt    58200
gaacatagac tggctgttag atggtatcaa taatttgtta atgattttgt tagagatgat    58260
gatggcatat agttgtataa gaaaatgtcc ttacttttta aatgcatatg gagttatgaa    58320
atgacataat gtctcaaatt tactttaaaa cagaaaaaaa aaatggcaca gttgatataa    58380
actcaagaca ttttcagaga caatcattgt gggtaccaat agaatcctac cgataaatta    58440
cattgtgaag aacatgctcc cgccctgctg aggaatatct gtgtttggga tctgctaaca    58500
tttaggcttg taagccgtat ttatgtcaaa gcaccagaga ataacagga aatagcttat    58560 gaatatgcct gagaattgtg gctctggaaa atcctggtc cagccagtga gtttaaattc    58620
aggtcacatt ttctttacta cttcccaaaa ttaaactatg atgattggag cctcctatga    58680
ccaacacagg gacagaacag cacctccagt cccgctccca gaggtcccct gagcatcctt    58740
cccggatgct cataactttg ctcaggaaga ggttgcagct cttccacttt agcctctgcc    58800
acccccgcct gggccagaag cactccagtg gcacagctg cgcctcctgg tgtctgctgt    58860
ggctgccact accccggtga cctaaggagt tccgctcttt gctcctccat cctaagacag    58920
gagcagaagc ttaattctcc aaagtgcagc tgagaccaca cttctactca ggacataatc    58980
tttgctaaag gtaaccaaaa gcagatgaaa caccaatggt gacatccaac tgctccctga    59040
aggggctccc agggcctctt aacagggatg cccctctgct tagctgcttg cctccaggag    59100
gctagagttc atctctaaag gtgttccaag cttttcctgca ccccagatcc cagaacctga    59160
caccaagttc taagaaggaa aaattccgct atcacacagg ccatcctgtc ctgacctgga    59220
gtgacctctt cctgggatgc ttgccattgt ggaatatcca cttcagagaa accccctc    59280 acggccacag ggggatagcc tttcctcgtg gacccatca ggagccttcc atagactcca    59340
taccatagta cctgctgggt tattgcaacc accctgcttg tagaacctgg gagtctgtcc    59400
aggtcaggct gggccaagtc catgccagtt cctgtgcaca tttcttcctc cagagcaagg    59460
agttgctcat tcctaaccct tcctgtgatg tcgcagctct ggatttccta aaaacgcctg    59520
ctcaaacaag ggcacacaca gctcctcaag aaacagcacc agtttgcagc tcagtggatg    59580
tcaagccaag cagatatcaa gccaagaaaa ctccctcctt tccctcctct ctcccccagg    59640
ccactgagtg tgagtcctag tactgattct gcttcctgga caagtcacat tattaaacac    59700
tagacgtcag gagaaaatat ttgcgttttg tttatcaatg actttcagtt tccaccagac    59760
actggttggg tgactggatt tacaattgag gatcttctcc aaagataaat ttaacactct    59820
acccttggaa gatttaaaaa acaaaaaatg ctccagactt ttagatgatt gttactccag    59880
ctttcatgtt aggatttcaa aattttttagg gcttgacctc aaccatagga tcagaggttt    59940
tctactactt tttgttggga aagggtggga agacagggtc tcattctatg cccaagctg    60000 gaatgcagtg gtaccagtat agctcactgt agtcttgaac tcctggactc aagccatcct    60060
tccacctaag ccttcctagt ggctgggact acggtggcc cacaccacca tgcctggcta    60120
attcttactt ttgtcgcgat agggtcttga tatattgcca gggctggtct caaactcctg    60180
gcctcaagtg agcctccac cttggcttcc caaactgctg tgattacagg aatgagccac    60240
cacacctgcc ctactttta accaagtaaa aaagtttaaa gccttataaa accttaggta    60300
tattcagtat ttattaaaca acagccagat gtagaatgca tatgtgagtt ggttgccttt    60360
caagcaagga ttttttctatg aagggcccaa tagtaaatat tctaggtttt acaggtcctg    60420 tgtatttgc ccaactaccc aactctgttt gtcatgggaa agcagccaca gaccgtatgt    60480
aaatgattga gggtgactgt gtgccaatga acattcatt tacaaaaaca ggaggccagc    60540
```

```
caggagctga cccctgccca gctagactct gacactccag atgcaatcta gttgaggttg    60600
aatccaggta acaaaataaa ctaccacatc aggcaaggag tatgaatgca ctgaagagac    60660
tgaagaatag agggtgagca gaataaagtg cagttggtga tagttttaga gcaccttatt    60720
tgtaaactca ggctttacag cagatgacac acttaaatct ttggggctga ggaaggcttt    60780
tttttaaagg ctatgtattc atttactcag aggcagctgt gtatctggaa acaatcccac    60840
atcctcctat gaaagaacc atgccacgtg cctccccgag acaaggttca gttttattca     60900
gctaacattt gttaactcca gctgcatgaa aacagactaa cagaaaacca ggtataagag    60960
ggtgaggccc taccactcac atggtcatgg agctgaggtc atctgatagt caggtccagg    61020
agtccctcgt tagcaagaat tgcaagactt gaagacgcat atcactttgt tgtacaactt    61080
gctattaaat gtaagctact gttcataaac ataggtggct aagagcattt aatgtcaatt    61140
ttagctacga gggaggagta tgcattcttt tcttgaaaca ttggtggtcc attatacagt    61200
ttagtttcta tgaaaattgc cattcaaggt ggtttataaa cttaaaactc caggcaggaa    61260
gacaagtttg ttgcctaaga ctgtacagtc tgagagtgaa cttcttgcct catttgcaac    61320
atctggaacc agtgggctct tcatgcactt taagtgctcc tttccctaag attatcaaga    61380
aatttgtgtt gagttagaat acagctgttg aagccaaagg acttattgta tcaatttgat    61440
ttctgaaatg cctggcctcc aaagacaaaa cgaccacata gtgtataagg aagagctccc    61500
ataatgaaca tgccatttgc aagtaataaa atgaatagtg gcaagagata aatatgccct    61560
gctttagtct ttcctgagac agtgaagccc agagaatcaa ccatgcatga gccttctttc    61620
tgactaaaca ggtattagac ttgttcatag ctctgttcag ctgtaagata acctgatttg    61680
attacttaaa aagggattct aaggaccttc tatatattgg aggcatggac ctggaagacc    61740
attcgttcat ttatttattt attcattcta tctttaatga gccaggctct gctagacaca    61800
caaggtgtaa aattaagtct tatctcagca agaaagagta cattacaatg ctgtgtgata    61860
agcactttct gggaatgagg tcagtgcagg ggacattgga aggagccatt tgaaggaag     61920 catagaaatc aagtgaaagg aagagggtgg gtattccagg caagagaaaa tagcatcttt    61980
gtcctcccaa aatagcatct tgggaggaca gtgagacttg aagtgcgatg ctggaaacgt    62040
gggcaagagg aatgggatgg aaaggggag cacaagggtt tactggcctc gtgtgccttg      62100 ccaagggac tggacttgag cctgcaggcg agggaagcaa ttctagcagt gactcccacc      62160
tgtgccattc tctacagagg gacacctgaa taagtatcca tcctagaggg gcaagagagt    62220
ccagtggtta agagtacaga caggagccac actgcctggg tttgaatcct ggttctgcca    62280
tggattagct gtgaaacctt ggatttact taacttgtcc tcagctttaa aatatggata      62340
ataataatgt ttcatagaac atctagaatg ccatacaatt tttttactta ctcttttttg    62400
tctgagacct tcagaagttc ctataaagta cctgaactgg cagcagaatc tacagggcca    62460
atatcagaat tgagctacgc agatatgaac acactgaatg cattcattct ggaaatgaga    62520
acaatataaa aagacttgct ctgccatcag tttgtaaagt tcaccagcat gtaagaagct    62580
tttgcctaga agtccgagat accaattta tggataaaga gaagcaaaga gacagctcag      62640
tcatatttag gttgtggcaa aaacccagaa aagtctcact gagccattag ctagctgctg    62700
ctgtcagagc attcatatgg actttggaaa agaacagttg agttcctcag attctttggg    62760
gtatatttaa tgcttttact ggacaataag ttcagggagt caaaaagttc atggagtctt    62820
ctgaaaaact ggtcctaact acaaatacca ccgtgttcca tagtaatgaa aaaaatgtta    62880
```

```
aaacagctcc tggactgctg aaaccaggac acagcccacc gcttctttt ttttttttt    62940 ttttttgaca gagtctcact gtgttgccca ggctggagtg cagtggtgcg atctcagctc    63000
acttgcaacc tccacctcct gggttcaagc gattctcctg cctcagcctc ccaagtagct    63060
gggactatag gtgtgtgcca ccaccaccgg ctaattttg tatttttagt agagatgagg    63120
ttacaccatg ttggccaggc tggtcttgaa ctcctgacct caagtgatcc acttgcctca    63180
gcctcccaaa gtgctgggat tacaggcatg aaccactgca cctggagagc ccactgcttc    63240
ttgatgcatg ttttgaactt caaatgtgga ccagctgaca gaggcttcaa ggggaccttt    63300
agctgattct gctcaaggac cagtttattt tgttaacatc accaaatagc ctagagtggt    63360
gatattacct attttaagag agttcttcat gtctctaaga aaagtagatg tcataggtga    63420
tgcatgcaca gaaagatttt gcatgctcct ctttgcctct tcctttccct ttgaacatcc    63480
agggagtact aatcaaggct gcagagattt ccctatgccc tggattaaca agtaagatc    63540 atatcctgcc ttgttttctc tggggaataa agaaacatt ttggaattta aaaatcatga    63600
acctgtttat ttaatcctca tagcagccct atgaagtcat caagtaggtg ggaccttaac    63660 tccatctta gagataagga aacaggaggt tgaagacaga ttaagccact ttttcaagat    63720
cacacagatc ataagggcag cagctggaac tggcaagttt tgttctggca acactctgct    63780
gccaaggggc cagagcctgg gagagggatc cagggcagtc agccatactt aaatacctgt    63840
tagtcattca atcagcatgt ttactgagca tctcctatgt gctgggcact gagtatacat    63900
tcgtgaacaa gcagatagct aggtctcctg ccttcatgga gcttaaaacc tagcaagaaa    63960
gagatataaa ataatgaacc aatgataaaa attgttgaga tatgatatgc acaggatgcc    64020
aagcaaggaa atcaggacac cctggtttag ggtggataat cagggaagga ttctgaggaa    64080
aggacttaaa agccaaatga agagtgagga agagcactcc aggcagaggg aagagcctgt    64140
gcaaaggcct tggggtggga aggagcttgg tctgttccag aagaggctgg aggaggggat    64200
gagacaggaa gatggcacaa agaggggctg gagaggcagg caggtgcctc ccctgcaagg    64260
cctgttggcc aagtaagga tttttctttt ttatcttcag tgccattgaa gggttatcct    64320
gatgtataaa atcacctgat ttatgttttt aaaggatctc tttagtgacc gtgtaatgaa    64380
ggaatgaatg agggagggaa tgaatgaatc agttaatgct tgttgaatac cttccatctg    64440
ctcagtgatg cacatcatct ttatcattta ttcagtaatc atgcaggcta tttactaaga    64500
acacactgtg ttctgggcac tgtactaggc ctgttataga cattatttct aatcctcaca    64560
acagctacgc aagctgaggt tgttcacttt gttcctcaca attaacctaa aggcgataga    64620
ggcatttcag atcctccaat ttatagatgg agaagctgag tctggggagga ggctgggatt    64680 tgagcccagt ctgtcccacc aaagcccatg ccttctctct gcacaggtgg cctctctgcc    64740
ggtgacagag acaggagtca tccacatggc gagttttaac tcctatgcaa caatgagttt    64800
cttggatgtg gtgtccactt ataatggcat aacaccacca aatgtcagac ctaaaagaac    64860
ttccaataag gggttgaatt ttgatacctt aacagcaatg tggagagatt gtcacgaaag    64920 cttgttctc agtgggtggt tgcttaatca gagagctcta ggaggagtct tttgccctca    64980
gatgtttatt tttaaaacat gctattgttt agccaggcaa ctgcttcctt tggagtgttt    65040
ttgtaaaaag ttcagatgat tactgctttg gctgggagcc aacacccttg ctcatcagag    65100
ccttctcctg aggtgaaaaa agcaaataaa tgcctttacc taaaataaag agctagcagg    65160 tgccctgac ttccaaggac aaccgggat tttatccctg tttctaggcc acagccgagc    65220
ctcaaaactg tcccaggttc taatggataa ccctgggttc acagggaact ggaatcgtgc    65280
```

```
tcttctttt   ctgcccaatt   caggtgccac   ctgttccatc   aagcctctcc   tgctcatctc    65340
aatctggtga  cagttcaggc   tcctctgaaa   gcccacagta   actggtctcc   gcaccagggc    65400
ttcacaaaac  atctagtttt   taaactggat   ggagcaaatc   cagttgttaa   aatttctgat    65460
ctgttacaga  tcaataacct   tcgtaaacta   tagttagagc   aaattactag   aaaagttata    65520
ttaaaaatag  acatacaaaa   tactagccct   attttttttt   tttttgaga    tggagtttca    65580 ctcctgttgc  ccaggctgaa   gtgcagtggc   atgatatcgg   ctcactgcaa   cctccacctc    65640
ccaggttcaa  gagattctcc   tgcctcagcc   tcctgagtag   ctgggattgc   aggtgcacac    65700
catcacaccc  agcaaatttg   tgtgtgtgtg   tggttttgtt   tttgtttttt   tgttttttta    65760
agtagagatg  gggtttcacc   atgttggcca   ggctggtctc   aaactcctga   cctcaggtga    65820
tccacctgcc  tgggcctccc   aaagtgctgg   gattaccggc   gtgagccact   acgcccgcc     65880 cctatctttt  attattacat   tcaacagaaa   taaagttact   gtccaattac   tataaacatt    65940
ttaaatactc  actgttgatt   tctgtgcaga   tgccatcaca   cctgcttagt   tcattctcat    66000 ttatcaccc   ctataggaca   gctttcaact   cccaggagaa   acgagttctg   atagtgaact    66060
gtaaagagag  gggtccttc    agacctcgcc   agccaccaaa   gatggcctga   gagcaagaaa    66120
cccgggggtc  cattgagaat   aaaaactcag   aactaaaggg   caaatgaggt   tttacttgtt    66180
tgggactaag  ttgggcctga   tcttcgacgt   caacgccagt   taagagtcta   atgcctggat    66240
tctcattctc  acagtcaaca   ttcattgcgc   tagaccacaa   gttctcacca   agacaatatc    66300
gtccccaagg  cagcaaaagc   tgtttttatt   tggtggtggt   gagttggggg   agaaaatctt    66360
actcttttta  tgtaaaaaaa   cacatgtatc   atttactata   taaccagata   tacagtttgc    66420
ggttttagaa  tttcagaggg   gtggtgatta   ggaaaacggc   tttgggggt    ggttttgcac    66480 aacaacaaca  acaataaaac   aaggttgaaa   aagactgaga   tgttacatgt   gttccctgt     66540 ggagtctttt  atggctgaaa   agtgttctcg   ttggctgccc   tgggaaccaa   actaaaccac    66600
catgtataag  cggtttctaa   ggggactacc   tgctgaggtc   caagtttcgg   acccagaaat    66660
ggatctttga  aatggggtca   tttgtaagca   gacgattact   tgcaaaaatg   cagctctttc    66720
tgtcatgtgg  aaagcttcaa   gtacaaacat   tcgtagagca   ccttatttaa   ggcactgggg    66780
gcccagtgaa  gaataagctt   caggccttac   agccatatga   tcagtgcagt   gatgaaacta    66840
cgtgccagga  gatttgcgcg   tagcatcttc   ctttcccctg   cccatgcttg   caaggcaaag    66900
agcttttcct  gaatttgata   atggagttaa   gctatagttt   gttcattcga   cattgtcgag    66960
cacccactaa  atgctaaaca   ctggtagggt   ctagagagat   tgggctgtcc   aatatgatag    67020
ccattagcca  cgtgtggcta   cttaaattga   gattaattaa   aactggccag   gtgtggtggc    67080
tcacaccaat  aatcctagca   atttgggagg   ccgaggtggg   aggatcgctg   agctcagga     67140 gttcaagacc  agcctgggca   acatagtgag   acctcatctc   tacaattaaa   aaaaaaatt     67200 aaaatagatt  aattaaaatg   aaaactcagt   tgtcagtca    cactagccac   tttccaagtg    67260
cttgctagcc  atatgcactt   tgtggctact   gcagggaca    gcacaaaaac   agaacgtttc    67320
tatcatcagg  aagctctact   gggcagcgct   agtctagaat   tttgtagcac   atggatagag    67380
ccaatatgga  atagtggtta   agaatatggc   ctttgaggta   aaatgtagat   tgagatccca    67440
gctctaccac  tcaccttacc   agctttatga   tcgtatggta   cttagccttt   ctgagctata    67500
gttttgtcct  ctgtaaaatg   ggggtaataa   tgcccgcctc   cttgggttgt   aatgagaatt    67560
aaagatgatg  cattaacatg   cagtcaatat   agtgtttatt   gtcatcatta   ttatttgtat    67620
```

```
tatgattatc atcctcatca ttattgacat tactcgcaga tggggtgttt acaaccatcc   67680
agacagatat tttatggtca ttaagttctg taatgttcct atttatagag gttttcaaag   67740
attaggctgt ttccctgtat ctgttctctc cctctatggt ggtcaccacc cttatcccca   67800
acaatgcatt ataaatcatc caacagcctg gacttggggg ccagctctgc ccccatgttg   67860
atgactagag aggtagaggg taactataga gtggtaacta tacagaggta gaggtaacta   67920
tacagtgtag agaagtataa tcgttgattt gtgtaaatat ctgatatatc cgggaaattg   67980
gtaggatgga ggtggattag aggaatggga aacaaagacc cgtgctgaaa gttactacaa   68040
gatagttgct gtgctccagg acagagggga aattggatga ctacttgggg atgtatttgt   68100
ttaagatatt ttcaccaaga tctcattatt atcaagcctt ttattgccag ctgagtcctg   68160
gagtacaagc agaggcacca gcccatggcc aaatcattaa gacaaattaa gacatattaa   68220
catatgctgg gaacaattat ccacatagat ttaatttgtt tcactgctgg aagaaaatcc   68280
tgagagagta ccaaacacat ccccgagaac agctctgtaa ctactctgtg actctcactt   68340
gtcagcactt caggggctgg aatctgctta aactggacat ctaccaaaga aggacgacat   68400
atctgaaaat agatcccata ttagggctac agatgagtta cttggagtct gttaaggtgg   68460
tgattctttt tgtttctttt taacctatgc atcttagaaa taattattac agttatcaaa   68520
acaatatacc aagctctaaa atgaaacagg cacatatttt ataatcatat aatatactta   68580
gcaagcttac atatttgtat tatgatttgc tctttcttta agagacctaa actaaatatg   68640
agatagtgaa cttgtttctg aattttggcc ttcaatctct cttgactttt ttgttgttgc   68700
tgttgtccct tgcctaattg ttatctttca ttgtcttact gggaggaaaa gaaagactct   68760
tcaacacagc aaactgcatt tttctcaaat cgaatagaat ctatcatcaa gattattcta   68820
gaatgtgact attgcagtat gcccattata tggcaattgc acaatctttt ctcagtggtt   68880
gatgaatggc gccttaacaa catcctgggg tagctgctac agaggccaga gcaccttctc   68940
tcaaaatatt aacttccaaa ggagcaatca acagccagag aaatggtgtg tttagagtga   69000
gaaatgactt gttctgtcat cataatggtg atcacttcct tgcagatttt cttcctgtac   69060
atcaaatatg tatgattata tatgagaagc ataaccccc agtcacttaa aaaaaatgga   69120
taggcctttt agtgtgggaa atgaacataa aagttaccta tgcatgctga tagccataca   69180
ggtttactgc cttttccttg gggttgcctt gtgacaacct cttccttttt cctgctaccc   69240
tgtaccttag gctttgcaaa tggttatggg acaactcatg cgtgttgaat atgcaaaatc   69300
attttctata atgctccttt gactcaaaat atgaccctca ttttggaaat caggcttggt   69360
agtgtctgaa acctccaatg acagcttgcc gaaagatgat tcagttgttt ctcaacttgg   69420
cccattcccc acgtccaagt ccaattggag aacggctttt gactccgttt atatgagcat   69480
ctttgataga gagcaaaggt ttctggcaag gcgggatgcc tgccttccac ctctaatcca   69540
gctgtccttg acactccaga cagcccttc aaatctgggc aacacttagt catcttactg   69600
gtagccaagg accatttgaa gtgagatcta acaatatgat cgtaagtctc tgacattacc   69660
tgtgccctgg gaattatttt attaatatct ttcctttttc aaatagaaat tttaagatgt   69720
ctcacaataa aagctataca caataaggtt gtttacacag aagcaatttg aaaatcatga   69780
aaagaggaag gaaacacact aaccagaatg gataatgaca ttactgtgaa tgtggccccg   69840
ggaccattta agatccagc aataagtgga tcattaaata cattctggta cagccacatg   69900
acagattact gagccattaa aattatcctc agggtgagtt tgtaacaatg tgggaaaatg   69960
cttacaacta taatattaag aagaagagag agggttagaa actataaaat tctcccagct   70020
```

-continued

```
gtttacaaaa aattgagaaa aatattagaa gaaaatcacc agaatattaa cttggttgat    70080
gagatgatgt gattttgtt gtcatcttta ccttttctcc tttttcagat agttgtaatg     70140
aatatatatt acttttataa ttgtatataa acattatttt ttccagttaa gcctaagctt    70200
cctgacagaa aaggcagaaa ggaaaactat catgagttac atgattctca agtgttaaaa    70260
aaaaaaaaaa tctcaggcag gacatgatga ctcacacctg taatcccagc actttgggag    70320
gccaaggttg tggatcacct gaggtcagga gttcgagaca agcctggcca acatggtgga    70380
acctcatctc tactaacaat acaaaaatta gctgggtgtg gtggtgtgca cctgtaatcc    70440
cagctactcg ggaagctgag gaaggagaat cgcttgaacc caggagatgg aggttgtaat    70500
gagccgagat cacaccattg cactccagcc tgggtgacag agtaagactc tgtctcaaaa    70560
caaacaaaca aacaaacaac aacaacaaca aacgatctca gttctttgag ataaattttt    70620
cctagataac tgaattccaa aggaggttta tcacaaggga tgttgaatga tataatacaa    70680
atcttggtaa agttcttagt gcaaatgtgg gacagggact ccttatgatt atttcctgac    70740
caactccagg aagatctgaa ggcaggacac tcctggaggt gaaggctgtg ggaagctgcc    70800
tgcaggggaa cttgcacctg actgggcttc cctctcttaa atctgtttgg aattttgaag    70860
tgttgctttt gcccattgca tgttattgcc cattgtctgt agatgagaac gcctctcagc    70920
tctttatttc acaacctgag gattaaatcg cgggtcctgg aaacctgtct tttaaaatta    70980
atgtaatttg atttctgtct ccccttcagg tgttgctgca ctggattcca acgtatccgg    71040
aaaaattggt ctgcgcgctg tcgtgtatta tttctgtacc actctcattg ctgttattct    71100
aggtaatact tatttctgaa tccttactac tttatgtaat ggtgattttt tcattcgaaa    71160
agtagttggt ggccagatgc ggtggctcag gcctgtaatc tcagaaatct gggaggctga    71220
tgtgggcaga tcccttgagg tcaggggttt gagaccagcc tggccaacat gaaaacccgt    71280
ttctaccaaa aatacaaaaa tattagccgg gtatggtaac atgcgcctgt agtcccagct    71340
acttgggagg ctgaggcagg agaatcactt gaacctggca gacagacttc aaaggaaaaa    71400
ctttatggta ctttgacaat actactttct gattttaaaa aattgtatgt taagaaaagc    71460
tcaactactt tttaaaatat gtattttttt aattaaaaag agacgtgggg agtcttctat    71520
gttgcccagg ctggtcttga actcttgggc tcaaggatc tgcctgcctc agcctcccaa     71580
agtgctggaa ttaccggcat gagccactgt gcctggccct aactactttt ttttttttt     71640
ttttttttca agagggagtc tcactcttgt cacccaggct agagtgcagt ggcatgatct    71700
cggctcactg caacctctgc ctcctgggtt caaatgattc tcctgcctca gcctcccgag    71760
tagctggat tacaggtgca caccaccatg cccagctaat ttttgtattt tttaaataga    71820
gacagggttt caccatgttg gccaggctgg tcttgaactc ctgacctcag gtgatctacc    71880
tgccttggcc tcccaaagtg ctgggattac aggtgtgagc caccatgccc agccacttac    71940
ataattctta aagtggatga ttggtctata atagtggagt tgagtataat tataaaatat    72000
ttccagaaat atagcatttt agtgcatttc acgtagtaac aagagctaac agctaataga    72060
tccttgttaa ggataaatcc cacttgtaag agggagaaaa ttctaataag ggaggagctg    72120
ctcttatacc cttagcatag ttttttgaag aatgcttggt ctttgtaacc ctgagtgaca    72180
ttttaagaag aatgcccaat tcccacctat gagtgagaat atgtggtgtt tggttttttg    72240
ttcttgcaat agtttactga gaatgatgat ttccaatttc aacctatgcc ctacaaagga    72300
catgaactca tcattttat ggctgcatag tattccatgg tgtatatgtg ccacattttc     72360
```

```
ttaatccagt ctatcattgt tggacatttg ggttggttcc aagtctttgc tattgtgaat   72420
aatgccgcaa taaacatacg tgtgcatgtg tctttatagc agcatgattt atagtccttt   72480
agatcacatg gacacaggaa ggggaacatc acactctggg gactgttgtg gggtgggggg   72540
aggggagagg gatagcattg ggagatatac ctaatgctag atgatgagtt agtgggtgca   72600
gcgcaccagc atggcacatg tatacatatg taactaacct gcacaatgtg cacatatacc   72660
ctaaaactta aagtataata ataaaagaaa aaaaagaga gagagagaaa aaaaaaaag    72720 aagaatgccc agaggggaa gacagaagga gcatatactc agatgtggca gcagctcggc   72780
ccttgtagcc ctgcttcaat gagctgataa aaggggtgg gatgtggtga ggctttagtg    72840
gtattaggcc aagggaccca ggagggcttg aactgtacca taaacaaaa ccacatcatc    72900 tcatgagttt cctgaggaag acagacacag agaaaaaata gcaatgagaa tcaagatact   72960
gctctcttat tagctggagg cgtatagccc ttctacaacc ctgagagagg aaaagagtgg   73020
gccatgccca gtcatggccc cttattgccc aggagttcct cccattagca aaatggaccc   73080
attcagcatc ccagagccct accccctgga ttaccattgc ctcttcttga gggaggagca   73140
ataaagagca tgaggacctt tttcttcttc acttccctcc agtcaaacac cctccaatgt   73200
cttggtctct tctacagcct cccatcttgg cttggatact caagtgacag gaacccatta   73260
cttcccaagg ccacaatgat gctgtcagat gctctgccat gtagacagtt cttccttaca   73320
gagagatgaa ccttctctcc ctataaatcc catctatttg tcctcattcc accccggaa    73380 cagcattttc ctacatgact gctttctaga tacttgaaga cctacggtat ggaaggaagg   73440
caaggcttgt tttgtatgat cctcaggaga ataaccagca tctgggtaaa agttgcagaa   73500
agacatcaga tgcattctct gggctagaaa atggatcatc cttaccctaa caccttccta   73560
ggctggtctc ataagttcaa gaaaagaat attctcatca gcaggtgttt ccagaagcaa    73620
ttctgggatg cagccccttc atttaaaaca cacatacaca cacacacaga cgcacacgca   73680
cgcacgcaag cacatggagt tctttctgct tactcattta aatggaagag taattaaggt   73740
ggctgctgag gttccagagg aggctcagca ttttggctgg acctcagggt cctccccatc   73800
acactattgc ctggtacaac catgcccatt gttctaaagg tgccagctgt gccaggtgcc   73860
ctggaaggtt cctaatgctc tgtggacgct gttcttggcc acaggtattg tgctggtggt   73920
gagcatcaag cctggtgtca cccagaaagt gggtgaaatt gcgaggacag gcagcacccc   73980
tgaagtcagt acggtggatg ccatgttaga tctcatcagg tgagtgtttt gccacaaggt   74040
ggcttcaagg gcatgcggat agcagcacaa ggccttgtat gtggtttaat attctgctgt   74100
tactgtattg aaattttttaa taactttga attattgtgc actttcattt tgcccaggaa   74160
cccacaaatt acatagccag tactgttttgc caagtcttgg ttccaagagg gaagggaaga   74220
aacaggcttc cgcatcagga tttaggatga acagagatgc agctacatgt tccagagaga   74280
tgctgggatg gattggtagt cagttctgaa gcgcacttag aaaaatacat cttttaattg    74340
tacaggagaa actctcttat ctaaagcaac cagagggta aataggtcag tcaataaaaa    74400
ataccagtta aagcagagac tcataaaaa agacataaga tacacattac aattttgttt    74460
tcacttaaaa cttagtgcat ttattccaca attgtttgac ataaagctaa ggtctttcct   74520
tcaagtttgt tagctcatgg taattttctta cgggttctgt tgcatataca gcccttataa   74580
atatatcatc tgcaatttcc aggtaaagtt tctatagaac agagcaccaa aacttttaga   74640
cattgcaaag aaagctaagt gcaaatcttt ccagttttc tttttaattt caataatctt   74700
cccataccta atctaaccat aaaaatttta gtcactggcc tttattgagt ttccaggtat   74760
```

```
gtggcttaga ttttatagaa accataccttt cttttttatgc tcatatttca ctggtttaca    74820
taatatgaaa tgcagtaatt atgatgatat ttgcaactgg tataaagaat ttgggaacaa      74880
ataaaatgaa cccttggtaa gtgtattagt ccattttcac actgctataa agaactacct     74940
gggactgggt aatttataac gggaagaggc ttaattaagt cacagttcct cacggctggg     75000
gaggcctcaa gaaacttaca atcatggcag aaggcaaagg ggaagcaagg cacatcttac    75060
atggctgcag gagagagagc aagggcgaag ggagaagtgc cacacacttt ctaacaacca    75120
gatcttgtga gaactcactc atgatcatga gaatagcatg ggagaaacca cccccatga    75180
tccaatcacc tcccacaagg cccctcccct gacatgtggg gattacaatt tgacatgaga    75240
tttgggtggg gacacagagc caaaccatat cagtaagcat acaacctcat tgatgaaaac    75300
agaagtgttc agaatattaa agaataaata gtctcttgac tgtgagtgtc catttcacca    75360
aggagcgtaa gcatgtcagt tactcagtga atcaattaag tgatggttga ttacagagct    75420
ttctatactt gggtgaagct cagcaggaaa aagaaatct caatacaagg aagtattacg    75480
caaagcaggg gccagaagag aaaccagagt actagttta tgttatacta atttctacca     75540
atatattagg tatgacaaaa caatactttt tgccctaaca taatactgcc ttttatgtct    75600
ccaacaggaa tatgttccct gagaatcttg tccaggcctg ttttcagcag gtaatattaa    75660
ttacttgtgc ccttaacttg ctaccctctt cccattatca attaaaaatg tttttttctg    75720
ctgtgactca agaaatggaa ttagccccgt gaaaatggca gcaggaagta aacctgtgac    75780
tggccaagtt taaggtgatg tctctgtttt gtatgcagcc tttctggctc acagtaaggt    75840
gcatgtcaca atttcactg cttccttttc ctttatgctt tttcccccaa aaaggctcaa    75900
atggtacaaa tcagaaatct gtcaaataat gagtatttta aaatgtggcc tccagtacct    75960
atttttggag aaccatagta tatttgtact gaagtttaaa cttttctgcag aaaaaaggta    76020
gctctctatc tcctctttgc ttttcctctg gtattagaac ccaggatcta accctcatgg    76080
tgtggtccac atctgggttc agtcttctcc ttaatcattg tgtcccagag aggcgtggaa    76140
gctcacacct gtaatcccag cactttggga ggccaaggtg ggcagatccc ttgagctcag    76200
gagttccaga ctagcctggg caacatggca agaccatgtc tctaaaaaga aataatttaa    76260
aaaaaaatat aaaaaatcgt tgtatcccca ttgctggagc tctacaatgc agtgtaacaa    76320
agccatgatt tttttttctg taggaaaatt gaacaatctc ttcactccat ttacttcaag    76380
cctttccctc ctatttatct atgtgcttta agacagctga gtccatcaca aactgctgta    76440
ttcattcaca taagttacat gaacacagac ttctgtgtat accaacaaaa atggcaactc    76500
tgttgctctc tgccggcctc cacgagggac agaacctcct ctattacagg gggcctttgc    76560
agatcagtca cagtggttgt ttgtaaggtt ctcagtgttg gcagagcctg gtagtggggg    76620
acatttatgc ctggtgtaat aatatactca ctctttctta aatccccatg tggaagctcc    76680
acagaaccaa acagggctga aagaagagaa ttcaactgca gtctcactca ctgaatagcc    76740
ccaaggggac tgttgatttt ggaacaacca tatcgttaaa cctttcttga tgcttattaa    76800
agttgtagtg atgttatcaa agtaatgaag tgtgtttgct cagattaaaa atcatttatt    76860
aattaataaa aacaaaaatg attgacagga atccttacag agtctgtctc tgacagcacc    76920
tgcagatcaa gcctgtactt tcttttgtat tattcttcta tcaacttgtc gtttattgtg    76980
aaagtgaagg aacattttga cataattgaa tggtgatcgt gggagtcagg ggtttaaatt    77040
tctgcctcgc ttttagttcc aaaacctgat gggaggtacc gttgacaact ggagccaaca    77100
```

```
gaggcattgg atgtagatcc cttcagtggc actgtttggc caaaataaca tgttcctgtg    77160
atttagtctc aaaagcttaa aaaaaattct tttttttgttt gcttgtcctt gattttctcc   77220
aacatgcagt acaaaactaa gcgtgaagaa gtgaagcctc ccagcgatcc agagatgaac    77280
atgacagaag agtccttcac agctgtcatg acaactgcaa tttccaaggt accattctta    77340
tttcctgttc ctcttcccca ggagacaggc actgagtcat gactgagcag gaaatacaat    77400
caatcctcgt cattcacaga atcgcatttg caaattcacc tacttgctaa aatttatgtg    77460
tgaccccaaa atccatactt aaggggcttt catggtcatc atctcgcaca caaagagcgg    77520
caaaatattt gagtcacccg acaggcacgt tcccagctaa ggtgaaaaag ctgtgctct     77580 gctttcttgc tttgattctc atgctggaaa caagtgtccc ttttgcagtg tgtttagtgt    77640 catattttt gcattttgt gattttctt gctgatttcg ctgttgaaa tggaccaagg       77700 tggggttcag tgactcatgt ctgtaatccc agcatgctgg gatgccgagg cgggaggatc    77760
gcttgagccc aggagttcca gaccagtctg cgcaacatag tgacacctca cctctacaaa    77820
aaatgaaaaa tagccgggtg tgatggtgca cacctattgt cccagctact cgggaggctg    77880
aagtgggagg attgcttgtt ccagggaatt caaggctgca gtgagccatg attgaatcat    77940
tgcacttcag cctgggtagc agactgagac cctgtctcaa aaaaaaaaa aaaggaccag     78000 gctgggcatg gtggctcaca cttgtaatct cagtactttg ggaggccaag acaggtggat    78060
cgcttgaaac caggagtttg agaccggcct gggaaatata gtgagacccc atatgcacaa    78120 aacatttaa tattacccag gtgtggtggc acatgcctgt agtcccagat acttgagagg     78180
ctgaggcagg aggatcgttt gagctatgat tgcaccactg cactcagcct gggtgacaga    78240
gcaagactct tgtttcaaaa aaaaaaaaa aaacatacac acaaaaaagc atcatattga     78300
agtggtctcc agtgttccta agcacaagaa gactgtgatg tgccttaggg agaaaatttg    78360
tgctttagat aagcttcatt caggcatgag ttatagtgct gttggctgtg aggtcagtat    78420
taataaatta acaatctata tgaaacaagg tgtctttaaa agaaacacat acaacaatgt    78480
tatatattga ttgtttgctg aaaaggatgt gtccaaggtt cccagaaact taaccctgta    78540
tttcccccag gagcaacggt tcagtatttg ctaattcagt gttcatgagc actttataga    78600
acataactac caggaataga gagagtcgac cacaaagagc aaaaaaagag ccctgttgcc    78660
tctacctctc tgggtctgct tacagtagag ctggccatct ctagaaactg ctatagattt    78720
gtcaggtaca taagcatgca atgcaggccc acaattccta gtctgaatct ctctgcccag    78780
atgtaattca gagttcagag tttctcagac tttagaaagg ccatgtggtg tatatactgc    78840
atattatgca acctttataa gtgggatggg caacaacatg ccagaatcaa ccacatcaat    78900 gttttttataa caaactcata aatattctgc caaggagaga aatggaccct tagtagccag    78960
tagcctcatc tcagtttagg atgggatttg ctgccaaaag agtttgctat aaacttatca    79020
ataaaatcaa catgctttga gagcttttgg gatttcagaa ttggagatca gaatgtgtgg    79080
gcctgcattg gtacctctgt aagcctgtag cagatttctc ccgaatgttc tctcaacttc    79140
acacaggaag gaatgattta aggagaaaag gagtgttcat tagacttaag aattcaaatt    79200
aaataaacca ccgttggctc cctgcttcct actgcagaaa gccttaactc ctctggctga    79260
gttcagaggc cctgcatgac ctggcttctc tctagttttc acagcttact tccagtgggc    79320
acctctcttc tttccagatt caccctcctcc atcactcctt attcctgcct tttgatgttg    79380
ttccacaaat actttctgag caccctctat accccaggcc ctgctgggca ttgggattat    79440
aatggtgaaa agacagatgc caggcctctg tcctcacaca aagaatgatg agtattataa    79500
```

```
tcaggaagaa tgggatgttt gggaggcatt cagcaaggga tgttaaatta gtctggaggc   79560
cataatgaat gagcaagaat tattcaagca gggtgcaaag gcccagtgca tgatcgtttt   79620
tgcctttgct tgccatcttt ctgaaacatg cttttctcc tggctgctga ttcctcagcc    79680
ctagctttcc ctaaccttga aacccacatt catgtcccac tcttcatatg acgcttgtat   79740
ctcatagttt gggcgcacaa ttaattacat accttcctgc tattattggc tcatgcttct   79800
cacagtcagt cttgtctctc cagctgaatc ttaagacctt atgctatagc cagtgcagta   79860
atactctagc ttttccctaa atatatgttt gatcataagt aagaaatgac tggtagccca   79920
gtgggtcctc aacataattt ttttttttt gagatggagt ctgactctat cgcccaggct    79980
ggagtgcagt ggcgtgacct tggctcactg cagcctccgc ctcctgggtt caagcaattt   80040
tctgcctcag cctcccaagc agctgggatt acaggcacgt gccacaatgc ctggctaatt   80100
tttgtatttt tagtagagac ggggtttcac catgttggcc aggctggtct tgaactccta   80160
acatcaggtg atccacctgc ctcagcctcc caaaatgctg ggattacagg tgtgagccac   80220
cgcacccagc taacataatt ctttataaac atagttggca ccactcagtt atctctctgt   80280
aaatctcagg ctattttac ccaggataaa gtgaagaaat taagccaggc atggtggcat    80340
gcccccgtag acccagctac ttgggaggct gaggtgagag gatcacttga gccctccttt   80400
gaggagtttg aggctgcagt gagctatgat catgccactg caccccagcc tggacaacat   80460
gagaccctgt ctgtttaaaa aaaaaaaaa ggtaaaaaca tgattcacag tagtaggtat    80520
ttggctaatt tttatatgtc taaaatccta ccaatgatag actggataaa gaaaatgtgt   80580
acatatatac catggaatgc tatgctgcca tttaaaaaga acaagatcat gtcctttgta   80640
agggacacgg atggagctag aggccattat ccttagccaa ctaacacagg aacagaaaac   80700
caaatactgc ctgttctttc ttataagtgg gagctaaatg atgagaacac atggacacat   80760 agagggaac aacacacact ggggcctatc agagggtaga gggtgggagg agggagagga    80820
tcaggaaaaa taattaatgg atactaggct taatacctgg gtgataaaat aatctataca   80880
acaaccccca tgcaccctg tacatcctgc accacatgta cccctgaatg taaaagttttt   80940 tttaaaaaaa tcctggctgg gcacagtggc tcacacctgt aatcccagca ctttgagagg   81000
ctgaggtggg cggatcacct gaggtcagga gttcgagacc accctggcca acacggcgaa   81060
accctgtctc tactaaaaat acaaaaaatt aattgggtgt ggggcggat gcctgtaatc    81120 ccagctacta gggaggctga ggcaggagaa ttgcttgaac ccgggaggtg gaggttgcag   81180
tgaactgaga taccaccact gcactccagc ctgggtaaca gagcgagact ccatctcaga   81240
aaaaataaat aaataaataa ataaataatc ctattggtca tccaagaccg caggcataaa   81300
gagtgttact gtgcttcatt atcagggtaa aacagaaggt aaaatgtcct aaaagtgttc   81360
acactggtaa gtattctgta cttcctgcat tattaattcc tgtgttttttt taagcagact   81420 ccaaatgtag ctagcagtta aaatgaccct gaaaagtgcc ttcaatctaa aattcataat   81480
aaaaatataa accattccag aataagaaat ctttataaga atattcaaa tatggacttg    81540 ttgaaagaag agaaagcatt ttaacttcgg ggagcaaggg taaagtttgt tacatgcata   81600
ggtgttttta ttattgtttt tatatttct atagttttgt tgactctgcc tgggagatca    81660
ccagtttatt atgtttggtc attgtatctt ctcatttctg gacctgtgct ttctaacaag   81720
attataatcg tgcatcaata tgttttcttg gttttgatcc acagaacaaa acaaaggaat   81780
acaaaattgt tggcatgtat tcagatggca taaacgtcct gggcttgatt gtcttttgcc   81840
```

-continued

```
ttgtctttgg acttgtcatt ggaaaaatgg gagaaaaggg acaaattctg gtggatttct   81900
tcaatgcttt gagtgatgca accatgaaaa tcgttcagat catcatgtgg tgagcagaca   81960
ctgtttaatg tcattttgct tccctgaca attctgtctc ctcaaaatta gaaagaagag   82020
gttttatgtt tgtcaactga tgaagctaga gaagttggac atttaatatt gaaccaccag   82080
agtattttgt gggggctttt gttgctgttc tttgttttg ttttagaggc agagtctcac   82140
tctgtcaccc cagggtggag tgcagtggtg caatctcggc tcactgcagc ctcaacttcc   82200
tgtgctcaag cgatcctccc gtctcagcta cctgagtagc tgggactata ggcatgtacc   82260
accatgccca gctattttt tgtattttt gtagagacag ggttttgcca tgttgcccag   82320
gctgatctca aactcctagg ctcaagcaat ctacccactt catcctccca aaatgctgga   82380
attacaggca ttagccacca cacccagcca ccactagagt attaaataat tccacatatt   82440
acccaggagt tagttcatga acagaagtct agctatcaac cattgtcttt tccctcaaag   82500
ccttgggaga tcatcttgca ctcaaccagc cttcgtgtaa gaagtaattc tttaaaaaat   82560
gatttgaagg atttcactgt acatgagaac acaaagtgct ttccctattg caccccatgc   82620
aaaagtgagt ttcaaaatat ttataactgg cactgcatgg gcactaaccc atctgaatga   82680
aagctaccat ccgtgagcat accagtgaca ccatttcagt gtctgtcctc tccctgaaaa   82740
tgccaaaaag tccacctttc ttaggatgca tctgtctcgc ttacctcata tttaattgt   82800 tcaacattat ttaatccaaa gtgtagatac tgacagtgat gtaaagggtt cagtaaaaat   82860
ggcaaggcag gtcacttaat actgcagaaa cctcagcttc atcatctgtt aaaaaggata   82920
ataaaagcta ccccagggga taggagaagt acattaaatg aaatgatgca tgtaaaatac   82980
tttccctcat gcaagataca acgatagctc cacaaataga gctattatga tcacttccag   83040
tactaatact atcgcctcta ttgctgatac ctgggaaaca gatgaccgtg gctagaaaga   83100
gccatatttg gcagtgaggg tcaagctcaa gtgagatctg cagataggac aatcagcagg   83160
atatatatgc actaggaaca cggcatgagg tgcgcaccca tctaaccaca tgttcttgcc   83220
aagtttgcaa actaccctat ggtagtttgg atgggtagaa tttaaggtgc acacaggtac   83280
taaaaactag agccaatatt gttcacccag gacttgaaac aactcttagc ttcaattccc   83340
atcctgtgct ccaccaagtg tgcatgccaa gctgagggtg cccacactgg agtgttcctt   83400
ccccaccaac ctagcatgag aaagcacttg atgacgaaat cacgcctctg ttgtgcttcc   83460
tttccagtta tatgccacta ggtatttgt tcctgattgc tgggaagatc atagaagttg   83520
aagactggga aatattccgc aagctgggcc tttacatggc cacagtcctg actgggtatg   83580
tcagactcaa gagaagagac agaaacctcc tttgatctaa taggatggcc gctgagaggt   83640
tgggtttcag ttggttaaaa ctggcttctg ccctatgtgc tgggaaagat agggttcaga   83700
gataagacag caggggagg agggctgccc tttaacagct gtactgtagg tggatcatgc   83760
tgtgctaatt gtcagctctt ggcagaacag cctggaccag gctttgtcac tgcctttatt   83820
ggttatgtta aaataatttt ttacaacaag agagaaaccc actcgtagcc tcccttggct   83880
ctctcctggc cttcatttcc ttaagaatgt aaactagcca agcaagcaag aatagcctcc   83940
atgtaccctg aacctgaaag aaattagcaa gggcctaaat gaaatcagac ttgagcaagt   84000
aggagcagga tggctgttgg ttcaaacact gttgctgggg ctgttaacca ccaccatgtc   84060
ctgcagcatc agagtgtcag agagggtgcc aggagaatct tgaggctggg aggaattgtg   84120
tgggcctttt tggaagccat taaacaggaa ggcagcaggg gttgggtagt ttccatattt   84180
attacagcct agctactgtt tccttgagaa aagatgaggt gggataagtt atgaatggtg   84240
```

```
cccctggaca cctagacagg ggcagaatat gtcacatacc ctaagaaata cagactaagg    84300
gaataaataa atatcattga tttgactctc acaagtcaat acctacaaac acccaacttg    84360
agcaatgaac tcacctattg gaacttgatc gtattggaga tttccaacac agcgcatttg    84420
gttcttaatc tgtgtttgcc aaaaacacag ccctgccagc caacacagag gcagatttgg    84480
tccctacagt gtgaggcccc tggcgctaag ggaggtggga cctccaattc actgaggcc     84540 accctgctgt agggctgctg aaacaggcag tgccagggat cgtgtctcag cagtgacgtg    84600
gctggggtgt atgagctgag ccatttcata accgagttct gctggtttct attctcttac    84660
cccagctagg tgtctaacag gaaactaaaa gtcagttcct catggttttt agctacaagc    84720
tctctatcaa gaagatcctc tcgccagaac tccaggatc atattttga tggccatttc      84780 ctatttcaaa cacacataac tgatctgtaa actctaagct gccagttaca tatatatcta    84840
tctgtgaaat gagtctcatt tcttaagcct cctagttcat gtaacctgtg tatttccatg    84900
tgaaacaatg aacagtttga gaaggcagga ataacaaaga aagaaataat cctaaagtat    84960
ggctgtggaa gagctgagac ttttttcctt actgtaactc tgacttccct cttagacagt    85020
gggcgccacc agcaagacag cagcttggtg cagggaatgg agtgggtgag gactgagcgc    85080
tgtgataagg ggtataatga ggtataaggt agtggtgaca tacagggtgc caaggaagga    85140
aggctcagcc ctacctgagg aagtgaggga aggcttcctg gaggaagggg gatgcctatc    85200
tgagtcttaa gaggagaaga actgagcagc aacagaagga aaaaagggca cttttgtgca    85260
tgtggcagga atagcacaca caggggtgtg gcagcatgat ataattctgt tctgtgaagc    85320
cttgaatttg gattcagcta ctggctttgt cattaactct gacaagatgc ttcatgtgct    85380
gagagagcct ctaaaccctc atacatggaa tgggacgtat attcctgccc tactcccatt    85440
tcttattggg ccattatgaa agtcaaacaa ttttataaat taaaaagatg tttgataaaa    85500
ggattaagtg tggggaggtg gtattatctt tgaaacttta atttctcttt cttgtttaca    85560
ggcttgcaat ccactccatt gtaattctcc cgctgatata tttcatagtc gtacgaaaga    85620 acccttccg atttgccatg gaatggccc aggctctcct gacagctctc atgatctctt      85680
ccaggtaaac agaagagggg tttctggaag aagcctccag gctcaacgtt atcaactctc    85740
acctcacttt acaaaacaga ctccagcttg cggttttgt agctgtcttt gagaaatgac     85800
ctccgtattc tcggcccctg ccctgaaca cattgcttca tgctgttgca tatttcctgc     85860
tctcttggca tgacctgcag ctcaggaagg ggttatggaa taactgggag cagtggtggg    85920
cacagcacct tctgattcct ggacctgcct aaagggctag catgatttgg atcctttgtt    85980
tcattttgtt ttgttatttt ctttactttt ctcgacaaga ttacctaaaa ggacccttg     86040 tttactttt ggaagacagg catgtcttca ggcagggact aaggtccagc atttctagac     86100
ataagttcct ttctattttt atcacacagt tcagcaacac tgcctgtcac cttccgctgt    86160
gctgaagaaa ataaccaggt ggacaagagg atcactcgat tcgtgttacc cgttggtgca    86220
acaatcaaca tggatgggac tgcgctctat gaagcagtgg cagcggtgtt tattgcacag    86280
ttgaatgacc tggacttggg cattgggcag atcatcacca tcaggtgggg catggtgtca    86340
cattcattgt catcactgat acagggatta ccgccagtaa aaattgtcca tgaagggaca    86400
ccaagaatgt cgcagtgatg aattcttttt cttgatctat aaagtccctt cccaagatta    86460
aatacgacta tatcctggta tgcaagattt ctgcttcggg gtctgggtag ccaaagccat    86520
cactctgtgc tcagtttact gaagccagta ggatctaggc acaggctagc acaaagactc    86580
```

```
aaggctgagt aagggccagt ccctgctttc aaactatccc tgctagatgg gcatgcacat    86640
atccaaatga atgctgaaga ccatgatgag ggatgtaaga gaactctgta tggtgttcac    86700
agaggactcc agagagggaa gggctggttc tagctgggaa ggtgaacgat ggcttcccag    86760
aggaggggaa catttagctg aatcttagaa gaataggaat ttagcaggca aaagaaaagc    86820
taggagcatt tggagtggca gaaatagctt gtgatgcagc catgggctag ttacagcata    86880
cagatttctt gctatggctg gcataaagga tacataaaca ttcctttatg tttaaacgaa    86940
tgaggaggca ggggtcatgt catgaaaggt tttgtacgaa gagcttgtgg aaagctctta    87000
gatgctttgt catattatgg acagatttgc attttatgta tttatttatt ttttgagatg    87060
gagttttgct ctgtcgccca ggctggagtg cagtggcaca atctcggctc accacaacct    87120
ccgcctccag ggttcaagca attctcctgc ctcagcctcc tgagtagctg ggactacagg    87180
cgtgcaccac cacacctggc taattttttga atttttagta gagatgggtt tcaccatgtt    87240
ggccaggctg gtcttgaact cctgacctca ggtgatttgc ccacctcaga ctcccaaagt    87300
gccgggatta taggtgtgag ccaccacgcc cggcagattt gcattttaca aagataagca    87360
gcaatatgga agatatattg gatgggagca gggaccaaat ctaggaaacc agttaggaga    87420
ccactgcaga agtccaggca gggtattaga aggcactgac actgaggttg gagaagagct    87480
aatgaattga agaagcatca gctggattca gggtgaaagg cgagggaatg ccaggatgac    87540
tcccaggatt ggcagatgat tctaaattgg tgggtggggc ttaccagaac aggaacgagt    87600
gtaagagaag cacatatagg tgggaaagat aaatagtaaa tacttttttga cagattgaat    87660 ttgaaatgcc tttaagactt ccagttgcac atatgcaatg agaaatatag gtctggctgc    87720
agatacagac atcaggaaca tgggcttaat aatggtcttc aaatgtgtaa gtcacaagtt    87780
attgcttgta ttggaatcgc ggctacatca tgattagctg tgatcttggg caagtgactt    87840 gaattttttaa acttctgttt tctcatctgt aaaatgaata atagtaccta caacttattc    87900
aagtagtggc aattaagtaa tatgcatata aaatgtttat aactgtgcct atgtagtgag    87960
tactcagtga atgttgaaaa tggatgacat gacgtaggga gagtttgcag agaagagaag    88020
gagattaagg actgaggctt ggaaaaatcc taatactaga agcaggtaga gaagggaaaa    88080
cccaagaggg agaggagaa ggacagagag atgggaggga agccagtaaa ccttggtatc    88140
atggaaaccc agaaaagaga gattttcaag ggtgaaatgg tccacagagt cagaagctgc    88200
agagaattct agtgaaatga ggatagacat tgtctgccca agtagatggt agaactgtca    88260
ttagtggatt ttgccagatt tgtttctcta ggacagcact attcaatatg gtaaccacta    88320
gccatgtggc ccactgaatt ggatagcaca gacacagaat agtttcatca ttgcagaaag    88380
ttcttttgga cagcactatg ttagagtgat aggctgggat tagagttaac ctgaagactt    88440
ttgttcagtt tagaatggaa gtttaagact aaactggtcc ctaggcctgc tcaaggttga    88500
atctgaactt tttagagtta attcattctt gtgtcccagc ctaaacataa attctaggga    88560
taaaatcaga gtttgttaac taacaatgtt ctaatacaat gcatttttta aatcctcccc    88620
aaccctaaat cgcaaagtat ttctgttggc tgaagacaag tgcaaaatac accatttggc    88680
acaccagctg gggaactatc ccaatgctgt gtaatctata aaagtgtta gcggctaaag    88740 aagcctgtgc caaagagatt gagcaaagtc ctgtaattat aacagcagag ggtatgtcaa    88800
aattgaaacc ttgaatcatg cctgaaaaag tttctgctcc acaaccaccc ctgtgcttcc    88860
aacagttgtt acttttacat ttccaagggt ttttccccac ttccctcacc ctgggctgtg    88920
gaacccagtc ttcactgaac tgatttccaa ggagtggttt atgaagtgcc tattcttttg    88980
```

```
tgtatttgac actttgtgat gaaatccctc cctcttttttt ggttgtaagt tttctagatc    89040
tttctaatca ttttttttaat ctcactgcca gaggaatgaa ctctgggcct agaagctaaa    89100
tagtcaattc tcattaaagc ctctccggct acctctggta tattcttaaa tcagatttgc    89160
tgaaaactac tggcccagag ccaataacaa ctgtgaggcc caagtaatc attggcttaa      89220 aattaaaaat cctcactggc tctacatgga aaataataaa agttggtttt gcttgacagt    89280
taccattata gttcatgtga ctaatggtta aagagatttt tagacccaaa gtatatttct    89340
gtggactgga catcaaagaa acataggtac catctaccca aaacataccc ttttgtggct    89400
ttatcataat actcaaaggt tacaacggat tgaaaattgt gtgagaatat gtgtcaaaat    89460
ggaaaaaaaa aggataaatt gtcttataaa aataattagg gccggaagcg atggctcaga    89520
cctgtaatcc cagcactttg ggagacctaa gtgggtgaat cacttgagtc caggagttcg    89580
agacaagcct gggcaaaatg gcaaaacccc atgtttacca aaatattct aaaaaagaaa      89640 aattagccag gcatggtggc atgtgcctgt agtcccagct actcaggagg ctgaagtggg    89700
cagactgctt gagcccagga ggcagaggtt gcagtgaact gagatggcgc cactgcactc    89760
tagcctaggc aacagagtga gattccatct caaagaaaag aaagaaagaa agaaagagag    89820
aaaagaaaaa gaaagaaaga aagtaaagc taattataca gcagggcgca gaggctcaca      89880
cctgtaatat cagcacttta agaggccaag gcgggcggat cactttagcc caggagtttg    89940
agaccagcct gagcaacaag gcgaggcccc gtctctacaa aaaatacaaa aattagccag    90000
gtgttatgga gtgcatctgt ggtctcagct actcaggagg ctgaggcaag aagatcgctt    90060
gagcccaata ggtggaggct gcagtgagct gtgatcatgc cactgaactc cagcctgggc    90120
aacagagtga gaccttgtct ctggaaaaaa aaaaaatata tatgtgtgtg tgtgtgtgtg    90180
tgtgtgtgtg tgtgtgtgtg tgtgtgtgtg tgtaaggaa ataagaaga aagacaattg        90240 taggatttgg ggcctagaaa gagctgagag aaaaaaaaag tagcagtagt aatagtagta    90300
gtagtagttg ttgtaatagt tgttgttttg gttgctgcag tagcagtagt aataatacca    90360
gtggcagcag cgacagcagc aatagaggaa gcattagcag caactgctgt tgttgcagaa    90420
gtagcagcag aaatggcacg tttttaatct ttttgtttgt ttttgtttt attttacttt      90480 aagctctggg atacgtgtgc agaacatgca ggtttgttac ataggtatac gtgtggaaat    90540
ggcatgtttt taagcatcta ctatacaagt gctatcccag atgccttacg tgtattaacc    90600
tcatttaatc ttcccagcag cttgcagtag acatactgtc cccatcttac aggcaaggaa    90660
ttgagattca gagaagtaac ttgcctgaag aaatgccatc agtaaaatgg tagagcccaa    90720
agtacatcac ccaggtgtgt ctgacactaa aacctgtgtt ccctccaagt cacaagccat    90780
ccttcaacct gtttagagag ccaagtccaa tggccggtcc taaaactagg acctcagtgt    90840
gaggaaagaa ctttgtacca ctgatattta tgttttcttc tgtggaaatc ctctaactca    90900
aagtagaata tgttcaagca gcaggaatag gttttttatat tattttctcc catctgaagg    90960
ttcatagttc tgagtttcag accaatgcca gtcaaacagc agtagtctgg taagcaaggt    91020
caaggctcaa ggacagagtt ttctttgact aaatgaattt tgagtttcaa gcccagcctc    91080
aggctataga gacatggatt actgtgcacac gtcagggttt ccaagaggga tcagctggca    91140
tggacacaaa tcacttctga caaagaaaac ctgttgatgc attccatta aatttttttc      91200 aaccagcatt aaaataaaact tgggcttttcc aaagagtact taggtcagaa gagatccaaa    91260
gggttataga ggccagaaac ctttgagact gaggcctgaa accttagag taattggtac     91320
```

-continued

| | |
|---|---|
| agccccagaa atctctaatt tactataatt tggtggtcaa aaccactgaa tgaaaataca | 91380 |
| cttgtcaaaa aactctggcc tgtgtttgac tgtaccctca aatgctttct gcaacacctc | 91440 |
| agtaggcaga tgaatgggca gtagaatcag cttcctaaga actctggctt tttttagccc | 91500 |
| caaagaatat gaatgtgtgg atagaatcag ggattcttcc agtttaaatt gccaattttt | 91560 |
| acattttcac ctttcaacac agtggaaccc gggcaacagt tcaggccttg gcccaagggc | 91620 |
| aaggacttgt ctccagaaag cactgtaggt gtggcctcca gcttatccaa gtcaagggat | 91680 |
| ttttcagggc atgttgaacc cttgtttcct tcagaatgat ccaattaaaa taaggaagat | 91740 |
| gttgctgata aagagactgc acattacaaa gaaaaaaatc cctactgcct cagctgatct | 91800 |
| taccaagagg gatcttttta aatacctggt aataaagttc acctggctgc ccctcctgga | 91860 |
| ttccagatct ttctttccca caaagtgcat ctactggcaa aaaggagcag tcaggagtaa | 91920 |
| atgcttgtac cttggacagg atcagctatt tctcaattca gtgccctgaa gagcagttcc | 91980 |
| cagaggtaaa gagtcctgtg atgtcaagag agtgcataaa gcctgcttaa ccattgtctc | 92040 |
| attcctttgc cttcacctga aatgcccttg cccatctgcc cctacaacta tccttctgtc | 92100 |
| catccttcag ggcaacttaa attcctgcca tatattaggt gctcagtaaa ttattgggtg | 92160 |
| gtgagtagat ggaacaaggg agtaggaagg caggtgcaga ggtacctggc acttatttag | 92220 |
| gatgagtgta tgtatacata gatgagtaca cgaagcctcc tattaacacc ccatttagta | 92280 |
| aactcctgct ttcctcttga gtatctctct tacttatttt ttggtgccac ttatgcagtt | 92340 |
| cttccttgca ttagagtgat gtgccatatc tccgtctgca aggagatggc atcatacccc | 92400 |
| tcatagtccc cctccccca cagctctaat cctgtaatga ggcagagctg gggctcagca | 92460 |
| agtcacagat tctaactacc caatttaggg acacagcagt aatagccatc gggactaagc | 92520 |
| gggagtaacc atttcaggcc agggctttaa cgggagaggt aagtgtctaa ctcctttcct | 92580 |
| gctggtatgt ttctgcagta tcacggccac atctgccagc atcggagctg ctggcgtgcc | 92640 |
| ccaggctggc ctggtgacca tggtgattgt gctgagtgcc gtgggcctgc ccgccgagga | 92700 |
| tgtcaccctg atcattgctg tcgactggct cctgtgagtt ggaataaatg cactgcctta | 92760 |
| gctggatgtg caggcgggct tcccagcctc gcaggcgctg cagtctgtca tcattctctc | 92820 |
| ctcagattgc ctaatgagcc acctgttgct gctttaattt tcctctgacc aggccatctg | 92880 |
| ataacatgcc taaaaattaa ctcctcataa cgtggagcag tgattttaaa aagccggtga | 92940 |
| gctccattag ctcattatac ctggtaacac tcaagcttag gagctgggtg tgggacagag | 93000 |
| ataaacacag aacaaggtga gaagccaggc agggccccag agccatcctg acctatccca | 93060 |
| gccctggttc agcatcatag gctcagaacc acctagttca aaatcagtcc gtcttcctaa | 93120 |
| gcatcttccg aaccatcagg gacagtggca caagcacttg ggtttgaatc tccgtcctgt | 93180 |
| gtcttaccag cttcttgacc tcgagcaagt ttccttaacc tgaggcccag ttgcataatc | 93240 |
| tgtgagatgg gaaaaaatct gcctatgtca ttgggttgtt ttaaggactg agtgagctca | 93300 |
| tgtgagtgga gcatctagaa cagcgtttgg cagcccatac atgctcaata aatggcaagt | 93360 |
| tttattgtta tgattagaat gagttggacc attcaggccc caatcaacaa cacttctctc | 93420 |
| tctctctctc tctctctctc tctcacacac acacacacac acacacacac acatatggaa | 93480 |
| tacagcagaa catctgggtg agaaagtacc ttcagtgacc ctcaaggtta aagttagaac | 93540 |
| cagcctggct ccaagcttta cccttgatgc ccacttctgt gcatggatct tacagcattt | 93600 |
| aggtctggct ctgtccctg gcattgcagg taagtattgc tccacatgga gcctttgctc | 93660 |
| agaaccagct caggctcact ggggagtcca gtgctatgta ctgtagtttg caggtgacag | 93720 |

```
atgagatgga aagggaagca gagacatcct attgggcttg aaaacacaga ttcacatttc   93780
aaatggcaaa agcccctgca cctggcttgg aagctgtgcc atgaggtggc ccctcagtag   93840
ctaactgggc tataggccca aatgaggtgg caccttctt gcaaagatat cctatcattg    93900
agtcaagatt tggttctttc tagtgatgct ggtggatttg cattttctc ctttccctga    93960
gtcttcctgg aaccagttac cttccctgcc aagataccca gatgagtcaa aggtccaatt   94020
ggaggtatgg gataaaaaga cactagggcc agttcaatcc ctggacttgt tctaaataac   94080
agaagggcat ccagggtggt catgtgtaag cattgtcagc cttttctgtt ctgcaggtgt   94140
agttttcaca agattccccc tgcatgcagt tcctgtcaac aaagtgccag tatcaaaatg   94200
gatcctctcc tctgcagtgt gccttctcta cctgtcttcc tgccaccagt ctcttcccca   94260
ggctctctgg aaattaagac tggatgaggg tggcccacag agaaatccat tcctgggctg   94320
acctgtgttt tctgaccccg tgctctgcac catgcctcct ggtttgctca taagtagagt   94380
gacctagatt ggtaaataaa caagtacacc atggacctga acaaacacat acatacccca   94440
catgcacatg gtacatactc cacccacaaa acacccaagt tctctgacct ttgcccaaag   94500
agagcccaca atggcatttg cattgaatct agaaaatccc aagatagagg ttagggctga   94560
aaaacttact gaattctgaa cctccctcag tcccccaaaa aatatctgga acgactctat   94620
tcatgtttct ttgggagaag aggaaggaat ttagggagac ttaggggagt cattgctact   94680
ttggggagc tcatgctgtg cctttatgaa caaccccagg cctgtgagga gccttcagtc    94740
agtcagccat gaggacagca cttctgcac ttactgaaat ctaaactgaa catgtcaggt    94800
ccttgcatct ctccagtgat gaaggaaaat gaaatctggg cctcctgtct gactcctccc   94860
gtctctcccc agggaccggt tcaggaccat ggtcaacgtc cttggtgatg cttttgggac   94920
gggcattgtg gaaaagctct ccaagaagga gctggagcag atggatgttt catctgaagt   94980
caacattgtg aatccctttg ccttggaatc cacaatcctt gacaacgaag actcagacac   95040
caagaagtct tatgtcaatg gaggctttgc agtagacaag tctgacacca tctcattcac   95100
ccagacctca cagttctagg gcccctggct gcagatgact ggaaacaagg aaggacattt   95160
ccgtgagagt catctcaaac actgcttaag gaaaagagaa acactaatgg ccaagtgtac   95220
atttgatttg atatacagac ctccagatta ttttctatat ttggattcac agcctttgcg   95280
ctctgggttt tgggatttgg gtgtggggta agttgaaggg aaatcaattt aaaggaaagt   95340
tctattatct gggttttaga aattctataa gagacaaagt ttggaagtac ataaagtaat   95400
aactgttaga attaggtaat ggatatgaaa gagaaaatgc tttctcatgc atagacaagt   95460
gttttgggtt tttaaaaaaa atattctgtc attggttaca aatttttact caggctttct   95520
attggcatgg atttcctttg acctctcact tttttataaa ttataatgca tctaaaccac   95580
ctgtccccag ttaatgtgcc aaaatgtcaa ttttaactt atctccagcc aatttcaaag    95640
aaaacagacc agcatagttc tgcaataaca gttttaagat gggcataggg tttggaagaa   95700
agggagaagg attcttttt caatgtactg tattgggacg ctggtaactg ttaacccagt    95760
gttcagcata gagctatata tatatatata tgtatatatt tattattttc atataatttg   95820
ccagacagag atcagaattg aaccgtcaat gtgaaataaa gagttctcct tgtacttgaa   95880
taataaccac gattccaacc caggtctgct ttggggctta tcagaactcc tttctaagga   95940
gcactgaaat gagaaatcat gttgttcgat cgtttcacat ctgtatatca gctctaaagc   96000
agagatgtat tatggtgata ctccaaggtg gcatagccat tcatttacaa cttccagatt   96060
```

-continued

```
tgagctgcct ggagggaatc catatcagct ctgcataaga ttatatacaa agctgtcact    96120
cacaaaaggc tggatgtgct ttcatccaac tggaaggctt tattcttcca agttcattca    96180
tactcaaaga ggccagtact ttgccatcct tgcacttctg ttatcagggc ccaaataaca    96240
gtggcaagct accaactaag ttgtattta ataaagattc catgggttga acaagccacg     96300
ttgcagaaaa agagcttccc ctaacctggg ttgttgcaga gtaaatccca cgacataagc    96360
tggtatcast ggttcggggg aaatagttcc attctatgac tcttgtctcc tcctccagga    96420
ggactgttct aactagtaat cttggcccta ttcattacat cctctgcttg tcattctgct    96480
aatttatgaa gatagtttat tatagtctgt acttcagttc tcatcttgta ataatgctt     96540 aacataaact tgtacttaca ctgaaatcca aaatagtcat gtttctgcag tattctgtag    96600
ccaacttaaa cctgtgcttt catgtttaag aaatgagaaa ttgtgccaaa gatagcagaa    96660
gagtagataa gtgctcagta ttgacgacct acatctgaaa tctacaacat aatgatactg    96720
aattgttatg taaacatcat aaatagtaaa taatgattca atgtgaattt taaaatgcaa    96780
atattgctat tgtttatagg aaataaatct aaatataaat g                        96821
```

```
<210> SEQ ID NO 5
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: Misc_feature
<222> LOCATION: (26)..(26)
<223> OTHER INFORMATION: R = A or G

<400> SEQUENCE: 5
ggataagctg gaggccacac ctacartgct ttctggagac aagtccttgc c             51

<210> SEQ ID NO 6
<211> LENGTH: 51
<212> TYPE: DNA
<213> ORGANISM: Artificial sequence
<220> FEATURE:
<223> OTHER INFORMATION: Primer
<220> FEATURE:
<221> NAME/KEY: Misc_feature
<222> LOCATION: (26)..(26)
<223> OTHER INFORMATION: R = A or G

<400> SEQUENCE: 6
ttagagctgt gggggagggg ggactrtgag gggtatgatg ccatctcctt g             51

<210> SEQ ID NO 7
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: Misc_feature
<222> LOCATION: (26)..(26)
<223> OTHER INFORMATION: S = C or G

<400> SEQUENCE: 7
aatcccacga cataagctgg tatcastggt tcgggggaaa tagttccatt c             51
```